(12) United States Patent
Clark et al.

(10) Patent No.: US 8,822,472 B2
(45) Date of Patent: Sep. 2, 2014

(54) PIPERAZINES, PHARMACEUTICAL COMPOSITIONS AND METHODS OF USE THEREOF

(75) Inventors: Roger B. Clark, Lexington, MA (US); Daniel Elbaum, Newton, MA (US)

(73) Assignee: Cornerstone Therapeutics, Inc., Cary, NC (US)

( * ) Notice: Subject to any disclaimer, the term of this patent is extended or adjusted under 35 U.S.C. 154(b) by 569 days.

(21) Appl. No.: 13/069,670

(22) Filed: Mar. 23, 2011

(65) Prior Publication Data

US 2012/0071652 A1      Mar. 22, 2012

Related U.S. Application Data

(63) Continuation of application No. 11/811,010, filed on Jun. 6, 2007, now Pat. No. 7,943,622.

(60) Provisional application No. 60/811,275, filed on Jun. 6, 2006, provisional application No. 60/852,836, filed on Oct. 19, 2006, provisional application No. 60/901,240, filed on Feb. 13, 2007.

(51) Int. Cl.
| | |
|---|---|
| *A61K 31/497* | (2006.01) |
| *C07D 401/08* | (2006.01) |
| *C07D 401/12* | (2006.01) |
| *C07D 413/08* | (2006.01) |
| *C07D 413/12* | (2006.01) |
| *C07D 405/14* | (2006.01) |
| *C07D 241/04* | (2006.01) |
| *C07D 401/14* | (2006.01) |
| *C07D 417/14* | (2006.01) |
| *C07D 513/14* | (2006.01) |
| *C07D 413/14* | (2006.01) |

(52) U.S. Cl.
CPC ............ *C07D 241/04* (2013.01); *C07D 401/12* (2013.01); *C07D 405/14* (2013.01); *C07D 401/14* (2013.01); *C07D 417/14* (2013.01); *C07D 513/14* (2013.01); *C07D 413/14* (2013.01)
USPC .............. 514/252.1; 514/252.12; 514/252.13; 514/253.01; 514/253.03; 544/121; 544/360; 544/362; 544/364

(58) Field of Classification Search
CPC .. A61K 31/497; C07D 401/08; C07D 401/12; C07D 413/08; C07D 413/12
USPC .......................... 544/121, 360, 362, 295, 364; 514/252.1, 252.12, 252.13, 253.01, 514/253.03
See application file for complete search history.

(56) References Cited

U.S. PATENT DOCUMENTS

| | | | |
|---|---|---|---|
| 5,880,128 | A | 3/1999 | Doll et al. |
| 5,891,872 | A * | 4/1999 | Doll et al. .................... 514/220 |
| 6,372,747 | B1 | 4/2002 | Taveras et al. |
| 6,878,700 | B1 | 4/2005 | Link et al. |
| 2002/0169155 | A1 | 11/2002 | Luly et al. |
| 2003/0073681 | A1 | 4/2003 | Hauske et al. |
| 2004/0180880 | A1 | 9/2004 | Lauffer et al. |

FOREIGN PATENT DOCUMENTS

| | | |
|---|---|---|
| WO | 95/00497 | 1/1995 |
| WO | 96/31478 | 10/1996 |
| WO | 96/31501 | 10/1996 |
| WO | 97/10219 | 3/1997 |
| WO | 98/20001 | 5/1998 |
| WO | 99/18095 | 4/1999 |
| WO | 03/44014 | 5/2003 |
| WO | 2004/014370 | 2/2004 |
| WO | 2004/071390 | 8/2004 |
| WO | 2004/087653 | 10/2004 |
| WO | 2005/044797 | 5/2005 |
| WO | 2005/080386 | 9/2005 |
| WO | 2006/014012 | 2/2006 |
| WO | 2006/012919 | 12/2006 |

OTHER PUBLICATIONS

Huang et al., "Guiding Farnesyltransferase Inhibitors from an ECLiPS Library to the Catalytic Zinc," *Bioorganic & Medicinal Chemistry Letters*, 2006, 16(3):507-511.

Brockunier et al., "Substituted Piperazines as Novel Dipeptidyl Peptidase IV Inhibitors," *Bioorganic & Medicinal Chemistry Letters*, 2004, 14(18):4763-4766.

Gundish, "Nictonic Acetylcholine Receptor Ligands as Potential Therapeutics," *Expert Opinion on Therapeutic Patents*, 2005, 15(9):1221-1239.

Chen, et al., "N, N-Disubstituted Piperazines: Synthesis and Affinities at alpha 4 beta 2 and alpha 7 neuronal nicotinic acetylcholine receptors," *Bioorganic & Medicinal Chemistry Letters*, 2003, 13(1):97-100.

Lin, et al., "Recent Developments in Neuronal Nicotinic Acetylcholine Receptor Modulators," *Expert Opinion on Therapeutic Patents*, 1998, 8(8):991-1015.

* cited by examiner

*Primary Examiner* — James O. Wilson
*Assistant Examiner* — Ebenezer O Sackey
(74) *Attorney, Agent, or Firm* — Saul Ewing LLP; Kathryn Doyle; Domingos J. Silva

(57) ABSTRACT

Disclosed are novel piperazine derivatives that act as agonists of the α7 nAChR. Also disclosed are pharmaceutical compositions, methods of treating inflammatory conditions, methods of treating CNS disorders, methods for inhibiting cytokine release from mammalian cells and methods for the preparation of the novel compounds.

2 Claims, 4 Drawing Sheets

PIPERAZINES, PHARMACEUTICAL COMPOSITIONS AND METHODS OF USE THEREOF

RELATED APPLICATIONS

This application is a continuation of U.S. application Ser. No. 11/811,010, filed Jun. 6, 2007, which claims the benefit of U.S. Provisional Application No. 60/811,275, filed on Jun. 6, 2006, U.S. Provisional Application No. 60/852,836, filed on Oct. 19, 2006, and U.S. Provisional Application No. 60/901, 240, filed on Feb. 13, 2007. The entire teachings of the above applications are incorporated herein by reference.

BACKGROUND OF THE INVENTION

Nicotinic acetylcholine receptors (nAChRs) are a family of ligand-gated ion channels found at the neuromuscular junction as well as throughout the central and peripheral nervous systems. In humans, 16 different nAChR subunits have been identified and include α1-α7, α9-α10, β1-4, δ, ε and γ (Lindstrom, 1995. Nicotinic acetylcholine receptors in "Handbook of Receptors and Channels: Ligand- and Voltage-Gated Ion Channels." Edited by R. Alan North. CRC Press, Inc.). These subunits can co-assemble to form numerous homo- and heteropentameric subtypes which in turn are characterized by distinct ligand-binding and pharmacologic properties (Lindstrom, 1995).

The α7 nAChR subtype has been reported to play a role in several diseases of the central nervous system (CNS) including Alzheimer's disease (Wang et al, J Biol. Chem. 275(8): 5626-32 (2000), Kem, Brain Biol. Res. 113(1-2): 169-81 (2000)), schizophrenia (Adler et al, Schizophr Bull 24(2): 189-202 (1998)), Parkinson's disease (Quik et al, Eur J Pharm 393(1-3) 223-30 (2000)) and attention deficit-hyperactivity disorder (Wilens et al, Am J Psychiatry 156(12): 1931-7 (1999), Levin et al, Eur J Pharmacol. 393(1-3): 141-6 (2000)). Selective agonists of the α7 nAChR subtype have therefore been proposed as useful for the treatment of these and other central nervous system conditions (U.S. Pat. Nos. 6,110,914, 5,902,814, 6,599,916, 6,432,975; Kem et al, Behav. Brain Res. 113(1-2): 169-81 (2000), Martin et al, Psychopharmacology (Berl.), 174(1):54-64 (2004).

The α7 nAChR subtype has also recently been shown to have involvement in the inflammatory response (Wang et al, Nature, 421(6921):384-8 (2003)). Wang et al demonstrated that activation of the α7 nAChR inhibits the release of proinflammatory cytokines, such as tumor necrosis factor alpha (TNF-α) and high mobility group box 1 protein (HMGB1), from macrophage cells and confers protection against lethality in a murine model of sepsis. Selective agonists/partial agonists of α7 nAChRs have been demonstrated to have utility as anti-inflammatory agents by inhibiting the release of TNF-α and other proinflammatory cytokines (WO 2004/052365 A2).

Given the therapeutic potential of α7 nAChR agonists in the treatment of inflammatory conditions, CNS conditions as well as other deleterious conditions, there remains a need in the art for additional α7 nAChR agonists.

SUMMARY OF THE INVENTION

It has now been discovered that certain novel piperazine compounds act as modulators of the α7 nAChR. Based on this discovery, novel compounds, pharmaceutical compositions, methods of treating inflammatory conditions, methods of treating CNS disorders, methods for inhibiting cytokine release from mammalian cells and methods for the preparation of the novel compounds are disclosed.

In one embodiment, the invention pertains to a compound of the Formula (I):

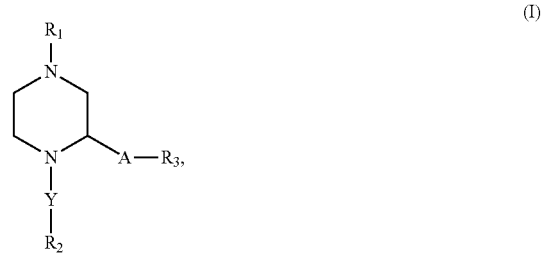

or a pharmaceutically acceptable salt thereof, wherein the variables are as defined below.

$R_1$ is selected from the group consisting of H, C1-C10 alkyl, C2-C10 alkenyl, C2-C10 alkynyl, C3-C10 cycloalkyl, C4-C10 cycloalkenyl, C(O)$R_5$, C(O)O$R_5$ and C(O)N$R_5R_5$. In another embodiment, $R_1$ is selected from the group consisting of H, C1-C10 alkyl and COR$_5$.

$R_2$ is selected from the group consisting of C1-C10 alkyl, C1-C10 alkyl substituted with one or more $R_7$, C2-C10 alkenyl, C2-C10 alkenyl substituted with one or more $R_{10}$, C2-C10 alkynyl, C2-C10 alkynyl substituted with one or more $R_7$, C3-C8 cycloalkyl, C3-C8 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, aryl, heteroaryl, wherein said aryl and heteroaryl are each optionally substituted with one or more $R_9$. In another embodiment, $R_2$ is selected from the group consisting of C1-C10 alkyl, C1-C10 alkyl substituted with one or more $R_7$, C2-C10 alkenyl, C2-C10 alkenyl substituted with one or more $R_{10}$, C3-C8 cycloalkyl, C3-C8 cycloalkyl substituted with one or more $R_8$, 3-8 membered heterocycloalkyl, 3-8 membered heterocycloalkyl substituted with one or more $R_8$, aryl and heteroaryl, wherein said aryl and heteroaryl are each optionally substituted with one or more $R_9$. In yet another embodiment, $R_2$ is aryl or heteroaryl, wherein said aryl and heteroaryl are each optionally substituted with one or more $R_9$. In a further embodiment, $R_2$ is aryl, wherein said aryl is optionally substituted with one or more $R_9$. In an additional embodiment, $R_2$ is heteroaryl, wherein said heteroaryl is optionally substituted with one or more $R_9$.

$R_3$ is aryl or heteroaryl, wherein said aryl and heteroaryl are each optionally substituted with one or more $R_9$. In another embodiment, $R_3$ is selected from the group consisting of 6 membered monocyclic aryl, 5 or 6 membered monocyclic heteroaryl comprising 1-3 heteroatoms, 8-12 membered bicyclic aryl, 8-12 membered bicyclic heteroaryl comprising 1-6 heteroatoms, 11-14 membered tricyclic aryl and 11-14 membered heteroaryl comprising 1-9 heteroatoms, wherein each of said heteroatoms is independently selected from the group consisting of O, N and S and wherein said aryl and heteroaryl are each optionally substituted with one or more $R_9$. In yet another embodiment, $R_3$ is 5-6 membered monocyclic aryl or 8-12 membered bicyclic aryl, wherein said aryl is optionally substituted with one or more $R_9$.

Y is selected from the group consisting of $C(R_4)_2$, $C(R_4)_2C(R_4)_2$, $C(R_4)_2C(R_4)_2R_6$, $C(R_4)_2C(R_4)_2C(R_4)_2R_6$, CO, $C(O)R_6$, C(S), $C(S)R_6$, $CH_2C(O)$, $CH_2C(O)R_6$, $CH_2C(S)$, $CH_2C(S)R_6$, $SO_2$, and $SO_2R_6$. In another embodiment, Y is selected from the group consisting of CO, $COR_6$, $SO_2$ and $SO_2R_6$. In an additional embodiment, Y is CO or $COR_6$. In a further embodiment, Y is $SO_2$ or $SO_2R_6$.

A is a linking group selected from the group consisting of:

$$-C(R_a)_2-X_a-, -C(R_b)=X_b- \text{ and } -C\equiv X_c-.$$

In another embodiment A is selected from the group consisting of $-C(R_a)-X_a-$ and $-C(R_b)=X_b-$. In a further embodiment, A is $-C(R_a)_2-X_a-$.

$X_a$ is selected from the group consisting of a bond, $C(R_4)_2$, $C(R_4)_2C(R_4)_2$, O, $C(R_4)_2O$, $OC(R_4)_2$, $NR_5$, CO, $C(R_4)_2CO$, $CONR_5$, $C(R_4)_2NR_5$, $NR_5C(R_4)_2$, $NR_5C(O)$, $C(R_4)_2NR_5C(O)$, $NC(O)R_5C(R_4)_2$, S, $C(R_4)_2S$, and $SC(R_4)_2$. In another embodiment, $X_a$ is selected from the group consisting of a bond, $C(R_4)_2$, $C(R_4)_2(R_4)_2$, O and $NR_5$.

$X_b$ is selected from the group consisting of $C(R_4)$ and $C(R_4)C(R_4)_2$.

$X_c$ is selected from the group consisting of C and $CC(R_4)_2$.

When $X_a$ is a bond, $C(R_4)_2$, $C(R_4)_2C(R_4)_2$, $C(R_4)_2O$, $C(R_4)_2$ $NR_5$, CO, $C(R_4)_2CO_3$ $CONR_5$ or $C(R_4)_2S$, then each $R_a$ is independently selected from the group consisting of H, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, halo, haloalkyl, $OR_5$, $SR_5$, $NR_5R_5$, $C(O)OR_5$, $NO_2$, CN, $C(O)R_5$, $C(O)C(O)R_5$, $C(O)NR_5R_5$, $N(R_5)C(O)R_5$, $NR_5S(O)_nR_5$, $N(R_5)(COOR_5)$, $NR_5C(O)C(O)R_5$, $NR_5C(O)R_5$, $NR_5S(O)_n$ $NR_5R_5$, $NR_5S(O)_nR_5$, $S(O)_nR_5$, $S(O)_nNR_5R_5$ and $OC(O)R_5$, or both $R_a$ are taken together to form a 3 to 6 membered ring containing 0 to 3 heteroatoms each independently selected from N, O and S, wherein said ring is substituted with one or more $R_8$. In another embodiment, each $R_a$ is independently selected from the group consisting of H, C1-C10 alkyl, C2-C10 alkenyl, $OR_5$, halo and haloalkyl.

When $X_a$ is O, $OC(R_4)_2$, $NR_5$, $NR_5C(R_4)_2NC(O)R_5$, $NC(O)R_5C(R_4)_2$, S, or $SC(R_4)_2$, then each $R_a$ is independently selected from the group consisting of H, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, haloalkyl, $C(O)OR_5$, CN, $C(O)R_5$, $C(O)C(O)R_5$ and $C(O)NR_5R_5$, or both $R_a$ are taken together to form a 3 to 6 membered ring containing 0 to 3 heteroatoms each independently selected from N, O and S, wherein said ring is substituted with one or more $R_8$. In another embodiment, each $R_a$ is independently selected from the group consisting of H, C1-C10 alkyl, C2-C10 alkenyl and haloalkyl.

$R_b$ is selected from the group consisting of H, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, halo, haloalkyl, $C(O)OR_5$, $NO_2$, CN, $C(O)R_5$, $C(O)C(O)R_5$, $C(O)NR_5R_5$, $S(O)_nR_5$ and $S(O)_nNR_5R_5$. In another embodiment, $R_b$ is selected from the group consisting of H, C1-C10 alkyl, C2-C10 alkenyl, $OR_5$, halo and haloalkyl.

Each $R_4$ is independently selected from the group consisting of H, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, halo, haloalkyl, $OR_5$, $SR_5$, $NR_5R_5$, $C(O)OR_5$, $NO_2$, CN, $C(O)R_5$, $C(O)C(O)R_5$, $C(O)NR_5R_5$, $N(R_5)C(O)R_5$, $NR_5S(O)_nR_5$, $N(R_5)(COOR_5)$, $NR_5C(O)C(O)R_5$, $NR_5C(O)R_5$, $NR_5S(O)_n$ $NR_5R_5$, $NR_5S(O)_nR_5$, $S(O)_nR_5$, $S(O)_nNR_5R_5$ and $OC(O)R_5$, or two $R_4$ are taken together to form a 3-6 membered ring comprising 0-3 heteroatoms, wherein said heteroatom is independently selected from N, O and S, and wherein said ring is substituted with one or more $R_8$. In another embodiment, each $R_4$ is independently selected from the group consisting of H, C1-C10 alkyl, C1-C10 alkyl substituted with one or more $R_7$, C2-C10 alkenyl, C2-C10 alkenyl substituted with one or more $R_7$ and haloalkyl.

Each $R_5$ is independently selected from the group consisting of H, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkenyl substituted with one or more $R_7$, C3-C10 cycloalkyl, C3-C10 cycloakyl substituted with one or more $R_8$, C4-C10 cycloalkenyl, C4-C10 cycloalkenyl substituted with one or more $R_8$, 3-10 membered heterocycloalkyl, 3-10 membered heterocylcloalkyl substituted with one or more $R_8$, 4-10 membered heterocycloalkenyl, 4-10 membered heterocycloalkenyl substituted with one or more $R_8$, haloalkyl, aryl, heteroaryl, wherein said aryl and heteroaryl are each optionally substituted with one or more $R_9$. In another embodiment, each $R_5$ is independently selected from the group consisting of H, C1-C10 alkyl, C2-C10 alkenyl, C2-C10 alkynyl, C3-C10 cycloalkyl, C4-C10 cycloalkenyl, 3-10 membered heterocycloalkyl, 4-10 membered heterocycloalkenyl, haloalkyl, aryl, heteroaryl, wherein said aryl and heteroaryl are each optionally substituted with one or more $R_9$. In another embodiment, each $R_5$ is independently selected from the group consisting of H, C1-C10 alkyl and C2-C10 alkenyl.

Each $R_6$ is independently selected from the group consisting of $C(R_4)_2$, $C(R_4)_2C(R_4)_2$, $NR_5$, O, C(O), $C(O)C(R_4)_2$, $C(O)O$, $OC(R_4)_2$, $CH_2O$, $C(R_4)_2S$, $C(R_4)_2NR_5$, $NR_5CH_2$, S and $SC(R_4)_2$. In another embodiment, each $R_6$ is independently selected from the group selected from $C(R_4)_2$, $C(R_4)_2(R_4)_2$, $OC(R_4)_2$, CO, O and $NR_5$.

Each $R_7$ is independently selected from the group consisting of halo, haloalkyl, $OR_5$, $SR_5$, $C(O)R_5$, $OC(O)R_5$, $C(O)OR_5$, $NR_5R_5$, $NO_2$, CN, $OC(O)NR_5R_5$, $C(O)NR_5R_5$, $N(R_5)C(O)R_5$, $N(R_5)(COOR_5)$, $S(O)_nNR_5R_5$, C3-C8 cycloalkyl, C4-C10 cycloalkenyl, 3-8 membered heterocycloalkyl, 4-10 membered heterocycloalkenyl, C5-C11 bicycloalkyl, C5-C11 bicycloalkenyl, 5-11 membered heterobicycloalkyl, 5-11 membered heterobicycloalkenyl, aryl and heteroaryl, wherein said aryl and heteroaryl are each optionally substituted with one or more $R_9$. In another embodiment, each $R_7$ is independently selected from the group consisting of C1-C10 alkyl, C1-C10 alkyl substituted with one or more $R_7$, halo, $OR_5$, $NR_5R_5$, $C(O)OR_5$, $NO_2$, CN and $SO_2NR_5R_5$.

Each $R_8$ is independently selected from the group consisting of $R_7$, C1-C10 alkyl, C1-C10 alkyl substituted with one or more $R_7$, C2-C10 alkenyl, C2-C10 alkenyl substituted with one or more $R_7$, C2-C10 alkynyl and C2-C10 alkynyl substituted with one or more $R_7$. In another embodiment, each $R_8$ is independently selected from the group consisting of halo, haloalkyl, $OR_5$, $NR_5R_5$, $NO_2$ and CN.

Each n is independently 1 or 2.

Each $R_9$ is independently selected from the group consisting of C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, halo, $OR_5$, $SR_5$, $NR_5R_5$, $C(O)OR_5$, $NO_2$, CN, $C(O)R_5$, $C(O)C(O)R_5$, $C(O)NR_5R_5$, $N(R_5)C(O)R_5$, $NR_5S(O)_nR_5$, $N(R_5)C(O)OR_5$, $NR_5C(O)C(O)R_5$, $NR_5C(O)NR_5R_5$, $NR_5S(O)_nNR_5R_5$, $NR_5S(O)_nR_5$, $S(O)_nR_5$, $S(O)_nNR_5R_5$, $OC(O)R_5$, optionally substituted aryl and optionally substituted heteroaryl. In another embodiment, each $R_9$ is independently selected from the group consisting of C1-C10 alkyl, C1-C10 alkyl substituted with one or more $R_7$, halo, $OR_5$, $NR_5R_5$, $C(O)OR_5$, $NO_2$, CN, $S(O)_nR_5$, optionally substituted aryl and optionally substituted heteroaryl.

Each $R_{10}$ is independently selected from the group consisting of halo, haloalkyl, $OR_5$, $SR_5$, $C(O)R_5$, $OC(O)R_5$, $C(O)OR_5$, $NR_5R_5$, $NO_2$, CN, $OC(O)NR_5R_5$, $C(O)NR_5R_5$, $N(R_5)C(O)R_5$, $N(R_5)(COOR_5)$, $S(O)_nNR_5R_5$, aryl and heteroaryl, wherein said aryl and heteroaryl are each optionally substituted with one or more $R_9$.

In another embodiment, the invention pertains to a compound of the Formula (II):

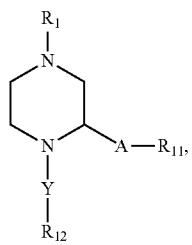

(II)

or a pharmaceutically acceptable salt thereof, wherein:

$R_1$, $R_4$, $R_5$, $R_6$, $R_7$, $R_8$, $R_9$, $R_{10}$, Y, A, $X_a$, $X_b$, $X_c$, $R_a$, $R_b$ and n are as defined above for Formula (I) and $R_{11}$ and $R_{12}$ are as defined below.

$R_{11}$ is selected from the group consisting of 5 or 6 membered monocyclic heteroaryl comprising 1 N atom and 0-2 additional heteroatoms, 8-12 membered bicyclic heteroaryl comprising 1 N atom and 0-5 additional heteroatoms, 11-14 membered heteroaryl comprising 1 N atom and 0-8 additional heteroatoms, wherein said heteroatoms are selected from O, N and S and wherein said heteroaryl is optionally substituted with one or more $R_9$. In another embodiment, $R_{11}$ is a 5 or 6 membered monocyclic heteroaryl comprising 1 N atom and 0-2 additional heteroatoms, wherein said heteroaryl is optionally substituted with one or more $R_9$. In a further embodiment, $R_{11}$ is pyridinyl, wherein said pyridinyl is optionally substituted with one more $R_9$.

$R_{12}$ is selected from the group consisting of C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C8 cycloalkyl, C3-C8 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_9$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, aryl, heteroaryl, wherein said aryl and heteroaryl are each optionally substituted with one or more $R_9$. In another embodiment, $R_{12}$ is selected from the group consisting of C1-C10 alkyl, C1-C10 alkyl substituted with one or more $R_7$, C2-C10 alkenyl, C2-C10 alkenyl substituted with one or more $R_7$, C3-C8 cycloalkyl, C3-C8 cycloalkyl substituted with one or more $R_8$, 3-8 membered heterocycloalkyl, 3-8 membered heterocycloalkyl substituted with one or more $R_8$, aryl and heteroaryl, wherein said aryl and heteroaryl are each optionally substituted with one or more $R_9$. In yet another embodiment, $R_{12}$ is aryl or heteroaryl, wherein said aryl and heteroaryl are each optionally substituted with one or more $R_9$. In a further embodiment, $R_{12}$ is aryl, wherein said aryl is optionally substituted with one or more $R_9$. In an additional embodiment, $R_{12}$ is heteroaryl, wherein said heteroaryl is optionally substituted with one or more $R_9$.

In yet another embodiment, $R_{12}$ is selected from the group consisting of C1-C10 alkyl, C1-C10 alkyl substituted with one or more $R_7$, C2-C10 alkenyl, C2-C10 alkenyl substituted with one or more $R_{10}$, C2-C10 alkynyl, C2-C10 alkynyl substituted with one or more $R_7$, C3-C8 cycloalkyl, C3-C8 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, aryl and heteroaryl, wherein said aryl and heteroaryl are each optionally substituted with one or more $R_9$.

In yet another embodiment, the invention pertains to a compound of the Formula (III):

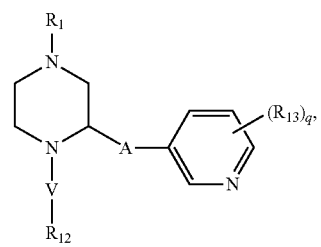

(III)

or a pharmaceutically acceptable salt thereof wherein $R_1$, $R_4$, $R_5$, $R_6$, $R_7$, $R_8$, $R_9$, $R_{10}$, $R_{12}$, A, $X_a$, $X_b$, $X_c$, $R_a$, $R_b$, and n are as defined above for Formula (II), q is an integer from 0 to 4, and V and $R_{13}$ are as defined below.

V is selected from the group consisting of a bond, $C(R_4)_2$, $C(R_4)_2C(R_4)_2$, $C(R_4)_2C(R_4)_2R_6$, $C(R_4)_2C(R_4)_2C(R_4)_2R_6$, CO, $C(O)R_6$, C(S), $C(S)R_6$, $CH_2C(O)$, $CH_2C(O)R_6$, $CH_2C(S)$, $CH_2C(S)R_6$, $SO_2$, and $SO_2R_6$. In another embodiment, V is selected from the group consisting of a bond, CO, $COR_6$, $SO_2$ and $SO_2R_6$. In yet another embodiment, V is a bond. In an additional embodiment, V is CO or $COR_6$. In a further embodiment, V is $SO_2$ or $SO_2R_6$.

Each $R_{13}$ is independently selected from the group consisting of C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, halo, $OR_5$, $SR_5$, $NR_5R_5$, $C(O)OR_5$, $NO_2$, CN, $C(O)R_5$, $C(O)C(O)R_5$, $C(O)NR_5R_5$, $N(R_5)C(O)R_5$, $NR_5S(O)_nR_5$, $N(R_5)C(O)OR_5$, $NR_5C(O)C(O)R_5$, $NR_5C(O)NR_5R_5$, $NR_5S(O)_nNR_5R_5$, $NR_5S(O)_nR_5$, $S(O)_nR_5$, $S(O)_nNR_5R_5$, $OC(O)R_5$, optionally substituted aryl and optionally substituted heteroaryl. In another embodiment, each $R_{13}$ is independently selected from the group consisting of C1-C10 alkyl, C1-C10 alkyl substituted with one or more $R_7$, halo, $OR_5$, $NR_5R_5$, $C(O)OR_5$, $NO_2$, CN, optionally substituted aryl and optionally substituted heteroaryl.

In an additional embodiment, the invention is directed to a compound of Formula (IV):

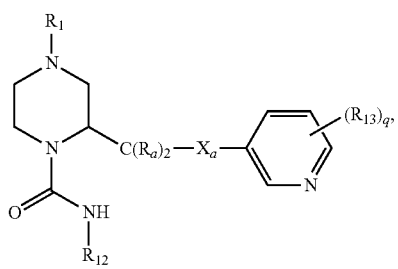

(IV)

or a pharmaceutically acceptable salt thereof wherein $R_1$, $R_4$, $R_5$, $R_6$, $R_7$, $R_8$, $X_a$, $R_a$, $R_9$, n, q, $R_{12}$ and $R_{13}$ are as defined above for Formula (III).

In another embodiment, the invention is directed to a compound of Formula (V):

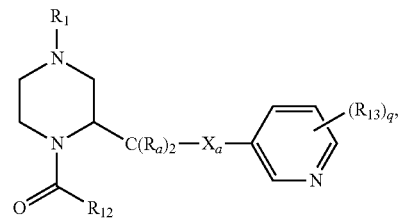

(V)

or a pharmaceutically acceptable salt thereof wherein $R_1$, $R_4$, $R_5$, $R_6$, $R_7$, $R_8$, $X_a$, $R_a$, $R_9$, n, q, $R_{12}$ and $R_{13}$ are as defined above for Formula (III).

In a further embodiment, the invention is directed to a compound of Formula (VI):

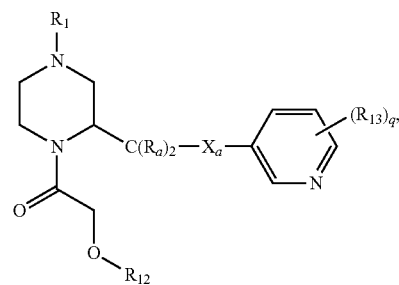

(VI)

or a pharmaceutically acceptable salt thereof wherein $R_1$, $R_4$, $R_5$, $R_6$, $R_7$, $R_8$, $X_a$, $R_a$, $R_9$, n, q, $R_{12}$ and $R_{13}$ are as defined above for Formula (III).

In yet another embodiment, the invention is directed to a compound of Formula (VII):

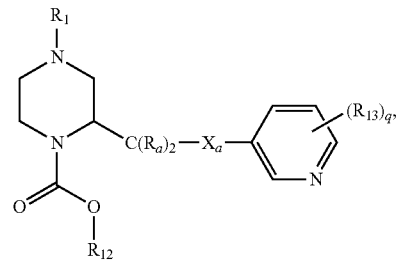

(VII)

or a pharmaceutically acceptable salt thereof wherein $R_1$, $R_4$, $R_5$, $R_6$, $R_7$, $R_8$, $X_a$, $R_a$, $R_9$, n, q, $R_{12}$ and $R_{13}$ are as defined above for Formula (III).

In another embodiment, the invention is directed to a compound of Formula (VIII):

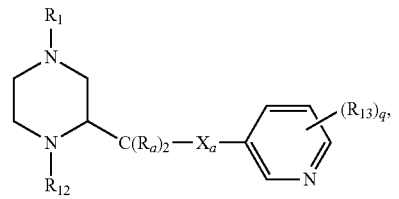

(VIII)

or a pharmaceutically acceptable salt thereof wherein $R_1$, $R_4$, $R_5$, $R_6$, $R_7$, $R_8$, $X_a$, $R_a$, $R_9$, n, q, $R_{12}$ and $R_{13}$ are as defined above for Formula (III).

In an additional embodiment, the invention is directed to a compound of Formula (IX):

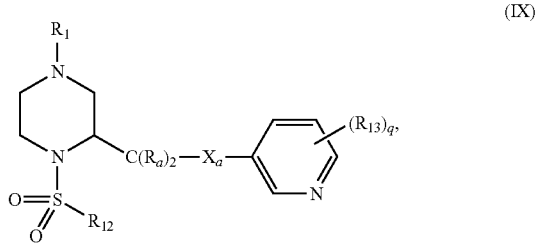

(IX)

or a pharmaceutically acceptable salt thereof wherein $R_1$, $R_4$, $R_5$, $R_6$, $R_7$, $R_8$, $X_a$, $R_a$, $R_9$, n, q, $R_{12}$ and $R_{13}$ are as defined above for Formula (III).

In a further embodiment, the invention is directed to a compound of Formula (X):

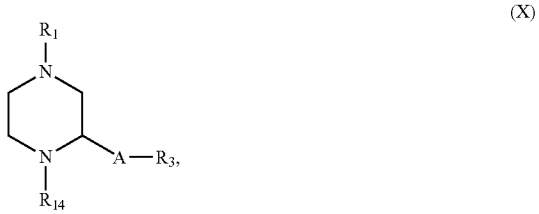

(X)

or a pharmaceutically acceptable salt thereof wherein $R_1$, $R_3$, $R_4$, $R_5$, $R_6$, $R_7$, $R_8$, $R_9$, A, $X_a$, $X_b$, $X_c$, $R_a$, $R_b$ and n are as defined above for Formula (I) and $R_{14}$ is as defined below.

$R_{14}$ is selected from the group consisting of C3-C8 cycloalkyl, C3-C8 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, aryl, heteroaryl, wherein said aryl and heteroaryl are each optionally substituted with one or more $R_9$.

In an additional embodiment, $R_{14}$ is selected from the group consisting of C3-C8 cycloalkyl, C3-C8 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl and 5-11 membered heterobicycloalkenyl substituted with one or more $R_8$. In another embodiment, $R_{14}$ is selected from the group consisting of selected from the group consisting of 6 membered monocyclic aryl, 5 or 6 membered monocyclic heteroaryl comprising 1-3 heteroatoms, 8-12 membered bicyclic aryl, 8-12 membered bicyclic heteroaryl comprising 1-6 heteroatoms, 11-14 membered tricyclic aryl and 11-14 membered heteroaryl comprising 1-9 heteroatoms, wherein each of said heteroatoms is independently selected from the group consisting of O, N and S and wherein said aryl and heteroaryl are each optionally substituted with one or more $R_9$. In yet another embodiment, $R_{14}$ is selected from the group consisting of 5 or 6 membered monocyclic heteroaryl comprising 1-3 heteroatoms, 8-12 membered bicyclic aryl, 8-12 membered bicyclic heteroaryl comprising 1-6 heteroatoms, 11-14 membered tricyclic aryl and 11-14 membered heteroaryl comprising 1-9 heteroatoms, wherein each of said heteroatoms is independently selected from the group consisting of O, N and S and wherein said aryl and heteroaryl are each optionally substituted with one or more $R_9$. In a further embodiment, $R_{14}$ is a substituted 6-membered aryl wherein said aryl is substituted with one or more $R_9$.

All stereoisomers and double bond geometries are encompassed.

In another embodiment, the invention is a pharmaceutical composition comprising a pharmaceutically acceptable carrier and a compound described herein.

In a further embodiment, the invention is directed to a method of treating a patient suffering from an inflammatory condition comprising administering to the patient a therapeutically effective amount of a compound described herein.

In an additional embodiment, the invention is directed to a method of treating a patient suffering from a CNS disorder comprising administering to the patient a therapeutically effective amount of a compound described herein.

DETAILED DESCRIPTION OF THE INVENTION

Figure 1:
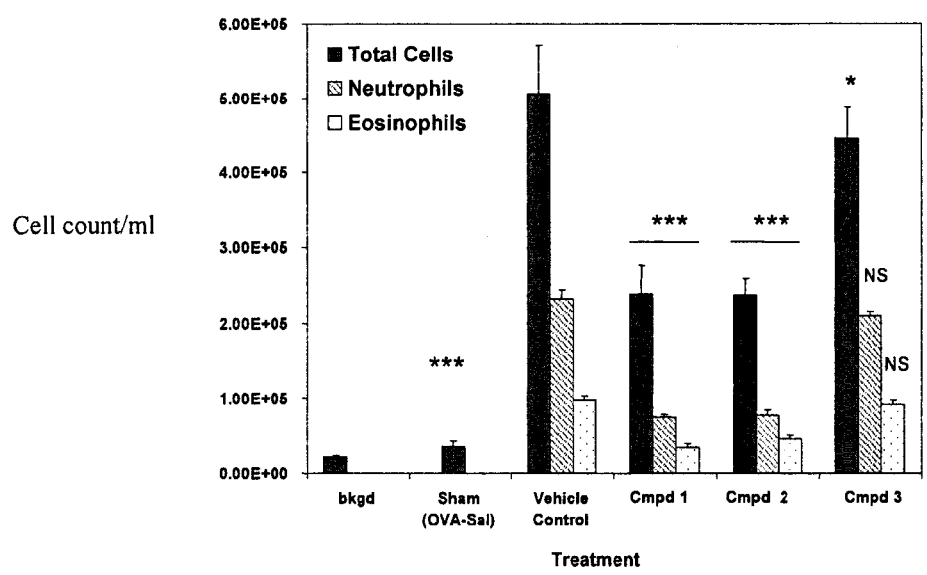
FIG. 1 is bar graph showing numbers of total cells, neutrophils and eosinophils per milliliter (mL) of bronchalveolar lavage (BAL) fluid from mice sensitized with ovalbumin (OVA) and challenged with saline (sham), mice sensitized and challenged with OVA and treated with saline (vehicle control) and mice sensitized and challenged with OVA and treated with three compounds of the invention designated as Compounds 1, 2 and 3 (Cmpd 1-Cmpd 3), respectively, in a murine model of allergic lung inflammation. The symbol "***" represents a significant difference compared to vehicle control and "NS" represents a non-significant difference.

The present invention encompasses novel compounds, methods for the preparation thereof, pharmaceutical compositions and methods for the treatment of inflammatory disorders and CNS disorders. The compounds and methods of the invention are particularly useful for treatment of inflammatory conditions.

In one embodiment, the invention is a compound represented by Formula (I) or a pharmaceutically acceptable salt thereof. The variables of Formula (I) are as described above.

In one embodiment, the compound is that of Formula (I) wherein Y is selected from the group consisting of a CO, $COR_6$, $SO_2$ and $SO_2R_6$.

In another embodiment, the compound is that of Formula (I) wherein $R_1$ is selected from the group consisting of H, C1-C5 alkyl and $COR_5$.

In an additional embodiment, the compound is that of Formula (I) wherein $R_2$ is selected from the group consisting of C1-C10 alkyl, C1-C10 alkyl substituted with one or more $R_7$, C2-C10 alkenyl, C2-C10 alkenyl substituted with one or more $R_{10}$, C3-C8 cycloalkyl, C3-C8 cycloalkyl substituted with one or more $R_8$, 3-8 membered heterocycloalkyl, 3-8 membered heterocycloalkyl substituted with one or more $R_8$, aryl and heteroaryl, wherein said aryl and heteroaryl are each optionally substituted with one or more $R_9$.

In an additional embodiment, the compound is that of Formula (I) wherein $R_2$ is aryl or heteroaryl, wherein said aryl and heteroaryl are each optionally substituted with one or more $R_9$.

In another embodiment, the compound is that of Formula (I) wherein $R_2$ is aryl, wherein said aryl is optionally substituted with one or more $R_9$.

In a further embodiment, the compound is that of Formula (I) wherein $R_2$ is a heteroaryl, wherein said heteroaryl is optionally substituted with one or more $R_9$.

In another embodiment, the compound is that of Formula (I) and $R_3$ is 5-6 membered monocyclic aryl or 8-12 membered bicyclic aryl, wherein said aryl is optionally substituted with one or more $R_9$.

In yet another embodiment, the compound is that of Formula (I) wherein $R_3$ is a 5-6 membered heteroaryl or 8-12 membered bicyclic heteroaryl, wherein said heteroaryl comprises at least one nitrogen atom, wherein said heteroaryl is optionally substituted with one or more $R_9$.

In one embodiment, the compound is that of Formula (I) wherein A is: —$C(R_a)_2$—$X_a$—. In another embodiment, each $R_a$ is independently selected from the group consisting of H, C1-C10 alkyl, C2-C10 alkenyl, $OR_5$, halo and haloalkyl. In a further embodiment, $X_a$ is selected from the group consisting of a bond, $C(R_4)_2$, $C(R_4)_2C(R_4)_2$, O and $NR_5$. In another embodiment, each $R_a$ is independently selected from the group consisting of H, C1-C10 alkyl, C2-C10 alkenyl, $OR_5$, halo and haloalkyl and $X_a$ is selected from the group consisting of a bond, $C(R_4)_2$, $C(R_4)_2C(R_4)_2$, O and $NR_5$.

In an additional embodiment, the compound is that of Formula (I) wherein A is: —$C(R_b)$=$X_b$—. In yet another embodiment, $R_b$ is selected from the group consisting of H, C1-C10 alkyl, C2-C10 alkenyl, $OR_5$, halo and haloalkyl and $X_b$ is selected from the group consisting of $C(R_4)$ and $C(R_4)C(R_4)_2$.

In a further embodiment, the compound is that of Formula (I) wherein A is: —C≡$X_c$—. In an additional embodiment, $X_c$ is selected from the group consisting of C and $CC(R_4)_2$.

In one embodiment, the compound is that of Formula (I) wherein $R_5$ is independently selected from the group consisting of H, C1-C10 alkyl, C2-C10 alkenyl, C2-C10 alkynyl, C3-C10 cycloalkyl, C4-C10 cycloalkenyl, 3-10 membered heterocycloalkyl, 4-10 membered heterocycloalkenyl, haloalkyl, aryl, heteroaryl, wherein said aryl and heteroaryl are each optionally substituted with one or more $R_9$. In another embodiment, each $R_5$ is independently selected from the group consisting of H, C1-C10 alkyl, C1-C10 alkyl substituted with one or more $R_7$, aryl and heteroaryl.

In an additional embodiment, the invention is a compound represented by Formula (II) or a pharmaceutically acceptable salt thereof. The variables of Formula (II) are as described above.

In one embodiment, the compound is that of Formula (II) wherein Y is selected from the group consisting of CO, $COR_E$, $SO_2$ and $SO_2R_6$.

In another embodiment, the compound is that of Formula (II) wherein $R_1$ is H or C1-C5 alkyl.

In an additional embodiment, the compound is that of Formula (II) wherein $R_{12}$ is selected from the group consisting of C1-C10 alkyl, C1-C10 alkyl substituted with one or more $R_7$, C2-C10 alkenyl, C2-C10 alkenyl substituted with one or more $R_7$, C3-C8 cycloalkyl, C3-C8 cycloalkyl substituted with one or more $R_8$, 3-8 membered heterocycloalkyl, 3-8 membered heterocycloalkyl substituted with one or more $R_8$, aryl and heteroaryl, wherein said aryl or heteroaryl are each optionally substituted with one or more $R_9$. In yet another embodiment, the compound is that of Formula (II) wherein $R_{12}$ is selected from the group consisting of C1-C10 alkyl, C1-C10 alkyl substituted with one or more $R_7$, C2-C10 alkenyl, C3-C8 cycloalkyl, C3-C8 cycloalkyl substituted with one or more $R_8$, 3-8 membered heterocycloalkyl, 3-8 membered heterocycloalkyl substituted with one or more $R_8$, aryl and heteroaryl, wherein said aryl or heteroaryl are each optionally substituted with one or more $R_9$.

In an additional embodiment, the compound is that of Formula (II) wherein $R_{12}$ is aryl or heteroaryl, wherein said aryl or heteroaryl are each optionally substituted with one or more $R_9$.

In another embodiment, the compound is that of Formula (II) wherein $R_{12}$ is aryl, wherein said aryl is optionally substituted with one or more $R_9$.

In a further embodiment, the compound is that of Formula (II) wherein $R_{12}$ is a heteroaryl, wherein said heteroaryl is optionally substituted with one or more $R_9$.

In one embodiment, the compound is that of Formula (II) wherein A is: —$C(R_a)_2$—$X_a$—. In another embodiment, each $R_a$ is independently selected from the group consisting of H, C1-C10 alkyl, C2-C10 alkenyl, $OR_5$, halo and haloalkyl.

In one embodiment, the compound is that of Formula (II) wherein $R_5$ is independently selected from the group consisting of H, C1-C10 alkyl, C2-C10 alkenyl, C2-C10 alkynyl, C3-C10 cycloalkyl, C4-C10 cycloalkenyl, 3-10 membered heterocycloalkyl, 4-10 membered heterocycloalkenyl, haloalkyl, aryl, heteroaryl, wherein said aryl and heteroaryl are each optionally substituted with one or more $R_9$. In another embodiment, each $R_5$ is independently selected from the group consisting of H, C1-C10 alkyl, C1-C10 alkyl substituted with one or more $R_7$, aryl and heteroaryl.

In an additional embodiment, the compound is that of Formula (II) and $R_{11}$ is 5-6 membered monocyclic heteroaryl or 8-12 membered bicyclic heteroaryl, wherein said heteroaryl is optionally substituted with one or more $R_9$. In yet another embodiment, $R_{11}$ is pyridinyl optionally substituted with one or more $R_9$.

In a further embodiment, the compound is that of Formula (II), wherein $R_{12}$ is aryl or heteroaryl, wherein said aryl and heteroaryl are each optionally substituted with one or more $R_9$.

In an additional embodiment, the compound is that of Formula (II), wherein $R_3$ is selected from the group consisting of 3-pyridinyl and 4-pyridinyl.

In yet another embodiment, the compound is represented by the Formula (III). The variables of Formula (III) are as described above.

In one embodiment, the compound is that of Formula (III) wherein V is selected from the group consisting of a bond, CO, $COR_E$, $SO_2$ and $SO_2R_6$.

In another embodiment, the compound is that of Formula (III) wherein $R_1$ is selected from the group consisting of H, C1-C10 alkyl, $C(O)R_5$ and $C(O)OR_5$.

In yet another embodiment, the compound is that of Formula (III) wherein $R_1$ is H or C1-C10 alkyl.

In one embodiment, the compound is that of Formula (III) wherein $R_5$ is independently selected from the group consisting of H, C1-C10 alkyl, C2-C10 alkenyl, C2-C10 alkynyl, C3-C10 cycloalkyl, C4-C10 cycloalkenyl, 3-10 membered heterocycloalkyl, 4-10 membered heterocycloalkenyl, haloalkyl, aryl, heteroaryl, wherein said aryl and heteroaryl are each optionally substituted with one or more $R_9$. In another embodiment, each $R_5$ is independently selected from the group consisting of H, C1-C10 alkyl, C1-C10 alkyl substituted with one or more $R_7$, aryl and heteroaryl.

In an additional embodiment, the compound is that of Formula (III) wherein $R_{12}$ is selected from the group consisting of C1-C10 alkyl, C1-C10 alkyl substituted with one or more $R_7$, C2-C10 alkenyl, C2-C10 alkenyl substituted with one or more $R_7$, C3-C8 cycloalkyl, C3-C8 cycloalkyl substituted with one or more $R_8$, 3-8 membered heterocycloalkyl, 3-8 membered heterocycloalkyl substituted with one or more $R_8$, aryl and heteroaryl, wherein said aryl and heteroaryl are each optionally substituted with one or more $R_9$.

In yet another embodiment, the compound is that of Formula (III) wherein $R_{12}$ is selected from the group consisting of C1-C10 alkyl, C1-C10 alkyl substituted with one or more $R_7$, C2-C10 alkenyl, C3-C8 cycloalkyl, C3-C8 cycloalkyl substituted with one or more $R_8$, 3-8 membered heterocycloalkyl, 3-8 membered heterocycloalkyl substituted with one or more $R_8$, aryl and heteroaryl, wherein said aryl or heteroaryl are each optionally substituted with one or more $R_9$.

In an additional embodiment, the compound is that of Formula (III) wherein $R_{12}$ is aryl or heteroaryl, wherein said aryl and heteroaryl are each optionally substituted with one or more $R_9$.

In another embodiment, the compound is that of Formula (III) wherein $R_{12}$ is aryl, wherein said aryl is optionally substituted with one or more $R_9$. In another embodiment, $R_2$ is phenyl or substituted phenyl.

In a further embodiment, the compound is that of Formula (III) wherein $R_{12}$ is heteroaryl, wherein said heteroaryl is optionally substituted with one or more $R_9$.

In one embodiment, the compound is that of Formula (III) wherein A is: —$C(R_a)_2$—$X_a$—. In another embodiment, each $R_a$ is independently selected from the group consisting of H, C1-C10 alkyl, C2-C10 alkenyl, $OR_5$, halo and haloalkyl. In a further embodiment, $X_a$ is selected from the group consisting of a bond, $C(R_4)_2$, $C(R_4)_2C(R_4)_2$, O and $NR_5$. In another embodiment, each $R_a$ is independently selected from the group consisting of H, C1-C10 alkyl, C2-C10 alkenyl, $OR_5$, halo and haloalkyl and $X_a$ is selected from the group consisting of a bond, $C(R_4)_2$, $C(R_4)_2C(R_4)_2$, O and $NR_5$.

In an additional embodiment, the compound is that of Formula (III) wherein A is: —$C(R_b)$=$X_b$—. In yet another embodiment, $R_b$ is selected from the group consisting of H, C1-C10 alkyl, C2-C10 alkenyl, $OR_5$, halo and haloalkyl and $X_b$ is selected from the group consisting of $C(R_4)$ and $C(R_4)C(R_4)_2$.

In a further embodiment, the compound is that of Formula (III) wherein A is: —C≡$X_c$—. In an additional embodiment, $X_c$ is selected from the group consisting of C and $CC(R_4)_2$.

In an additional embodiment, the compound is that of Formula (III) wherein each $R_9$ is independently selected from the group consisting of C1-C10 alkyl, C1-C10 alkyl substituted with one or more $R_7$, halo, $OR_5$, $NR_5R_5$, $C(O)OR_5$, $NO_2$, CN, $S(O)_nR_5$, optionally substituted aryl and optionally substituted heteroaryl.

In a further embodiment, the compound is that of Formula (III), wherein $R_{12}$ is:

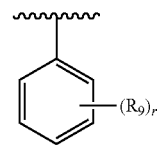

wherein r is an integer from 0 to 5. In one embodiment, r is 0. In another embodiment, r is 1, 2 or 3.

In one embodiment, the compound is that of Formula (IV), (V), (VI), (VII) (VIII) or (IX), wherein each $R_a$ is independently selected from the group consisting of H, C1-C10 alkyl, C2-C10 alkenyl, $OR_5$, halo and haloalkyl and $X_a$ is selected from the group consisting of $C(R_4)_2$, $C(R_4)_2C(R_4)_2$, O and $NR_5$.

In another embodiment, the compound is that of Formula (IV), (V), (VI), (VII) (VIII) or (IX), wherein $R_{12}$ is selected from the group consisting of C1-C10 alkyl, C1-C10 alkyl substituted with one or more $R_7$, C2-C10 alkenyl, C2-C10 alkenyl substituted with one or more $R_7$, C3-C8 cycloalkyl, C3-C8 cycloalkyl substituted with one or more $R_8$, 3-8 membered heterocycloalkyl, 3-8 membered heterocycloalkyl substituted with one or more $R_8$, aryl and heteroaryl, wherein said aryl and heteroaryl are each optionally substituted with one or more $R_9$.

In an additional embodiment, the compound is that of Formula (IV), (V), (VI), (VII) (VIII) or (IX) wherein $R_{12}$ is aryl or heteroaryl, wherein said aryl and heteroaryl are each optionally substituted with one or more $R_9$.

In a further embodiment, the compound is that of Formula (X), wherein $R_3$ is selected from the group consisting of 5 or 6 membered monocyclic heteroaryl comprising 1 N atom and 0-2 additional heteroatoms, 8-12 membered bicyclic heteroaryl comprising 1 N atom and 0-5 additional heteroatoms, 11-14 membered heteroaryl comprising 1 N atom and 0-8 additional heteroatoms, wherein said heteroatoms are selected from O, N and S and wherein said heteroaryl is optionally substituted with one or more $R_9$. In another embodiment, $R_3$ is a 5 or 6 membered monocyclic heteroaryl comprising 1 N atom and 0-2 additional heteroatoms, wherein said heteroaryl is optionally substituted with one or more $R_9$. In a further embodiment, $R_3$ is pyridinyl, wherein said pyridinyl is optionally substituted with one more $R_9$.

Representative compounds of the invention include, but are not limited to, the following:
N-phenyl-2-((pyridin-3-yloxy)methyl)piperazine-1-carboxamide,
N-(2-methoxyphenyl)-2-((pyridin-3-yloxy)methyl)piperazine-1-carboxamide,
N-(3-fluorophenyl)-2-((pyridin-3-yloxy)methyl)piperazine-1-carboxamide,
N-(3-methoxyphenyl)-2-((pyridin-3-yloxy)methyl)piperazine-1-carboxamide, N-(3-chlorophenyl)-2-((pyridin-3-yloxy)methyl)piperazine 1-carboxamide,
N-(4-chlorophenyl)-2-((pyridin-3-yloxy)methyl)piperazine 1-carboxamide,
N-(4-bromophenyl)-2-((pyridin-3-yloxy)methyl)piperazine-1-carboxamide,
N-(4-fluorophenyl)-2-((pyridin-3-yloxy)methyl)piperazine-1-carboxamide,
N-(4-methoxyphenyl)-2-((pyridin-3-yloxy)methyl)piperazine-1-carboxamide,
2-((pyridin-3-yloxy)methyl)-N-p-tolylpiperazine-1-carboxamide dihydrochloride,
N-(4-ethoxyphenyl)-2((pyridin-3-yloxy)methyl)piperazine-1-carboxamide,
2-((pyridin-3-yloxy)methyl)-N-(4-(trifluoromethoxy)phenyl)piperazine-1-carboxamide,
N-(4-phenoxyphenyl)-2-((pyridin-3-yloxy)methyl)piperazine-1-carboxamide,
N-(2,4-dimethoxyphenyl)-2-((pyridin-3-yloxy)methyl)piperazine-1-carboxamide,
N-(3,4-dichlorophenyl)-2-((pyridin-3-yloxy)methyl)piperazine-1-carboxamide,
N-(2,4-dichlorophenyl)-2-((pyridin-3-yloxy)methyl)piperazine-1-carboxamide,
N-(2,5-dimethoxyphenyl)-2-((pyridin-3-yloxy)methyl)piperazine-1-carboxamide,
N-(2,3-dichlorphenyl)-2-((pyridin-3-yloxy)methyl)piperazine-1-carboxamide,
N-(2,5-dichlorophenyl)-2-((pyridin-3-yloxy)methyl)piperazine-1-carboxamide,
N-(2,6-dichlorophenyl)-2-((pyridin-3-yloxy)methyl)piperazine-carboxamide,
N-benzyl-2-((pyridin-3-yloxy)methyl)piperazine-1-carboxamide,
N-(4-methoxybenzyl)-2-((pyridin-3-yloxy)methyl)piperazine-1-carboxamide,
N-(3-methoxybenzyl)-2-((pyridin-3-yloxy)methyl)piperazine-1-carboxamide,
N-(4-chlorobenzyl)-2-((pyridin-3-yloxy)methyl)piperazine-1-carboxamide,
N-(4-bromobenzyl)-2-((pyridin-3-yloxy)methyl)piperazine-1-carboxamide,
N-cyclopentyl-2-((pyridin-3-yloxy)methyl)piperazine-1-carboxamide,
N-(4-benzylphenyl)-2-((pyridin-3-yloxy)methyl)piperazine-1-carboxamide,
N-(4-benzoylphenyl)-2-((pyridin-3-yloxy)methyl)piperazine-1-carboxamide,
N-(biphenyl-4-yl)-2-((pyridin-3-yloxy)methyl)piperazine-1-carboxamide,
N-(4-methoxyphenyl)-3-(phenoxymethyl)piperidine-4-carboxamide,
2-((4-methoxyphenoxy)methyl)-N-4-methoxyphenyl)piperazine-1-carboxamide,
N-(4-chlorophenyl)-2-(4-methoxyphenyl)piperazine-1-carboxamide,
2-((4-chlorophenoxy)methyl)-N-(4-methoxyphenyl)piperazine-1-carboxamide,
2-((4-chlorophenoxy)methyl-N-(4-chlorophenyl)piperazine-1-carboxamide,
2-((4-chlorophenoxy)methyl-N-(3,4-dichlorophenyl)piperazine-1-carboxamide,
2-((3-fluorophenoxy)methyl)-N-(4-methoxyphenyl)piperazine-1-carboxamide,
N-(4-chlorophenyl)-2-((3-fluorophenoxy)methyl)piperazine-1-carboxamide,
2-((5-chloropyridin-3-yloxy)methyl)-N-(4-methoxyphenyl) piperazine-1-carboxamide,
N-(4-chlorophenyl)-2((5-chloropyridin-3-yloxy)methyl) piperazine-1-carboxamide,
N-(4-bromophenyl)-2-((5-chloropyridin-3-yloxy)methyl) piperazine-1-carboxamide,
2-((5-chloropyridin-3-yloxy)methyl)-N-(4-phenoxyphenyl) piperazine-1-carboxamide,
N-(4-methoxyphenyl)-2-((6-methylpyridin-3-yloxy)methyl) piperazine-1-carboxamide,
N-(4-chlorophenyl)-2-((6-methylpyridin-3-yloxy)methyl) piperazine-1-carboxamide,
N-(4-bromophenyl)-2-((6-methylpyridin-3-yloxy)methyl) piperazine-1-carboxamide,
2-((6-methylpyridin-3-yloxy)methyl)-N-(4-phenoxyphenyl) piperazine-1-carboxamide,
N-(4-chlorophenyl)-4-methyl-2-((pyridin-3-yloxy)methyl) piperazine-1-carboxamide,
N-(4-methoxyphenyl)-4-methyl-2-((pyridin-3-yloxy)methyl)piperazine-1-carboxamide,
N-(4'-methoxybiphenyl-4-yl)-2-((pyridin-3-yloxy)methyl) piperazine-1-carboxamide,
N-(3'-methoxybiphenyl-4-yl)-2-((pyridin-3-yloxy)methyl) piperazine-1-carboxamide,
N-(4'-chlorobiphenyl-4-yl)-2-((pyridin-3-yloxy)methyl)piperazine-1-carboxamide,
N-(3'-chlorobiphenyl-4-yl)-2-((pyridin-3-yloxy)methyl)piperazine-1-carboxamide,
Piperidin-1-yl(2-((pyridin-3-yloxy)methyl)piperazin-1-yl) methanone,
Morpholino(2-((pyridin-3-yloxy)methyl)piperazin-1-yl) methanone,
Phenyl(2-pyridin-3-yloxy)methyl)piperazin-1-yl)methanone,
(2-methoxyphenyl)(2-((pyridin-3-yloxy)methyl)piperazin-1-yl)methanone,
(3-methoxyphenyl)(2-((pyridin-3-yloxy)methyl)piperazin-1-yl)methanone,
(3-chlorophenyl)(2-((pyridin-3-yloxy)methyl)piperazin-1-yl)methanone,
(4-bromophenyl)(2-((pyridin-3-yloxy)methyl)pipearazin-1-yl)methanone,
(4-chlorophenyl)(2-((pyridin-3-yloxy)methyl)pipearazin-1-yl)methanone,
(2-((pyridin-3-yloxy)methyl)piperazin-1-yl)(4-trifluoromethoxy)phenyl)methanone,
(4-methoxyphenyl)(2-((pyridin-3-yloxy)methyl)piperazin-1-yl)methanone,
(2,4-dimethoxyphenyl)(2-((pyridine-3-yloxy)methyl)piperazine-1-yl)methanone,
2-phenyl-1-(2-((pyridin-3-yloxy)methyl)piperazin-1-yl) ethanone,
2-(4-chlorophenoxy)-1-(2-((pyridine-3-yloxy)methyl)piperazin-1-yl)ethanone,
2-(4-methoxyphenyl)-1-(2-((pyridin-3-yloxy)methyl)piperazin-1-yl)ethanone,
3-phenyl-1-(2-((pyridin-3-yloxy)methyl)piperazin-1-yl)propan-1-one,
2-phenoxy-1-(2-((pyridin-3-yloxy)methyl)piperazin-1-yl) ethanone,
2-(4-chlorophenoxy)-1-(2-((pyridin-3-yloxy)methyl)piperazin-1-yl)ethanone,
Furan-2-yl(2-((pyridin-3-yloxy)methyl)piperazin-1-yl) methanone,
2-(4-methoxyphenyl)-1-(2-((pyridin-3-yloxy)methyl)piperazin-1-yl)ethanone, (benzofuran-2-yl)(2-((pyridin-3-yloxy)methyl)piperazine-1-yl)methanone,
1-phenyl-2-(2-((pyridin-3-yloxy)methyl)piperazin-1-yl)ethane-1,2-dione,
(1H-indol-2-yl)(2-((pyridin-3-yloxy)methyl)piperazin-1-yl)methanone,
(1H-indol-3-yl)(2-((pyridin-3-yloxy)methyl)piperazin-1-yl)methanone,
(1H-indol-5-yl)(2-((pyridin-3-yloxy)methyl)piperazin-1-yl)methanone, phenyl 2-((pyridin-3-yloxy)methyl)piperazine-1-carboxylate,
4-fluorophenyl 2-((pyridin-3-yloxy)methyl)piperazine-1-carboxylate,
3-methoxyphenyl 2-((pyridin-3-yloxy)methyl)piperazine-1-carboxylate,
3-chlorophenyl 2-((pyridin-3-yloxy)methyl)piperazine-1-carboxylate,
4-methoxyphenyl 2-((pyridin-3-yloxy)methyl)piperazine-1-carboxylate,
4-chlorophenyl 2-((pyridin-3-yloxy)methyl)piperazine-1-carboxylate,
p-tolyl 2-((pyridin-3-yloxy)methyl)piperazine-1-carboxylate,
4-bromophenyl 2-((pyridin-3-yloxy)methyl)piperazine-1-carboxylate,
4-chlorobenzyl 2-((pyridin-3-yloxy)methyl)piperazine-1-carboxylate,
4-bromobenzyl 2-((pyridin-3-yloxy)methyl)piperazine-1-carboxylate,
3,4-dichlorobenzyl 2-((pyridin-3-yloxy)methyl)piperazine-1-carboxylate,
cyclohexyl 2-((pyridin-3-yloxy)methyl)piperazine-1-carboxylate,
cyclopentyl 2-((pyridin-3-yloxy)methyl)piperazine-1-carboxylate,
4-chlorophenyl-2-((3-fluorophenoxy)methyl)piperazine-1-carboxylate,
1-(benzyloxycarbonyl)piperidin-4-yl-2-((pyrdin-3-yloxy)methyl)piperazine-1-carboxylate,
Piperidin-4-yl-2-((pyridin-3-yloxy)methyl)piperazine-1-carboxylate,
Tert-butyl 2-((pyridin-3-yloxy)methyl)piperazine-1-carboxylate,
Benzyl 2-((pyridin-3-yloxy)methyl)piperazine-1-carboxylate,
2-(2-((pyridin-3-yloxy)methyl)piperazin-1-yl)benzo[d]oxazole,
5-chloro-2-(2-((pyridin-3-yloxy)methyl)piperazin-1-yl)benzo[d]oxazole,
6-chloro-2-(2-((pyridin-3-yloxy)methyl)piperazin-1-yl)benzo[d]oxazole,
6-methyl-2-(2-((pyridin-3-yloxy)methyl)piperazin-1-yl)benzo[d]oxazole,
6-methoxy-2-(2-((pyridin-3-yloxy)methyl)piperazin-1-yl)benzo[d]oxazole,
5-methyl-2-(2-((pyridin-3-yloxy)methyl)piperazin-1-yl)benzo[d]oxazole,
2-(2-((pyridin-3-yloxy)methyl)piperazin-1-yl)benzo[d]thiazole,
6-chloro-2-(2-((pyridin-3-yloxy)methyl)piperazin-1-yl)benzo[d]thiazole,
6-methoxy-2-(2-((pyridin-3-yloxy)methyl)piperazin-1-yl)benzo[d]thiazole,
N-methyl-N-phenyl-2-((pyridin-3-yloxy)methyl)piperazine-1-carboxamide,
N-(4-chlorophenyl)-N-methyl-2-((pyridin-3-yloxy)methyl)piperazine-1-carboxamide,
N-(4-methoxyphenyl)-N-methyl-2-((pyridin-3-yloxy)methyl)piperazine-1-carboxamide,
Benzyl 2-(2-(pyridin-3-yl)ethyl)piperazine-1-carboxylate,
2-(2-(pyridin-3-yl)ethyl)-N-p-tolylpiperazine-1-carboxamide,
N-(4-chlorophenyl)-2-(2-(pyridin-3-yl)ethyl)piperazine-1-carboxamide,
N-(4-methoxyphenyl)-2-(2-(pyridin-3-yl)ethyl)piperazine-1-carboxamide,
N-(4-phenoxyphenyl)-2-(2-(pyridin-3-yl)ethyl)piperazine-1-carboxamide,
N-(4-bromophenyl)-2-(2-(pyridin-3-yl)ethyl)piperazine-1-carboxamide,
N-(4-ethoxyphenyl)-2-(2-(pyridin-3-yl)ethyl)piperazine-1-carboxamide,
N-(3,4-dichlorophenyl)-2-(2-(pyridin-3-yl)ethyl)piperazine-1-carboxamide.
Benzo[d]thiazol-2-yl(2-((pyridin-3-yloxy)methyl)piperazin-1-yl)methanone dihydrochloride,
(5-phenylfuran-2-yl)(2-((pyridin-3-yloxy)methyl)piperazin-1-yl)methanone,
(5-(2,4-dichlorophenyl)furan-2-yl)(2-((pyridin-3-yloxy)methyl)piperazin-1-yl)methyl)piperazin-1-yl)methanone,
(5-(2,5-dichlorophenyl)furan-2-yl)(2-((pyridin-3-yloxy)methyl)piperazin-1-yl)methanone,
5-(4-chlorophenyl)furan-2-yl)(2-((pyridin-2-yloxy)methyl)piperazin-1-yl)methanone,
(5-(4-methoxyphenyl)furan-2-yl)(2-((pyridin-3-yloxy)methyl)piperazin-1-yl)methanone,
(5-(4-bromophenyl)furan-2-yl)(2-((pyridin-3-yloxy)methyl)piperazin-1-yl)methanone,
(2-((pyridin-3-yloxy)methyl)piperazin-1-yl)(5-p-tolylfuran)_2-yl)methanone,
(3-phenylisoxazol-5-yl)(2-((pyridin-3-yloxy)methyl)piperazin-1-yl)methanone,
(5-bromothiophen-2-yl)(2-((pyridin-3-yloxy)methyl)piperazin-1-yl)methanone,
(5-bromofuran-2-yl)(2-((pyridin-3-yloxy)methyl)piperazin-1-yl)methanone,
(5-(2-chlorophenyl)thiophen-2-yl)(2-((pyridin-3-yloxy)methyl)piperazin-1-yl)methanone,
(5-(2-chlorphenyl)furan-2-yl)(2-((pyridin-3-yloxy)methyl)piperazin-1-yl)methanone,
(5-phenylthiophen-2-yl)(2-((pyridin-2-yloxy)methyl)piperazin-1-yl)methanone,
(5-(3-chlorophenyl)thiophen-2-yl)(2-((pyridin-3-yloxy)methyl)piperazin-1-yl)methanone,
(2-((pyridin-2-yloxy)methyl)piperazin-1-yl)(5-o-tolylfuran-2-yl)methanone,
(5-(2-methoxyphenyl)furan-2-yl)(2-((pyridin-3-yloxy)methyl)piperazin-1-yl)methanone dihydrochloride,
4-chloro-5-methoxy-2-(2-((pyridin-3-yloxy)methyl)piperazin-1-yl)benzo[d]thiazole,
5-chloro-2-(2-((pyridin-3-yloxy)methyl)piperazin-1-yl)benzo[d]thiazole,
2-(2-((5-chloropyridin-3-yloxy)methyl)piperazin-1-yl)-6-methoxybenzo[d]thiazole,
6-methoxy-2-(2-((6-methylpyridin-3-yloxy)methyl)piperazin-1-yl)benzo[d]thiazole,
5-bromo-2-(2-((pyridin-3-yloxy)methyl)piperazin-1-yl)methyl)piperazin-1-yl)benzo[d]oxazole,
4-methyl-2-(2-((pyridin-3-yloxy)methyl)piperazin-1-yl)benzo[d]oxazole,
6-chloro-2-(2-((5-chloropyridin-3-yloxy)methyl)piperazin-1-yl)benzo[d]oxazole,
6-chloro-2-(2-((6-methylpyridin-3-yloxy)methyl)piperazin-1-yl)benzo[d]oxazole, 2-(2-((pyridin-3-yloxy)methyl)piperazin-1-yl)thiazole,
1-(phenylsulfonyl)-2-((pyridin-3-yloxy)methyl)piperazine,
1-(4-chlorophenylsulfonyl)-2-((pyridin-3-yloxy)methyl) piperazine,
1-(4-bromophenylsulfonyl)-2-((pyridin-3-yloxy)methyl) piperazine,
1-(4-methoxyphenylsulfonyl)-2-((pyridin-3-yloxy)methyl) piperazine,
N-(4-methoxyphenyl)-2-(pyridin-3-ylmethyl)piperazine-1-carboxamide,
N-(4-chlorophenyl)-2-(pyridin-3-ylmethyl)piperazine-1-carboxamide,
N—((R)-1-phenylethyl)-2-((pyridin-3-yloxy)methyl)piperazine-1-carboxamide,
N—((S)-1-phenylethyl)-2-((pyridin-3-yloxy)methyl)piperazine-1-carboxamide,
(R)—N-(4-methoxyphenyl)-2-((pyridin-3-yloxy)methyl) piperazine-1-carboxamide,
(R)—N-(4-phenoxyphenyl)-2-((pyridin-3-yloxy)methyl) piperazine-1-carboxamide,
(R)—N-(3,4-dichlorophenyl)-2-((pyridin-3-yloxy)methyl) piperazine-1-carboxamide,
(R)—N—((R)-1-phenylethyl)-2-((pyridin-3-yloxy)methyl) piperazine-1-carboxamide,
(R)—N—((S)-1-phenylethyl)-2-((pyridin-3-yloxy)methyl) piperazine-1-carboxamide,
(S)—N-(4-methoxyphenyl)-2-((pyridin-3-yloxy)methyl) piperazine-1-carboxamide,
(S)—N-(4-phenoxyphenyl)-2-((pyridin-3-yloxy)methyl) piperazine-1-carboxamide,
(S)—N-(3,4-dichlorophenyl)-2-((pyridin-3-yloxy)methyl) piperazine-1-carboxamide,
(S)—N—((R)-1-phenylethyl)-2-((pyridin-3-yloxy)methyl) piperazine-1-carboxamide,
(S)—N—((S)-1-phenylethyl)-2-((pyridin-3-yloxy)methyl) piperazine-1-carboxamide,
(2-chlorothiazol-4-yl)(2-((pyridin-3-yloxy)methyl)piperazin-1-yl)methanone,
(2-phenylthiazol-4-yl)(2-((pyridin-3-yloxy)methyl)piperazin-1-yl)methanone,
(2-(4-fluorophenyl)thiazol-4-yl)(2-((pyridin-3-yloxy)methyl)piperazin-1-yl)methanone,
(2-(4-methoxyphenyl)thiazol-4-yl)(2-((pyridin-3-yloxy)methyl)piperazin-1-yl)methanone,
(2-((pyridin-3-yloxy)methyl)piperazin-1-yl)(2-p-tolylthiazol-4-yl)methanone,
(2-((pyridin-3-yloxy)methyl)piperazine-1-yl)(2-(4-(trifluoromethoxy)phenyl)thiazol-4-yl)methanone,
(2-phenyloxazol-4-yl)(2-((pyridin-3-yloxy)methyl)piperazin-1-yl)methanone,
(2-(4-fluorophenyl)oxazol-4-yl)(2-((pyridin-3-yloxy)methyl)piperazin-1-yl)methanone dihydrochloride,
(2-(4-methoxyphenyl)oxazol-4-yl)(2-((pyridin-3-yloxy)methyl)piperazin-1-yl)methanone,
furan-3-yl(2-((pyridin-3-yloxy)methyl)piperazin-1-yl) methanone,
(3-methylfuran-2-yl)(2-((pyridin-3-yloxy)methyl)piperazin-1-yl)methanone,
(5-methylisoxazol-3-yl)(2-((pyridin-3-yloxy)methyl)piperazin-1-yl)methanone
(1-phenylcyclopropyl)(2-((pyridin-3-yloxy)methyl)piperazin-1-yl)methanone,
(R)-(5-phenylfuran-2-yl)(2-((pyridin-3-yloxy)methyl)piperazin-1-yl)methanone,
(R)-(5-(4-methoxyphenyl)furan-2-yl)(2-((pyridin-3-yloxy) methyl)piperazin-1-yl)methanone,
(S)-(5-phenylfuran-2-yl)(2-((pyridin-3-yloxy)methyl)piperazin-1-yl)methanone,
(S)-(5-(4-methoxyphenyl)furan-2-yl)(2-((pyridin-3-yloxy) methyl)piperazin-1-yl)methanone,
4-(4-methoxyphenyl)-2-(2-((pyridin-3-yloxy)methyl)piperazin-1-yl)thiazole
4-phenyl-2-(2-((pyridin-3-yloxy)methyl)piperazin-1-yl) thiazole,
4-(4-chlorophenyl)-2-(2-((pyridin-3-yloxy)methyl)piperazin-1-yl)thiazole,
6-bromo-2-(2-((pyridin-3-yloxy)methyl)piperazin-1-yl) benzo[d]thiazole,
(R)-5-methoxy-2-(2-((pyridin-3-yloxy)methyl)piperazin-1-yl)benzo[d]oxazole,
(R)-5-bromo-2-(2-((pyridin-3-yloxy)methyl)piperazin-1-yl) benzo[d]oxazole,
(R)-6-methoxy-2-(2-((pyridin-3-yloxy)methyl)piperazine-1-yl)benzo[d]thiazole,
(S)-5-methoxy-2-(2-((pyridin-3-yloxy)methyl)piperazin-1-yl)benzo[d]oxazole,
(S)-5-bromo-2-(2-((pyridin-3-yloxy)methyl)piperazin-1-yl) benzo[d]oxazole,
(S)-6-methoxy-2-(2-((pyridin-3-yloxy)methyl)piperazine-1-yl)benzo[d]thiazole,
6-fluoro-2-(2-((pyridin-3-yloxy)methyl)piperazin-1-yl) benzo[d]oxazole,
5-fluoro-2-(2-((pyridin-3-yloxy)methyl)piperazin-1-yl) benzo[d]oxazole,
2-(2-((pyridin-3-yloxy)methyl)piperazin-1-yl)-5-(trifluoromethyl)benzo[d]oxazole,
2-(2-((pyridin-3-yloxy)methyl)piperazin-1-yl)oxazolo[4,5-b]pyridine,
5-methoxy-2-(2-((pyridin-3-yloxy)methyl)piperazin-1-yl) benzo[d]thiazole,
2-(2-((pyridin-3-yloxy)methyl)piperazin-1-yl)-5-(trifluoromethyl)benzo[d]thiazole,
5-fluoro-2-(2-((pyridin-3-yloxy)methyl)piperazin-1-yl) benzo[d]thiazole,
6-isopropyl-2-(2-((pyridin-3-yloxy)methyl)piperazin-1-yl) benzo[d]thiazole,
2-(2-((pyridin-3-yloxy)methyl)piperazin-1-yl)-6-(trifluoromethyl)benzo[d]thiazole,
2-(2-((pyridin-3-yloxy)methyl)piperazin-1-yl)-6-(trifluoromethoxy)benzo[d]thiazole,
5,6-difluoro-2-(2-((pyridin-3-yloxy)methyl)piperazin-1-yl) benzo[d]thiazole,
4-fluoro-2-(2-((pyridin-3-yloxy)methyl)piperazin-1-yl) benzo[d]thiazole,
6-methyl-2-(2-((pyridin-3-yloxy)methyl)piperazin-1-yl) benzo[d]thiazole,
6-fluoro-2-(2-((pyridin-3-yloxy)methyl)piperazin-1-yl) benzo[d]thiazole,
5,6-dimethyl-2-(2-((pyridin-3-yloxy)methyl)piperazin-1-yl) benzo[d]thiazole,
6-(methylsulfonyl)-2-(2-((pyridin-3-yloxy)methyl)piperazin-1-yl)benzo[d]thiazole,
6-isopropoxy-2-(2-((pyridin-3-yloxy)methyl)piperazin-1-yl)benzo[d]thiazole,
6-(benzyloxy)-2-(2-((pyridin-3-yloxy)methyl)piperazin-1-yl)benzo[d]thiazole,
4,6-difluoro-2-(2-((pyridin-3-yloxy)methyl)piperazin-1-yl) benzo[d]thiazole,
6,7-difluoro-2-(2-((pyridin-3-yloxy)methyl)piperazin-1-yl) benzo[d]thiazole,
7-fluoro-2-(2-((pyridin-3-yloxy)methyl)piperazin-1-yl) benzo[d]thiazole, 4-(6-(benzyloxy)benzo[d]thiazol-2-yl)-3-((pyridin-3-yloxy)methyl)piperazine-1-carbaldehyde,
4-(6-hydroxybenzo[d]thiazol-2-yl)-3-((pyridin-3-yloxy)methyl)piperazine-1-carbaldehyde,
2-(2-((pyridin-3-yloxy)methyl)piperazin-1-yl)benzo[d]thiazol-6-ol,
1-(4-(6-methoxybenzo[d]thiazol-2-yl)-3-((pyridin-3-yloxy)methyl)piperazin-1-yl)ethanone,
(2-((pyridin-3-yloxy)methyl)piperazin-1-yl)(2-p-tolyloxazol-4-yl)methanone,
(2-(phenylamino)oxazol-4-yl)(2-((pyridin-3-yloxy)methyl)piperazin-1-yl)methanone,
(2-(4-methoxyphenylamino)oxazol-4-yl)(2-((pyridin-3-yloxy)methyl)piperazin-1-yl)methanone,
(2-morpholinooxazol-4-yl)(2-((pyridin-3-yloxy)methyl)piperazin-1-yl)methanone,
(5-(3-methoxyphenyl)furan-2-yl)(2-((pyridin-3-yloxy)methyl)piperazin-1-yl)methanone,
(2-((pyridin-3-yloxy)methyl)piperazin-1-yl)(5-(4-(trifluoromethoxy)phenyl)furan-2-yl)methanone,
(2-((pyridin-3-yloxy)methyl)piperazin-1-yl)(5-(4-(trifluoromethyl)phenyl)furan-2-yl)methanone,
(5-(4-isopropoxyphenyl)furan-2-yl)(2-((pyridin-3-yloxy)methyl)piperazin-1-yl)methanone,
(5-(3,4-dimethoxyphenyl)furan-2-yl)(2-((pyridin-3-yloxy)methyl)piperazin-1-yl)methanone,
(2-(4-chlorophenyl)-4-methyloxaxzol-5-yl)(2-((pyridin-3-yloxy)methyl)piperazin-1-yl)methanone,
(4-methyl-2-phenyloxazol-5-yl)(2-((pyridin-3-yloxy)methyl)piperazin-1-yl)methanone,
(2-(4-methoxyphenyl)-4-methyloxazol-5-yl)(2-((pyridin-3-yloxy)methyl)piperazin-2-yl)methanone,
(2-(4-fluorophenyl)-4-methyloxazol-5-yl)(2-((pyridin-3-yloxy)methyl)piperazin-1-yl)methanone,
(3-bromophenyl)(2-((pyridin-3-yloxy)methyl)piperazin-1-yl)methanone,
(4'-fluorobiphenyl-3-yl)(2-((pyridin-3-yloxy)methyl)piperazin-1-yl)methanone,
(4'-chlorobiphenyl-3-yl)(2-((pyridin-3-yloxy)methyl)piperazin-1-yl)methanone,
(4'-methoxybiphenyl-3-yl)(2-((pyridin-3-yloxy)methyl)piperazin-1-yl)methanone,
(4'-fluorobiphenyl-4-yl)(2-((pyridin-3-yloxy)methyl)piperazin-1-yl)methanone,
(4'-methoxybiphenyl-4-yl)(2-((pyridin-3-yloxy)methyl)piperazin-1-yl)methanone,
(4'-chlorobiphenyl-4-yl)(2-((pyridin-3-yloxy)methyl)piperazin-1-yl)methanone,
(6-chloropyridin-2-yl)(2-((pyridin-3-yloxy)methyl)piperazin-1-yl)methanone,
(6-phenylpyridin-2-yl)(2-((pyridin-3-yloxy)methyl)piperazin-1-yl)methanone,
(6-(3-methoxyphenyl)pyridin-2-yl)(2-((pyridin-3-yloxy)methyl)piperazin-1-yl)methanone,
(6-(4-fluorophenyl)pyridin-2-yl)(2-((pyridin-3-yloxy)methyl)piperazin-1-yl)methanone,
6-(2-fluorophenyl)pyridin-2-yl)(2-((pyridin-3-yloxy)methyl)piperazin-1-yl)methanone,
(6-(4-methoxyphenyl)pyridin-2-yl)(2-((pyridin-3-yloxy)methyl)piperazin-1-yl)methanone,
(3-chloro-2-fluorophenyl)(2-((pyridin-3-yloxy)methyl)piperazin-1-yl)methanone,
(2-fluorobiphenyl-3-yl)(2-((pyridin-3-yloxy)methyl)piperazin-1-yl)methanone,
(2-fluorobiphenyl)(2-((pyridin-3-yloxy)methyl)piperazin-1-yl)methanone,
(5-phenylfuran-2-yl)(2-((pyridin-3-yloxy)methyl)piperazin-1-yl)methanone,
(5-(2,4-dichlorophenyl)furan-2-yl)(2-((pyridin-3-yloxy)methyl)piperazin-1-yl)methanone,
(5-(4-chlorophenyl)furan-2-yl)(2-((pyridin-3-yloxy)methyl)piperazin-1-yl)methanone,
(5-(4-methoxyphenyl)furan-2-yl)(2-((pyridin-3-yloxy)methyl)piperazin-1-yl)methanone,
(5-(4-bromophenyl)furan-2-yl)(2-((pyridin-3-yloxy)methyl)piperazin-1-yl)methanone,
(2-((pyridin-3-yloxy)methyl)piperazin-1-yl)(5-p-tolylfuran-2-yl)methanone,
(3-phenylisoxazol-5-yl)(2-((pyridin-3-yloxy)methyl)piperazin-1-yl)methanone,
Furan-3-yl(2-((pyridin-3-yloxy)methyl)piperazin-1-yl)methanone,
(5-methylisoxazol-3-yl)(2-((pyridin-3-yloxy)methyl)piperazin-1-yl)methanone,
(1-phenylcyclopropyl)(2-((pyridin-3-yloxy)methyl)piperazin-1-yl)methanone,
N-benzyl-4-methyl-2-(2-((pyridin-3-yloxy)methyl)piperazin-1-yl)oxazole-5-carboxamide,
2-((pyridin-3-yloxy)methyl)-N-(4-trifluoromethyl)phenyl)piperazine-1-carboxamide,
N-(2,4-difluorophenyl)-2-((pyridin-3-yloxy)methyl)piperazine-1-carboxamide,
N-(2-fluorophenyl)-2-((pyridin-3-yloxy)methyl)piperazine-1-carboxamide,
N-(4-bromo-2-fluorophenyl)-2-((pyridin-3-yloxy)methyl)piperazine-1-carboxamide,
N-(3-chloro-4-methylphenyl)-2-((pyridin-3-yloxy)methyl)piperazine-1-carboxamide,
N-(4-bromo-3-methylphenyl)-2-((pyridin-3-yloxy)methyl)piperazine-1-carboxamide,
N-(3-fluoro-4-methylphenyl)-2-((pyridin-3-yloxy)methyl)piperazine-1-carboxamide,
N-(4-methyl-3-(trifluoromethyl)phenyl)-2-((pyridin-3-yloxy)methyl)piperazine-1-carboxamide,
N-(3,4-dimethylphenyl)-2-((pyridin-3-yloxy)methyl)piperazine-1-carboxamide,
N-(3-chloro-4-methoxyphenyl)-2-((pyridin-3-yloxy)methyl)piperazine-1-carboxamide,
N-(4-isopropylphenyl)-2-((pyridin-3-yloxy)methyl)piperazine-1-carboxamide,
N-(4-tert-butylphenyl)-2-((pyridin-3-yloxy)methyl)piperazine-1-carboxamide,
Methyl 4-(2-((pyridin-3-yloxy)methyl)piperazine-1-carboxamido)benzoate,
N-(2,3-dihydrobenzofuran-5-yl)-2-((pyridin-3-yloxy)methyl)piperazine-1-carboxamide,
N-(2,3-dihydrobenzo[b][1,4]dioxin-6-yl)-2-((pyridin-3-yloxy)methyl)piperazine-1-carboxamide,
N-(4-(benzyloxy)phenyl)-2-((pyridin-3-yloxy)methyl)piperazine-1-carboxamide,
N-(benzo[d][1,3]dioxol-5-yl)-2-((pyridin-3-yloxy)methyl)piperazine-1-carboxamide,
N-(4-(methylthio)phenyl)-2-((pyridin-3-yloxy)methyl)piperazine-1-carboxamide,
N-(4-(dimethylamine)phenyl)-2-((pyridin-3-yloxy)methyl)piperazine-1-carboxamide,
N-(3,4-dichlorophenyl)-2-((3-methoxyphenoxy)methyl)piperazine-1-carboxamide,
N-(3,4-dichlorophenyl)-2-((2-methoxyphenoxy)methyl)piperazine-1-carboxamide,
N-(3-4-dichlorophenyl)-2-((4-(trifluoromethoxy)phenoxy)methyl)piperazine-1-carboxamide, N-(4-methoxyphenyl)-2-((2-methlypryidin-3-yloxy)methyl)piperazine-1-carboxamide,
N-(3,4-dichlorophenyl)-2-((2-methylpyridin-3-yloxy)methyl)piperazine-1-carboxamide,
N-(3-chloro-4-methoxyphenyl)-2-((2-methylpyridin-3-yloxy)methyl)piperazine-1-carboxamide,
N-(4-bromo-3-methylphenyl)-2-((2-methylpyridin-3-yloxy)methyl)piperazine-1-carboxamide,
(2-(3-fluorophenyl)oxazol-4-yl)(2-((pyridin-3-yloxy)methyl)piperazin-1-yl)methanone,
(2-(3-chlorophenyl)oxazol-4-yl)(2-((pyridin-3-yloxy)methanone,
(2-((pyridin-3-yloxy)methyl)piperazin-1-yl)(2-m-tolyloxazol-4-yl)methanone,
2-((pyridin-3-yloxy)methyl)piperazin-1-yl)(2-(3-(trifluoromethoxy)phenyl)oxazol-4-yl)methanone,
(2-(2-fluorophenyl)oxazol-4-yl)(2-((pyridin-3-yloxy)methyl)piperazin-1-yl)methanone,
(2-(2-methoxyphenyl)oxazol-4-yl)(2-((pyridin-3-yloxy)methyl)piperazin-1-yl)methanone,
(R)-2-(2-((pyridin-3-yloxy)methyl)piperazin-1-yl)oxazolo[4,5-b]pyridine,
(S)-2-(2-((pyridin-3-yloxy)methyl)piperazin-1-yl)oxazolo[4,5-b]pyridine,
2-(2-((3-fluorophenoxy)methyl)piperazin-1-yl)oxazolo[4,5-b]pyridine,
2-(2-((2-methylpyridin-3-yloxy)methyl)piperazin-1-yl)oxazolo[4,5-b]pyridine,
2-2-((pyridin-3-yloxy)methyl)piperazin-1-yl)thiazolo[4,5-b]pyridine,
2-(2-((pyridin-3-yloxy)methyl)piperazin-1-yl)-6-(trifluoromethyl)thiazolo[4,5-b]pyridine,
6-chloro-2-(2-((pyridin-3-yloxy)methyl)piperazin-1-yl)thiazolo[4,5-b]pyridine,
6-bromo-2-(2-((pyridin-3-yloxy)methyl)piperazin-1-yl)thiazolo[4,5-b]pyridine,
6-bromo-4-fluoro-2-(2-((pyridin-3-yloxy)methyl)piperazin-1-yl)benzo[d]thiazole,
4,6-difluoro-2-(2-((2-methylpyridin-3-yloxy)methyl)piperazin-1-yl)benzo[d]thiazole,
Methyl 2-(2-((pyridin-3-yloxy)methyl)piperazin-1-yl)thiazole-4-carboxylate,
N-methyl-2-(2-((pyridin-3-yloxy)methyl)piperazin-1-yl)thiazole-4-carboxamide,
Morpholino(2-(2-((pyridin-3-yloxy)methyl)piperazin-1-yl)thiazol-4-yl)methanone,
N-phenyl-2-(2-((pyridin-3-yloxy)methyl)piperazin-1-yl)thiazol-4-carboxamide
N-benzyl-2-(2-((pyridin-3-yloxy)methyl)piperazin-1-yl)thiazol-4-carboxamide,
N-(6-fluorobenzo[d]thiazol-2-yl)-2-((pyridin-3-yloxy)methyl)piperazine-1-carboxamide,
N-(6-methylbenzo[d]thiazol-2-yl)-2-((pyridin-3-yloxy)methyl)piperazine-1-carbaxoamide,
N-(4-methoxybenzo[d]thiazol-2-yl)-2-((pyridin-3-yloxy)methyl)piperazine-1-carboxamide,
N-(4-methylbenzo[d]thiazol-2-yl)-2-((pyridin-2-yloxy)methyl)piperazine-1-carboxamide,
N-(6-chlorobenzo[d]thiazol-2-yl)-2-((pyridin-3-yloxy)methyl)piperazine-1-carboxamide,
N-(6-methoxybenzo[d]thiazol-2-yl)-2-((pyridin-3-yloxy)methyl)piperazine-1-carboxamide,
N-(benzo[d]thiazol-2-yl)-2-((pyridin-3-yloxy)methyl)piperazine-1-carboxamide,
N-(5-chlorobenzo[d]oxazol-2-yl)-2-((pyridin-3-yloxy)methyl)piperazine-1-carboxamide,
N-(1H-indol-5-yl)-2-((pyridin-3-yloxy)methyl)piperazine-1-carboxamide,
N-(4-phenylthiazol-2-yl)-2-((pyridin-3-yloxy)methyl)piperazine-1-carboxamide,
N-(4-(4-chlorophenyl)thiazol-2-yl)-2-((pyridin-3-yloxy)methyl)piperazine-1-carboxamide,
N-(5-phenyl-1,3,4-thiadiazol-2-yl)-2-((pyridin-3-yloxy)methyl)piperazine-1-carboxamide,
N-(3-methylisothiazol-5-yl)-2-((pyridin-3-yloxy)methyl)piperazine-1-carboxamide,
N-(3-methylisoxazol-5-yl)-2-((pyridin-3-yloxy)methyl)piperazine-1-carboxamide,
N-(benzo[d]thiazol-6-yl)-2-((pyridin-3-yloxy)methyl)piperazine-1-carboxamide,
N-(2-methylbenzo[d]thiazol-5-yl)-2-((pyridin-3-yloxy)methyl)piperazine-1-carboxamide,
N-(2,3-dihydro-1H-inden-5-yl)-2-((pyridin-3-yloxy)methyl)piperazine-1-carboxamide,
N-(4-(methylcarbamoyl)phenyl)-2-((pyridin-3-yloxy)methyl)piperazine-1-carboxamide,
N-(4-dimethylcarbamoyl)phenyl)-2-((pyridin-3-yloxy)methyl)piperazine-1-carboxamide,
N-(4-(phenylcarbamoyl)phenyl)-2-((pyridin-3-yloxy)methyl)piperazine-1-carboxamide,
N-(4-(benzylcarbamoyl)phenyl)-2-((pyridin-3-yloxy)methyl)piperazine-1-carboxamide,
N-(4-hydroxphenyl)-2-((pyridin-3-yloxy)methyl)piperazine-1-carboxamide,
N-(4-methoxyphenyl)-2-((pyridin-3-ylamino)methyl)piperazine-1-carboxamide,
N-(3-chloro-4-methoxyphenyl)-2-((pyridin-3-ylamino)methyl)piperazine-1-carboxamide,
2-((pyridin-3-ylamino)methyl)-N-(4-(trifluoromethoxy)phenyl)piperazine-1-carboxamide,
2-(2-((pyridin-3-ylamino)methyl)piperazin-1-yl)pyrimidine,
5-bromo-2-(2-((pyridin-3-ylamino)methyl)piperazin-1-yl)pyrimidine,
N-(3,4-dimethoxyphenyl)-2-((pyridin-3-yloxy)methyl)piperazine-1-carboxamide dihydrochloride,
(R)—N-(4-bromo-2-fluorophenyl)-2-((pyridin-3-yloxy)methyl)piperazine-1-carboxamide,
N-(pyridin-3-yl)-2-((pyridin-3-yloxy)methyl)piperazine-1-carboxamide,
N-(4-morpholinophenyl)-2-((pyridin-3-yloxy)methyl)piperazine-1-carboxamide,
N-(2-fluoro-4-methylphenyl)-2-((pyridin-3-yloxy)methyl)piperazine-1-carboxamide,
N-(4-(methylsulfonyl)phenyl)-2-((pyridin-3-yloxy)methyl)piperazine-1-carboxamide,
(R)-(5-bromofuran-2-yl)(2-((pyridin-3-yloxy)methyl)piperazin-1-yl)methanone,
(R)-(2-((pyridin-3-yloxy)methyl)piperazin-1-yl)(5-(4-(trifluoromethoxy)phenyl)furan-2-yl)methanone,
(R)-6-methyl-2-(2-((pyridin-3-yloxy)methyl)piperazin-1-yl)benzo[d]oxazole,
(R)-5-methyl-2-(2-((pyridin-3-yloxy)methyl)piperazin-1-yl)benzo[d]oxazole,
(R)-5-phenyl-2-(2-((pyridin-3-yloxy)methyl)piperazin-1-yl)benzo[d]oxazole,
(R)-4-fluoro-2-(2-((pyridin-3-yloxy)methyl)piperazin-1-yl)benzo[d]thiazole,
(R)-5,6-difluoro-2-(2-((pyridin-3-yloxy)methyl)piperazin-1-yl)benzo[d]thiazole,
(R)-6,7-difluoro-2-(2-((pyridin-3-yloxy)methyl)piperazin-1-yl)benzo[d]thiazole, (R)-4,6-difluoro-2-(2-((pyridin-3-yloxy)methyl)piperazin-1-yl)benzo[d]thiazole,
5-methyl-2-(2-((pyridin-3-yloxy)methyl)piperazin-1-yl)oxazolo[4,5-b]pyridine,
6-methyl-2-(2-((pyridin-3-yloxy)methyl)piperazin-1-yl)oxazolo[4,5-b]pyridine,
(R)-2-(2-((pyridin-3-yloxy)methyl)piperazin-1-yl)oxazolo[4,5-b]pyridine,
(R)-5-methyl-2-(2-((pyridin-3-yloxy)methyl)piperazin-1-yl)oxazolo[4,5-b]pyridine, and
(R)-6-methyl-2-(2-((pyridin-3-yloxy)methyl)piperazin-1-yl)oxazolo[4,5-b]pyridine.

Compounds were named using ChemDraw Ultra 9.0.1 (CambrideSoft, Cambridge, Mass.).

The term "alkyl", as used herein, unless otherwise indicated, refers to both branched and straight-chain saturated aliphatic hydrocarbon groups having the specified number of carbon atoms; for example, "C1-C10 alkyl" denotes alkyl having 1 to 10 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond.

The term, "alkynyl", as used herein, refers to both straight and branched-chain moieties having the specified number or carbon atoms and having at least one carbon-carbon triple bond.

The term "cycloalkyl," as used herein, refers to cyclic alkyl moieties having 3 or more carbon atoms. Examples of cycloalkyl include, but are not limited to, cyclopropyl, cyclobutyl, cyclopentyl, cyclohexyl, and cycloheptyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

The term "heterocycloalkyl" as used herein refers to cycloalkyl groups containing one or more heteroatoms (O, S, or N) within the ring.

The term "heterocycloalkenyl" as used herein refers to cycloalkenyl groups containing one or more heteroatoms (O, S or N) within the ring.

The term "bicycloalkyl" as used herein refers to a non-aromatic saturated carbocyclic group consisting of two rings. Examples of bicycloalkyl groups include, but are not limited to, bicyclo-[2.2.2]-octyl and norbornyl.

The term "bicycloalkenyl" as used herein refers to bicycloalkyl groups as defined above, except comprising one or more double bonds connecting carbon ring members (an "endocyclic double bond") and/or one or more double bonds connecting a carbon ring member and an adjacent non-ring carbon (an "exocyclic double bond").

The term "heterobicycloalkyl" as used herein refers to bicycloalkyl groups containing one or more heteroatoms (O, S or N) within a ring.

The term "heterobicycloalkenyl" as used herein refers to bicycloalkenyl groups containing one or more heteroatoms (O, S or N) within a ring.

Cycloalkyl, cycloalkenyl, bicycloalkyl, bicycloalkenyl, heterocycloalkyl, heterocycloalkyl, heterobicycloalkyl and heterobicycloalkenyl groups also include groups similar to those described above for each of these respective categories, but which are substituted with one or more oxo moieties and/or are fused to one or more aromatic rings.

The term "aryl", as used herein, refers to an aromatic carbocyclic group containing one or more rings wherein such rings may be attached together in a fused manner. The term "aryl" embraces aromatic radicals, such as, phenyl, naphthyl, indenyl, tetrahydronaphthyl, and indanyl. An aryl group may be substituted or unsubstituted.

A suitable substituent on an aryl is any substituent that does not substantially interfere with the pharmaceutical activity of the disclosed compound. An aryl may have one or more substituents, which can be identical or different. Examples of suitable substituents for a substitutable carbon atom in an aryl group include, but are not limited to, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, halo, $OR_5$, $SR_5$, $NR_5R_5$, $C(O)OR_5$, $NO_2$, CN, $C(O)R_5$, $C(O)C(O)R_5$, $C(O)NR_5R_5$, $N(R_5)C(O)R_5$, $NR_5S(O)_2R_5$, $N(R_5)(C(O)OR_5)$, $NR_5C(O)C(O)R_5$, $NR_5C(O)NR_5R_5$, $NR_5S(O)_nNR_5R_5$, $NR_5S(O)_nR_5$, $S(O)_nR_5$, $S(O)_nNR_5R_5$, $OC(O)R_5$, optionally substituted aryl and optionally substituted heteroaryl. Non-limiting examples of optionally substituted aryl are phenyl, substituted phenyl, phenyl substituted with one or more $R_9$, napthyl and substituted naphthyl.

The term "heteroaryl", as used herein, refers to aromatic carbocyclic groups containing one or more heteroatoms (O, S, or N) within a ring. A heteroaryl group can be monocyclic or polycyclic. A heteroaryl group may additionally be substituted or unsubstituted. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl.

The foregoing heteroaryl groups may be C-attached or heteroatom-attached (where such is possible). For instance, a group derived from pyrrole may be pyrrol-1-yl (N-attached) or pyrrol-3-yl (C-attached).

A suitable substituent on a heteroaryl group is one that does not substantially interfere with the pharmaceutical activity of the disclosed compound. A heteroaryl may have one or more substituents, which can be identical or different. Examples of suitable substituents for a substitutable carbon atom in a heteroaryl group include, but are not limited to, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, halo, $OR_5$, $SR_5$, $NR_5R_5$, $COOR_5$, $NO_2$, CN, $C(O)R_5$, $C(O)C(O)R_5$, $C(O)NR_5R_5$, $N(R_5)C(O)R_5$, $NR_5S(O)_2R_5$, $N(R_5)(COOR_5)$, $NR_5C(O)C(O)R_5$, $NR_5C(O)NR_5R_5$, $NR_5S(O)_nNR_5R_5$, $NR_5S(O)_nR_5$, $S(O)_nR_5$, $S(O)_nNR_5R_5$, $OC(O)R_5$, optionally substituted aryl and optionally substituted heteroaryl.

In one embodiment, the heteroaryl is selected from the group consisting of:

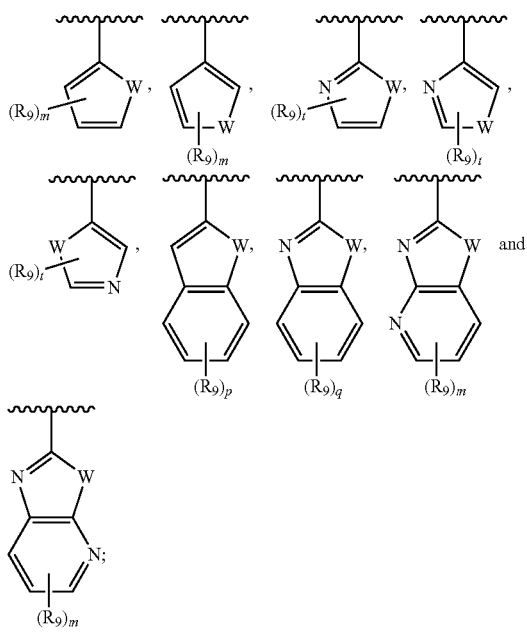

wherein W is selected from the group consisting of $NR_5$, O and S; m is an integer from 0 to 3; p is an integer from 0 to 5; q is an integer from 0 to 4 and t is an integer 0 to 2.

In one embodiment, an "optionally substituted aryl" or "optionally substituted heteroaryl" is an aryl or heteroaryl group substituted with a group selected from the group consisting of C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, halo, $OR_5$, $SR_5$, $NR_5R_5$, $C(O)OR_5$, $NO_2$, CN, $C(O)R_5$, $C(O)C(O)R_5$, $C(O)NR_5R_5$, $N(R_5)C(O)R_5$, $NR_5S(O)_nR_5$, $N(R_5)C(O)OR_5$, $NR_5C(O)C(O)R_5$, $NR_5C(O)NR_5R_5$, $NR_5S(O)_nNR_5R_5$, $NR_5S(O)_nR_5$, $S(O)_nR_5$, $S(O)_nNR_5R_5$, $OC(O)R_5$, phenyl and phenyl substituted with one or more C1-C10 alkyl, C1-C10 alkyl substituted with one or more $R_7$, C2-C10 alkenyl, halo, $OR_5$, $SR_5$, $NR_5R_5$, $C(O)OR_5$, $NO_2$, CN and $S(O)_nR_5$. In another embodiment, an "optionally substituted aryl" or "optionally substituted heteroaryl" is an aryl or heteroaryl group substituted with a group selected from the group consisting of C1-C10 alkyl, C1-C10 alkyl substituted with one or more $R_7$, halo, $OR_5$, $NR_5R_5$, $C(O)OR_5$, $NO_2$, CN, $S(O)_nR_5$, phenyl and phenyl substituted with one or more C1-C10 alkyl, C1-C10 alkyl substituted with one or more $R_7$, C2-C10 alkenyl, halo, $OR_5$, $SR_5$, $NR_5R_5$, $C(O)OR_5$, $NO_2$, CN and $S(O)_nR_5$. In a further embodiment, an "optionally substituted aryl" or "optionally substituted heteroaryl" is an aryl or heteroaryl group substituted with a group selected from C1-C10 alkyl, C1-C10 alkyl substituted with one or more $R_7$, halo, $OR_5$, $NR_5R_5$, $C(O)OR_5$, $NO_2$, CN and $S(O)_nR_5$.

The term "haloalkyl" as used herein refers to an alkyl group having 1 to (2n+1) substituent(s) independently selected from F, Cl, Br or I, where n is the maximum number of carbon atoms in the alkyl group.

The term "pyridinyl," as used herein is meant to encompass 2-pyridinyl, 3-pyridinyl and 4-pyridinyl groups.

Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. "Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. When the compounds described herein contain olefinic double bonds or other centers of geometric asymmetry, and unless specified otherwise, it is intended that the compounds include both E and Z geometric isomers. Likewise, all tautomeric forms are also intended to be included.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position. In one embodiment, the compound has an R-configuration at the 2-position of the piperazine ring. In another embodiment, the compound has an S-configuration at the 2-position of the piperazine ring. In one embodiment, a compound has an R-configuration at the 2-position if it is present at least 5%, 10%, 20%, 30%, 40%, 50%, 60%, 70%, 80%, 85%, 90%, 95% or 99% excess compared with a compound having an S-configuration at the 2-position. In another embodiment, a compound has an S-configuration at the 2-position if it is present at least 5%, 10%, 20%, 30%, 40%, 50%, 60%, 70%, 80%, 85%, 90%, 95% or 99% excess compared with a compound having an R-configuration at the 2-position.

In a further embodiment, the compound is present as a mixture of (S)- and (R)-isomers at the 2-position of the piperazine ring in any ratio between 1:99 and 99:1. In yet another embodiment, the (S)- and (R)-isomers are present in any ratio between 10:90 and 90:10, 20:80 and 80:20, and 60:40 and 40:60. In an additional embodiment, the compound is present as a mixture of the (S)- and (R)-isomers at the 2-position of the piperazine ring at a ratio of 50:50.

As used herein, a "pharmaceutically acceptable salt" is an ionic bond-containing product of the reaction between the disclosed compound with either an acid or a base, suitable for administering to a subject. Pharmaceutically acceptable salts are well known in the art and are described, for example, in Berge et al (1977), Pharmaceutical Salts. Journal of Pharmaceutical Sciences, 69(1): 1-19, the contents of which are herein incorporated by reference. A non-limiting example of a pharmaceutically acceptable salt is an acid salt of a compound containing an amine or other basic group which can be obtained by reacting the compound with a suitable organic or inorganic acid. Examples of pharmaceutically acceptable salts also can be metallic salts including, but not limited to, sodium, magnesium, calcium, lithium and aluminum salts. Further examples of pharmaceutically acceptable salts include hydrochlorides, hydrobromides, sulfates, methanesulfonates, nitrates, maleates, acetates, citrates, fumarates, tartrates (e.g. (+)-tartrates, (-)-tartrates or mixtures thereof including racemic mixtures), succinates, benzoates and salts with amino acids such as glutamic acid. Salts can also be formed with suitable organic bases when the compound comprises an acid functional group such as —COOH or —SO$_3$H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylenediamine, tris(hydroxymethyl)aminomethane and the like.

The compounds of the present invention can be synthesized as illustrated in the following synthetic schemes:

Scheme 1

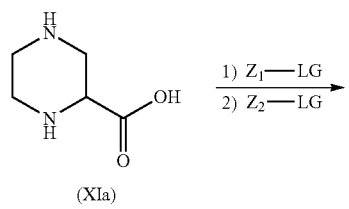

(XIa)

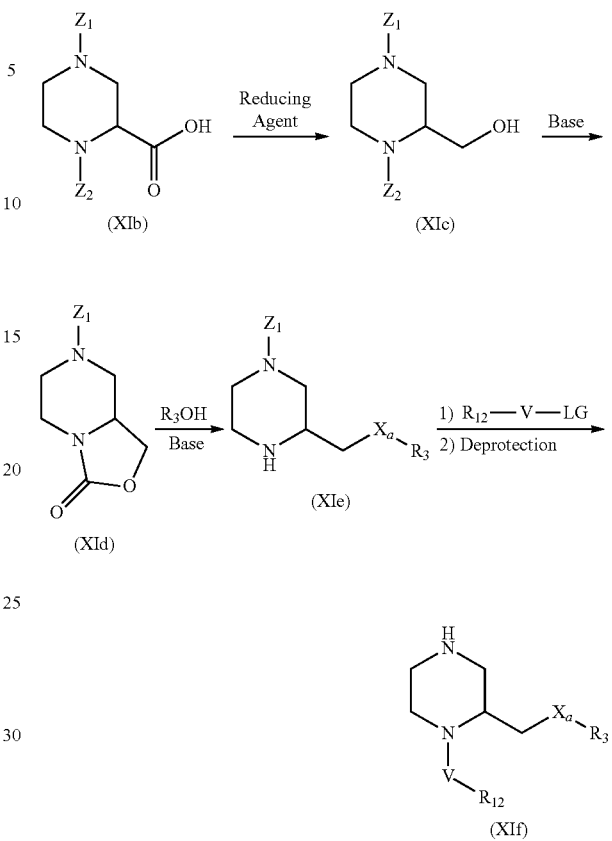

Compounds having the Formula (XIf) can be prepared as outlined in Scheme 1 wherein $X_a$, $R_{12}$ and V are as defined for Formula (III), $R_3$ is as described above for Formula (I), $Z_1$ is a nitrogen protecting group, $Z_2$ is a carbamate nitrogen protecting group, and LG is a leaving group. In general, a compound of Formula (XIf) can be prepared by reacting a compound of Formula (XIe) with an electrophilic reactant, $R_{12}$—V-LG, followed by removal of the $Z_1$ protecting group. More specific examples are outlined in Schemes 5-15 below. The compound of Formula (XIe) wherein $X_a$ is O can be prepared in several steps from piperazine-2-carboxylic acid, Formula (XIa). The protecting group $Z_1$ is introduced on the less hindered nitrogen of (XIa), followed by introduction of $Z_2$ on the second nitrogen to yield a compound of Formula (XIb). A compound of Formula (XIc) can then be prepared by treating the compound of Formula (XIb) with an appropriate reducing agent, such as borane-tetrahydrofuran complex. Under some reducing conditions, the compound of Formula (XIc) may cyclize to form a compound of Formula (XId). In other cases, the compound of Formula (XIc) can be converted to a compound of Formula (XId) by heating at about 50° C. to about 100° C. for about 1 to about 24 hours in the presence of an appropriate base, such as K$_2$CO$_3$ or sodium hydride. It will be recognized that in the case where $Z_1$ is a protecting group, such as a t-butoxycarbonyl or benzyloxycarbonyl, $Z_1$ and $Z_2$ can be identical. Reacting a compound of Formula (XId) with an appropriate alcohol in the presence of an appropriate base at about 80° C. to about 150° C. for about 12 hours to about 72 hours yields a compound of Formula (XIe).

Scheme 2

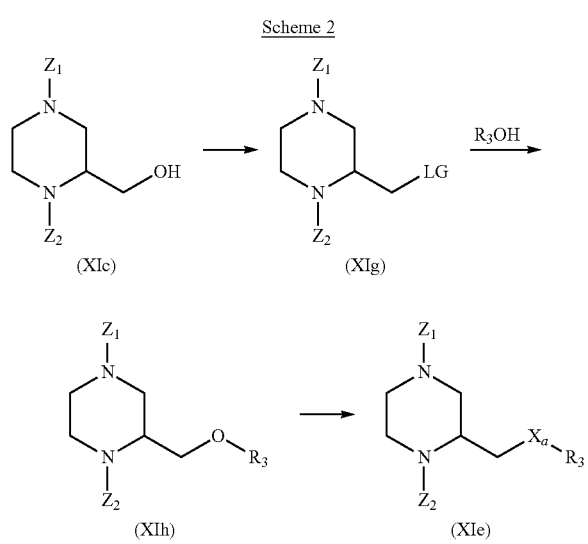

Alternatively, compounds having the Formula (XIe) wherein $X_a$ is O, $NR_5$ or S can be prepared as outlined in Scheme 2 wherein $Z_1$, $Z_2$, LG and $R_3$ are as defined for Scheme 1 above. The alcohol group of the compound of Formula (XIc) can be converted to a leaving group, such as a tosylate, mesylate, bromide, or iodide, to give a compound of Formula (XIg). The compound of Formula (XIg) is then reacted with an appropriate alcohol in the presence of an appropriate base at about room temperature to about 100° C. to give a compound of Formula (XIh). The compound of Formula (XIh) can also be prepared by in situ conversion of the alcohol of the compound of Formula (XIc) to a leaving group using an azodicarboxylate reagent, such as diisopropylazodicarboxylate, and phosphine reagent, such as triphenylphosphine, and displacement by an appropriate alcohol, a reaction commonly known as a Mitsunobu reaction. The $Z_2$ protecting group of the compound of Formula (XIh) can then be removed to provide the compound of Formula (XIe).

Scheme 3

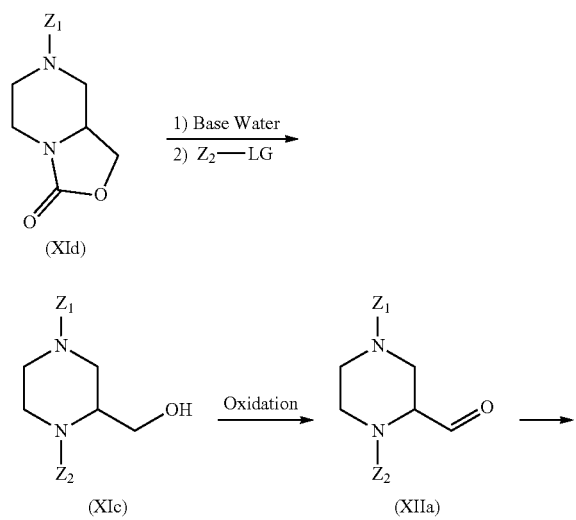

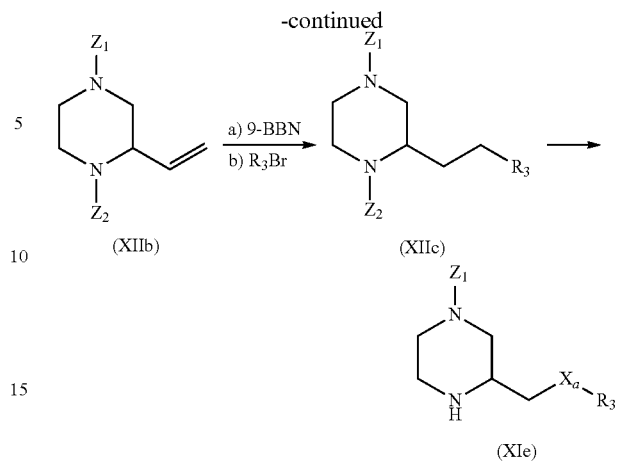

Compounds having the Formula (XIe) wherein $X_a$ is $CH_2$ can be prepared as outlined in Scheme 3 wherein $Z_1$, $Z_2$, and $R_3$ are as described above for Scheme 1. A compound having the Formula (XIc) can be prepared as described in Scheme 1 above or by heating a compound of Formula (XId) to about 70° C. in the presence of water and an appropriate base followed by introduction of a protecting group, $Z_2$. The compound of Formula (XIc) can then be oxidized by a number of methods, including the Swern oxidation, to give a compound of Formula (XIIa). The compound of Formula (XIIa) can be converted to the compound of Formula (XIIb) by reaction with methyltriphenylphosphonium bromide and n-BuLi. The compound of Formula (XIIb) is then hydroborated with an appropriate borohydride reagent, such as 9-BBN, the product of which is coupled to an appropriate arylhalide in the presence of a palladium catalyst, such as tetrakistriphenylphosphinepalladium(0), to give a compound of Formula (XIIc). The $Z_2$ protecting group of the compound of Formula (XIIc) is then removed to provide the compound of Formula (XIe).

Scheme 4

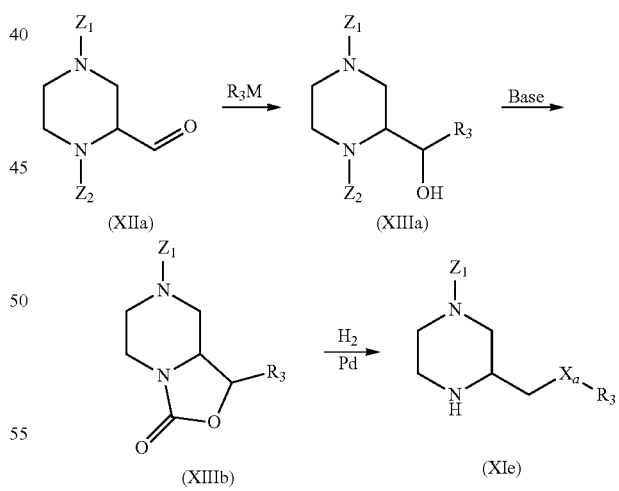

Compounds having the Formula (XIe) wherein $X_a$ is a bond can be prepared as outlined in Scheme 4 wherein $Z_1$, $Z_2$, and $R_3$ are as described above for Scheme 1 and M is a metal, such as lithium or magnesium. A compound having the Formula (XIIIa) can be prepared by reacting the compound of Formula (XIIa) with a suitable organometallic reagent, $R_3M$, at between about −78° C. and room temperature. Under some reaction conditions, the compound of Formula (XIIIa) may cyclize to form a compound of Formula (XIIIb). Alternatively, the compound of Formula (XIIIb) can be prepared by heating the compound of Formula (XIIIa) at about 50° C. to about 100° C. in the presence of a suitable base. It will be recognized that in the case where $Z_1$ is a carbamate protecting group, such as a t-butoxycarbonyl or benzyloxycarbonyl, $Z_1$ and $Z_2$ can be identical. The compound of Formula (XIIIb) is then treated with hydrogen or a hydrogen source, such as ammonium formate, in the presence of a palladium catalyst, such as palladium on carbon or palladium hydroxide on carbon, to yield the compound of Formula (XIe) wherein X is a bond.

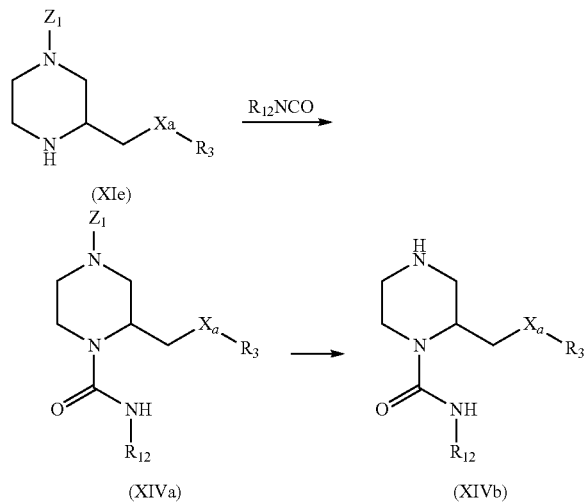

Compounds having the Formula (XIVb) can be prepared as outlined in Scheme 5, wherein $Z_1$, $X_a$, $R_3$ and $R_{12}$ are as defined in Scheme 1 above. The compound of Formula (XIe) can be reacted with an appropriate isocyanate with or without a suitable base for a period of about 30 minutes to about 12 hours to prepare the compound of Formula (XIVa). The compound of Formula (XIVa) can then be deprotected to yield a compound of Formula (XIVb).

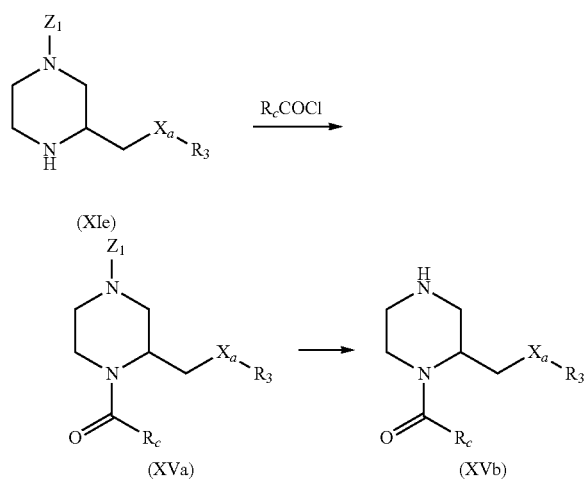

Compounds having the Formula (XVb) can be prepared as outlined in Scheme 6 wherein $X_a$, $Z_1$, and $R_3$ are as described above for Scheme 1 and $R_c$ is $R_{12}$ or $R_6$-$R_{12}$, wherein $R_6$ and $R_{12}$ are as defined in Formula (III). The compound of Formula (XIe) can be reacted with an appropriate acid chloride, chloroformate, or carbamoyl chloride for about 1 to about 12 hours in the presence of a suitable base to prepare the compound of Formula (XVa) which can then be deprotected to yield a compound having the Formula (XVb).

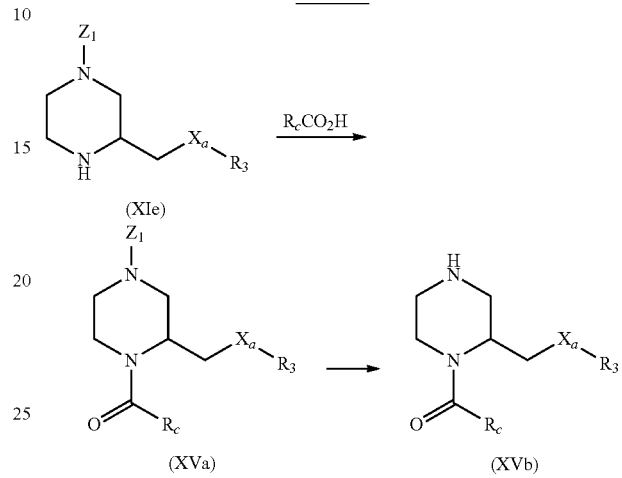

Alternatively, compounds having the Formula (XVb) can be prepared as outlined in Scheme 7 wherein $X_a$, $Z_1$ and $R_3$ are as described above for Scheme 1 and $R_c$ is $R_{12}$ or $R_6$-$R_{12}$, wherein $R_6$ is $CH_2$, $CH_2CH_2$, $C(O)$, $C(O)CH_2$, $C(O)O$, $CH_2O$, $CH_2S$, or $CH_2NR_5$, and $R_{12}$ is as defined in Formula (III). The compound of Formula (XVa) can be prepared by the addition of a suitable coupling agent, such as N,N-diisopropylcarbodiimide, to a mixture of a compound of Formula (XIe) and an appropriate carboxylic acid. Other reactants may also be present, such as 1-hydroxybenzotriazole and a suitable base. The compound of Formula (XVa) can then be deprotected to yield a compound of Formula (XVb).

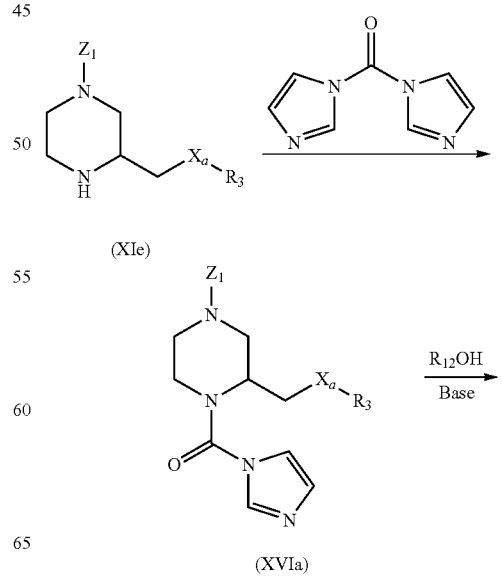

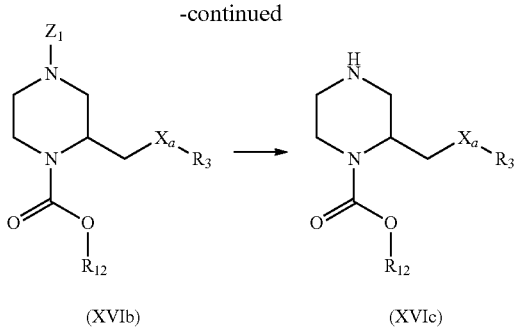

(XVIb)          (XVIc)

Compounds having the Formula (XVIc) can be prepared as outlined in Scheme 8 wherein $X_a$, $Z_1$, $R_{12}$ and $R_3$ are as described above for Scheme 1. A compound of Formula (XVIb) can be prepared by reacting a compound of Formula (XVIa) and an appropriate alcohol in the presence of a base at room temperature to about 70° C. for about 1 hour to about 12 hours. A compound of Formula (XVIb) can be deprotected to give a compound of Formula (XVIc). A compound of Formula (XVIa) can be prepared by reacting a compound of Formula (XVIe) and N,N'-carbonyldiimidazole for about 12 hours.

Scheme 9

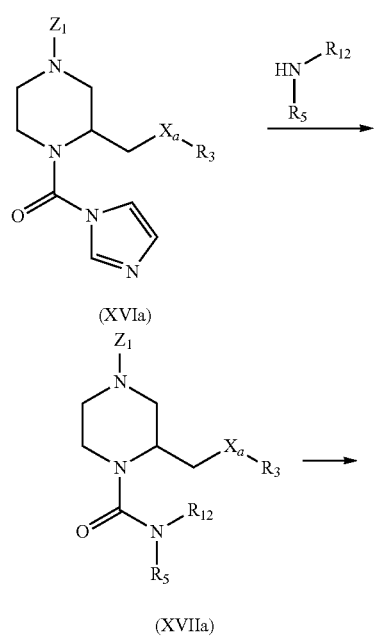

(XVIIa)          (XVIIb)

Compounds having the Formula (XVIIb) can be prepared as outlined in Scheme 9 wherein $X_a$, $Z_1$ and $R_3$ are as described above for Scheme 1, $R_5$ is as defined for Formula (I) and wherein $R_{12}$ is selected from the group consisting of a 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$ or alternatively, $R_{12}$ and $R_5$ are taken together to form a 3 to 8 membered ring containing 0 to 2 additional heteroatoms each independently selected from N, O and S, wherein said ring is substituted with one or more $R_8$. A compound of Formula (XVIIa) can be prepared by heating an appropriate primary or secondary amine and a compound of Formula (XVIa) with or without a suitable base for about 16 to about 72 hours. A compound of Formula (XVIIa) can then be deprotected to yield a compound of Formula (XVIIb).

Scheme 10

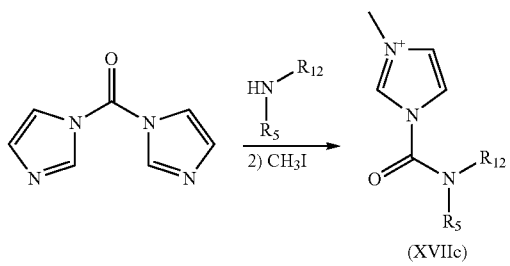

(XVIIc)

(XIe)

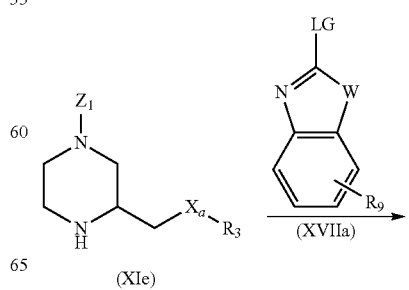

(XVIIa)          (XVIIb)

Alternatively, compounds having the Formula (XVIIb) can be prepared as outlined in Scheme 10 wherein $X_a$, $Z_1$ and $R_3$ are as described above for Scheme 1 and $R_{12}$ and $R_5$ are as defined above for Scheme 9. A compound of Formula (XVIIa) can be prepared by heating a compound of Formula (XIe) and a compound of Formula (XVIIc) in the presence of a suitable base for about 12 to about 24 hours. A compound of Formula (XVIIa) can then be deprotected to yield a compound of Formula (XVIIb). A compound of Formula (XVIIc) is prepared by treating a primary or secondary amine with N,N'-carbonyldiimidazole. After an appropriate workup and isolation, the material is heated with iodomethane.

Scheme 11

(XIe)

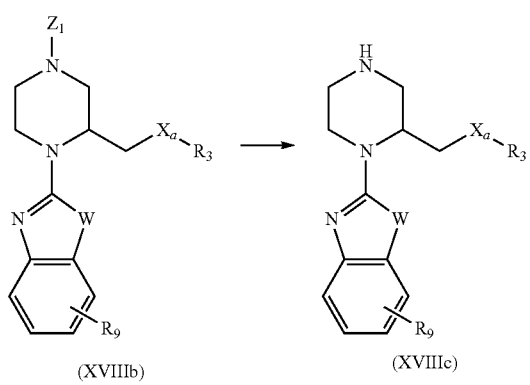

Compounds having the Formula (XVIIIc) can be prepared as outlined in Scheme 11 wherein $X_a$, $Z_1$ and $R_3$ are as described above for Scheme 1, W is O or S, and LG is Cl, Br, SH, SOCH$_3$, or SO$_2$CH$_3$. $R_9$ is defined as in Formula (I). A compound of Formula (XVIIIb) can be prepared by heating a compound of Formula (IVe) and a compound of Formula (XVIIIa) with or without a suitable base for about 16 to about 72 hours. In the case where LG is Cl or Br, a suitable catalyst, such as Pd(OAc)$_2$, and additive, such as triphenylphosphine, may also be used. A compound of Formula (XVIIIb) can then be deprotected to yield a compound of Formula (XVIIIc).

Scheme 12

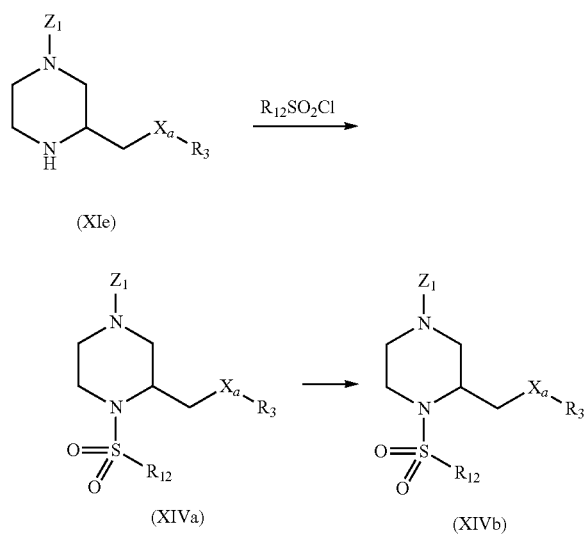

Compounds having the Formula (XIVb) can be prepared as outlined in Scheme 12 wherein $X_a$, $Z_1$, $R_{12}$ and $R_3$ are as described above for Scheme 1. The compound of Formula (XIe) can be reacted with an appropriate sulfonyl chloride in the presence of a suitable base for about 1 to about 16 hours to prepare the compound of Formula (XIVa). The compound of Formula (XIVa) can then be deprotected to yield a compound having the Formula (XIVb).

Scheme 13

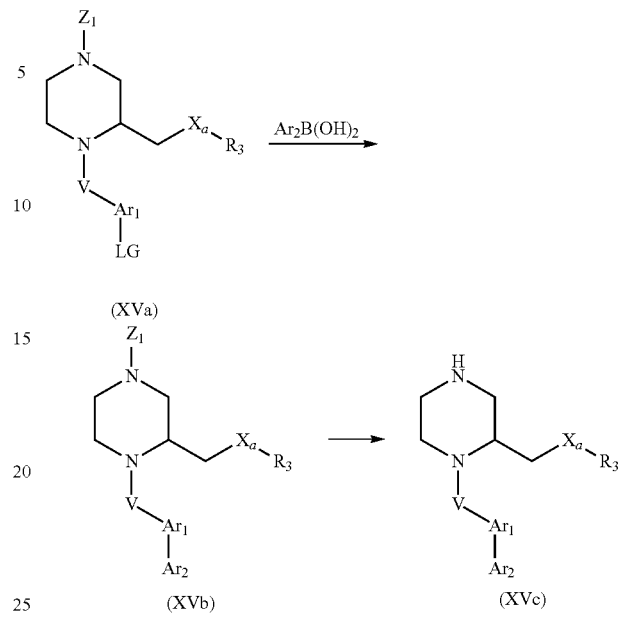

Compounds having the Formula (XVc) can be prepared as outlined in Scheme 13 wherein $X_a$, V, $Z_1$, and $R_3$ are as described above for Scheme 1, and Ar$_1$ and Ar$_2$ are each independently aryl or heteroaryl and LG is bromine, chlorine, iodine, or triflate. The compound of Formula (XVa) can be reacted with an appropriate boronic acid in the presence of a suitable catalyst, such as tetrakistriphenylphoshinepalladium (0), and a suitable base for about 3 to about 16 hours to prepare the compound of Formula (XVb). The compound of Formula (XVb) can then be deprotected to yield a compound having the Formula (XVc). Compounds of Formula (XVa) are prepared as in Schemes 1-12 above.

Scheme 14

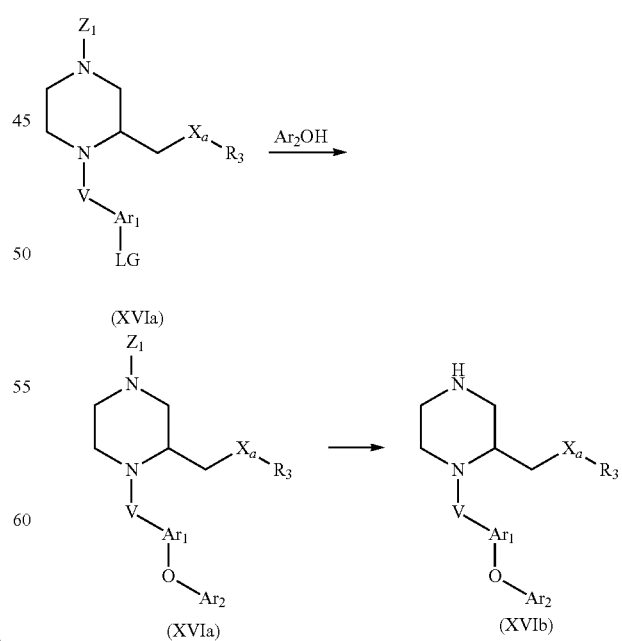

Compounds having the Formula (XVIb) can be prepared as outlined in Scheme 14 wherein $X_a$, V, $Z_1$, and $R_3$ are as described above for Scheme 1, and $Ar_1$ and $Ar_2$ are each independently aryl or heteroaryl and LG is bromine, chlorine, iodine, or triflate. The compound of Formula (XVIa) can be reacted with an appropriate aryl or heteroaryl alcohol in the presence of a suitable catalyst, such as copper(I) iodide, a suitable cocatalyst, such as N,N-dimethylglycine, and a suitable base for about 12 to about 48 hours to prepare the compound of Formula (XVIa). The compound of Formula (XVIa) can then be deprotected to yield a compound having the Formula (XVIb).

Scheme 15

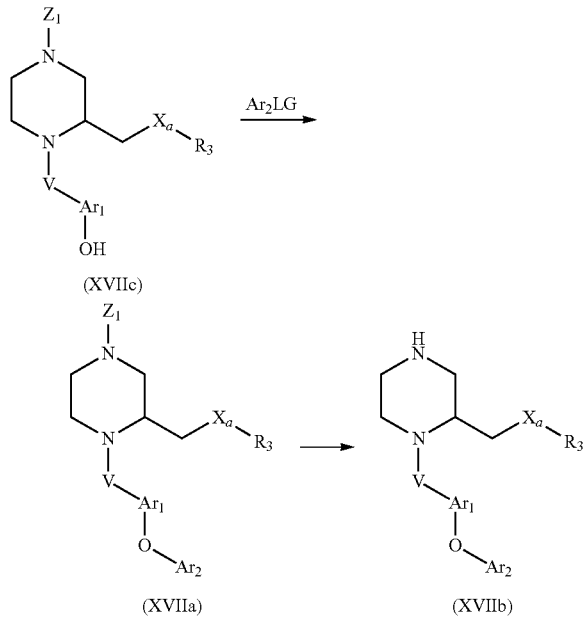

(XVIIc)

(XVIIa)   (XVIIb)

Alternatively, compounds having the Formula (XVIIb) can be prepared as outlined in Scheme 15 wherein $X_a$, V, $Z_1$, and $R_3$ are as described above for Scheme 1, and $Ar_1$ and $Ar_2$ are each independently aryl or heteroaryl and LG is bromine, chlorine, or iodine. The compound of Formula (XVIIc) can be reacted with an appropriate aryl or heteroaryl halide in the presence of a suitable catalyst, such as copper(I) iodide, a suitable cocatalyst, such as N,N-dimethylglycine, and a suitable base for about 12 to about 48 hours to prepare the compound of Formula (XVIIa). The compound of Formula (XVIIa) can then be deprotected to yield a compound having the Formula (XVIIb). The compounds of Formula (XVIIc) are prepared as described in Schemes 1-12 above.

In one embodiment, the invention is directed to a method for the preparation of a compound having the Formula (I) comprising the step of reacting a compound having the Formula (XId):

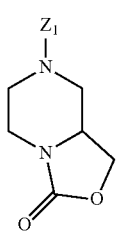

(XId)

with an alcohol having the Formula $R_3OH$ under basic conditions to yield a compound having the Formula (XIe):

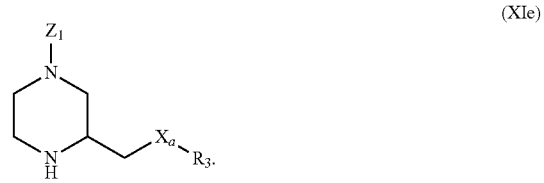

(XIe)

The chemicals used in the above synthetic schemes may include, for example, appropriate solvents, reagents, catalysts, protecting groups and their associated deprotecting reagents, and the like.

One skilled in the art will appreciate that the above synthetic schemes are not intended to comprise a comprehensive list of all methods by which the compounds described and claimed herein may be synthesized. Further methods of preparing the compounds will be evident to those of ordinary skill in the art. Other compounds of the invention that can be prepared using these methods and the appropriate starting material, reagents and/or reactants will also be evident to those of skill in the art. Additionally, the various synthetic steps described above may be performed in an alternative sequence to give the desired compounds. In some instances, it may be desirable to use protecting groups. Suitable protecting groups are known to the one of ordinary skill in the art and are found, for example, in Green and Wuts, "Protective Groups in Organic Synthesis", John Wiley and Sons (1991), the entire relevant teachings of which are incorporated herein by reference.

In one embodiment, the invention pertains to a pharmaceutical composition comprising a pharmaceutically acceptable excipient and a compound of Formula (I), Formula (II), Formula (III), Formula (IV), Formula (V), Formula (VI), Formula (VII), Formula (VIII), Formula (IX) or Formula (X). As used herein, a "pharmaceutical composition" is a formulation comprising a compound of the invention in a therapeutically effective amount and a pharmaceutically acceptable diluent or carrier, in a form suitable for administration to a subject. The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration. A variety of routes are contemplated, including, but not limited to, parenteral, oral, pulmonary, ophthalmic, nasal, rectal, vaginal, aural, topical, buccal, transdermal, mucosal, intravenous, intramuscular, subcutaneous, intradermal, intraocular, intracerebral, intracerbroventricular, intralymphatic, intraarticular, intrathecal and intraperitoneal.

The compounds described herein can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

In a further embodiment, the invention pertains to the treatment or alleviation of a condition mediated by the α7 nAChR. Conditions that are mediated by the α7 nAChR include, but are not limited to, an inflammatory condition, a CNS disorder, symptoms of nicotine withdrawal, cessation of smoking, treatment of chronic pain and treating a learning or memory impairment. As used herein, the "α7 nAChR," is a receptor comprising an α7 subunit. The receptor can comprise only the α7 subunit; alternatively the receptor comprises α7 subunit(s) and other nicotinic receptor subunit(s). In one embodiment, the receptor is a homopentamer of α7 subunits. In another embodiment, the receptor of is a heteropentamer of the α7 subunit and other nicotinic receptor subunits. An "α7 subunit" is intended to include all α7 subunit isoforms and/or variants including, but not limited to, the α7 duplicate nicotinic acetylcholine receptor ("dupα7") described in Villiger et al., Journal of Immunology 126: 86-98 (2002) and Gault et al., Genomics 52:173-85 (1998), the splice variant α7-2 described in US 20040152160 and the promoter variant(s) of the α7 nicotinic receptor described in U.S. Pat. No. 6,875,606.

In another embodiment, the invention pertains to treating a patient suffering from an inflammatory condition comprising administering a compound disclosed herein. In one embodiment, the inflammatory condition is selected from the group consisting of appendicitis, peptic, gastric or duodenal ulcers, peritonitis, pancreatitis, pseudomembranous colitis, acute colitis, ulcerative colitis, ischemic colitis, diverticulitis, epiglottitis, achalasia, cholangitis, cholecystitis, hepatitis, Crohn's disease, enteritis, ileus, Whipple's disease, asthma, chronic obstructive pulmonary disease, acute lung injury, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcet's syndrome, allograft rejection, graft-versus-host disease, interstitial cystitis, Type I diabetes, ankylosing spondylitis, Berger's disease, Type II diabetes, Retier's syndrome and Hodgkins disease.

In another embodiment, the inflammatory condition is selected from the group consisting of peritonitis, pancreatitis, ulcerative colitis, Crohn's disease, asthma, organ ischemia, reperfusion injury, sepsis, cachexia, burns, myocardial ischemia, adult respiratory distress syndrome, acute lung injury, multiple sclerosis, rheumatoid arthritis, systemic lupus erythematous, chronic obstructive pulmonary disease, psoriasis, Behcet's syndrome, allograft rejection, graft-versus-host disease and ileus.

In yet another embodiment, the inflammatory condition is selected from the group consisting of peritonitis, pancreatitis, ulcerative colitis, Crohn's disease, asthma, sepsis, acute lung injury, adult respiratory distress syndrome, rheumatoid arthritis, systemic lupus erythematosus, chronic obstructive pulmonary disease, psoriasis and ileus.

In a further embodiment, the invention is directed to a method for inhibiting the release of a cytokine from a mammalian cell. As used herein, a cytokine is a soluble protein or peptide which is naturally produced by mammalian cells and which act in vivo as humoral regulators at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodialation, hyperemia, increased permeability of vessels with associated edema, accumulation of granulocytes and mononuclear phagocytes, or deposition of fibrin. In some cases, the proinflammatory cytokine can also cause apoptosis, such as chronic heart failure, where TNF has been shown to stimulate cardiomyocyte apoptosis (Pulkki, 1997; Tsutsui et al. 2000). Nonlimiting examples of proinflammatory cytokines are tumor necrosis factor alpha (TNF-α), interleukin (IL)-1α, IL-1β, IL-6, IL-8, IL-18, interferon-γ, HMGB1, platelet-activating factor (PAF), and macrophage migration inhibitory factor (MIF). In one embodiment, the invention is directed to a method for inhibiting the release of a cytokine from a mammalian cell, wherein the cytokine is selected from the group consisting of TNF-α, IL-1α, IL-1β, IL-6, IL-8, IL-18, IFN-γ, HMGB1, PAF and MIF. In yet another embodiment, the cytokine is selected from the group consisting of TNF-α, HMGB1, IL-1α, IL-1β, IL-6 and IL-18. In an additional embodiment, the cytokine is selected from the group consisting of TNF-α and HMGB1. Any mammalian cell that produces proinflammatory cytokines may be inhibited by the practice of the disclosed method. Nonlimiting examples are monocytes, macrophages, mast cells, neutrophils, epithelial cells, osteoblasts, fibroblasts, smooth muscle cells, and neurons. In one embodiment of the invention, the mammalian cell is selected from the group consisting of a monocyte, a macrophage and a neutrophil. In another embodiment, the mammalian cell is a macrophage.

In yet another embodiment, the invention is directed to a method for the treatment of a CNS disorder in a mammal suffering therefrom comprising administering a compound described herein to the mammal. As used herein, the term "CNS disorder," includes neurological disorders, neuropsychiatric disorders, neurologic diseases, mental illnesses, neurodegenerative diseases, behavioral disorders, cognitive disorders and cognitive affective disorders. A CNS disorder can be drug induced, attributed to genetic predisposition, infection or trauma or can be of unknown etiology. In one embodiment, the CNS disorder is selected from the group consisting of dementia, Parkinson's disease, Huntington's chorea, tardive dyskinesia, hyperkinesia, mania, attention deficit disorder, anxiety, schizophrenia, Tourette's syndrome, mania, manic depression, anxiety, Alzheimer's disease, learning deficit, cognitive deficit, memory loss, autism, amyotrophic lateral sclerosis and neuroendocrine disorders (e.g., obesity, bulemia and diabetes insipidus). In a further embodiment, the CNS disorder is Alzheimer's disease. In a preferred embodiment of the disclosed methods, the mammal is a human.

In a further embodiment, the CNS disorder is pain. The method of the invention can be used to treat acute, chronic or recurrent pain including, but not limited to, pain from migraine, postoperative pain, pain from chronic headache, and neuropathic pain.

As used herein, "treatment" and/or "treating" refer to the therapeutic treatment as well as prophylactic treatment or preventative measures. As used herein, an "effective amount" of a compound of the disclosed invention is the quantity which, when administered to a subject in need of treatment, improves the prognosis of the subject, e.g., delays or prevents the onset of and/or reduces the severity of one or more of the subject's symptoms associated with an inflammatory condition and/or a CNS disorder and/or a condition mediated by an $\alpha 7$ receptor. The amount of the disclosed compound to be administered to a subject will depend on the particular disease or condition, the mode of administration, and the characteristics of the subject, such as general health, other diseases, age, sex, genotype, body weight and tolerance to drugs. The skilled artisan will be able to determine appropriate dosages depending on these and other factors.

The disclosed compounds can be co-administered with one or more additional agents such as antibiotics, anti-inflammatory agents (e.g., ibuprofen, prednisone, corticosteroid, pentofylline), anti-fungals (e.g., Amphotericin B, Fluconazole, Ketoconazol and Itraconazol), steroids, decongestants, bronchodialators, and the like. The disclosed compounds can also be co-administered with anti-TNF agents, such as infliximab, etanercept, adalimumab, CDP870, CDP571, Lenercept or Thalidomide. The formulation may also contain preserving agents, solubilizing agents, chemical buffers, surfactants, emulsifiers, colorants, odorants and sweetenters. The disclosed compounds may be co-administered with one or more additional agents separately or in the same formulation.

The excipient included with the compounds of the pharmaceutical compositions of the invention is chosen based on the expected route of administration of the composition in therapeutic applications. The route of administration of the composition depends on the condition to be treated. For example, intravenous injection may be preferred for treatment of a systemic disorder such as endotoxic shock, and oral administration may be preferred to treat a gastrointestinal disorder such as a gastric ulcer. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the composition can be administered orally, parenterally, intranasally, vaginally, rectally, lingually, sublingually, bucally, intrabuccally and transdermally to the patient.

Accordingly, compositions designed for oral, lingual, sublingual, buccal and intrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the compound prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administer to a wound site.

The composition of the present invention can be administered parenterally such as, for example, by intravenous, intramuscular, intrathecal or subcutaneous injection. Parenteral administration can be accomplished by incorporating a composition of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes).

Embodiments of the invention are illustrated by the following examples which are not intended to be limiting in any way.

EXEMPLIFICATION

General Experimental Methods

Air and moisture sensitive liquids and reagents were transferred via syringe or cannula and were introduced into oven-dried glassware under a positive pressure of dry nitrogen through rubber septa. All reactions were stirred magnetically. Commercial reagents were used without further purification. Unless otherwise stated, the term "concentrated under reduced pressure" refers to the use of a Buchi rotary evaporator at 10-500 mbar. All temperatures are reported uncorrected in degrees Celsius (° C.). Thin-layer chomatography (TLC) was performed on EM Science pre-coated glass-backed silica gel 60 Å F-254 250 μm plates. Visualization of the plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in cerium sulfate solution followed by heating, (e) immersion of the plate in acidic ethanol solution of 2,4-dinitrophenylhydrazine followed by heating and/or (f) immersion of the plate in acidic ethanol solution of anisaldehyde followed by heating. Column chomatography was performed on an Argonaut FlashMaster Personal or FlashMaster Personal+ System using ISOLUTE Flash Si II silica gel pre-packed cartridges. Preparative reversed-phase HPLC chomatography (HPLC) was accomplished using an Agilent 1100 Series system and an Agilent Prep-C18 (21.2 mm I.D.× 150 mm) column equipped with an Agilent Prep-C18 (21.2 mm I.D.) guard column. Typically, the mobile phase used was a mixture of $H_2O$ (A) and MeCN (B) containing 0.1% TFA. A typical gradient was:

| Time (min.) | % A | % B | Flow (mL/min.) |
|---|---|---|---|
| 0.00 | 90 | 10 | 30 |
| 1.00 | 90 | 10 | 30 |
| 11.00 | 10 | 90 | 30 |
| 14.00 | 10 | 90 | 30 |
| 15.00 | 90 | 10 | 30 |
| 16.00 | 90 | 10 | 30 |

A typical gradient for more polar compounds was:

| Time (min.) | % A | % B | Flow (mL/min.) |
|---|---|---|---|
| 0.00 | 95 | 5 | 30 |
| 2.00 | 95 | 5 | 30 |
| 10.00 | 50 | 50 | 30 |
| 12.00 | 5 | 95 | 30 |
| 15.00 | 5 | 95 | 30 |
| 16.00 | 95 | 5 | 30 |
| 17.00 | 95 | 5 | 30 |

High performance liquid chomatography-electrospray mass spectra (LC-MS) were obtained using an Agilent 1100 Series HPLC equipped with a binary pump, a diode array detector monitored at 254 nm and 214 nm, an Agilent Zorbax Eclipse XDB-C8 (4.6 mm I.D.×150 mm, 5 micron) column, and an Agilent 1100 Series LC/MSD mass spectrometer with electrospray ionization. Spectra were scanned from 100-1000 amu. The eluent was a mixture of $H_2O$ (A) and MeCN (B) containing 0.1% AcOH. A typical gradient was:

| Time (min.) | % A | % B | Flow (mL/min.) |
|---|---|---|---|
| 0.00 | 90 | 10 | 1 |
| 9.00 | 10 | 90 | 1 |
| 9.50 | 90 | 10 | 1 |
| 12.00 | 90 | 10 | 1 |

Routine one-dimensional NMR spectroscopy was performed on a Varian 400 MHz spectrometer at 293 K. The samples were dissolved in deuterated solvents obtained from Cambridge Isotope Labs (Andover, Mass.). The chemical shifts were recorded on the ppm scale and were referenced to the appropriate residual solvent signals, such as 2.50 ppm for DMSO-$d_6$, 1.93 ppm for $CD_3CN$, 3.30 for $CD_3OD$, 5.32 ppm for $CD_2Cl_2$, and 7.26 ppm for $CDCl_3$ for $^1H$ NMR spectra, and 39.5 ppm for DMSO-$d_6$, 1.3 ppm for $CD_3CN$, 49.0 for $CD_3OD$, 53.8 ppm for $CD_2Cl_2$, and 77.0 ppm for $CDCl_3$ for $^{13}C$ NMR spectra.

ABBREVIATIONS AND ACRONYMS

When the following abbreviations are used throughout the disclosure, they have the following meanings:

| | |
|---|---|
| Ac | acetyl |
| AcOH | acetic acid |
| 9-BBN | 9-borabicyclo[3.3.1]nonane |
| Boc | t-butoxycarbonyl |
| Bu | butyl |
| Cbz | benzyloxycarbonyl |
| CDCl$_3$ | deuterochloroform |
| Celite ® | registered trademark of Celite Corp. brand of diatomaceous earth |
| d | doublet |
| dd | doublet of doublet |
| ddd | doublet of doublet of doublet |
| DIAD | diisopropyl azodicarboxylate |
| DIEA | diisopropylethylamine |
| DMAP | 4-(N,N-dimethyl)amino pyridine |
| DME | dimethoxyethane |
| DMF | N,N-dimethylformamide |
| DMSO | dimethylsulfoxide |
| DMSO-d$_6$ | dimethylsulfoxide-d$_6$ |
| dppf | 1,1'-bis(diphenylphosphino)ferrocene |
| EI | electron impact ionization |
| EI-MS | electron impact-mass spectrometry |
| Et | ethyl |
| EtOH | ethanol |
| Et$_2$O | diethyl ether |
| EtOAc | ethyl acetate |
| FACS | fluorescence activated cell sorting |
| FBS | fetal bovine serum |
| g | gram(s) |
| h | hour(s) |
| HBTU | O-benzotriazol-1-yl-N,N,N',N'-tetramethyluronium hexafluorophosphate |
| $^1$H NMR | proton nuclear magnetic resonance |
| Hex | hexanes |
| HPLC | high performance liquid chromatography |
| iPrOH | isopropanol |
| LC-MS | liquid chomatography-mass spectrometry |
| LDA | lithium diisopropylamide |
| m | multiplet |
| M | molar |
| m/z | mass over charge |
| Me | methyl |
| MeOH | methanol |
| MeCN | acetonitrile |
| mg | milligram(s) |
| MHz | megahertz |
| min | minute(s) |
| mL | milliliter(s) |
| mol | mole(s) |
| mmol | millimole(s) |
| MS | mass spectrometry |
| N | normal |
| n-BuLi | n-butyllithium |
| NMR | nuclear magnetic resonance |
| NaOAc | sodium acetate |
| PBS | phosphate buffered saline |
| PC-12 | rat pheochromocytoma cells |
| Pd/C | palladium on carbon |
| PdCl$_2$(dppf)-CH$_2$Cl$_2$ | [1,1'-bis(diphenylphosphino)ferrocene] dichloropalladium (II) complex with dichloromethane (1:1) |
| Ph | phenyl |
| PPh$_3$ | triphenylphosphine |
| ppm | parts per million |
| psi | pounds per square inch |
| Pr | propyl |
| q | quartet |
| qt | quintet |
| quant. | quantitative |
| R$_f$ | TLC retention factor |
| rt | room temperature |
| RT | retention time |
| s | singlet |
| TBS | tert-butyldimethylsilyl |
| TBSCl | tert-butyldimethylsilyl chloride |
| TBTU | 2-(1H-benzotriazol-1-yl)-1,1,3,3-tetramethyluronium tetrafluoroborate |
| TFA | trifluoroacetic acid |
| THF | tetrahydrofuran |
| TLC | thin layer chomatography |
| TMS | tetramethylsilane |
| v/v | volume per unit volume |
| vol | volume |
| w/w | weight per unit weight |

Example 1

Preparation of Intermediates

A. Synthesis of Intermediate A: Benzyl tetrahydro-3-oxo-1H-oxazolo[3,4-a]pyrazine-7(3H)-carboxylate)

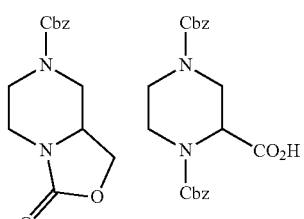

Step 1. Synthesis of 1,4-di((benzyloxy)carbonyl)piperazine-2-carboxylic acid

Piperazine-2-carboxylic acid dihydrochloride (10.0 g, 49.2 mmol) was dissolved in H$_2$O (125 mL) and 1,4-dioxane (200 mL), and the solution was brought to pH 11 with 50% NaOH in H$_2$O. Benzyl chloroformate (14 mL, 98 mmol) was added while maintaining the pH at 11 with 50% NaOH in H$_2$O. After 1 h, an additional portion of benzyl chloroformate (2 mL, 14 mmol) was added. After 30 min, the solution was extracted with Et$_2$O (3×100 mL). The aqueous layer was brought to pH 2 with concentrated HCl and extracted with EtOAc (3×200 mL). The combined EtOAc extracts were dried over Na$_2$SO$_4$, filtered, and concentrated under reduced pressure to give 18.9 g (96%) of the desired product as a thick oil. The material was used without further purification. LC-MS: RT=9.250 min; [M+H]$^+$=421.1.

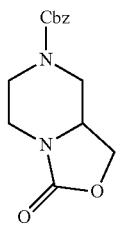 [SMILES: O=C(OCc1ccccc1)N1CCN2C(=O)OCC2C1]

Step 2. Synthesis of benzyl tetrahydro-3-oxo-1H-oxazolo[3,4-a]pyrazine-7(3H)-carboxylate 1,4-Di((benzyloxy)carbonyl)piperazine-2-carboxylic acid (18.9 g, 47.4 mmol) was dissolved in THF (200 mL), and borane-THF complex (1.0 M solution in THF, 100 mL, 100 mmol) was added over about 15 min. Upon complete addition, the reaction mixture was heated to 50° C. After 3 h, the reaction mixture was allowed to cool to rt and was slowly quenched by the dropwise addition of MeOH. After gas evolution ceased, the reaction mixture was heated to 50° C. for 1 h. Upon cooling to rt, the reaction mixture was concentrated under reduced pressure. The material was dissolved in EtOH (200 mL) and K$_2$CO$_3$ (6.9 g, 49.9 mmol) was added. The reaction mixture was heated to 70° C. overnight. Upon cooling to rt, the reaction mixture was concentrated under reduced pressure, diluted with H$_2$O (200 mL) and extracted with EtOAc (3×200 mL). The combined organics were dried over Na$_2$SO$_4$, filtered, and concentrated under reduced pressure. The material was purified by column chomatography (10 to 40% EtOAc in Hexanes gradient) to give 10.26 g (78%) of the desired product as a white solid. An additional 0.452 g (3%) of the desired product was isolated from impure chomatography fractions by recrystallization from methyl tert-butyl ether. LC-MS: RT=7.848 min; [M+Na]$^+$=299.1.

B. Synthesis of Intermediate B: tert-butyl tetrahydro-3-oxo-1H-oxazolo[3,4-a]pyrazine-7(3H)-carboxylate)

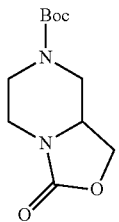

Method A.

Ammonium formate (1.99 g, 31.6 mmol) was added to a mixture of benzyl tetrahydro-3-oxo-1H-oxazolo[3,4-a]pyrazine-7(3H)-carboxylate (4.37 g, 15.8 mmol) and palladium hydroxide on carbon (~10% Pd, 1.11 g, 0.79 mmol) in EtOH (150 mL). The reaction mixture was heated to reflux for 1 h. Upon cooling to rt, the reaction mixture was filtered though Celite®, and the filtrate was concentrated under reduced pressure and dissolved in THF (100 mL). Di-tert-butyl dicarbonate (3.79 g, 17.4 mmol) and diisopropylethylamine (3.0 mL, 17.4 mmol) were added. After 2 h, the reaction mixture was diluted with EtOAc (200 mL), washed with H$_2$O (2×100 mL) and brine (100 mL), dried over Na$_2$SO$_4$, filtered, and concentrated under reduced pressure. The solid was recrystallized from EtOAc/Hexanes (1:3) to give 3.37 g (88%) of the desired product as a white, crystalline solid. LC-MS: RT=6.46 min; [M+Na]$^+$=265.1.

Method B.

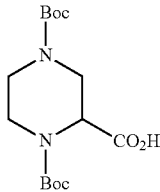

Step 1. Synthesis of 1,4-di(tert-butoxycarbonyl)piperazine-2-carboxylic acid

Piperazine-2-carboxyilc acid dihydrochloride (15.0 g, 73.9 mmol) was dissolved in H$_2$O (240 mL) and 1,4-dioxane (360 mL), and the solution was brought to pH 10 with 6 N NaOH in H$_2$O. Di-tert-butyldicarbonate (28.3 g, 162 mmol) was added while maintaining the pH at 10 with 6 N NaOH in H$_2$O. After 2 h, the reaction mixture was extracted with Et$_2$O (3×200 mL). The aqueous layer was brought to pH 3 with 6 N HCl and was extracted with EtOAc (4×300 mL). The combined EtOAc extracts were dried over Na$_2$SO$_4$, filtered, and concentrated under reduced pressure to give 14.45 g (59%) of the desired product as an off-white solid. The material was used without further purification. LC-MS: RT=8.16 min; [M+Na]$^+$=353.1.

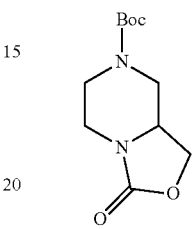

Step 2. Synthesis of tert-butyl tetrahydro-3-oxo-1H-oxazolo[3,4-a]pyrazine-7(3H)-carboxylate 1,4-Di(tert-butoxycarbonyl)piperazine-2-carboxylic acid (14.45 g, 43.7 mmol) was dissolved in THF (200 mL), and borane-THF complex (1.0 M solution in THF, 100 mL, 100 mmol) was added slowly. Upon complete addition, the reaction mixture was heated to 50° C. After 2 h, the reaction mixture was allowed to cool to rt and was slowly quenched by the dropwise addition of MeOH (50 mL). After gas evolution ceased, the reaction mixture was heated to 50° C. for 1 h. Upon cooling to rt, the reaction mixture was concentrated under reduced pressure. The material was dissolved in THF (200 mL) and NaH (60% dispersion in mineral oil, 1.75 g, 43.7 mmol) was added portion wise. The reaction mixture was heated to 50° C. overnight. Upon cooling to rt, the reaction mixture was quenched with H$_2$O (300 mL) and extracted with EtOAc (3×400 mL). The combined organics were dried over Na$_2$SO$_4$, filtered, and concentrated under reduced pressure. The material was purified by column chromatography (10 to 40% EtOAc in Hexanes gradient) to give 6.31 g (59%) of the desired product as a white solid. R$_f$=0.43 in 80% EtOAc in Hexanes. 1.10 g (8%) of di-tert-butyl 2-(hydroxymethyl)piperazine-1,4-dicarboxylate was also isolated. R$_f$=0.63 in 80% EtOAc in Hexanes.

Method C.

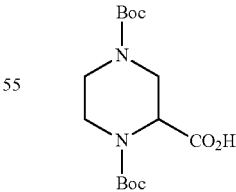

Step 1. Synthesis of 1,4-di(tert-butoxycarbonyl)piperazine-2-carboxylic acid

A solution of di-tert-butyldicarbonate (63 g, 290 mmol) in MeOH (100 mL) was added portionwise to a solution of piperazine-2-carboxyilic acid dihydrochloride (25.0 g, 123 mmol) and triethylamine (48 mL, 340 mmol) in MeOH (150 mL) over 30 minutes. Upon complete addition, the reaction mixture was heated to 50° C. for 2 h. Upon cooling to rt, the reaction mixture was concentrated under reduced pressure. The material was dissolved in water (300 mL) and the solution was brought to pH 2 with 1 M aqueous HCl. This was extracted with EtOAc (4×200 mL), and the combined extracts were dried over $Na_2SO_4$, filtered, and concentrated under reduced pressure until ~100 mL EtOAc remained. The solution was diluted with hexanes (150 mL) and cooled to 0° C. The resulting solid was collected by filtration, washed with hexanes (2×) and air-dried. This gave 38.9 g (96%) of the title compound as a white solid. Analytical data: $^1$H NMR (400 MHz, DMSO-$d_6$) δ 13.02-12.80 (br, 1H), 4.50-4.24 (m, 2H), 3.94-3.72 (br, 1H), 3.66 (d, J=12.8 Hz, 1H), 3.22-2.92 (m, 2H), 2.90-2.68 (br, 1H), 1.42-1.34, (m, 18H).

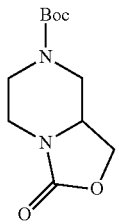

Step 2. Synthesis of tert-butyl tetrahydro-3-oxo-1H-oxazolo[3,4-a]pyrazine-7(3H)-carboxylate Borane-THF complex (1.0 M solution in THF, 200 mL, 200 mmol) was added slowly to a solution of 1,4-bis(tert-butoxycarbonyl)piperazine-2-carboxylic acid (30.3 g, 91.7 mmol) in THF (100 mL). Upon complete addition, the reaction mixture was heated to 50° C. for 2 h. Upon cooling to rt, the reaction mixture was carefully quenched by the dropwise addition of MeOH. After gas evolution ceased, the reaction mixture was concentrated under reduced pressure. The material was dissolved in EtOAc (300 mL) and washed with 1 N NaOH (2×200 mL) and brine (200 mL). The organics were dried over Na2SO4, filtered, and concentrated under reduced pressure. The material was twice dissolved in THF (50 mL) and concentrated under reduced pressure. The material was dissolved in THF (200 mL) and NaH (60% dispersion in mineral oil, 0.366 g, 0.916 mmol) was added portionwise. The reaction mixture was heated to reflux. After 1 h, the reaction mixture was allowed to cool to rt and was concentrated under reduced pressure. The material was dissolved in EtOAc (300 mL), washed with water (2×200 mL) and brine (200 mL), dried over Na2SO4, filtered, and concentrated under reduced pressure. The resulting solid was dissolved in EtOAc (200 mL) with heating, diluted with hexanes (200 mL) and allowed to cool to rt. The white, crystalline solid was collected by filtration after 5 h, washed with hexanes (2×), and dried under vacuum. This gave 13.29 g (60%) of the product. The filtrate was concentrated under reduced pressure, dissolved in EtOAc (50 mL) with heating, and diluted with hexanes (200 mL). This was allowed to cool to rt and sit over the weekend. The white, crystalline solid was collected by filtration, washed with hexanes (2×), and dried under vacuum. This gave an additional 4.49 g (20%) of the product. Analytical data: Rf=0.43 in 80% EtOAc/Hexanes; $^1$H NMR (400 MHz, CDCl$_3$) δ 4.41 (t, J=8.4 Hz, 1H), 4.35-3.98 (br, 2H), 3.92 (dd, J=5.6 and 8.8 Hz, 1H), 3.80-3.72 (m, 2H), 2.98 (dt, J=3.6 and 12.4 Hz, 1H), 2.86-2.70 (br, 1H), 2.70-2.55, (br, 1H), 1.45 (s, 9H); $^{13}$C NMR (100 MHz, CDCl$_3$) δ 156.7, 154.2, 81.1, 65.5, 52.9, 47.7 (br), 43.4 (br), 41.1, 28.7. LC-MS: RT=6.46 min; [M+Na]+=264.9. Anal. Calcd for $C_{11}H_{18}N_2O_4$: C, 54.53; H, 7.49; N, 11.56. Found: C, 54.38; H, 7.44; N, 11.35.

C. Synthesis of Intermediate C: tert-butyl 3-((pyridin-3-yloxy)methyl)piperazine-1-carboxylate)

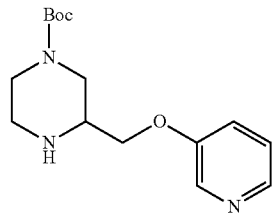 [SMILES: CC(C)(C)OC(=O)N1CCNC(COc2cccnc2)C1]

Method A.

Sodium hydride (60% dispersion in mineral oil, 4.50 g, 113 mmol) was added portionwise to a solution of 3-hydroxypyridine (13.2 g, 139 mmol) and tert-butyl tetrahydro-3-oxo-1H-oxazolo[3,4-a]pyrazine-7(3H)-carboxylate (3.37 g, 13.9 mmol) in DMF (100 mL). Upon complete addition, the reaction mixture was heated to 120° C. for 60 h. Upon cooling to rt, water (10 mL) was added and the reaction mixture was concentrated under reduced pressure. The material was dissolved in $H_2O$ (150 mL) and EtOAc (100 mL). The organic layer was separated, and the aqueous layer was extracted with EtOAc (2×100 mL). The combined organics were concentrated under reduced pressure. The material was dissolved in EtOAc (150 mL) and washed with 1 N NaOH (3×50 mL) and brine (50 mL), dried over $Na_2SO_4$, filtered, and concentrated under reduced pressure. Purification by column chomatography (0 to 5% MeOH in $CH_2Cl_2$ gradient) gave 1.7096 g (42%) of the desired product as a white solid. LC-MS: RT=3.81 min, [M+H]$^+$=294.2.

Method B.

3-Hydroxypyridine sodium salt (Acros, 7.23 g, 61.7 mmol) was added to a solution of tert-butyl tetrahydro-3-oxo-1H-oxazolo[3,4-a]pyrazine-7(3H)-carboxylate (5.00 g, 20.6 mmol) in DMF (50 mL). The reaction mixture was heated to 120° C. for 60 h. Upon cooling to rt, the reaction mixture was concentrated under reduced pressure. The material was dissolved in $H_2O$ (100 mL) and was extracted with EtOAc (3×150 mL). The combined organics were washed with 1 N NaOH (3×200 mL) and brine (200 mL), dried over dried over $Na_2SO_4$, filtered, and concentrated under reduced pressure. Recrystallization from EtOAc/Hexanes (1:4) gave 3.068 g (51%) of the desired product as an off-white solid.

Method C.

Potassium tert-butoxide (1.18 g, 10.5 mmol) was added to a solution of 3-hydroxypyridine (0.979 g, 10.3 mmol) in DMF (10 mL). After 30 min, tert-butyl tetrahydro-3-oxo-1H-oxazolo[3,4-a]pyrazine-7(3H)-carboxylate (0.500 g, 2.06 mmol) was added, and the reaction mixture was heated to 90° C. After 48 h, a second batch of 3-hydroxypyridine potassium salt was prepared by adding potassium tert-butoxide (1.18 g, 10.5 mmol) to a solution of 3-hydroxypyridine (0.979 g, 10.3 mmol) in DMF (5 mL). This was added to the reaction mixture and heating was continued at 90° C. for 3 days. Upon cooling to rt, water (50 mL) was added, and the reaction mixture was extracted with EtOAc (3×500 mL). The combined extracts were washed with 1 N NaOH (2×100 mL) and brine (100 mL), dried over $Na_2SO_4$, filtered, and concentrated under reduced pressure. Purification by column chomatography (0 to 4% MeOH in $CH_2Cl_2$ with 0.5% $NH_4OH$ gradient) gave 0.487 g (80%) of the desired product as a white solid.

D. Synthesis of Intermediates $C_i$, $C_{ii}$, and D through M

Intermediate $C_i$ and $C_{ii}$ were prepared as described for Intermediate C in which piperazine-2-carboxylic acid dihydrochloride was replaced with (R)-piperazine-2-carboxylic acid dihydrochloride or (S)-piperazine-2-carboxylic acid dihydrochloride (ChemPacific Corporation, Baltimore, Md.).

Intermediate Ci: (R)-tert-butyl 3-((pyridin-3-yloxy)methyl)piperazine-1-carboxylate: LC-MS: RT=3.74 min, [M+H]$^+$=294.1.

Intermediate Cii: (S)-tert-butyl 3-((pyridin-3-yloxy)methyl)piperazine-1-carboxylate: LC-MS: RT=3.81 min, [M+H]$^+$=294.1.

Intermediate D through M (shown in Table 1 below) were prepared as described for Intermediate C in which 3-hydroxypyridine was replaced with the appropriate aryl or heteroaryl alcohol.

TABLE 1

| Intermediate | Ar | Yield | HPLC RT (min) | LC-MS [M + H]$^+$ |
|---|---|---|---|---|
| D | phenyl | 66% | 5.30 | 293.5 |
| E | 4-methoxyphenyl | 63% | 4.98 | 323.5 |
| F | 4-chlorophenyl | 75% | 5.52 | 327.5 |
| G | 3-fluorophenyl | 62% | 5.30 | 311.5 |
| H | 3-methoxyphenyl | 76% | 5.31 | 323.5 |
| I | 2-methoxyphenyl | 48% | 5.20 | 323.5 |
| J | 4-(trifluoromethoxy)phenyl | 58% | 6.07 | 377.6 |
| K | 5-chloropyridin-3-yl | 69% | 4.58 | 328.1 |
| L | 6-methylpyridin-3-yl | 66% | 3.48 | 308.2 |

TABLE 1-continued

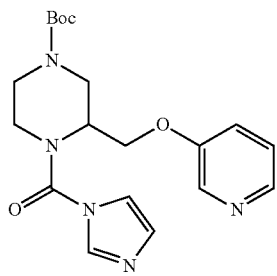 [SMILES: CC(C)(C)OC(=O)N1CCN(C(=O)n2ccnc2)C(COc2cccnc2)C1]

| Intermediate | Ar | Yield | HPLC RT (min) | LC-MS [M + H]+ |
|---|---|---|---|---|
| M | 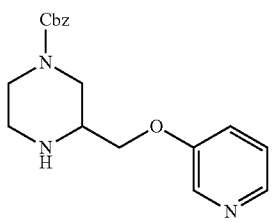 | 60% | 3.37 | 308.1 |

E. Synthesis of Intermediate N: tert-butyl 4-(1H-imidazole-1-carbonyl)-3-((pyridin-3-yloxy)methyl)piperazine-1-carboxylate)

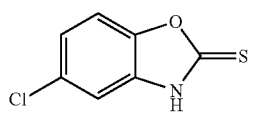 [SMILES: S=c1[nH]c2cc(Cl)ccc2o1]

N,N'-Carbonyldiimidazole (1.05 g, 6.48 mmol) was added to a solution of Intermediate C (0.380 g, 1.30 mmol) in CH$_2$Cl$_2$ (20 mL). After 12 h, the reaction mixture was diluted with EtOAc (30 mL) and washed with water (3×20 mL) and brine (20 mL). The organics were dried over Na$_2$SO$_4$, filtered, and concentrated under reduced pressure, yielding 0.350 g (70%) of the desired product which was used without further purification. LC-MS: RT=5.98 min, [M+H]$^+$=388.2.

F. Synthesis of Intermediate O: Benzyl 3-((pyridin-3-yloxy)methyl)piperazine-1-carboxylate)

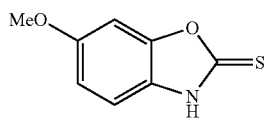 [SMILES: COc1ccc2[nH]c(=S)oc2c1]

Potassium tert-butoxide (2.57 g, 22.9 mmol) was added to a solution of 3-hydroxypyridine (2.18 g, 22.9 mmol) and Intermediate A (3.17 g, 11.5 mmol) in DMF (50 mL), and the reaction mixture was heated to 100° C. for 60 h. Upon cooling to rt, water (200 mL) was added and the reaction mixture was extracted with EtOAc (3×200 mL). The combined organics were concentrated under reduced pressure. The material was dissolved in EtOAc (200 mL) and washed with 1 N NaOH (3×50 mL) and brine (50 mL), dried over Na$_2$SO$_4$, filtered, and concentrated under reduced pressure. Purification by column chomatography (0 to 6% MeOH in CH$_2$Cl$_2$ gradient) gave 0.544 g (14%) of the desired product as an oil. 2.165 g of Intermediate A were also recovered. LC-MS: RT=4.092 min, [M+H]$^+$=328.2.

G. Synthesis of Intermediate P: 5-chlorobenzo[d]oxazole-2(3H)-thione)

2-Amino-4-chlorophenol (5.0 g, 35 mmol) and potassium hydroxide (2.34 g, 41.8 mmol) were dissolved in carbon disulfide (50 mL) and EtOH (75 mL), and the reaction mixture was heated to reflux. After 7 h, the reaction mixture was concentrated under reduced pressure. The material was taken up in EtOAc (100 mL) and 1M HCl (50 mL). The aqueous layer was separated, and the organic layer was washed with water (50 mL) and brine (50 mL). The organics were dried over Na$_2$SO$_4$, filtered, and concentrated under reduced pressure, yielding 5.71 g (89%) of the desired product as a brown solid. LC-MS: RT=7.60 min., [M+H]$^+$=186.1.

H. Synthesis of Intermediate Q: 6-methoxybenzo[d]oxazole-2(3H)-thione)

2-Hydroxy-4-methoxyaniline (1.00 g, 7.19 mmol) and potassium O-ethyl xanthate (1.27 g, 7.91 mmol) were heated to reflux in pyridine (20 mL). After 2 h, the reaction mixture was allowed to cool to rt and was poured into a solution of conc. HCl (10 mL) in ice water (80 mL). The resulting white solid was collected by filtration, washed with water (3×), and dried in a vacuum oven. This gave 0.733 g (56%) of the desired product. LC-MS: RT=6.67 min., [M+H]$^+$=182.1.

I. Synthesis of Intermediates R through X

Intermediates R through X (shown in Table 2 below) were prepared as described for Intermediates P or Q, substituting the appropriate 2-aminophenol.

TABLE 2

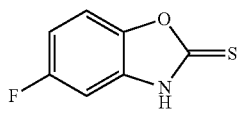

| Intermediate | $R_d$ | $R_e$ | $R_f$ | HPLC RT (min) | LC-MS [M + H]$^+$ | Prepared using method in Intermediate No. |
|---|---|---|---|---|---|---|
| P | H | Cl | H | 7.60 | 186.1 | P |
| Q | Cl | H | H | 7.66 | 186.1 | Q |
| R | OMe | H | H | 6.67 | 182.1 | Q |
| S | CH$_3$ | H | H | 7.26 | 166.1 | Q |
| T | H | CH$_3$ | H | 7.28 | 166.1 | Q |
| U | H | OMe | H | 6.84 | 182.1 | P |
| V | H | Ph | H | 8.67 | 228.1 | P |
| W | H | Br | H | 7.77 | 230.0 | P |
| X | H | H | CH$_3$ | 7.16 | 166.1 | P |

J. Synthesis of Intermediate Y. 5-fluorobenzo[d]oxazole-2(3H)-thione

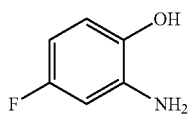

Step 1. Synthesis of 2-amino-4-fluorophenol

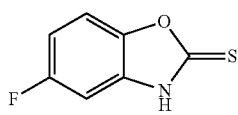

Tin(II) chloride (12.1 g, 63.6 mmol) was added to a solution of 4-fluoro-2-nitrophenol (2.00 g, 12.7 mmol) in EtOH (45 mL), and the reaction mixture was heated to 70° C. After 2 h, the reaction mixture was allowed to cool to rt and was poured onto ice (~200 mL). After warming to rt, the pH was adjusted to ~9 with 2 N aqueous NaOH, and the mixture was filtered. The filtrate was extracted with EtOAc (3×), and the combined EtOAc extracts were dried over Na$_2$SO$_4$, filtered, and concentrated under reduced pressure. This gave 1.21 g (75%) of the title compound. LC-MS: RT=4.48 min., [M+H]$^+$=128.0.

Step 2. Synthesis of 5-fluorobenzo[d]oxazole-2(3H)-thione

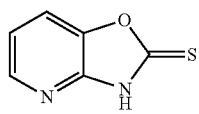

2-Amino-4-fluorophenol (1.21 g, 9.52 mmol) and potassium hydroxide (0.64 g, 11.4 mmol) were dissolved in carbon disulfide (15 mL) and EtOH (25 mL), and the reaction mixture was heated to reflux overnight. Upon cooling to rt, the reaction mixture was concentrated under reduced pressure. The resulting solid was suspended in 1 M aqueous HCl and collected by filtration. This was washed with 1 M aqueous HCl (2×) and water (2×) and was air-dried. This gave 1.115 g (69%) of the title compound as a yellow solid. LC-MS: RT=6.89 min., [M+H]$^+$=169.9.

K. Synthesis of Intermediates Z and AA

Intermediates Z through AA (shown in Table 3 below) were prepared as described for Intermediate Y, substituting the appropriate 2-nitrophenol.

TABLE 3

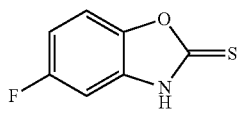

| Intermediate | $R_d$ | $R_e$ | $R_f$ | HPLC RT (min) | LC-MS [M + H]$^+$ |
|---|---|---|---|---|---|
| Z | F | H | H | 6.91 | 169.9 |
| Y | H | F | H | 6.89 | 169.9 |
| AA | H | CF$_3$ | H | 8.17 | 220.0 |

L. Synthesis of Intermediate AB: Oxazolo[4,5-b]pyridine-2(3H)-thione

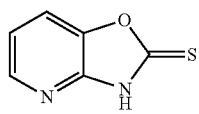

3-Hydroxy-2-aminopyridine (2.00 g, 18.2 mmol) and potassium hydroxide (1.22 g, 21.8 mmol) were dissolved in carbon disulfide (15 mL) and EtOH (25 mL), and the reaction mixture was heated to reflux overnight. Upon cooling to rt, the reaction mixture was concentrated under reduced pressure. The resulting solid was suspended in 1 M aqueous HCl, collected by filtration, washed with water (2×) and air-dried. Further drying in a 35° C. vacuum oven gave 2.52 g (91%) of the title compound as a tan solid. LC-MS: RT=4.82 min., [M+H]$^+$=153.1

M. Synthesis of Intermediate AC: 5-chloro-2-(methylsulfinyl)benzo[d]oxazole)

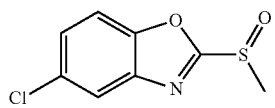

Iodomethane (1.35 mL, 21.6 mmol) was added to a mixture of 5-chlorobenzo[d]oxazole-2(3H)-thione (2.00 g, 10.8 mmol) and K$_2$CO$_3$ (2.99 g, 21.6 mmol) in THF (43 mL). After 2 h, the reaction mixture was filtered and concentrated under reduced pressure. The crude material was dissolved in CH$_2$Cl$_2$ (40 mL) and meta-chloroperbenzoic acid (50-55%, 3.73 g, 10.8 mmol) was added at 0° C. The reaction was allowed to warm to rt. After stirring overnight, the reaction mixture was diluted with sodium thiosulfate (saturated, aqueous) and the organics were separated. The organics were washed with NaHCO$_3$ (saturated, aqueous, 50 mL) and brine, dried over Na$_2$SO$_4$, filtered, and concentrated under reduced pressure. This gave 3.32 g (>100% crude yield) of the desired product as an orange solid. The material was used without further purification. LC-MS: RT=6.60 min., [M+H]$^+$=216.2.

N. Synthesis of Intermediate AD:
6-chloro-2-(methylsulfinyl)benzo[d]oxazole)

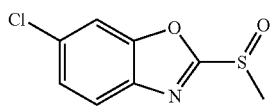

Iodomethane (1.35 mL, 21.6 mmol) was added to a mixture of 6-chlorobenzo[d]oxazole-2(3H)-thione (2.00 g, 10.8 mmol) and K$_2$CO$_3$ (2.99 g, 21.6 mmol) in THF (43 mL). After 2 h, the reaction mixture was filtered and concentrated under reduced pressure. The crude material was dissolved in CH$_2$Cl$_2$ (40 mL) and meta-chloroperbenzoic acid (50-55%, 3.73 g, 10.8 mmol) was added at 0° C. The reaction was allowed to warm to rt. After stirring overnight, the reaction mixture was diluted with sodium thiosulfate (saturated, aqueous) and the organics were separated. The organics were washed with NaHCO$_3$ (saturated, aqueous, 50 mL) and brine, dried over Na$_2$SO$_4$, filtered, and concentrated under reduced pressure. This gave 3.22 g (>100% crude yield) of the desired product as an orange solid. The material was used without further purification. LC-MS: RT=6.57 min., [M+H]$^+$=216.2.

O. Preparation of Intermediate AE: Tert-butyl 3-(2-(pyridin-3-yl)ethyl)piperazine-1-carboxylate)

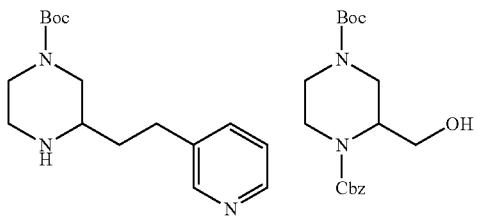

Step 1. Synthesis of 1-benzyl 4-test-butyl 2-(hydroxymethyl)piperazine-1,4-dicarboxylate Sodium hydroxide (1N aqueous solution, 20 mL, 20 mmol) was added to a solution of Intermediate B (2.59 g, 10.7 mmol) in EtOH (20 mL), and the reaction mixture was heated to 70° C. for 1 h. Upon cooling to rt, the EtOH was removed under reduced pressure. The aqueous solution was diluted with THF (40 mL) and benzyl chloroformate (1.60 mL, 10.7 mmol) was added. After 1 h, the reaction mixture was diluted with water (50 mL) and was extracted with EtOAc (3×50 mL). The combined organics were dried over Na$_2$SO$_4$, filtered, and concentrated under reduced pressure. The material was purified by column chomatography (20 to 40% EtOAc in Hexane gradient) to give 3.16 g (85%) of the desired product as a thick oil. LC-MS: RT=8.41 min., [M+H]$^+$=373.1.

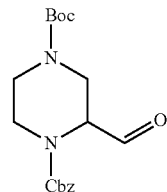 [SMILES: CC(C)(C)OC(=O)N1CCN(C(=O)OCc2ccccc2)C(C=O)C1]

Step 2. Synthesis of 1-benzyl 4-tert-butyl 2-formylpiperazine-1,4-dicarboxylate

A solution of DMSO (1.41 mL, 19.9 mmol) in CH$_2$Cl$_2$ (5 mL) was added to a solution of oxalyl chloride (0.87 mL, 9.9 mmol) in CH$_2$Cl$_2$ (25 mL) at −60° C. After 5 min, a solution of 1-benzyl 4-tert-butyl 2-(hydroxymethyl)piperazine-1,4-dicarboxylate (3.16 g, 9.03 mmol) in CH$_2$Cl$_2$ (5 mL) was added. After 15 min., triethylamine (6.3 mL, 45 mmol) was added, and the reaction mixture was allowed to warm to rt. After 1 h, water (100 mL) was added, the organics were separated, and the aqueous layer was extracted with CH$_2$Cl$_2$ (3×100 mL). The combined organics were washed with brine (3×150 mL), 1% HCl (3×150 mL), water (150 mL), and 5% NaHCO$_3$ (3×150 mL). The organics were dried over Na$_2$SO$_4$, filtered, and concentrated under reduced pressure. This gave 3.07 g (98%) of the desired product as a thick oil. R$_f$=0.10 in 30% EtOAc/Hexane.

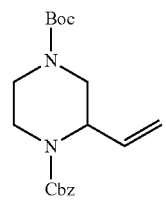 [SMILES: C=CC1CN(C(=O)OC(C)(C)C)CCN1C(=O)OCc1ccccc1]

Step 3. Synthesis of 1-benzyl 4-tert-butyl 2-vinylpiperazine-1,4-dicarboxylate n-Butyl lithium (2.5M solution in hexane, 4.0 mL, 10 mmol) was added to a suspension of methyltriphenylphosphonium bromide (4.19 g, 11.7 mmol) in THF (100 mL) at −78° C. After 10 min., the reaction mixture was allowed to warm to rt. After 1 h, the reaction mixture was cooled to −78° C., and a solution of 1-benzyl 4-tert-butyl 2-formylpiperazine-1,4-dicarboxylate (3.07 g, 8.81 mmol) in THF (10 mL) was added dropwise. After 2 h, the reaction mixture was allowed to warm to rt and was quenched with NH$_4$Cl (saturated, aqueous solution). The reaction mixture was diluted with water (100 mL) and was extracted with EtOAc (3×150 mL). The combined organics were dried over Na$_2$SO$_4$, filtered, and concentrated under reduced pressure. Purification by column chomatography (0 to 20% EtOAc in Hexane gradient) gave 2.33 g (76%) of the desired product as a thick oil. R$_f$=0.35 in 30% EtOAc/Hexane. LC-MS: RT=10.1 min., [M+H]$^+$=369.1.

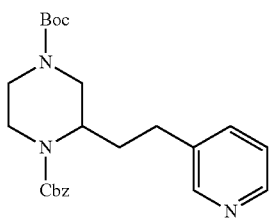 [SMILES: CC(C)(C)OC(=O)N1CCN(C(=O)OCc2ccccc2)C(CCc2cccnc2)C1]

Step 4. Synthesis of 1-benzyl 4-tert-butyl 2-(2-(pyridin-3-yl)ethyl)piperazine-1,4-dicarboxylate 9-Borabicyclo[3.3.1]nonane (0.5M solution in THF, 54 mL, 27 mmol) was added to 1-benzyl 4-tert-butyl 2-vinylpiperazine-1,4-dicarboxylate (2.33 g, 6.73 mmol). After 3 h, 3-bromopyridine (0.99 mL, 10.1 mmol), triphenylphosphine (0.53 g, 2.0 mmol), and tetrakis(triphenylphosphine) palladium(0) (0.311 g, 0.27 mmol) were added. Sodium hydroxide (1N aqueous solution, 16.8 mL, 16.8 mmol) was added slowly. Once bubbling ceased, the reaction mixture was heated to reflux overnight. Upon cooling to rt, the reaction mixture was diluted with water (200 mL) and extracted with EtOAc (3×200 mL). The combined organics were dried over $Na_2SO_4$, filtered, and concentrated under reduced pressure. Purification by column chomatography (10 to 40% EtOAc in Hexane gradient) gave 1.79 g (63%) of the desired product as a thick oil. $R_f$=0.57 in 80% EtOAc/Hexane. LC-MS: RT=7.69 min., [M+H]$^+$=426.2. The material was contaminated with ~15% triphenylphosphine, and was used without further purification.

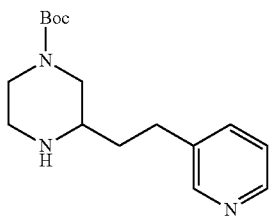

Step 5. Synthesis of tert-butyl 3-(2-(pyridin-3-yl)ethyl)piperazine-1-carboxylate, Intermediate AE Ammonium formate (0.492 g, 7.80 mmol) was added to a mixture of 1-benzyl 4-tert-butyl 2-(2-(pyridin-3-yl)ethyl)piperazine-1,4-dicarboxylate (1.66 g, 3.90 mmol) and palladium hydroxide on carbon (~20% Pd, 0.137 g, 0.20 mmol) in EtOH (100 mL). The reaction mixture was heated to reflux for 3 h. Upon cooling to rt, the reaction mixture was filtered though Celite®, and the filtrate was concentrated under reduced pressure. Purification by column chomatography (0 to 5% MeOH in $CH_2Cl_2$ gradient) gave 0.683 g (60%) of the desired product. $R_f$=0.34 in 10% MeOH/$CH_2Cl_2$. LC-MS: RT=3.33 min., [M+H]$^+$=292.2.

P. Synthesis of Intermediate AF: Tert-butyl 3-(pyridin-3-ylmethyl)piperazine-1-carboxylate

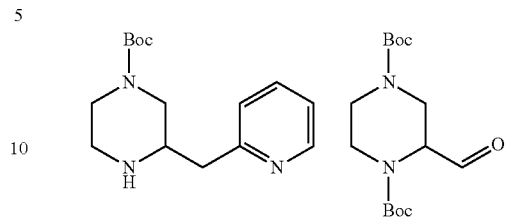

Step 1. Synthesis of di-tert-butyl 2-formylpiperazine-1,4-dicarboxylate

A solution of DMSO (0.54 mL, 7.66 mmol) in $CH_2Cl_2$ (1 mL) was added to a solution of oxalyl chloride (0.33 mL, 3.8 mmol) in $CH_2Cl_2$ (8 mL) at −60° C. After 5 min, a solution of di-tert-butyl 2-(hydroxymethyl)piperazine-1,4-dicarboxylate (1.10 g, 3.48 mmol) in $CH_2Cl_2$ (3 mL) was added. After 15 min, triethylamine (2.4 mL, 17 mmol) was added, and the reaction mixture was allowed to warm to rt. After 1 h, water (25 mL) was added, the organics were separated, and the aqueous layer was extracted with $CH_2Cl_2$ (3×25 mL). The combined organics were washed with brine (3×50 mL), 1% HCl (3×50 mL), water (50 mL), and 5% $NaHCO_3$ (3×50 mL). The organics were dried over $Na_2SO_4$, filtered, and concentrated under reduced pressure. The material was purified by column chromatography (10 to 20% EtOAc in Hexanes gradient), yielding 0.873 g (80%) of the desired product as a white solid. $R_f$=0.70 in 50% EtOAc/Hexane.

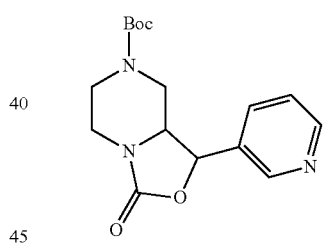

Step 2. Synthesis of tert-butyl 3-oxo-1-(pyridin-3-yl)tetrahydro-1H-oxazolo[3,4-a]pyrazine-7(3H)-carboxylate A solution of 3-bromopyridine (0.545 mL, 5.55 mmol) in THF (10 mL) was added to a solution of tert-butyllithium (1.7 M solution in pentane, 6.53 mL, 11.1 mmol) in THF (15 mL) at −78° C. over about 15 min. The solution was then transferred portion wise into a −78° C. solution of di-tert-butyl 2-formylpiperazine-1,4-dicarboxylate (0.873 g, 2.78 mmol) in THF (20 mL). After addition of all of the organolithium, a significant amount of the aldehyde starting material still remained as indicated by LC-MS. A second batch of the organolithium was prepared as above, staring with 5.0 equivalents of 3-bromopyridine. After complete addition, the aldehyde starting material still remained, but the reaction mixture was quenched with ammonium chloride (saturated aqueous solution). The reaction mixture was extracted with EtOAc (3×200 mL). The combined organics were dried over $Na_2SO_4$, filtered, and concentrated under reduced pressure.

The material was taken up in THF (20 mL) and was slowly added to a suspension of sodium hydride (60% dispersion in mineral oil, 0.111 g, 2.78 mmol) in THF (20 mL). The reaction mixture was heated to 70° C. overnight. The reaction mixture was quenched with water (75 mL) and was extracted with EtOAc (3×100 mL). The combined organics were dried over Na$_2$SO$_4$, filtered, and concentrated under reduced pressure. The material was purified by column chromatography (40 to 75% EtOAc in Hexanes gradient), yielding 340 mg of impure product. This material was purified by HPLC (5 to 50% MeCN/0.1% TFA in H$_2$O/0.1% TFA gradient), yielding 239 mg (20%) of the TFA salt of the desired product. LC-MS: RT=6.39 min; [M+H]$^+$=320.1.

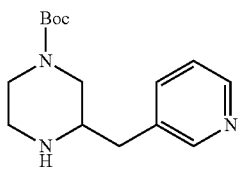 [SMILES: CC(C)(C)OC(=O)N1CCNC(Cc2cccnc2)C1]

Step 3. Synthesis of tert-butyl
3-(pyridin-3-ylmethyl)piperazine-1-carboxylate

Palladium hydroxide on carbon (~10% Pd, 62 mg, 0.044 mmol) was added to a solution of tert-butyl 3-oxo-1-(pyridin-3-yl)tetrahydro-1H-oxazolo[3,4-a]pyrazine-7(3H)-carboxylate TFA salt (239 mg, 0.552 mmol) and ammonium formate (70 mg, 1.1 mmol) in EtOH (5 mL). The reaction mixture was heated to reflux for 2 h. Upon cooling to rt, the reaction mixture was filtered though Celite®, and the filtrate was concentrated under reduced pressure to give 213 mg (99%) of the TFA salt of the desired product as a white solid.

Q. Synthesis of Intermediate AG:
2,4-dichloro-5-methoxybenzo[d]thiazole

Sulfuryl chloride (10 mL) was added to 5-methoxy-2-mercaptobenzothiazole at 0° C. After complete addition, the reaction mixture was allowed to warm to rt. After 2 h, the reaction mixture was poured into ice water (100 mL). This was allowed to warm to rt and was extracted with EtOAc (3×). The combined organics were dried over Na$_2$SO$_4$, filtered, and concentrated under reduced pressure. The material was used without further purification. LC-MS: RT=9.08 min., [M+H]$^+$=234.0.

R. Synthesis of Intermediate AH:
2,5-dichlorobenzo[d]thiazole

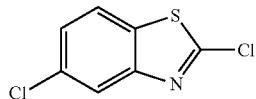 [SMILES: Clc1ccc2sc(Cl)nc2c1]

Sulfuryl chloride (10 mL) was added to 5-chloro-2-mercaptobenzothiazole at 0° C. After complete addition, the reaction mixture was allowed to warm to rt. After 2 h, the reaction mixture was poured into ice water (100 mL). This was allowed to warm to rt and was extracted with EtOAc (3×). The combined organics were dried over Na$_2$SO$_4$, filtered, and concentrated under reduced pressure. The material was used without further purification. LC-MS: RT=10.03 min., compound does not ionize.

S. Synthesis of Intermediate AI.
6-bromo-2-chlorobenzo[d]thiazole

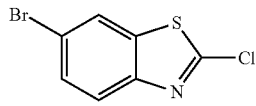

DMF (0.807 mL, 10.4 mmol) was added to phosphorous oxychloride (8.10 mL, 86.9 mmol), and the reaction mixture was stirred for 15 min. 6-bromobenzo[d]thiazol-2(3H)-one (2.00 g, 8.69 mmol) was added and the reaction mixture was heated to 100° C. overnight. Upon cooling to rt, the reaction mixture was slowly added to a solution of K$_2$CO$_3$ (75 g) in water (200 mL) while maintaining the temperature below 35° C. Additional K$_2$CO$_3$ was added in order to maintain the pH above 10. Upon complete addition, the mixture was allowed to stir for 1 h. The solid was collected by filtration, washed with water (2×25 mL), and air dried. Further drying in a vacuum oven gave 2.06 g (95%) of the desired product as a brown solid. The material was used without further purification. LC-MS: RT=9.94 min., compound does not ionize.

T. Synthesis of Intermediate AJ:
2-chloro-5-methoxybenzo[d]thiazole

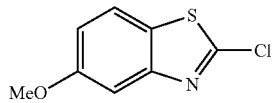 [SMILES: COc1ccc2sc(Cl)nc2c1]

Sulfuryl chloride (1.64 mL) was added to a solution of 5-methoxy-2-mercaptobenzothiazole in THF (20 mL). After stirring overnight, ice water was added. The reaction mixture was allowed to warm to rt and was diluted with EtOAc (100 mL). This was washed with water (50 mL) and brine (50 mL), dried over Na$_2$SO$_4$, filtered, and concentrated under reduced pressure. The material was purified by column chromatography (0 to 3% EtOAc in hexanes gradient), yielding 0.407 g (20%) of the title compound as a white solid. LC-MS: RT=9.05 min., [M+H]$^+$=200.0. $R_f$=0.38 in 10% EtOAc/Hexanes.

U. Synthesis of Intermediate AK: 2-chloro-5-(trifluoromethyl)benzo[d]thiazole

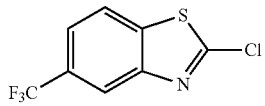

3-Amino-4-bromobenzotrifluoride (1.00 g, 4.17 mmol) and potassium ethyl xanthate (1.60 g, 10.0 mmol) were heated to 130° C. in DMF (5 mL) overnight. After cooling to rt, the reaction mixture was diluted with 1 M aqueous HCl (15 mL) and stirred at rt for an additional 30 min. The resulting solid was collected by filtration and washed with water (2×). The solid was dissolved in EtOAc, dried over Na$_2$SO$_4$, filtered, and concentrated under reduced pressure. This gave 0.895 g (91%) of the 2-mercapto intermediate as a yellow solid. LC-MS: RT=8.60 min., [M+H]$^+$=236.2. The material was suspended in sulfuryl chloride (5 mL) and CH$_2$Cl$_2$ (2 mL). After 2 h, water (20 mL) was added and stirring continued for an additional 30 min. The reaction mixture was extracted with EtOAc (3×), and the combined extracts were dried over Na$_2$SO$_4$, filtered, and concentrated under reduced pressure. This gave 0.886 g (98%) of the title compound as an off-white solid. LC-MS: RT=10.12 min., compound does not ionize.

V. Synthesis of Intermediates AL through AW

Intermediates AL through AW (shown in Table 4 below) were prepared as described for Intermediate AK, substituting the appropriate 2-haloaniline.

TABLE 4

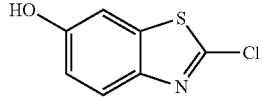 [SMILES: Oc1ccc2nc(Cl)sc2c1]

| Intermediate | $R_d$ | $R_e$ | $R_f$ | $R_g$ | HPLC RT (min) | LC-MS [M + H]$^+$ |
|---|---|---|---|---|---|---|
| AK | H | CF$_3$ | H | H | 10.12 | * |
| AL | H | F | H | H | 9.16 | 188.1 |
| AM | i-Pr | H | H | H | 10.84 | * |
| AN | CF$_3$ | H | H | H | 10.18 | * |
| AO | OCF$_3$ | H | H | H | 10.37 | 254.2 |
| AP | F | F | H | H | 9.32 | * |
| AS | H | H | F | H | 8.91 | * |
| AT | H | H | H | F | 9.62 | * |
| AU | F | H | F | H | 9.18 | 206.2 |
| AV | F | H | H | F | 9.81 | * |
| AW | Br | H | F | H | 10.13 | * |

* Compound does not ionize under standard LC-MS conditions.

W. Synthesis of Intermediate AX: 2-chloro-6-isopropoxybenzo[d]thiazole

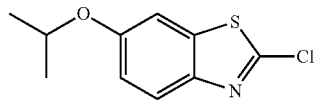

Step 1. Synthesis of 2-chlorobenzo[d]thiazol-6-ol

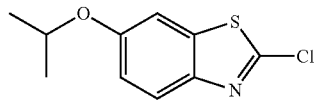

Aluminum chloride (1.98 g, 14.9 mmol) was added to a solution of 6-methoxy-2-chlorobenzothiazole (1.06 g, 5.31 mmol) in toluene (40 mL), and the reaction mixture was heated to 110° C. After 1 h, the reaction mixture was allowed to cool to rt and 1 M aqueous HCl (40 mL) was added. The resulting precipitate was collected by filtration and washed with water (2×), saturated aqueous NaHCO$_3$ (2×) and water (2×). The solid was air-dried, yielding 0.800 g (81%) of the title compound as a brown solid. LC-MS: RT=7.18 min., [M+H]$^+$=185.9.

Step 2. Synthesis of 2-chloro-6-isopropoxybenzo[d]thiazole

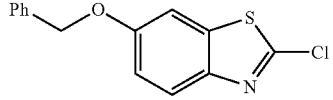 [SMILES: Clc1nc2ccc(OCc3ccccc3)cc2s1]

2-Chlorobenzo[d]thiazol-6-ol (0.800 g, 4.31 mmol), isopropanol (0.36 mL, 4.74 mmol) and triphenylphosphine (1.24 g, 4.74 mmol) were mixed in THF (1.4 mL) and sonicated. DIAD (0.933 mL, 4.74 mmol) was added dropwise over ~2 min. After 1 h, the reaction mixture was concentrated under reduced pressure. The material was purified by column chromatography (0 to 10% EtOAc in Hexanes gradient), yielding 0.894 g (91%) of the title compound as a light brown oil. LC-MS: RT=10.21 min., [M+H]$^+$=228.0. $R_f$=0.50 in 10% EtOAc/Hexanes.

X. Synthesis of Intermediate AY: 6-(benzyloxy)-2-chlorobenzo[d]thiazole

Benzyl bromide (0.921 g, 5.39 mmol) was added to a mixture of 2-chlorobenzo[d]thiazol-6-ol (1.00 g, 5.39 mmol) and cesium carbonate (1.76 g, 5.39 mmol) in CH$_3$CN (15 mL). After 2 h at rt, the reaction mixture was heated to 70° C.

overnight. Upon cooling to rt, the reaction mixture was diluted with EtOAc (100 mL) and washed with water (3×75 mL) and brine (75 mL). The EtOAc layer was dried over Na$_2$SO$_4$, filtered, and concentrated under reduced pressure. The material was purified by column chromatography (0 to 8% EtOAc in Hexanes gradient), yielding 1.396 g (94%) of the title compound as a reddish, waxy solid. LC-MS: RT=10.51 min., [M+H]$^+$=275.9. R$_f$=0.41 in 10% EtOAc/Hexanes.

Y. Synthesis of Intermediate AZ:
2-chlorothiazolo[4,5-b]pyridine

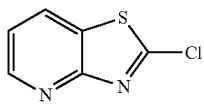

2-Amino-3-bromopyridine (1.0 g, 5.8 mmol) and potassium ethyl xanthate (2.22 g, 13.9 mmol) were heated to 130° C. in DMF (5 mL) overnight. After cooling to rt, the reaction mixture was diluted with 1 M aqueous HCl (30 mL) and stirred at rt for an additional 1 h. The resulting solid was collected by filtration, washed with water (2×), and air-dried. The material was suspended in CH$_2$Cl$_2$ (2 mL) and sulfuryl chloride (5 mL) was added. After 2 h, water (30 mL) was added to decompose the excess sulfuryl chloride. The reaction mixture was diluted with EtOAc (30 mL) and washed with water (2×) and brine. The EtOAc layer was discarded. The combined aqueous washes were brought to pH ~12 with 1 N aqueous NaOH and were extracted with EtOAc (3×). The combined EtOAc extracts were dried over Na$_2$SO$_4$, filtered, and concentrated under reduced pressure. This gave 0.933 g (95%) of the title compound as a yellow solid. LC-MS: RT=5.81 min., [M+H]$^+$=171.1.

Z. Synthesis of Intermediates BA through BD

Intermediates BA through BD (shown in Table 5 below) were prepared as described for Intermediate AZ, substituting the appropriate 2-amino-3-halopyridine.

TABLE 5

| Intermediate | R$_d$ | R$_e$ | HPLC RT (min) | LC-MS [M + H]$^+$ |
|---|---|---|---|---|
| BA | CF$_3$ | H | 8.32 | 239.2 |
| BB | Cl | H | 7.73 | 205.1 |
| BC | Br | H | 8.02 | 248.8 |
| BD | CH$_3$ | H | 6.97 | 184.9 |

AA. Synthesis of Intermediate BE:
2-chloro-6-methylbenzo[d]thiazole

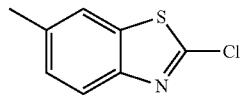

t-Butyl nitrite (3.25 mL, 27.4 mmol) was added to a suspension of copper (II) chloride (2.95 g, 22.0 mmol) in CH$_3$CN (31 mL). 6-Methyl-2-aminobenzothiazole (3.0 g, 18 mmol) was added portionwise over ~30 min., and the reaction mixture was stirred at rt overnight. The reaction mixture was poured into 20% aqueous HCl (100 mL) and was extracted with EtOAc (3×). The combined extracts were dried over Na$_2$SO$_4$, filtered, and concentrated under reduced pressure. The material was purified by column chromatography (0 to 10% EtOAc in Hexanes gradient), yielding 2.50 g (74%) of the title compound as a yellowish oil that solidified on standing. LC-MS: RT=9.71 min., [M+H]$^+$=184.0.

BB. Synthesis of Intermediates BF through BH

Intermediates BF through BH (shown in Table 5 below) were prepared as described for Intermediate BE, substituting the appropriate 2-aminobenzothiazole.

TABLE 6

| Intermediate | R$_d$ | R$_e$ | R$_f$ | R$_g$ | HPLC RT (min) | LC-MS [M + H]$^+$ |
|---|---|---|---|---|---|---|
| BE | CH$_3$ | H | H | H | 9.71 | 184.0 |
| BF | F | H | H | H | 9.09 | * |
| BG | CH$_3$ | CH$_3$ | H | H | 10.17 | * |
| BH | CH$_3$SO$_2$ | H | H | H | 7.17 | 248.1 |

* Compound does not ionize under standard LC-MS conditions.

Intermediate BI:
5-Methyloxazolo[4,5-b]pyridine-2(3H)-thione

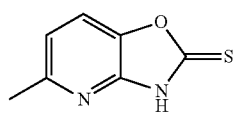

Ammonium formate (1.64 g, 26 mmol) was added to a suspension of Pd(OH)$_2$ on carbon (~20% Pd, 0.73 g, 1.0 mmol) and 2-nitro-3-hydroxy-6-methylpyridine (2.0 g, 13 mmol) in EtOH (20 mL). The reaction mixture was heated to 70° C. for 1 h at which point the reaction mixture was allowed to cool to rt and was filtered through Celite®. The filtrate was concentrated under reduced pressure, yielding a thick orangish oil. The material was dissolved in EtOH (25 mL) and potassium hydroxide (0.875 g, 15.6 mmol) and carbon disulfide (15 mL) were added. The reaction mixture was heated to reflux overnight. Upon cooling to rt, the reaction mixture was acidified with 1 N HCl, and the resulting solid was collected by filtration. The solid was washed with water (2×) and air dried followed by drying in a 35° C. vacuum oven. LC-MS: RT=5.58 min, [M+H]$^+$=167.0.

Intermediate BJ:
6-methyloxazolo[4,5-b]pyridine-2(3H)-thione

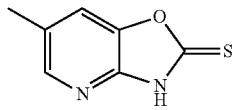

3-Bromo-2-amino-5-methylpyridine (1.0 g, 5.3 mmol), potassium hydroxide (1.19 g, 21.2 mmol) and copper powder (17 mg, 0.27 mmol) were heated to 150° C. in ethylene glycol (2.3 mL). After 4 h, the reaction mixture was allowed to cool to rt, carbon disulfide (10 mL) was added, and heating was continued at 70° C. overnight. Upon cooling to rt, the reaction mixture concentrated under reduced pressure. 1 N HCl (20 mL) was added, and the resulting dark solid was collected by filtration. The solid was washed with water (2×) and air dried followed by drying in a 35° C. vacuum oven, yielding 0.817 g (93%) of the title compound. LC-MS: RT=4.14 min, [M+H]$^+$=167.0, ~80% pure.

Example 2

N-Phenyl-2-((pyridin-3-yloxy)methyl)piperazine-1-carboxamide dihydrochloride

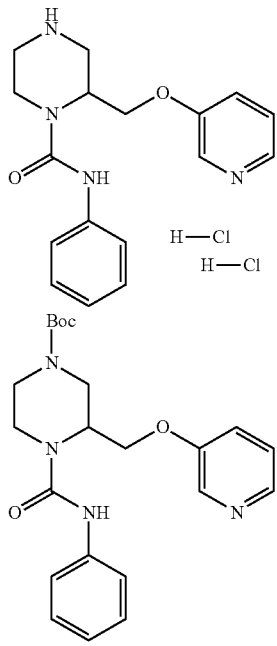

Step 1. Synthesis of tert-butyl 4-(phenylcarbamoyl)-3-((pyridin-3-yloxy)methyl)piperazine-1-carboxylate Phenylisocyanate (41 mg, 0.34 mmol) was added to a solution of Intermediate C (101 mg, 0.34 mmol) in CH$_2$Cl$_2$ (5 mL). After 1 h, the reaction mixture was concentrated under reduced pressure, and the material was purified by HPLC (10 to 95% MeCN/0.1% TFA in H$_2$O/0.1% TFA gradient). The desired fractions were brought to pH 12 with 1 N NaOH in H$_2$O and were extracted with EtOAc (3×20 mL). The combined organics were dried over Na$_2$SO$_4$, filtered, and concentrated under reduced pressure. This gave 114.5 mg (81%) of the desired product as a white solid. LC-MS: RT=8.793 min, [M+H]$^+$=413.2.

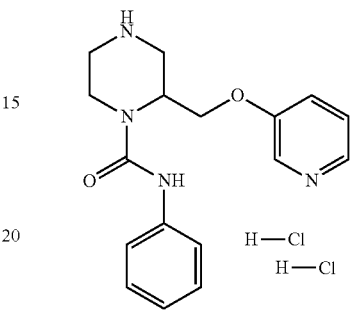

Step 2. Synthesis of N-phenyl-2-((pyridin-3-yloxy)methyl)piperazine-1-carboxamide dihydrochloride 4 M HCl in 1,4-dioxane (6 mL, 24 mmol) was added to tert-butyl 4-(phenylcarbamoyl)-3-((pyridin-3-yloxy)methyl)piperazine-1-carboxylate (114.5 mg, 0.278 mmol). After 12 h, the reaction mixture was concentrated under reduced pressure, yielding 105.2 mg (98%) of the desired product as a white solid. LC-MS: RT=5.284 min, [M+H]$^+$=313.1

Examples 3-52

The examples shown in Table 7 below were prepared by similar methods as described for Example 2, substituting the appropriate isocyanate. All reagents were commercially available unless otherwise noted. All compounds were isolated as the dihydrochloride salts unless otherwise noted.

TABLE 7

| Example No. | R$_{12}$ | IUPAC Name | HPLC RT (min) | LC-MS [M + H]$^+$ |
|---|---|---|---|---|
| 2 | phenyl | N-phenyl-2-((pyridin-3-yloxy)methyl)-piperazine-1-carboxamide dihydrochloride | 5.28 | 313.1 |

TABLE 7-continued

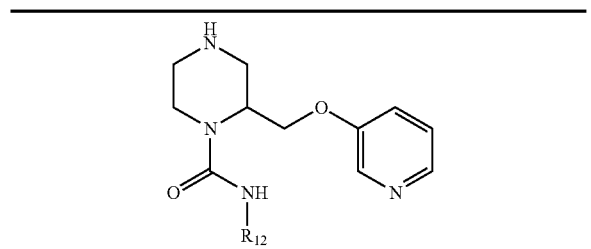
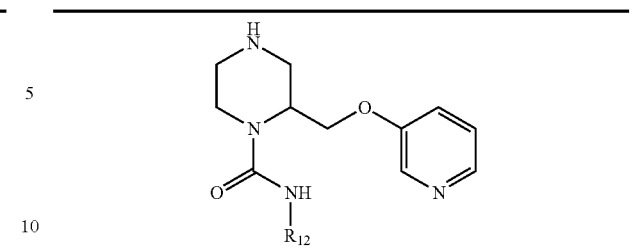

| Example No. | R₁₂ | IUPAC Name | HPLC RT (min) | LC-MS [M + H]⁺ |
|---|---|---|---|---|
| 3 | 2-methoxyphenyl | N-(2-methoxyphenyl)-2-((pyridin-3-yloxy)methyl)-piperazine-1-carboxamide dihydrochloride | 3.73 | 343.2 |
| 4 | 3-fluorophenyl | N-(3-fluorophenyl)-2-((pyridin-3-yloxy)methyl)-piperazine-1-carboxamide dihydrochloride | 5.54 | 331.1 |
| 5 | 3-methoxyphenyl | N-(3-methoxyphenyl)-2-((pyridin-3-yloxy)methyl)-piperazine-1-carboxamide dihydrochloride | 3.61 | 343 |
| 6 | 3-chlorophenyl | N-(3-chlorophenyl)-2-((pyridin-3-yloxy)methyl)-piperazine-1-carboxamide dihydrochloride | 4.2 | 346.9 |
| 7 | 4-chlorophenyl | N-(4-chlorophenyl)-2-((pyridin-3-yloxy)methyl)-piperazine-1-carboxamide dihydrochloride | 4.38 | 347.1 |
| 8 | 4-bromophenyl | N-(4-bromophenyl)-2-((pyridin-3-yloxy)methyl)-piperazine-1-carboxamide dihydrochloride | 4.48 | 391 |
| 9 | 4-fluorophenyl | N-(4-fluorophenyl)-2-((pyridin-3-yloxy)methyl)-piperazine-1-carboxamide dihydrochloride | 5.43 | 331.1 |
| 10 | 4-methoxyphenyl | N-(4-methoxyphenyl)-2-((pyridin-3-yloxy)methyl)-piperazine-1-carboxamide dihydrochloride | 5.26 | 343.1 |
| 11 | 4-methylphenyl | 2-((pyridin-3-yloxy)methyl)-N-p-tolylpiperazine-1-carboxamide dihydrochloride | 3.95 | 327.1 |
| 12 | 4-ethoxyphenyl | N-(4-ethoxyphenyl)-2-((pyridin-3-yloxy)methyl)-piperazine-1-carboxamide dihydrochloride | 3.97 | 357.2 |
| 13 | 4-(trifluoromethoxy)phenyl | 2-((pyridin-3-yloxy)methyl)-N-(4-(trifluoromethoxy)phenyl)-piperazine-1-carboxamide dihydrochloride | 4.91 | 397.1 |

TABLE 7-continued

| Example No. | R₁₂ | IUPAC Name | HPLC RT (min) | LC-MS [M + H]⁺ |
|---|---|---|---|---|
| 14 | 4-phenoxyphenyl | N-(4-phenoxyphenyl)-2-((pyridin-3-yloxy)methyl)-piperazine-1-carboxamide dihydrochloride | 5.06 | 405.2 |
| 15 | 2,4-dimethoxyphenyl | N-(2,4-dimethoxyphenyl)-2-((pyridin-3-yloxy)methyl)-piperazine-1-carboxamide dihydrochloride | 3.45 | 373.1 |
| 16 | 3,4-dichlorophenyl | N-(3,4-dichlorophenyl)-2-((pyridin-3-yloxy)methyl)-piperazine-1-carboxamide dihydrochloride | 4.91 | 381 |
| 17 | 2,4-dichlorophenyl | N-(2,4-dichlorophenyl)-2-((pyridin-3-yloxy)methyl)-piperazine-1-carboxamide dihydrochloride | 4.58 | 381 |
| 18 | 2,5-dimethoxyphenyl | N-(2,5-dimethoxyphenyl)-2-((pyridin-3-yloxy)methyl)-piperazine-1-carboxamide dihydrochloride | 3.9 | 373.2 |
| 19 | 2,3-dichlorophenyl | N-(2,3-dichlorophenyl)-2-((pyridin-3-yloxy)methyl)-piperazine-1-carboxamide dihydrochloride | 4.44 | 381.1 |
| 20 | 2,5-dichlorophenyl | N-(2,5-dichlorophenyl)-2-((pyridin-3-yloxy)methyl)-piperazine-1-carboxamide dihydrochloride | 4.54 | 381 |
| 21 | 2,6-dichlorophenyl | N-(2,6-dichlorophenyl)-2-((pyridin-3-yloxy)methyl)-piperazine-1-carboxamide dihydrochloride | 3.61 | 381 |
| 22 | benzyl | N-benzyl-2-((pyridin-3-yloxy)methyl)-piperazine-1-carboxamide dihydrochloride | 3.38 | 327.1 |
| 23 | 4-methoxybenzyl | N-(4-methoxybenzyl)-2-((pyridin-3-yloxy)methyl)-piperazine-1-carboxamide dihydrochloride | 3.65 | 357 |
| 24 | 3-methoxybenzyl | N-(3-methoxybenzyl)-2-((pyridin-3-yloxy)methyl)-piperazine-1-carboxamide dihydrochloride | 3.77 | 357 |

TABLE 7-continued

| Example No. | R₁₂ | IUPAC Name | HPLC RT (min) | LC-MS [M + H]⁺ |
|---|---|---|---|---|
| 25 | 4-chlorobenzyl | N-(4-chlorobenzyl)-2-((pyridin-3-yloxy)methyl)-piperazine-1-carboxamide dihydrochloride | 4.28 | 361.1 |
| 26 | 4-bromobenzyl | N-(4-bromobenzyl)-2-((pyridin-3-yloxy)methyl)-piperazine-1-carboxamide dihydrochloride | 4.36 | 405.1 |
| 27 | cyclopentyl | N-cyclopentyl-2-((pyridin-3-yloxy)methyl)-piperazine-1-carboxamide dihydrochloride | 3.28 | 305.2 |
| 28 | 4-benzylphenyl | N-(4-benzylphenyl)-2-((pyridin-3-yloxy)methyl)-piperazine-1-carboxamide dihydrochloride | 5.22 | 403.2 |
| 29 | 4-benzoylphenyl | N-(4-benzoylphenyl)-2-((pyridin-3-yloxy)methyl)-piperazine-1-carboxamide dihydrochloride | 4.7 | 417.1 |
| 30 | biphenyl-4-yl | N-(biphenyl-4-yl)-2-((pyridin-3-yloxy)methyl)-piperazine-1-carboxamide dihydrochloride | 5.1 | 389.2 |
| 31 | (R)-1-phenylethyl | N-((R)-1-phenylethyl)-2-((pyridin-3-yloxy)methyl)-piperazine-1-carboxamide dihydrochloride | 3.95 | 341.0 |
| 32 | (S)-1-phenylethyl | N-((S)-1-phenylethyl)-2-((pyridin-3-yloxy)methyl)-piperazine-1-carboxamide dihydrochloride | 3.84 | 341.0 |
| 33 | 4-(trifluoromethyl)phenyl | 2-((pyridin-3-yloxy)methyl)-N-(4-(trifluoromethyl)phenyl)piperazine-1-carboxamide dihydrochloride | 4.85 | 381.6 |
| 34 | 2,4-difluorophenyl | N-(2,4-difluorophenyl)-2-((pyridin-3-yloxy)methyl)-piperazine-1-carboxamide dihydrochloride | 3.59 | 349.5 |

TABLE 7-continued

| Example No. | R₁₂ | IUPAC Name | HPLC RT (min) | LC-MS [M + H]⁺ |
|---|---|---|---|---|
| 35 | 2-fluorophenyl | N-(2-fluorophenyl)-2-((pyridin-3-yloxy)methyl)-piperazine-1-carboxamide dihydrochloride | 3.42 | 331.5 |
| 36 | 4-bromo-2-fluorophenyl | N-(4-bromo-2-fluorophenyl)-2-((pyridin-3-yloxy)methyl)-piperazine-1-carboxamide dihydrochloride | 4.45 | 409.6 |
| 37 | 3-chloro-4-methylphenyl | N-(3-chloro-4-methylphenyl)-2-((pyridin-3-yloxy)methyl)-piperazine-1-carboxamide dihydrochloride | 4.56 | 361.6 |
| 38 | 4-bromo-3-methylphenyl | N-(4-bromo-3-methylphenyl)-2-((pyridin-3-yloxy)methyl)-piperazine-1-carboxamide dihydrochloride | 4.68 | 405.6 |
| 39 | 3-fluoro-4-methylphenyl | N-(3-fluoro-4-methylphenyl)-2-((pyridin-3-yloxy)methyl)-piperazine-1-carboxamide dihydrochloride | 4.57 | 345.6 |
| 40 | 4-methyl-3-(trifluoromethyl)phenyl | N-(4-methyl-3-(trifluoromethyl)phenyl)-2-((pyridin-3-yloxy)methyl)-piperazine-1-carboxamide dihydrochloride | 5.03 | 395.6 |
| 41 | 3,4-dimethylphenyl | N-(3,4-dimethylphenyl)-2-((pyridin-3-yloxy)methyl)-piperazine-1-carboxamide dihydrochloride | 4.34 | 341.6 |
| 42 | 3-chloro-4-methoxyphenyl | N-(3-chloro-4-methoxyphenyl)-2-((pyridin-3-yloxy)methyl)-piperazine-1-carboxamide dihydrochloride | 4.02 | 377.6 |
| 43 | 4-isopropylphenyl | N-(4-isopropylphenyl)-2-((pyridin-3-yloxy)methyl)-piperazine-1-carboxamide dihydrochloride | 4.94 | 355.6 |
| 44 | 4-tert-butylphenyl | N-(4-tert-butylphenyl)-2-((pyridin-3-yloxy)methyl)-piperazine-1-carboxamide dihydrochloride | 5.28 | 369.7 |

TABLE 7-continued

| Example No. | R₁₂ | IUPAC Name | HPLC RT (min) | LC-MS [M + H]⁺ |
|---|---|---|---|---|
| 45 | (4-methoxycarbonylphenyl) | methyl 4-(2-((pyridin-3-yloxy)methyl)-piperazine-1-carboxamido)-benzoate dihydrochloride | 3.99 | 371.1 |
| 46 | (2,3-dihydrobenzofuran-5-yl) | N-(2,3-dihydro-benzofuran-5-yl)-2-((pyridin-3-yloxy)methyl)-piperazine-1-carboxamide dihydrochloride | 3.87 | 355.1 |
| 47 | (2,3-dihydrobenzo[b][1,4]dioxin-6-yl) | N-(2,3-dihydrobenzo[b][1,4]dioxin-6-yl)-2-((pyridin-3-yloxy)methyl)-piperazine-1-carboxamide dihydrochloride | 3.90 | 371.2 |
| 48 | (4-(benzyloxy)phenyl) | N-(4-(benzyloxy)-phenyl)-2-((pyridin-3-yloxy)methyl)-piperazine-1-carboxamide dihydrochloride | 5.29 | 419.2 |
| 49 | (benzo[d][1,3]dioxol-5-yl) | N-(benzo[d][1,3]-dioxol-5-yl)-2-((pyridin-3-yloxy)methyl)-piperazine-1-carboxamide dihydrochloride | 3.92 | 357.1 |
| 50 | (4-(methylthio)phenyl) | N-(4-(methylthio)-phenyl)-2-((pyridin-3-yloxy)methyl)-piperazine-1-carboxamide dihydrochloride | 4.63 | 359.1 |
| 51 | (4-(dimethylamino)phenyl) | N-(4-(dimethyl-amino)phenyl)-2-((pyridin-3-yloxy)methyl)-piperazine-1-carboxamide trihydrochloride | 2.32 | 356.1 |
| 52 | (3,4-dimethoxyphenyl) | N-(3,4-dimethoxy-phenyl)-2-((pyridin-3-yloxy)methyl)-piperazine-1-carboxamide dihydrochloride | 2.28 | 373.1 |

Examples 53-58

The examples shown in Table 8 below were prepared by similar methods as described for Example 2, substituting Intermediate $C_i$ for Intermediate C and substituting the appropriate isocyanate. All reagents were commercially available unless otherwise noted. All compounds were isolated as the dihydrochloride salts unless otherwise noted.

TABLE 8

| Example No. | R₁₂ | IUPAC Name | HPLC RT (min) | LC-MS [M + H]⁺ |
|---|---|---|---|---|
| 53 | 4-methoxyphenyl | (R)-N-(4-methoxyphenyl)-2-((pyridin-3-yloxy)methyl)-piperazine-1-carboxamide dihydrochloride | 3.43 | 343.0 |
| 54 | 4-phenoxyphenyl | (R)-N-(4-phenoxyphenyl)-2-((pyridin-3-yloxy)methyl)-piperazine-1-carboxamide dihydrochloride | 5.10 | 405.0 |
| 55 | 3,4-dichlorophenyl | (R)-N-(3,4-dichlorophenyl)-2-((pyridin-3-yloxy)methyl)-piperazine-1-carboxamide dihydrochloride | 4.92 | 380.9 |
| 56 | (R)-1-phenylethyl | (R)-N-((R)-1-phenylethyl)-2-((pyridin-3-yloxy)methyl)-piperazine-1-carboxamide dihydrochloride | 3.93 | 341.0 |
| 57 | (S)-1-phenylethyl | (R)-N-((S)-1-phenylethyl)-2-((pyridin-3-yloxy)methyl)-piperazine-1-carboxamide dihydrochloride | 3.91 | 341.1 |

TABLE 8-continued

| Example No. | R₁₂ | IUPAC Name | HPLC RT (min) | LC-MS [M + H]⁺ |
|---|---|---|---|---|
| 58 | 4-bromo-2-fluorophenyl | (R)-N-(4-bromo-2-fluorophenyl)-2-((pyridin-3-yloxy)methyl)-piperazine-1-carboxamide dihydrochloride | 5.04 | 408.8 |

Examples 59-63

The examples shown in Table 9 below were prepared by similar methods as described for Example 2, substituting Intermediate C$_{ii}$ for Intermediate C and substituting the appropriate isocyanate. All reagents were commercially available unless otherwise noted. All compounds were isolated as the dihydrochloride salts unless otherwise noted.

TABLE 9

| Example No. | R₁₂ | IUPAC Name | HPLC RT (min) | LC-MS [M + H]⁺ |
|---|---|---|---|---|
| 59 | 4-methoxyphenyl | (S)-N-(4-methoxyphenyl)-2-((pyridin-3-yloxy)methyl)-piperazine-1-carboxamide dihydrochloride | 3.45 | 343.1 |

TABLE 9-continued

| Example No. | R12 | IUPAC Name | HPLC RT (min) | LC-MS [M + H]+ |
|---|---|---|---|---|
| 60 | 4-phenoxyphenyl | (S)-N-(4-phenoxyphenyl)-2-((pyridin-3-yloxy)methyl)-piperazine-1-carboxamide dihydrochloride | 5.11 | 405.0 |
| 61 | 3,4-dichlorophenyl | (S)-N-(3,4-dichlorophenyl)-2-((pyridin-3-yloxy)methyl)-piperazine-1-carboxamide dihydrochloride | 4.94 | 380.9 |
| 62 | (R)-1-phenylethyl | (S)-N-((R)-1-phenylethyl)-2-((pyridin-3-yloxy)methyl)-piperazine-1-carboxamide dihydrochloride | 3.92 | 341.1 |
| 63 | (S)-1-phenylethyl | (S)-N-((S)-1-phenylethyl)-2-((pyridin-3-yloxy)methyl)-piperazine-1-carboxamide dihydrochloride | 3.94 | 341.1 |

Examples 64-74

The examples found in Table 10 below were prepared by similar methods as described for Example 2, using Intermediates D-J instead of Intermediate C, as appropriate, and substituting the appropriate isocyanate. All reagents were commercially available unless otherwise noted. All compounds were isolated as the hydrochloride salts.

TABLE 10

| Example No. | Ar | R12 | IUPAC Name | HPLC RT (min) | LC-MS [M + H]+ |
|---|---|---|---|---|---|
| 64 | phenyl | 4-methoxyphenyl | N-(4-methoxyphenyl)-2-(phenoxymethyl)piperazine-1-carboxamide hydrochloride | 4.89 | 342.2 |

TABLE 10-continued

| Example No. | Ar | R₁₂ | IUPAC Name | HPLC RT (min) | LC-MS [M + H]⁺ |
|---|---|---|---|---|---|
| 65 | 4-methoxyphenyl | 4-methoxyphenyl | 2-((4-methoxyphenoxy)methyl)-N-(4-methoxyphenyl)piperazine-1-carboxamide hydrochloride | 4.91 | 372.2 |
| 66 | 4-methoxyphenyl | 4-chlorophenyl | N-(4-chlorophenyl)-2((4-methoxyphenoxy)methyl)piperazine-1-carboxamide hydrochloride | 5.47 | 376.1 |
| 67 | 4-chlorophenyl | 4-methoxyphenyl | 2-((4-chlorophenoxy)methyl)-N-(4-methoxyphenyl)piperazine-1-carboxamide hydrochloride | 5.40 | 376.1 |
| 68 | 4-chlorophenyl | 4-chlorophenyl | 2-((4-chlorophenoxy)methyl)-N-(4-chlorophenyl)piperazine-1-carboxamide hydrochloride | 5.81 | 380.1 |
| 69 | 4-chlorophenyl | 3,4-dichlorophenyl | 2-((4-chlorophenoxy)methyl)-N-(3,4-dichlorophenyl)piperazine-1-carboxamide hydrochloride | 6.12 | 414 |

TABLE 10-continued

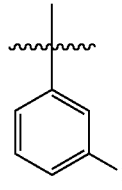

| Example No. | Ar | R$_{12}$ | IUPAC Name | HPLC RT (min) | LC-MS [M + H]$^+$ |
|---|---|---|---|---|---|
| 70 | 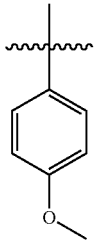 | 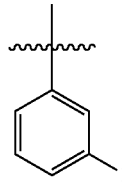 | 2-((3-fluorophenoxy)methyl)-N-(4-methoxyphenyl)piperazine-1-carboxamide hydrochloride | 4.90 | 360.1 |
| 71 | 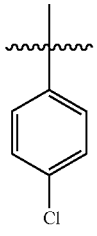 | 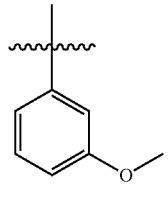 [SMILES: *c1cccc(OC)c1] | N-(4-chlorophenyl)-2-((3-fluorophenoxy)methyl)piperazine-1-carboxamide hydrochloride | 5.54 | 364.1 |
| 72 | 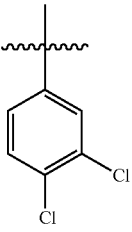 [SMILES: *c1ccc(Cl)c(Cl)c1] | 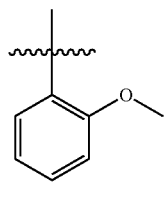 [SMILES: *c1ccccc1OC] | N-(3,4-dichlorophenyl)-2-((3-methoxyphenoxy)methyl)piperazine-1-carboxamide hydrochloride | 6.13 | 410.0 |
| 73 | 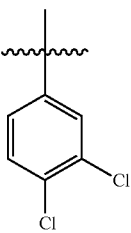 [SMILES: *c1ccc(Cl)c(Cl)c1] | 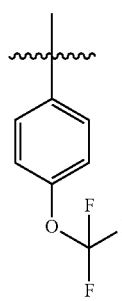 | N-(3,4-dichlorophenyl)-2-((2-methoxyphenoxy)methyl)piperazine-1-carboxamide hydrochloride | 6.16 | 410.1 |
| 74 | 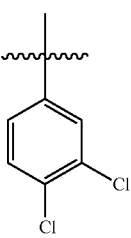 [SMILES: *c1ccc(Cl)c(Cl)c1] | | N-(3,4-dichlorophenyl)-2-((4-(trifluoromethoxy)phenoxy)methyl)piperazine-1-carboxamide hydrochloride | 6.67 | 464.0 |

Examples 75-86

The examples found in Table 11 below were prepared by similar methods as described for Example 2, using Intermediates K-M instead of Intermediate C, as appropriate, and substituting the appropriate isocyanate. All reagents were commercially available unless otherwise noted. All compounds were isolated as the dihydrochloride salts.

TABLE 11

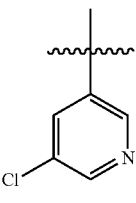 [SMILES: *c1cncc(Cl)c1]

| Example No. | Ar | $R_{12}$ | IUPAC Name | HPLC RT (min) | LC-MS $[M + H]^+$ |
|---|---|---|---|---|---|
| 75 | 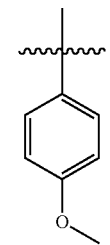 | 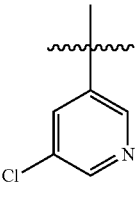 [SMILES: *c1cncc(Cl)c1] | 2-((5-chloropyridin-3-yloxy)methyl)-N-(4-methoxyphenyl)piperazine-1-carboxamide dihydrochloride | 4.63 | 377.1 |
| 76 | 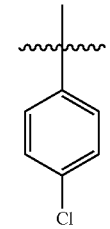 | 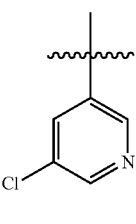 | N-(4-chlorophenyl)-2-((5-chloropyridin-3-yloxy)methyl)piperazine-1-carboxamide dihydrochloride | 5.21 | 381 |
| 77 | 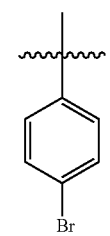 | 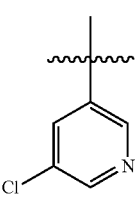 [SMILES: *c1cncc(Cl)c1] | N-(4-bromophenyl)-2-((5-chloropyridin-3-yloxy)methyl)piperazine-1-carboxamide dihydrochloride | 5.24 | 425 |
| 78 | 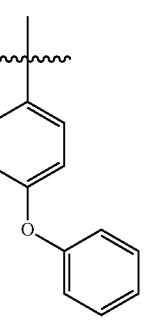 | | 2-((5-chloropyridin-3-yloxy)methyl)-N-(4-phenoxyphenyl)piperazine-1-carboxamide dihydrochloride | 5.77 | 439.1 |

TABLE 11-continued

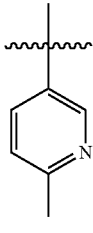

| Example No. | Ar | $R_{12}$ | IUPAC Name | HPLC RT (min) | LC-MS $[M + H]^+$ |
|---|---|---|---|---|---|
| 79 | 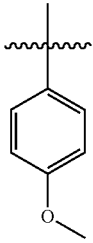 | 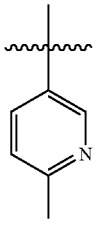 | N-(4-methoxyphenyl)-2-((6-methylpyridin-3-yloxy)methyl)piperazine-1-carboxamide dihydrochloride | 3.08 | 357.1 |
| 80 | 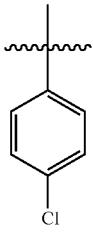 | 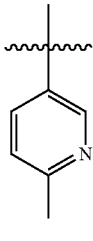 | N-(4-chlorophenyl)-2-((6-methylpyridin-3-yloxy)methyl)piperazine-1-carboxamide dihydrochloride | 4.08 | 361.1 |
| 81 | 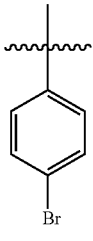 | 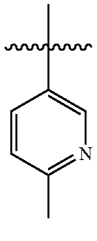 | N-(4-bromophenyl)-2-((6-methylpyridin-3-yloxy)methyl)piperazine-1-carboxamide dihydrochloride | 4.24 | 405.1 |
| 82 | 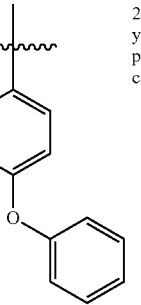 | 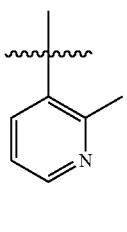 [SMILES: *c1cccnc1C] | 2-((6-methylpyridin-3-yloxy)methyl)-N-(4-phenoxyphenyl)piperazine-1-carboxamide dihydrochloride | 4.89 | 419.1 |
| 83 | 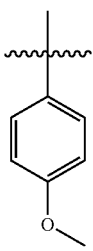 | | N-(4-methoxyphenyl)-2-((2-methylpyridin-3-yloxy)methyl)piperazine-1-carboxamide dihydrochloride | 2.32 | 357.1 |

TABLE 11-continued

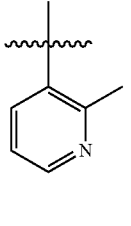 [SMILES: *c1cccnc1C]

| Example No. | Ar | R₁₂ | IUPAC Name | HPLC RT (min) | LC-MS [M + H]⁺ |
|---|---|---|---|---|---|
| 84 | 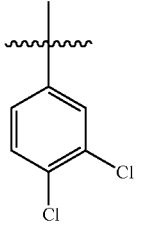 [SMILES: *c1ccc(Cl)c(Cl)c1] | 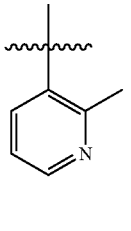 [SMILES: *c1cccnc1C] | N-(3,4-dichlorophenyl)-2-((2-methylpyridin-3-yloxy)methyl)piperazine-1-carboxamide dihydrochloride | 4.42 | 395.0 |
| 85 | 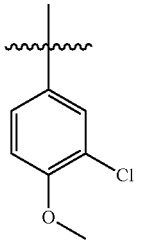 [SMILES: *c1ccc(OC)c(Cl)c1] | 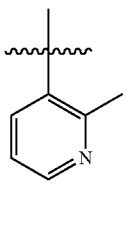 [SMILES: *c1cccnc1C] | N-(3-chloro-4-methoxyphenyl)-2-((2-methylpyridin-3-yloxy)methyl)piperazine-1-carboxamide dihydrochloride | 3.50 | 391.1 |
| 86 | 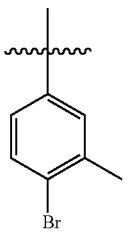 [SMILES: *c1ccc(Br)c(C)c1] | 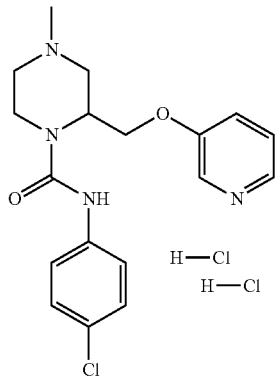 | N-(4-bromo-3-methylphenyl)-2-((2-methylpyridin-3-yloxy)methyl)piperazine-1-carboxamide dihydrochloride | 4.25 | 419.1 |

Example 87

N-(4-Chlorophenyl)-4-methyl-2-((pyridin-3-yloxy)methyl)piperazine-1-carboxamide dihydrochloride N-(4-chlorophenyl)-2-((pyridin-3-yloxy)methyl)piperazine-1-carboxamide dihydrochloride (prepared as described in Example 7) (141 mg, 0.335 mmol) was dissolved in formaldehyde (37% aqueous solution, 1 mL) and formic acid (1 mL) and heated to 60° C. After 16 h, the reaction mixture was brought to pH 12 with 1 N NaOH in water and was extracted with CH₂Cl₂ (3×10 mL). The combined organics were dried over Na₂SO₄, filtered, and concentrated under reduced pressure. The material was purified by HPLC (5 to 30% MeCN/0.1% TFA in H₂O/0.1% TFA gradient). The desired fractions were concentrated under reduced pressure, dissolved in MeOH (1 mL) and treated with 4M HCl in 1,4-dioxane. The mixture was concentrated under reduced pressure, yielding 10.3 mg (7%) of the desired product as a white solid. LC-MS: RT=4.48 min, [M+H]⁺=361.1.

Example 88

N-(4-methoxyphenyl)-4-methyl-2-((pyridin-3-yloxy)methyl)piperazine-1-carboxamide dihydrochloride

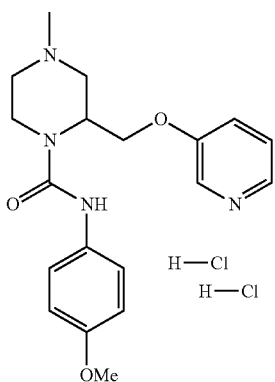

N-(4-methoxyphenyl)-2-((pyridin-3-yloxy)methyl)piperazine-1-carboxamide dihydrochloride (prepared as described in Example 10) (123 mg, 0.295 mmol), was dissolved in formaldehyde (37% aqueous solution, 1 mL) and formic acid (1 mL) and heated to 60° C. After 16 h, the reaction mixture was brought to pH 12 with 1 N NaOH in water and was extracted with $CH_2Cl_2$ (3×10 mL). The combined organics were dried over $Na_2SO_4$, filtered, and concentrated under reduced pressure. The material was purified by HPLC (5 to 30% MeCN/0.1% TFA in $H_2O$/0.1% TFA gradient). The desired fractions were concentrated under reduced pressure, dissolved in MeOH (1 mL) and treated with 4M HCl in 1,4-dioxane. The mixture was concentrated under reduced pressure, yielding 16.2 mg (13%) of the desired product as an off-white solid. LC-MS: RT=3.59 min, $[M+H]^+$=357.1.

Example 89

N-(4'-methoxybiphenyl-4-yl)-2-((pyridin-3-yloxy)methyl)piperazine-1-carboxamide

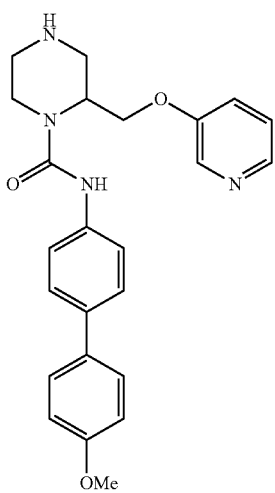 [SMILES: COc1ccc(-c2ccc(NC(=O)N3CCNCC3COc3cccnc3)cc2)cc1]

Step 1. Synthesis of tert-butyl 4-(4'-methoxybiphenyl-4-ylcarbamoyl)-3-((pyridin-3-yloxy)methyl)piperazine-1-carboxylate

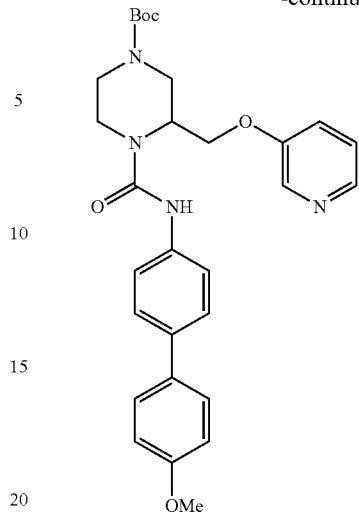

[1,1'-bis(diphenylphosphino)ferrocene]-dichloropalladium(II) complex with dichloromethane (1:1) (8.3 mg, 0.010 mmol) was added to a mixture of tert-butyl 4-(4-bromophenylcarbamoyl)-3-((pyridin-3-yloxy)methyl)piperazine-1-carboxylate (100 mg, 0.204 mmol, prepared as in Example 2, Step 1), (4-methoxyphenyl)boronic acid (61.9 mg, 0.407 mmol) and sodium carbonate (42.4 mg, 0.407 mmol) in toluene (4 mL), 1,4-dioxane (1 mL), and water (1 mL). The reaction mixture was heated to 80° C. for 3 h. Upon cooling to room temperature, the reaction mixture was filtered though Celite®, concentrated under reduced pressure, and purified by HPLC (10 to 90% MeCN/0.1% TFA in $H_2O$/0.1% TFA gradient). This gave 114.9 mg (89%, ~90% pure) of the TFA salt of the desired product as a thick, brownish oil. LC-MS: RT=8.69 min, $[M+H]^+$=519.2.

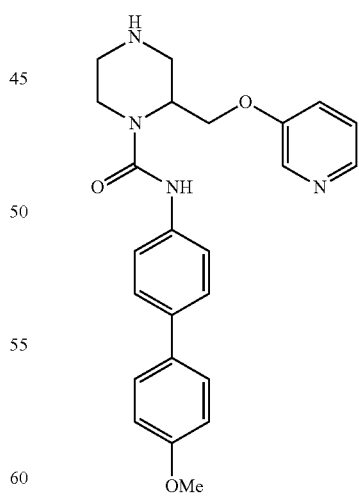

Step 2. Synthesis of N-(4'-methoxybiphenyl-4-yl)-2-((pyridin-3-yloxy)methyl)piperazine-1-carboxamide 4 M HCl in 1,4-dioxane (6 mL, 24 mmol) was added to a solution of tert-butyl 4-(4'-methoxybiphenyl-4-ylcarbamoyl)-3-((pyridin-3-yloxy)methyl)piperazine-1-carboxylate (114.9 mg, 0.182 mmol) in MeOH (1 mL). After 2 h, the reaction mixture was concentrated under reduced pressure, and the material was purified by HPLC (5 to 50% MeCN/0.1% TFA in H₂O/0.1% TFA gradient). The desired fractions were brought to pH 12 with 1 N NaOH in H₂O and were extracted with EtOAc (3×). The combined organics were dried over Na₂SO₄, filtered, and concentrated under reduced pressure. This gave 28.6 mg (38%) of the desired product as a white solid. LC-MS: RT=4.97 min, [M+H]⁺=419.2.

Examples 90-92

The examples shown in Table 12 below were prepared by similar methods as described for Example 89, substituting the appropriate boronic acid. All reagents were commercially available unless otherwise noted.

TABLE 12

| Example No. | R_d | IUPAC Name | HPLC RT (min) | LC-MS [M + H]⁺ |
|---|---|---|---|---|
| 89 | 4'-methoxyphenyl | N-(4'-methoxy-biphenyl-4-yl)-2-((pyridin-3-yloxy)methyl)piperazine-1-carboxamide | 4.97 | 419.2 |
| 90 | 3'-methoxyphenyl | N-(3'-methoxy-biphenyl-4-yl)-2-((pyridin-3-yloxy)methyl)piperazine-1-carboxamide | 5.1 | 419.2 |
| 91 | 4'-chlorophenyl | N-(4'-chloro-biphenyl-4-yl)-2-((pyridin-3-yloxy)methyl)piperazine-1-carboxamide | 5.46 | 423.1 |
| 92 | 3'-chlorophenyl | N-(3'-chloro-biphenyl-4-yl)-2-((pyridin-3-yloxy)methyl)piperazine-1-carboxamide | 5.46 | 423.1 |

Example 93

Piperidin-1-yl(2-((pyridin-3-yloxy)methyl)piperazin-1-yl)methanone dihydrochloride

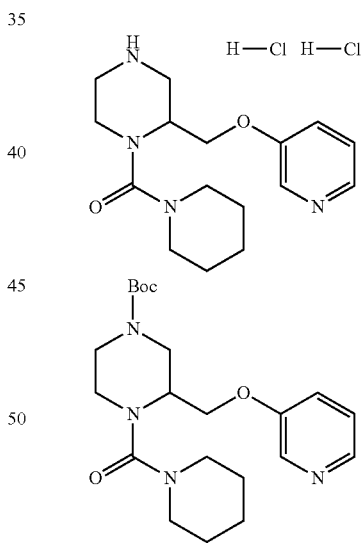

Step 1. Synthesis of tert-butyl 4-(piperidine-1-carbonyl)-3-((pyridin-3-yloxy)methyl)piperazine-1-carboxylate A solution of Intermediate N (108.5 mg, 0.280 mmol), piperidine (47.7 mg, 0.560 mmol) and triethylamine (0.078 mL, 0.56 mmol) in MeCN (4 mL) was heated to 70° C. After 12 h, piperidine (1 mL) was added and heating was continued at 70° C. After an additional 24 h, Cs₂CO₃ (0.182 g, 0.560 mmol) was added and heating was continued at 70° C. for 72 h. Upon cooling to rt, the reaction mixture was filtered, concentrated under reduced pressure and purified by HPLC (10 to 95% MeCN/0.1% TFA in H₂O/0.1% TFA gradient). This gave 43.0 mg (30%) of the TFA salt of the desired product. LC-MS: RT=7.53 min, [M+H]⁺=405.2.

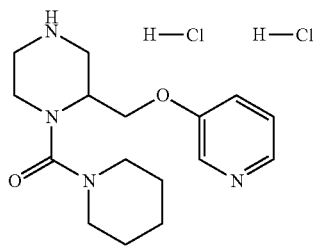 [SMILES: O=C(N1CCCCC1)N1CCNCC1COc1cccnc1 ; Cl ; Cl]

Step 2. Synthesis of piperidin-1-yl(2-((pyridin-3-yloxy)methyl)piperazin-1-yl)methanone dihydrochloride 4 M HCl in 1,4-dioxane (6 mL, 24 mmol) was added to a solution of tert-butyl 4-(piperidine-1-carbonyl)-3-((pyridin-3-yloxy)methyl)piperazine-1-carboxylate TFA salt (43.0 mg, 0.083 mmol) in MeOH (1 mL). After 12 h, the reaction mixture was concentrated under reduced pressure, yielding 31.3 mg (100%) of the desired product as a white solid. LC-MS: RT=3.34 min, [M+H]⁺=305.2.

Example 94

Morpholino(2-((pyridin-3-yloxy)methyl)piperazin-1-yl)methanone dihydrochloride

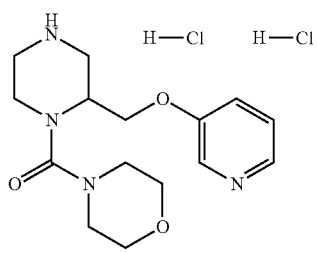 [SMILES: O=C(N1CCOCC1)N1CCNCC1COc1cccnc1 ; Cl ; Cl]

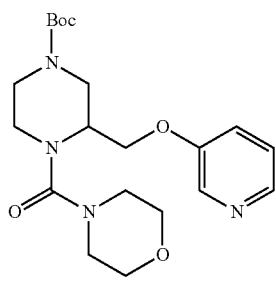

Step 1. Synthesis of tert-butyl 4-(morpholine-4-carbonyl)-3-((pyridin-3-yloxy)methyl)piperazine-1-carboxylate A solution of Intermediate N (87.5 mg, 0.226 mmol) and morpholine (196 mg, 2.26 mmol) in THF (5 mL) was heated to 70° C. After 7 days, the reaction mixture was diluted with EtOAc (20 mL). The organics were washed with water (3×15 mL) and brine (15 mL), dried over Na₂SO₄, filtered, and concentrated under reduced pressure. The material was purified by HPLC (5 to 50% MeCN/0.1% TFA in H₂O/0.1% TFA gradient). This gave 20.0 mg (17%) of the TFA salt of the desired product. LC-MS: RT=6.02 min, [M+H]⁺=407.2.

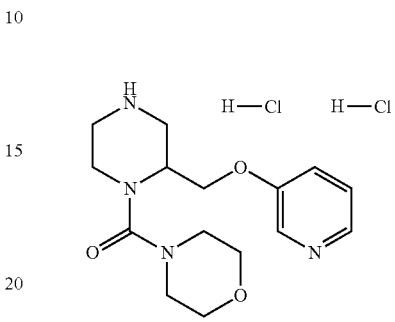

Step 2. Synthesis of morpholino(2-((pyridin-3-yloxy)methyl)piperazin-1-yl)methanone dihydrochloride 4 M HCl in 1,4-dioxane (6 mL, 24 mmol) was added to a solution of tert-butyl 4-(morpholine-4-carbonyl)-3-((pyridin-3-yloxy)methyl)piperazine-1-carboxylate TFA salt (20.0 mg, 0.038 mmol) in MeOH (1 mL). After 1 h, the reaction mixture was concentrated under reduced pressure, yielding 14.5 mg (99%) of the desired product. LC-MS: RT=1.49 min, [M+H]⁺=307.1.

Example 95

N-(6-fluorobenzo[d]thiazol-2-yl)-2-((pyridin-3-yloxy)methyl)piperazine-1-carboxamide dihydrochloride

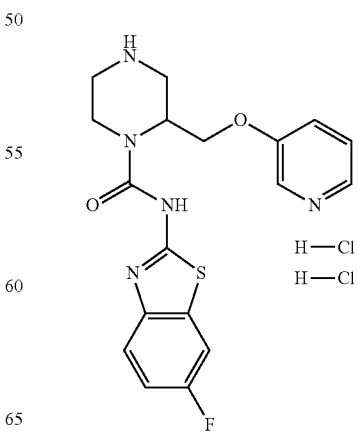

Step 1. Synthesis of tert-butyl 4-(6-fluorobenzo[d]thiazol-2-ylcarbamoyl)-3-((pyridin-3-yloxy)methyl)piperazine-1-carboxylate

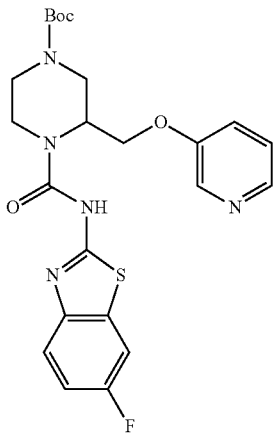

2-Amino-6-fluorobenzothiazole (66 mg, 0.392 mmol) was added to a suspension of sodium hydride (60% dispersion in mineral oil, 16 mg, 0.392 mmol) in THF (2 mL). After 5 min, a solution of Intermediate N (138 mg, 0.356 mmol) in THF (2 mL) was added, and the reaction mixture was heated to 70° C. After 4 h, the reaction mixture was diluted with $H_2O$ (20 mL) and was extracted with EtOAc (3×20 mL). The combined extracts were washed dried over $Na_2SO_4$, filtered, and concentrated under reduced pressure. The material was purified by HPLC (10 to 90% MeCN/0.1% TFA in $H_2O$/0.1% TFA gradient). This gave 122 mg (57%) of the TFA salt of the title compound. LC-MS: RT=8.33 min, $[M+H]^+$=488.1.

Step 2. Synthesis of N-(6-fluorobenzo[d]thiazol-2-yl)-2-((pyridin-3-yloxy)methyl)piperazine-1-carboxamide dihydrochloride

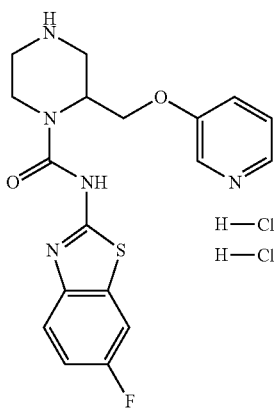

4 M HCl in 1,4-dioxane (6 mL, 24 mmol) was added to a solution of tert-butyl 4-(6-fluorobenzo[d]thiazol-2-ylcarbamoyl)-3-((pyridin-3-yloxy)methyl)piperazine-1-carboxylate TFA salt (122 mg, 0.203 mmol) in MeOH (1 mL). After 1 h, the reaction mixture was concentrated under reduced pressure, yielding 83.9 mg (90%) of the title compound as a white solid. LC-MS: RT=4.61 min, $[M+H]^+$=388.1.

Examples 96-108

The examples shown in Table 13 below were prepared by similar methods as described for Example 95, substituting the appropriate amine. All reagents were commercially available unless otherwise noted. All compounds were isolated as the dihydrochloride salts unless otherwise noted.

TABLE 13

| Example No. | $R_{12}$ | IUPAC Name | HPLC RT (min) | LC-MS $[M + H]^+$ |
|---|---|---|---|---|
| 96 | 6-methylbenzothiazol-2-yl | N-(6-methylbenzo[d]thiazol-2-yl)-2-((pyridin-3-yloxy)methyl)-piperazine-1-carboxamide dihydrochloride | 4.79 | 384.1 |
| 97 | 4-methoxybenzothiazol-2-yl | N-(4-methoxybenzo[d]thiazol-2-yl)-2-((pyridin-3-yloxy)methyl)-piperazine-1-carboxamide dihydrochloride | 4.40 | 400.1 |
| 98 | 4-methylbenzothiazol-2-yl | N-(4-methylbenzo[d]thiazol-2-yl)-2-((pyridin-3-yloxy)methyl)-piperazine-1-carboxamide dihydrochloride | 4.57 | 384.1 |
| 99 | 6-chlorobenzothiazol-2-yl | N-(6-chlorobenzo[d]thiazol-2-yl)-2-((pyridin-3-yloxy)methyl)-piperazine-1-carboxamide dihydrochloride | 5.10 | 404.1 |

TABLE 13-continued

Structure: piperazine with 2-((pyridin-3-yloxy)methyl) substituent and 1-carboxamide-NH-R₁₂

| Example No. | R₁₂ | IUPAC Name | HPLC RT (min) | LC-MS [M + H]⁺ |
|---|---|---|---|---|
| 100 | 6-methoxybenzo[d]thiazol-2-yl | N-(6-methoxybenzo[d]thiazol-2-yl)-2-((pyridin-3-yloxy)methyl)-piperazine-1-carboxamide dihydrochloride | 4.64 | 400.1 |
| 101 | benzo[d]thiazol-2-yl | N-(benzo[d]thiazol-2-yl)-2-((pyridin-3-yloxy)methyl)-piperazine-1-carboxamide dihydrochloride | 4.46 | 370.1 |
| 102 | 5-chlorobenzo[d]oxazol-2-yl | N-(5-chlorobenzo[d]oxazol-2-yl)-2-((pyridin-3-yloxy)methyl)-piperazine-1-carboxamide dihydrochloride | 4.90 | 388.2 |
| 103 | 1H-indol-5-yl | N-(1H-indol-5-yl)-2-((pyridin-3-yloxy)methyl)-piperazine-1-carboxamide dihydrochloride | 1.44 | 352.1 |
| 104 | 4-phenylthiazol-2-yl | N-(4-phenylthiazol-2-yl)-2-((pyridin-3-yloxy)methyl)-piperazine-1-carboxamide dihydrochloride | 5.08 | 396.1 |
| 105 | 4-(4-chlorophenyl)thiazol-2-yl | N-(4-(4-chlorophenyl)-thiazol-2-yl)-2-((pyridin-3-yloxy)methyl)-piperazine-1-carboxamide dihydrochloride | 5.59 | 430.1 |
| 106 | 5-phenyl-1,3,4-thiadiazol-2-yl | N-(5-phenyl-1,3,4-thiadiazol-2-yl)-2-((pyridin-3-yloxy)methyl)-piperazine-1-carboxamide dihydrochloride | 4.79 | 397.1 |
| 107 | 3-methylisothiazol-5-yl | N-(3-methylisothiazol-5-yl)-2-((pyridin-3-yloxy)methyl)-piperazine-1-carboxamide dihydrochloride | 2.81 | 334.1 |
| 108 | 3-methylisoxazol-5-yl | N-(3-methylisoxazol-5-yl)-2-((pyridin-3-yloxy)methyl)-piperazine-1-carboxamide dihydrochloride | 2.89 | 318.1 |

Example 109

N-(benzo[d]thiazol-6-yl)-2-((pyridin-3-yloxy)methyl)piperazine-1-carboxamide

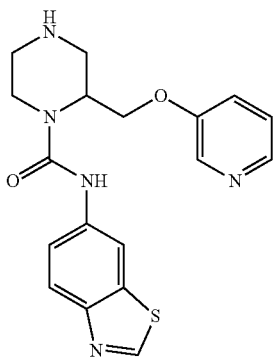 [SMILES: O=C(Nc1ccc2ncsc2c1)N1CCNCC1COc1cccnc1]

Step 1. Synthesis of 4-nitrophenyl benzo[d]thiazol-6-ylcarbamate hydrochloride

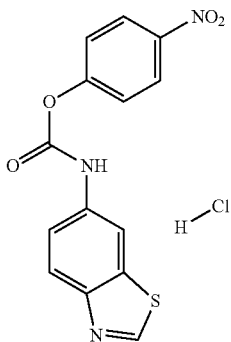

6-Aminobenzothiazole (100 mg, 0.666 mmol) and p-nitrophenyl chloroformate (148 mg, 0.733 mmol) were stirred at rt in CH$_2$Cl$_2$ (5 mL) overnight. The resulting solid was collected by filtration, yielding 183 mg (81%) of the title compound. LC-MS: RT=8.17 min, [M+H]$^+$=316.0.

Step 2. Synthesis of tert-butyl 4-(benzo[d]thiazol-6-ylcarbamoyl)-3-((pyridin-3-yloxy)methyl)piperazine-1-carboxylate

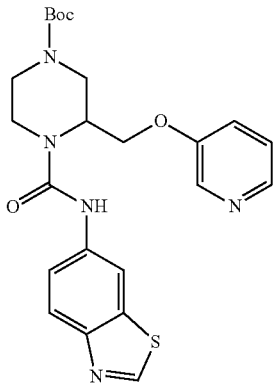 [SMILES: CC(C)(C)OC(=O)N1CCN(C(=O)Nc2ccc3ncsc3c2)C(COc2cccnc2)C1]

4-Nitrophenyl benzo[d]thiazol-6-ylcarbamate hydrochloride (143 mg, 0.409 mmol), Intermediate C (100 mg, 0.341 mmol) and triethylamine (0.048 mL, 0.341 mmol) were stirred in CH$_2$Cl$_2$ (5 mL). After 2 h, the reaction mixture was diluted with EtOAc (30 mL) and was washed with 1 N NaOH (3×20 mL) and brine (20 mL), dried over Na$_2$SO$_4$, filtered, and concentrated under reduced pressure. The material was purified by HPLC (10 to 90% MeCN/0.1% TFA in H$_2$O/0.1% TFA gradient). This gave 154 mg (65%) of the di-TFA salt of the title compound. LC-MS: RT=6.88 min, [M+H]$^+$=470.2.

Step 3. Synthesis of N-(benzo[d]thiazol-6-yl)-2-((pyridin-3-yloxy)methyl)piperazine-1-carboxamide

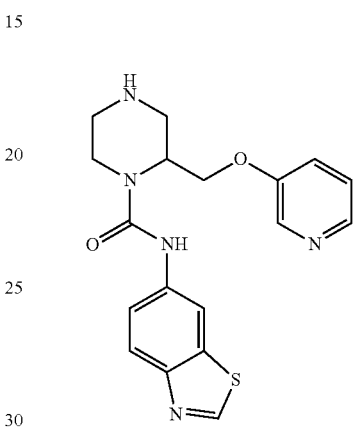

4 M HCl in 1,4-dioxane (6 mL, 24 mmol) was added to a solution of tert-butyl 4-(benzo[d]thiazol-6-ylcarbamoyl)-3-((pyridin-3-yloxy)methyl)piperazine-1-carboxylate di-TFA salt (154 mg, 0.221 mmol) in MeOH (1 mL). After stirring overnight, the reaction mixture was concentrated under reduced pressure, dissolved in 1 N NaOH, and extracted with EtOAc (3×). The combined extracts were dried over Na$_2$SO$_4$, filtered, and concentrated under reduced pressure, yielding 69.5 mg (85%) of the title compound as an off-white solid. LC-MS: RT=3.62 min, [M+H]$^+$=370.1.

Example 110

N-(2-methylbenzo[d]thiazol-5-yl)-2-((pyridin-3-yloxy)methyl)piperazine-1-carboxamide hydrochloride

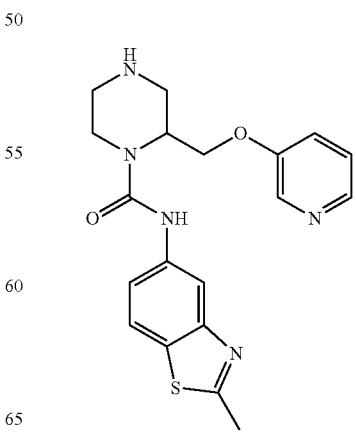

Step 1. Synthesis of 4-nitrophenyl 2-methylbenzo[d]thiazol-5-ylcarbamate hydrochloride

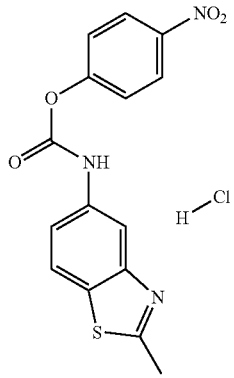

5-Amino-2-methylbenzothiazole dihydrochloride (530 mg, 2.23 mmol) was dissolved in 1 N NaOH (10 mL) and was extracted with EtOAc (3×20 mL). The combined extracts were dried over $Na_2SO_4$, filtered, and concentrated under reduced pressure. The material was dissolved in $CH_2Cl_2$ (10 mL), p-nitrophenyl chloroformate (586 mg, 2.91 mmol) was added, and the reaction mixture was stirred at rt overnight. The resulting solid was collected by filtration, was washed with $CH_2Cl_2$, and was dried under vacuum. This gave 853 mg of the title compound contaminated with some 5-amino-2-methylbenzothiazole. LC-MS: RT=8.49 min, [M+H]$^+$=330.0.

Step 2. Synthesis of tert-butyl 4-(2-methylbenzo[d]thiazol-5-ylcarbamoyl)-3-((pyridin-3-yloxy)methyl)piperazine-1-carboxylate

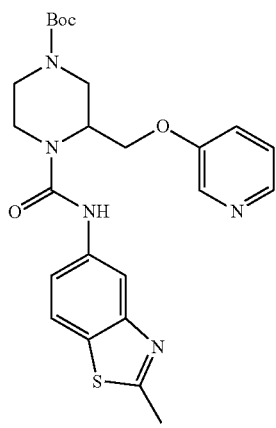 [SMILES: Cc1nc2cc(NC(=O)N3CCN(C(=O)OC(C)(C)C)CC3COc3cccnc3)ccc2s1]

4-Nitrophenyl 2-methylbenzo[d]thiazol-5-ylcarbamate hydrochloride (149 mg, 0.409 mmol), Intermediate C (100 mg, 0.341 mmol) and triethylamine (0.057 mL, 0.409 mmol) were stirred in $CH_2Cl_2$ (5 mL). After 2 h, the reaction mixture was concentrated under reduced pressure and purified by HPLC (10 to 90% MeCN/0.1% TFA in $H_2O$/0.1% TFA gradient). This gave 129.9 mg (54%) of the di-TFA salt of the title compound. LC-MS: RT=7.22 min, [M+H]$^+$=484.2.

Step 3. Synthesis of N-(2-methylbenzo[d]thiazol-5-yl)-2-((pyridin-3-yloxy)methyl)piperazine-1-carboxamide hydrochloride

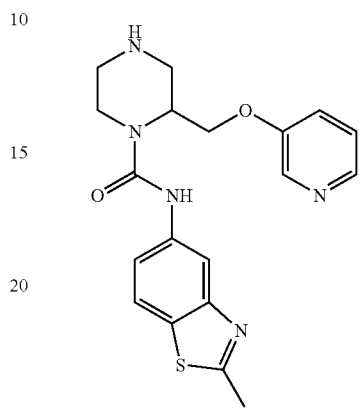

4 M HCl in 1,4-dioxane (6 mL, 24 mmol) was added to a solution of tert-butyl 4-(2-methylbenzo[d]thiazol-5-ylcarbamoyl)-3-((pyridin-3-yloxy)methyl)piperazine-1-carboxylate di-TFA salt (129.9 mg, 0.183 mmol) in MeOH (1 mL). After 1 h, the reaction mixture was concentrated under reduced pressure and purified by HPLC (5 to 50% MeCN/0.1% TFA in $H_2O$/0.1% TFA gradient). The fractions containing the desired product were combined and brought to pH 12 with 1 N NaOH and were extracted with EtOAc (3×). The combined organics were dried over $Na_2SO_4$, filtered, and concentrated under reduced pressure. The material was dissolved in MeOH (1 mL) and 4 M HCl in 1,4-dioxane (1 equiv. HCl, 0.028 mL) was added. The mixture was concentrated under reduced pressure to give 44.6 mg (58%) of the title compound as the hydrochloride salt. LC-MS: RT=4.22 min, [M+H]$^+$=384.1.

Example 111

N-(2,3-dihydro-1H-inden-5-yl)-2-((pyridin-3-yloxy)methyl)piperazine-1-carboxamide dihydrochloride

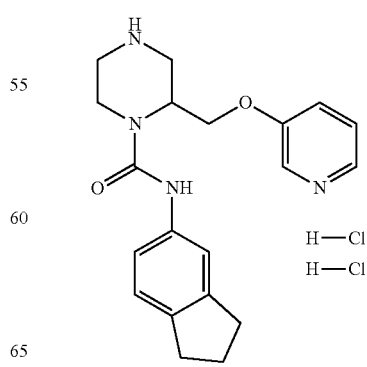

Step 1. Synthesis of 4-nitrophenyl 2,3-dihydro-1H-inden-5-ylcarbamate

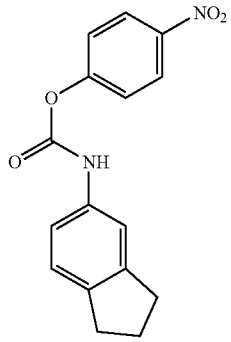 [SMILES: O=C(Nc1ccc2c(c1)CCC2)Oc1ccc([N+](=O)[O-])cc1]

5-Aminoindan (212 mg, 1.59 mmol) was dissolved in CH$_2$Cl$_2$ (10 mL), p-nitrophenyl chloroformate (417 mg, 2.07 mmol) was added, and the reaction mixture was stirred at rt overnight. The solid was removed by filtration (discarded), and the filtrate was concentrated under reduced pressure. This gave the title compound as a grey solid which was about 50% pure and was used without further purification. LC-MS: RT=9.98 min, [M+H]$^+$=299.1.

Step 2. Synthesis of tert-butyl 4-(2,3-dihydro-1H-inden-5-ylcarbamoyl)-3-((pyridin-3-yloxy)methyl)piperazine-1-carboxylate

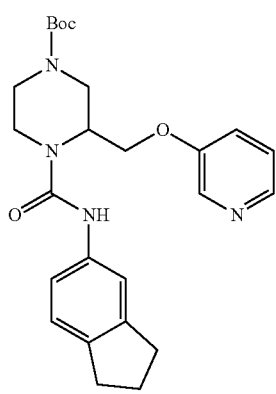 [SMILES: CC(C)(C)OC(=O)N1CCN(C(=O)Nc2ccc3c(c2)CCC3)C(COc2cccnc2)C1]

4-Nitrophenyl 2,3-dihydro-1H-inden-5-ylcarbamate (122 mg, 0.409 mmol), Intermediate C (100 mg, 0.341 mmol) and triethylamine (0.057 mL, 0.409 mmol) were stirred in CH$_2$Cl$_2$ (5 mL). After 2 h, the reaction mixture was concentrated under reduced pressure and purified by HPLC (10 to 90% MeCN/0.1% TFA in H$_2$O/0.1% TFA gradient). This gave 62.6 mg (32%) of the TFA salt of the title compound. LC-MS: RT=8.57 min, [M+H]$^+$=453.2.

Step 3. Synthesis of N-(2,3-dihydro-1H-inden-5-yl)-2-((pyridin-3-yloxy)methyl)piperazine-1-carboxamide dihydrochloride

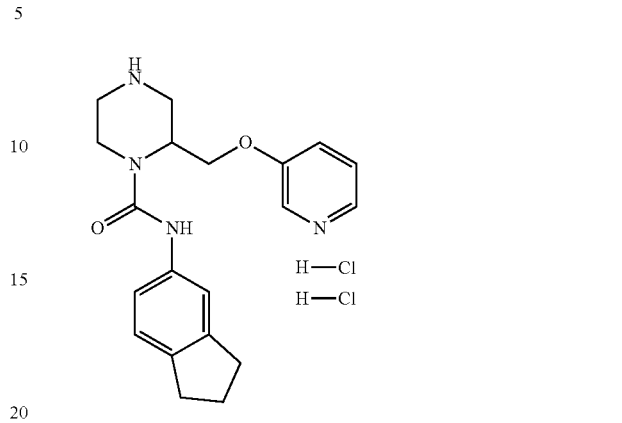

4 M HCl in 1,4-dioxane (6 mL, 24 mmol) was added to a solution of tert-butyl 4-(2,3-dihydro-1H-inden-5-ylcarbamoyl)-3-((pyridin-3-yloxy)methyl)piperazine-1-carboxylate TFA salt (62.6 mg, 0.110 mmol) in MeOH (1 mL). After 1 h, the reaction mixture was concentrated under reduced pressure and purified by HPLC (5 to 50% MeCN/0.1% TFA in H$_2$O/0.1% TFA gradient). The fractions containing the desired product were concentrated under reduced pressure. The material was dissolved in MeOH (1 mL) and treated with 4 M HCl in 1,4-dioxane (6 mL). The mixture was concentrated under reduced pressure to give 30.7 mg (65%) of the title compound. LC-MS: RT=4.79 min, [M+H]$^+$=353.2.

Examples 112-115

Examples 112-115 were prepared as described for Example 111, substituting the appropriate amines.

Example 112

N-(pyridin-3-yl)-2-((pyridin-3-yloxy)methyl)piperazine-1-carboxamide trihydrochloride LC-MS: RT=1.81 min, [M+H]$^+$=314.1.

Example 113

N-(4-morpholinophenyl)-2-((pyridin-3-yloxy)methyl)piperazine-1-carboxamide trihydrochloride LC-MS: RT=3.35 min, [M+H]$^+$=398.2.

Example 114

N-(2-fluoro-4-methylphenyl)-2-((pyridin-3-yloxy)methyl)piperazine-1-carboxamide dihydrochloride LC-MS: RT=3.93 min, [M+H]$^+$=345.1.

Example 115

N-(4-(methylsulfonyl)phenyl)-2-((pyridin-3-yloxy)methyl)piperazine-1-carboxamide dihydrochloride LC-MS: RT=1.64 min, [M+H]$^+$=391.1.

Example 116

N-(4-(methylcarbamoyl)phenyl)-2-((pyridin-3-yloxy)methyl)piperazine-1-carboxamide dihydrochloride

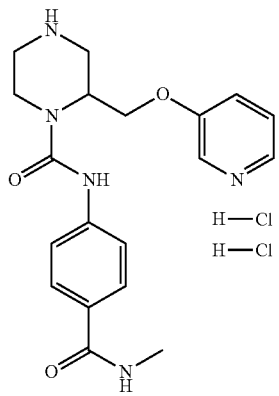

Step 1. Synthesis of tert-butyl 4-(4-(methoxycarbonyl)phenylcarbamoyl)-3-((pyridin-3-yloxy)methyl)piperazine-1-carboxylate

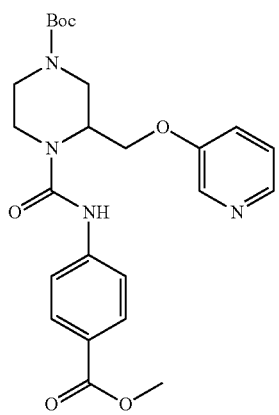 [SMILES: COC(=O)c1ccc(NC(=O)N2CCN(C(=O)OC(C)(C)C)CC2COc2cccnc2)cc1]

Methyl 4-isocyanatobenzoate (254 mg, 1.43 mmol) was added to a solution of Intermediate C (420 mg, 1.43 mmol) in CH$_2$Cl$_2$ (15 mL). After stirring overnight, the reaction mixture was concentrated under reduced pressure, and the material was purified by HPLC (10 to 90% MeCN/0.1% TFA in H$_2$O/0.1% TFA gradient). The desired fractions were brought to pH 12 with 1 N NaOH in H$_2$O and were extracted with EtOAc (3×). The combined organics were dried over Na$_2$SO$_4$, filtered, and concentrated under reduced pressure. This gave 601 mg (89%) of the title compound as a white solid. LC-MS: RT=7.65 min, [M+H]$^+$=471.2.

Step 2. Synthesis of 4-(4-(tert-butoxycarbonyl)-2-((pyridin-3-yloxy)methyl)piperazine-1-carboxamido)benzoic acid Lithium hydroxide (84 mg, 3.5 mmol) was added to a solution of tert-butyl 4-(4-(methoxycarbonyl)phenylcarbamoyl)-3-((pyridin-3-yloxy)methyl)piperazine-1-carboxylate (0.550 g, 1.17 mmol) in THF (5 mL), MeOH (5 mL), and H$_2$O (2.5 mL), and the reaction mixture was heated to 50° C. After 4 h, the reaction mixture was concentrated under reduced pressure. The material was purified by HPLC (10 to 90% MeCN/0.1% TFA in H$_2$O/0.1% TFA gradient), yielding 537 mg (81%) of the TFA salt of the title compound. LC-MS: RT=6.55 min, [M+H]$^+$=457.2.

Step 3. Synthesis of tert-butyl 4-(4-(methylcarbamoyl)phenylcarbamoyl)-3-((pyridin-3-yloxy)methyl)piperazine-1-carboxylate

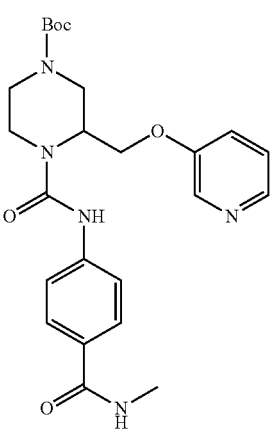 [SMILES: CNC(=O)c1ccc(NC(=O)N2CCN(C(=O)OC(C)(C)C)CC2COc2cccnc2)cc1]

Diisoproylcarbodiimide (0.037 mL, 0.24 mmol) was added to a solution of 4-(4-(tert-butoxycarbonyl)-2-((pyridin-3-yloxy)methyl)piperazine-1-carboxamido)benzoic acid TFA salt (123 mg, 0.215 mmol), methylamine hydrochloride (16 mg, 0.237 mmol), diisopropylethylamine (0.123 mL, 0.710 mmol), and N-hydroxybenzotriazole (32 mg, 0.237 mmol) in CH$_2$Cl$_2$ (2 mL) and DMF (0.5 mL). After stirring overnight, the reaction mixture was concentrated under reduced pressure and was purified by HPLC (10 to 90% MeCN/0.1% TFA in H$_2$O/0.1% TFA gradient). This gave 103 mg (82%) of the TFA salt of the title compound as a white solid. LC-MS: RT=5.99 min, [M+H]$^+$=470.2.

Step 4. Synthesis of N-(4-(methylcarbamoyl)phenyl)-2-((pyridin-3-yloxy)methyl)piperazine-1-carboxamide dihydrochloride

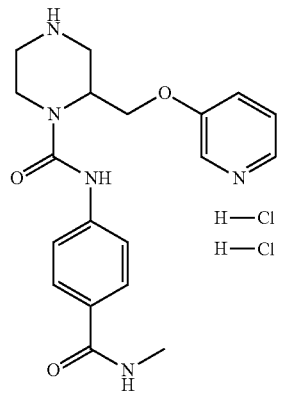

4 M HCl in 1,4-dioxane (6 mL, 24 mmol) was added to a solution of tert-butyl 4-(4-(methylcarbamoyl)phenylcarbamoyl)-3-((pyridin-3-yloxy)methyl)piperazine-1-carboxylate TFA salt (103 mg, 0.177 mmol) in MeOH (1 mL). After stirring overnight, the reaction mixture was concentrated under reduced pressure and purified by HPLC (5 to 50% MeCN/0.1% TFA in H$_2$O/0.1% TFA gradient). The fractions containing the desired product were concentrated under reduced pressure. The material was dissolved in MeOH (1 mL) and treated with 4 M HCl in 1,4-dioxane (6 mL). The mixture was concentrated under reduced pressure to give 42.8 mg (55%) of the title compound as a white solid. LC-MS: RT=2.22 min, [M+H]$^+$=370.1.

Examples 117-119

The examples shown in Table 14 below were prepared by similar methods as described for Example 116, substituting the appropriate amine. All reagents were commercially available unless otherwise noted. All compounds were isolated as the dihydrochloride salts unless otherwise noted.

TABLE 14

| Example No. | R | IUPAC Name | HPLC RT (min) | LC-MS [M + H]$^+$ |
|---|---|---|---|---|
| 117 | | N-(4-(dimethylcarbamoyl)phenyl)-2-((pyridin-3-yloxy)methyl)-piperazine-1-carboxamide dihydrochloride | 3.02 | 384.2 |
| 118 | | N-(4-(phenylcarbamoyl)phenyl)-2-((pyridin-3-yloxy)methyl)-piperazine-1-carboxamide dihydrochloride | 4.42 | 432.2 |
| 119 | | N-(4-(benzylcarbamoyl)phenyl)-2-((pyridin-3-yloxy)methyl)-piperazine-1-carboxamide dihydrochloride | 4.34 | 446.2 |

Example 120

N-(4-Hydroxyphenyl)-2-((pyridin-3-yloxy)methyl)piperazine-1-carboxamide dihydrochloride

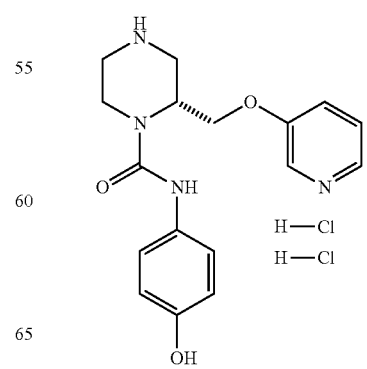

Step 1. Synthesis of (R)-tert-butyl 4-(4-(benzyloxy)phenylcarbamoyl)-3-((pyridin-3-yloxy)methyl)piperazine-1-carboxylate

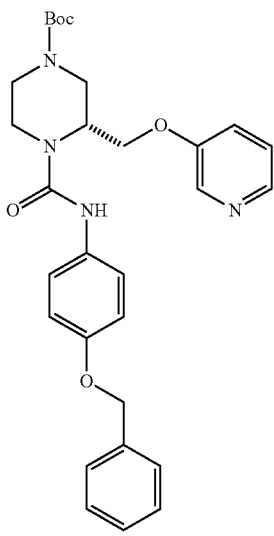 [SMILES: CC(C)(C)OC(=O)N1CCN(C(=O)Nc2ccc(OCc3ccccc3)cc2)[C@@H](COc2cccnc2)C1]

4-Benzyloxyphenyl isocyanate (131 mg, 0.579 mmol) was added to a solution of Intermediate C$_t$ (170 mg, 0.579 mmol) in CH$_2$Cl$_2$ (5 mL). After 1 h, the reaction mixture was concentrated under reduced pressure, and the material was purified by HPLC (10 to 90% MeCN/0.1% TFA in H$_2$O/0.1% TFA gradient). This gave 328 mg (90%) of the TFA salt of the title compound as a white solid. LC-MS: RT=8.92 min, [M+H]$^+$=519.3.

Step 2. Synthesis of (R)-tert-butyl 4-(4-hydroxyphenylcarbamoyl)-3-((pyridin-3-yloxy)methyl)piperazine-1-carboxylate

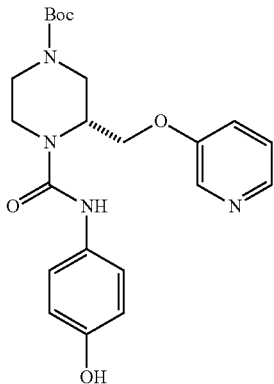 [SMILES: CC(C)(C)OC(=O)N1CCN(C(=O)Nc2ccc(O)cc2)[C@@H](COc2cccnc2)C1]

Ammonium formate (44 mg, 0.70 mmol) was added to a mixture of (R)-tert-butyl 4-(4-(benzyloxy)phenylcarbamoyl)-3-((pyridin-3-yloxy)methyl)piperazine-1-carboxylate TFA salt (220 mg, 0.348 mmol) and palladium hydroxide on carbon (~20% Pd, 20 mg, 0.028 mmol) in EtOH (5 mL). The reaction mixture was heated to 70° C. for 1 h. Upon cooling to rt, the reaction mixture was filtered though Celite®, and the filtrate was concentrated under reduced pressure. The material was purified by HPLC (10 to 90% MeCN/0.1% TFA in H$_2$O/0.1% TFA gradient), yielding 182 mg (97%) of the TFA salt of the title compound. LC-MS: RT=6.30 min, [M+H]$^+$=429.2.

Step 3. Synthesis of N-(4-hydroxyphenyl)-2-((pyridin-3-yloxy)methyl)piperazine-1-carboxamide dihydrochloride

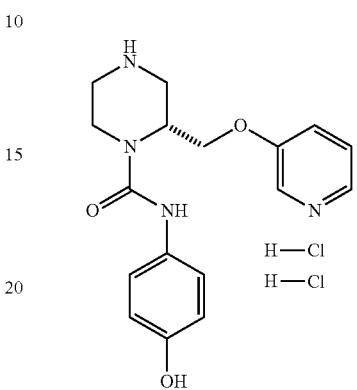

4 M HCl in 1,4-dioxane (6 mL, 24 mmol) was added to a solution of (R)-tert-butyl 4-(4-hydroxyphenylcarbamoyl)-3-((pyridin-3-yloxy)methyl)piperazine-1-carboxylate TFA salt (182 mg, 0.335 mmol) in MeOH (1 mL). After 1 h, the reaction mixture was concentrated under reduced pressure, yielding 118 mg (88%) of the title compound as a white solid. LC-MS: RT=2.11 min, [M+H]$^+$=329.1.

Example 121

Phenyl(2-((pyridin-3-yloxy)methyl)piperazin-1-yl)methanone dihydrochloride

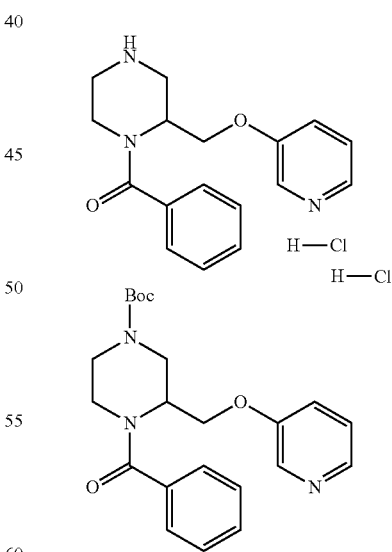

Step 1. Synthesis of tert-butyl 4-(benzoyl)-3-((pyridin-3-yloxy)methyl)piperazine-1-carboxylate Benzoyl chloride (36 mg, 0.26 mmol) was added to a solution of Intermediate C (72 mg, 0.25 mmol) in CH$_2$Cl$_2$ (4 mL). After 12 h, the reaction mixture was concentrated under reduced pressure, and the material was purified by HPLC (10 to 95% MeCN/0.1% TFA in H$_2$O/0.1% TFA gradient). This gave 89.5 mg (71%) of the TFA salt of the desired product as a white solid. LC-MS: RT=7.45 min, [M+H]$^+$=398.2.

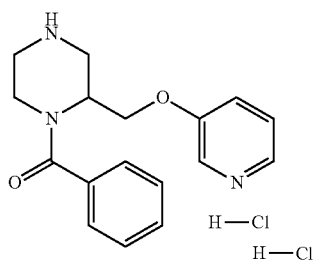

Step 2. Synthesis of phenyl(2-((pyridin-3-yloxy)methyl)piperazin-1-yl)methanone dihydrochloride 4 M HCl in 1,4-dioxane (6 mL, 24 mmol) was added to tert-butyl 4-(benzoyl)-3-((pyridin-3-yloxy)methyl)piperazine-1-carboxylate TFA salt (89.5 mg, 0.175 mmol). After 12 h, the reaction mixture was concentrated under reduced pressure, yielding 63.8 mg (98%) of the desired product as a white solid. LC-MS: RT=3.05 min, [M+H]$^+$=298.1.

Examples 122-137

The examples found in Table 15 below were prepared by similar methods as described for Example 121, substituting the appropriate acid chloride. All reagents were commercially available unless otherwise noted. All compounds were isolated as the dihydrochloride salts unless otherwise noted.

TABLE 15

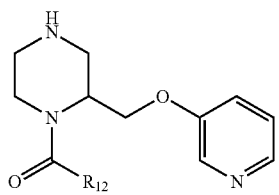

| Example No. | R$_{12}$ | IUPAC Name | HPLC RT (min) | LC-MS [M + H]$^+$ |
|---|---|---|---|---|
| 121 | 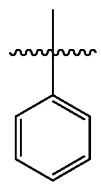 | phenyl(2-((pyridin-3-yloxy)methyl)piperazin-1-yl)methanone dihydrochloride | 3.05 | 298.1 |
| 122 | 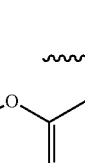 | (2-methoxyphenyl)(2-((pyridin-3-yloxy)methyl)piperazin-1-yl)methanone dihydrochloride | 4.59 | 328.1 |
| 123 | 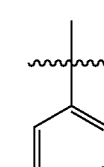 | (3-methoxyphenyl)(2-((pyridin-3-yloxy)methyl)piperazin-1-yl)methanone dihydrochloride | 4.49 | 328.1 |
| 124 |  | (3-chlorophenyl)(2-((pyridin-3-yloxy)methyl)piperazin-1-yl)methanone dihydrochloride | 5.66 | 332.1 |

TABLE 15-continued

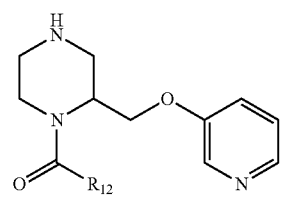

| Example No. | R$_{12}$ | IUPAC Name | HPLC RT (min) | LC-MS [M + H]$^+$ |
|---|---|---|---|---|
| 125 | 4-bromophenyl group | (4-bromophenyl)(2-((pyridin-3-yloxy)methyl)piperazin-1-yl)methanone dihydrochloride | 5.36 | 376.1 |
| 126 | 4-chlorophenyl group | (4-chlorophenyl)(2-((pyridin-3-yloxy)methyl)piperazin-1-yl)methanone dihydrochloride | 5.03 | 332.1 |
| 127 | 4-(trifluoromethoxy)phenyl group | (2-((pyridin-3-yloxy)methyl)piperazin-1-yl)(4-(trifluoromethoxy)phenyl)methanone dihydrochloride | 6.27 | 328.1 |
| 128 | 4-methoxyphenyl group | (4-methoxyphenyl)(2-((pyridin-3-yloxy)methyl)piperazin-1-yl)methanone dihydrochloride | 4.57 | 328.1 |
| 129 | 2,4-dimethoxyphenyl group | (2,4-dimethoxyphenyl)(2-((pyridin-3-yloxy)methyl)piperazin-1-yl)methanone dihydrochloride | 5.2 | 358.2 |

TABLE 15-continued

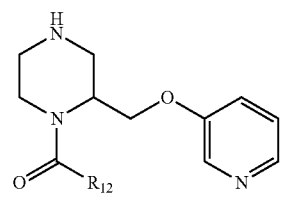

| Example No. | R₁₂ | IUPAC Name | HPLC RT (min) | LC-MS [M + H]⁺ |
|---|---|---|---|---|
| 130 | benzyl | 2-phenyl-1-(2-((pyridin-3-yloxy)methyl)piperazin-1-yl)ethanone dihydrochloride | 3.61 | 312.1 |
| 131 | 4-chlorobenzyl | 2-(4-chlorophenyl)-1-(2-((pyridin-3-yloxy)methyl)piperazin-1-yl)ethanone dihydrochloride | 4.28 | 346.1 |
| 132 | 4-methoxybenzyl | 2-(4-methoxyphenyl)-1-(2-((pyridin-3-yloxy)methyl)piperazin-1-yl)ethanone dihydrochloride | 3.71 | 342.1 |
| 133 | phenethyl | 3-phenyl-1-(2-((pyridin-3-yloxy)methyl)piperazin-1-yl)propan-1-one dihydrochloride | 4.01 | 326.2 |
| 134* | phenoxymethyl | 2-phenoxy-1-(2-((pyridin-3-yloxy)methyl)piperazin-1-yl)ethanone | 3.66 | 328.1 |

TABLE 15-continued

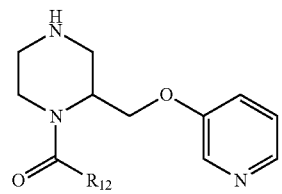

| Example No. | R₁₂ | IUPAC Name | HPLC RT (min) | LC-MS [M + H]⁺ |
|---|---|---|---|---|
| 135* | (4-chlorophenoxymethyl) | 2-(4-chlorophenoxy)-1-(2-((pyridin-3-yloxy)methyl)piperazin-1-yl)ethanone | 4.48 | 362.1 |
| 136 | (furan-2-yl) | furan-2-yl(2-((pyridin-3-yloxy)methyl)piperazin-1-yl)methanone dihydrochloride | 2.11 | 288.1 |
| 137 | (benzo[d]thiazol-2-yl) | benzo[d]thiazol-2-yl(2-((pyridin-3-yloxy)methyl)piperazin-1-yl)methanone dihydrochloride | 4.35 | 355.1 |

*Compounds were isolated following HPLC purification as the free bases.

Example 138

2-(4-Methoxyphenoxy)-1-(2-((pyridin-3-yloxy)methyl)piperazin-1-yl)ethanone

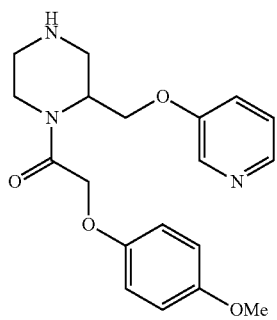 [SMILES: COc1ccc(OCC(=O)N2CCNCC2COc2cccnc2)cc1]

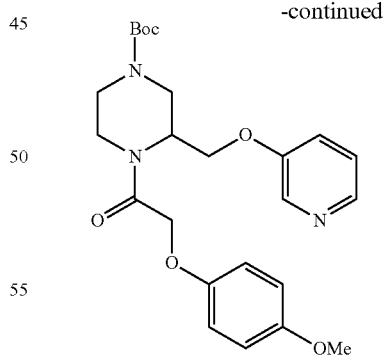

Step 1. Synthesis of tert-butyl 4-(2-(4-methoxyphenoxy)acetyl)-3-((pyridin-3-yloxy)methyl)piperazine-1-carboxylate N,N'-Diisopropylcarbodiimide (0.0526 mL, 0.336 mmol) was added to a mixture of Intermediate C (89.5 mg, 0.305 mmol), 4-methoxyphenoxyacetic acid (61.2 mg, 0.336 mmol), 1-hydroxybenzotriazole (45.4 mg, 0.336 mmol) and N,N-diisopropylethylamine (0.117 mL, 0.672 mmol) in CH₂Cl₂ (4 mL). After 12 h, the reaction mixture was diluted with EtOAc (15 mL), washed with 1 N NaOH (10 mL), H₂O (10 mL), and brine (10 mL), dried over Na₂SO₄, filtered, and concentrated under reduced pressure. The material was purified by HPLC (10 to 95% MeCN/0.1% TFA in H₂O/0.1% TFA gradient). This gave 182 mg (>100%) of the product as the TFA salt contaminated with minor impurities. LC-MS: RT=7.71 min, [M+H]⁺=458.2.

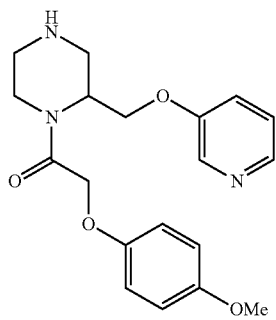

Step 2. Synthesis of 2-(4-Methoxyphenoxy)-1-(2-((pyridin-3-yloxy)methyl)piperazin-1-yl)ethanone 4 M HCl in 1,4-dioxane (6 mL, 24 mmol) was added to tert-butyl 4-(2-(4-methoxyphenoxy)acetyl)-3-((pyridin-3-yloxy)methyl)piperazine-1-carboxylate TFA salt (182 mg, ≤0.305 mmol). After 12 h, the reaction mixture was concentrated under reduced pressure and purified by HPLC (5 to 50% MeCN/0.1% TFA in H₂O/0.1% TFA gradient). The desired chomatography fractions were brought to pH ~12 with 1 N NaOH and were extracted with EtOAc (3×10 mL). The combined organics were dried over Na₂SO₄, filtered, and concentrated under reduced pressure, yielding 20.9 mg (19%) of the desired product as a thick oil. LC-MS: RT=3.76 min, [M+H]⁺=358.1.

Examples 139-143

The examples shown below in Table 16 were prepared by similar methods as described for Example 138, substituting the appropriate carboxylic acid. All reagents were commercially available unless otherwise noted. All compounds were isolated as the dihydrochloride salts unless otherwise noted.

TABLE 16

| Example No. | R₁₂ | IUPAC Name | HPLC RT (min) | LC-MS [M+H]⁺ |
|---|---|---|---|---|
| 139 | benzofuran-2-yl | benzofuran-2-yl(2-((pyridin-3-yloxy)methyl)piperazin-1-yl)methanone dihydrochloride | 4.08 | 338.1 |
| 140 | 1-phenyl-2-oxoethan-1-yl (phenylglyoxyl) | 1-phenyl-2-(2-((pyridin-3-yloxy)methyl)piperazin-1-yl)ethane-1,2-dione dihydrochloride | 3.83 | 326.1 |
| 141 | 1H-indol-2-yl | (1H-indol-2-yl)(2-((pyridin-3-yloxy)methyl)piperazin-1-yl)methanone dihydrochloride | 4.08 | 337.1 |
| 142 | 1H-indol-3-yl | (1H-indol-3-yl)(2-((pyridin-3-yloxy)methyl)piperazin-1-yl)methanone dihydrochloride | 3.17 | 337.1 |
| 143 | 1H-indol-5-yl | (1H-indol-5-yl)(2-((pyridin-3-yloxy)methyl)piperazin-1-yl)methanone dihydrochloride | 2.76 | 337.1 |

Example 144

(5-phenylfuran-2-yl)(2-((pyridin-3-yloxy)methyl)piperazin-1-yl)methanone dihydrochloride

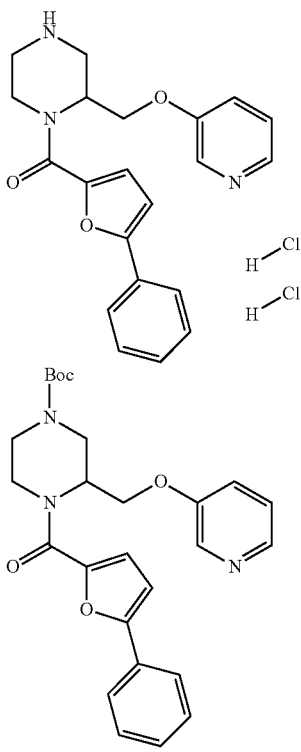

Step 1. Synthesis of tert-butyl 4-(5-phenylfuran-2-carbonyl)-3-((pyridin-3-yloxy)methyl)piperazine-1-carboxylate TBTU (169 mg, 0.527 mmol) was added to a solution of Intermediate C (82 mg, 0.28 mmol), 5-phenyl-2-furoic acid (66 mg, 0.35 mmol), and triethylamine (0.099 mL, 0.70 mmol) in DMF (2 mL). After stirring overnight, 1N NaOH (2 mL) was added, and the reaction mixture was stirred for 1 h. Additional 1N NaOH (4 mL) was added, and the reaction mixture was extracted with EtOAc (3×10 mL). The combined organics were dried over $Na_2SO_4$, filtered, and concentrated under reduced pressure. The material was purified by HPLC (10 to 90% MeCN/0.1% TFA in $H_2O$/0.1% TFA gradient). This gave 58.9 mg (36%) of the desired product as the TFA salt. LC-MS: RT=8.79 min, $[M+H]^+$=464.2.

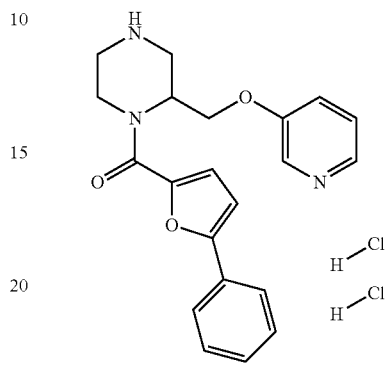

Step 2. Synthesis of (5-phenylfuran-2-yl)(2-((pyridin-3-yloxy)methyl)piperazin-1-yl)methanone dihydrochloride 4 M HCl in 1,4-dioxane (6 mL, 24 mmol) was added to tert-butyl 4-(5-phenylfuran-2-carbonyl)-3-((pyridin-3-yloxy)methyl)piperazine-1-carboxylate TFA salt (58.9 mg, 0.102 mmol). After 1 h, the reaction mixture was concentrated under reduced pressure, yielding 39.6 mg (89%) of the desired product as a white solid. LC-MS: RT=4.63 min, $[M+H]^+$=364.1.

Examples 145-156

The examples shown below in Table 17 were prepared by similar methods as described for Example 144, substituting the appropriate carboxylic acid. All reagents were commercially available unless otherwise noted. All compounds were isolated as the dihydrochloride salts unless otherwise noted.

TABLE 17

| Example No. | $R_{12}$ | IUPAC Name | HPLC RT (min) | LC-MS $[M + H]^+$ |
|---|---|---|---|---|
| 144 | | (5-phenylfuran-2-yl)(2-((pyridin-3-yloxy)methyl)piperazin-1-yl)methanone dihydrochloride | 4.63 | 364.1 |

TABLE 17-continued

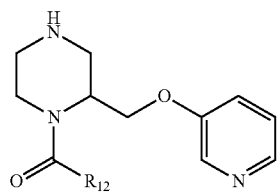

| Example No. | R₁₂ | IUPAC Name | HPLC RT (min) | LC-MS [M + H]⁺ |
|---|---|---|---|---|
| 145 | (2,4-dichlorophenyl-furan) | (5-(2,4-dichlorophenyl)furan-2-yl)(2-((pyridin-3-yloxy)methyl)piperazin-1-yl)methanone dihydrochloride | 5.34 | 432 |
| 146 | (2,5-dichlorophenyl-furan) | (5-(2,5-dichlorophenyl)furan-2-yl)(2-((pyridin-3-yloxy)methyl)piperazin-1-yl)methanone dihydrochloride | 5.32 | 432 |
| 147 | (4-chlorophenyl-furan) | (5-(4-chlorophenyl)furan-2-yl)(2-((pyridin-3-yloxy)methyl)piperazin-1-yl)methanone dihydrochloride | 5.04 | 398.1 |
| 148 | (4-methoxyphenyl-furan) | (5-(4-methoxyphenyl)furan-2-yl)(2-((pyridin-3-yloxy)methyl)piperazin-1-yl)methanone dihydrochloride | 4.54 | 394 |

TABLE 17-continued

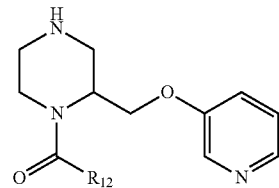

| Example No. | R₁₂ | IUPAC Name | HPLC RT (min) | LC-MS [M + H]⁺ |
|---|---|---|---|---|
| 149 | (furan with 4-bromophenyl) | (5-(4-bromophenyl)furan-2-yl)(2-((pyridin-3-yloxy)methyl)piperazin-1-yl)methanone dihydrochloride | 5.13 | 441.9 |
| 150 | (furan with p-tolyl) | (2-((pyridin-3-yloxy)methyl)piperazin-1-yl)(5-p-tolylfuran-2-yl)methanone dihydrochloride | 4.95 | 378 |
| 151 | (3-phenylisoxazol-5-yl) | (3-phenylisoxazol-5-yl)(2-((pyridin-3-yloxy)methyl)piperazin-1-yl)methanone dihydrochloride | 4.62 | 365.1 |
| 152 | (furan-3-yl) | furan-3-yl(2-((pyridin-3-yloxy)methyl)piperazin-1-yl)methanone dihydrochloride | 2.08 | 288.0 |
| 153 | (3-methylfuran-2-yl) | (3-methylfuran-2-yl)(2-((pyridin-3-yloxy)methyl)piperazin-1-yl)methanone dihydrochloride | 2.84 | 302.0 |

TABLE 17-continued

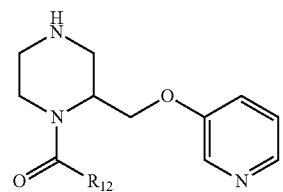

| Example No. | R₁₂ | IUPAC Name | HPLC RT (min) | LC-MS [M + H]⁺ |
|---|---|---|---|---|
| 154 | (5-methylisoxazol-3-yl group) | (5-methylisoxazol-3-yl)(2-((pyridin-3-yloxy)methyl)piperazin-1-yl)methanone dihydrochloride | 2.46 | 303.0 |
| 155 | (1-phenylcyclopropyl group) | (1-phenylcyclopropyl)(2-((pyridin-3-yloxy)methyl)piperazin-1-yl)methanone dihydrochloride | 3.93 | 338.0 |
| 156 | (biphenyl-2-yl group) | biphenyl-2-yl(2-((pyridin-3-yloxy)methyl)piperazin-1-yl)methanone dihydrochloride | 4.30 | 374.6 |

Examples 157-159

The examples shown below in Table 18 were prepared by similar methods as described for Example 144, substituting the appropriate carboxylic acid and Intermediate $C_i$ for Intermediate C. All reagents were commercially available unless otherwise noted. All compounds were isolated as the dihydrochloride salts unless otherwise noted.

TABLE 18

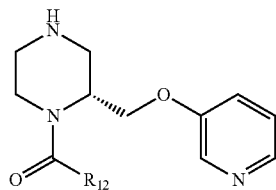

| Example No. | R₁₂ | IUPAC Name | HPLC RT (min) | LC-MS [M + H]⁺ |
|---|---|---|---|---|
| 157 | (5-phenylfuran-2-yl group) | (R)-(5-phenylfuran-2-yl)(2-((pyridin-3-yloxy)methyl)piperazin-1-yl)methanone dihydrochloride | 4.55 | 364.0 |

TABLE 18-continued

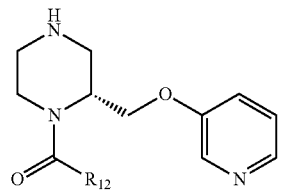

| Example No. | R$_{12}$ | IUPAC Name | HPLC RT (min) | LC-MS [M + H]$^+$ |
|---|---|---|---|---|
| 158 | | (R)-(5-(4-methoxyphenyl)furan-2-yl)(2-((pyridin-3-yloxy)methyl)piperazin-1-yl)methanone dihydrochloride | 4.56 | 394.0 |
| 159 | | (R)-(5-bromofuran-2-yl)(2-((pyridin-3-yloxy)methyl)piperazin-1-yl)methanone dihydrochloride | 4.23 | 365.8 |

Examples 160-161

The examples shown below in Table 19 were prepared by similar methods as described for Example 144, substituting the appropriate carboxylic acid and Intermediate C$_{ii}$ for Intermediate C. All reagents were commercially available unless otherwise noted. All compounds were isolated as the dihydrochloride salts unless otherwise noted.

TABLE 19

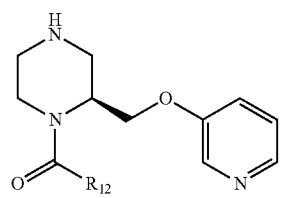

| Example No. | R$_{12}$ | IUPAC Name | HPLC RT (min) | LC-MS [M + H]$^+$ |
|---|---|---|---|---|
| 160 | | (S)-(5-phenylfuran-2-yl)(2-((pyridin-3-yloxy)methyl)piperazin-1-yl)methanone dihydrochloride | 4.56 | 364.0 |

TABLE 19-continued

| Example No. | R₁₂ | IUPAC Name | HPLC RT (min) | LC-MS [M + H]⁺ |
|---|---|---|---|---|
| 161 | | (S)-(5-(4-methoxyphenyl)furan-2-yl)(2-((pyridin-3-yloxy)methyl)piperazin-1-yl)methanone dihydrochloride | 4.61 | 394.0 |

Example 162

(5-Bromothiophen-2-yl)(2-((pyridin-3-yloxy)methyl)piperazin-1-yl)methanone dihydrochloride

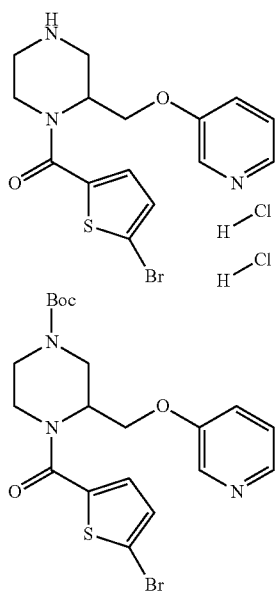

Step 1. Synthesis of tert-butyl 4-(5-bromothiophene-2-carbonyl)-3-((pyridin-3-yloxy)methyl)piperazine-1-carboxylate N,N'-Diisopropylcarbodiimide (0.189 mL, 1.21 mmol) was added to a mixture of Intermediate C (322 mg, 1.10 mmol), 5-bromo-2-thiophenecarboxylic acid (250 mg, 1.21 mmol), 1-hydroxybenzotriazole (163 mg, 1.21 mmol) and N,N-diisopropylethylamine (0.421 mL, 2.42 mmol) in CH₂Cl₂ (10 mL). After stirring overnight, TBTU (353 mg, 1.10 mmol) was added and stirring was continued overnight. The reaction mixture was filtered, concentrated under reduced pressure, and purified by HPLC (10 to 90% MeCN/0.1% TFA in H₂O/0.1% TFA gradient). The desired chromatography fractions were brought to pH ~12 with 1 N NaOH and were extracted with EtOAc (3×). The combined organics were dried over Na₂SO₄, filtered, and concentrated under reduced pressure. This gave 436 mg (82%) of an off-white solid that was ~80% pure by HPLC. LC-MS: RT=8.58 min, [M+H]⁺=482.2.

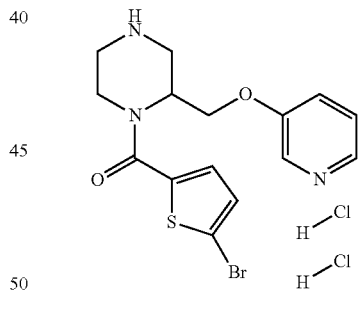

Step 2. Synthesis of (5-bromothiophen-2-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(5-bromothiophene-2-carbonyl)-3-((pyridin-3-yloxy)methyl)piperazine-1-carboxylate (192.6 mg, 0.399 mmol) in MeOH (1 mL). After 1 h, the reaction mixture was concentrated under reduced pressure and purified by HPLC (5 to 50% MeCN/0.1% TFA in H₂O/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 108 mg (59%) of the desired product as a white solid. LC-MS: RT=4.16 min, [M+H]⁺=382.0.

Example 163

(5-Bromofuran-2-yl)(2-((pyridin-3-yloxy)methyl)piperazin-1-yl)methanone dihydrochloride

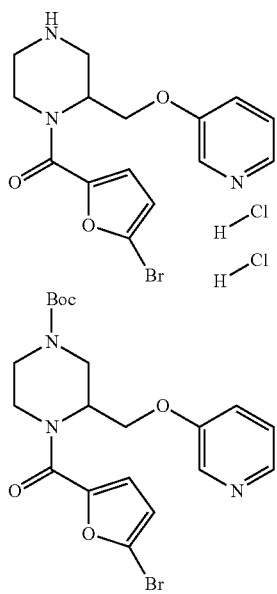

Step 1. Synthesis of tert-butyl 4-(5-bromofuran-2-carbonyl)-3-((pyridin-3-yloxy)methyl)piperazine-1-carboxylate N,N'-Diisopropylcarbodiimide (0.142 mL, 0.910 mmol) was added to a mixture of Intermediate C (243 mg, 0.827 mmol), 5-bromo-2-furoic acid (174 mg, 0.910 mmol), 1-hydroxybenzotriazole (123 mg, 0.910 mmol) and N,N-diisopropylethylamine (0.317 mL, 1.82 mmol) in CH$_2$Cl$_2$ (10 mL). After stirring overnight, TBTU (265 mg, 0.827 mmol) was added and stirring was continued overnight. The reaction mixture was filtered, concentrated under reduced pressure, and purified by HPLC (10 to 90% MeCN/0.1% TFA in H$_2$O/ 0.1% TFA gradient). The desired chromatography fractions were brought to pH ~12 with 1 N NaOH and were extracted with EtOAc (3×). The combined organics were dried over Na$_2$SO$_4$, filtered, and concentrated under reduced pressure. This gave 304 mg (79%) of an off-white solid that was ~92% pure by HPLC. LC-MS: RT=7.97 min, [M+H]$^+$=466.2.

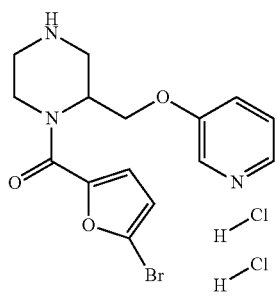

Step 2. Synthesis of (5-bromofuran-2-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(5-bromofuran-2-carbonyl)-3-((pyridin-3-yloxy)methyl)piperazine-1-carboxylate (75 mg, 0.16 mmol) in MeOH (1 mL). After stirring overnight, the reaction mixture was concentrated under reduced pressure and purified by HPLC (5 to 50% MeCN/0.1% TFA in H$_2$O/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 66 mg (94%) of the desired product as a white solid. LC-MS: RT=3.54 min, [M+H]$^+$=366.0.

Example 164

(5-(2-Chlorophenyl)thiophen-2-yl)(2-((pyridin-3-yloxy)methyl)piperazin-1-yl)methanone dihydrochloride

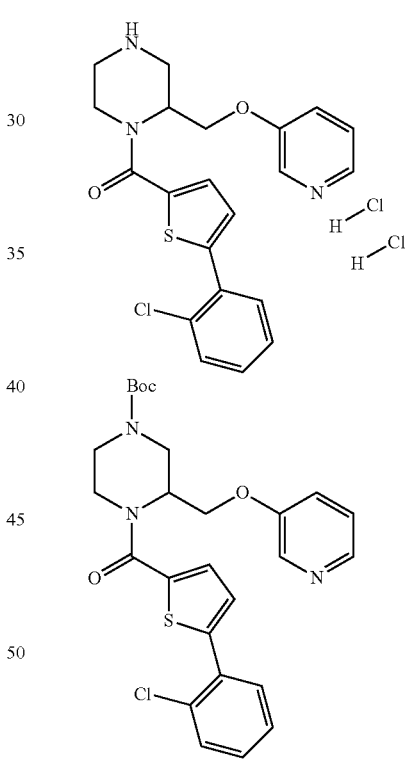

Step 1. tert-butyl 4-(5-(2-chlorophenyl)thiophene-2-carbonyl)-3-((pyridin-3-yloxy)methyl)piperazine-1-carboxylate

[1,1'-bis(diphenylphosphino)ferrocene]-dichloropalladium(II) complex with dichloromethane (1:1) (7 mg, 0.008 mmol) was added to a mixture of tert-butyl 4-(5-bromothiophene-2-carbonyl)-3-((pyridin-3-yloxy)methyl)piperazine-1-carboxylate (79 mg, 0.16 mmol), 2-chlorobenzeneboronic acid (51 mg, 0.33 mmol) and sodium carbonate (35 mg, 0.33 mmol) in toluene (4 mL), 1,4-dioxane (1 mL), and water (1 mL). The reaction mixture was heated to 80° C. for 2 h. Upon cooling to room temperature, the reaction mixture was filtered, concentrated under reduced pressure, and purified by HPLC (10 to 90% MeCN/0.1% TFA in H$_2$O/0.1% TFA gradient). This gave 75.9 mg (74%, ~60% pure) of the TFA salt of the desired product. LC-MS: RT=9.60 min, [M+H]$^+$=514.2.

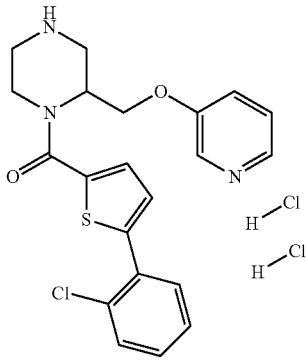

Step 2. Synthesis of (5-(2-chlorophenyl)thiophen-2-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(5-(2-chlorophenyl)thiophene-2-carbonyl)-3-((pyridin-3-yloxy)methyl)piperazine-1-carboxylate TFA salt (75.9 mg, 0.121 mmol) in MeOH (1 mL). After 1 h, the reaction mixture was concentrated under reduced pressure and purified by HPLC (5 to 50% MeCN/0.1% TFA in H$_2$O/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 23.8 mg (40%) of the desired product as a white solid. LC-MS: RT=5.27 min, [M+H]$^+$=414.1.

Example 165

(5-(2-Chlorophenyl)furan-2-yl)(2-((pyridin-3-yloxy)methyl)piperazin-1-yl)methanone dihydrochloride

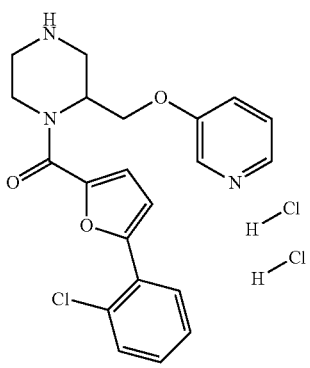

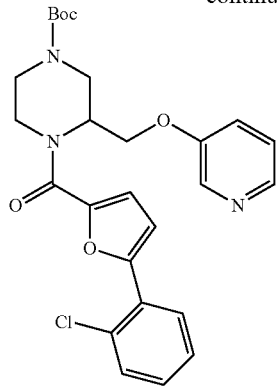

Step 1. Synthesis tert-butyl 4-(5-(2-chlorophenyl)furan-2-carbonyl)-3-((pyridin-3-yloxy)methyl)piperazine-1-carboxylate

[1,1'-bis(diphenylphosphino)ferrocene]-dichloropalladium(II) complex with dichloromethane (1:1) (7 mg, 0.008 mmol) was added to a mixture of tert-butyl 4-(5-bromofuran-2-carbonyl)-3-((pyridin-3-yloxy)methyl)piperazine-1-carboxylate (75 mg, 0.16 mmol), 2-chlorobenzeneboronic acid (50 mg, 0.32 mmol) and sodium carbonate (34 mg, 0.32 mmol) in toluene (4 mL), 1,4-dioxane (1 mL), and water (1 mL). The reaction mixture was heated to 80° C. for 2 h. Upon cooling to room temperature, the reaction mixture was filtered, concentrated under reduced pressure, and purified by HPLC (10 to 90% MeCN/0.1% TFA in H$_2$O/0.1% TFA gradient). This gave 66.6 mg (68%, ~85% pure) of the TFA salt of the desired product. LC-MS: RT=10.08 min, [M+H]$^+$=498.2.

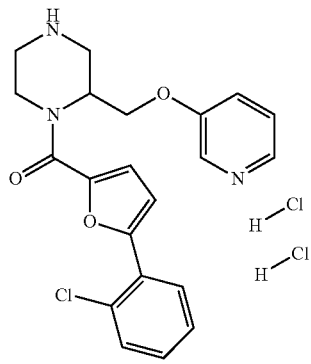

Step 2. Synthesis of (5-(2-chlorophenyl)furan-2-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(5-(2-chlorophenyl)furan-2-carbonyl)-3-((pyridin-3-yloxy)methyl)piperazine-1-carboxylate TFA salt (66.6 mg, 0.109 mmol) in MeOH (1 mL). After 1 h, the reaction mixture was concentrated under reduced pressure and purified by HPLC (5 to 50% MeCN/0.1% TFA in H$_2$O/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 30 mg (59%) of the desired product as a white solid. LC-MS: RT=5.00 min, [M+H]$^+$=398.1.

Examples 166-175

The examples shown below in Table 20 were prepared by similar methods as described for Examples 164 and 165, substituting the appropriate boronic acid. All reagents were commercially available unless otherwise noted. All compounds were isolated as the dihydrochloride salts unless otherwise noted.

TABLE 20

| Example No. | W | $R_d$ | IUPAC Name | HPLC RT (min) | LC-MS [M + H]$^+$ |
|---|---|---|---|---|---|
| 164 | S | 2-chlorophenyl | (5-(2-chlorophenyl)thiophen-2-yl)(2-((pyridin-3-yloxy)methyl)piperazin-1-yl)methanone dihydrochloride | 5.27 | 414.1 |
| 165 | O | 2-chlorophenyl | (5-(2-chlorophenyl)furan-2-yl)(2-((pyridin-3-yloxy)methyl)piperazin-1-yl)methanone dihydrochloride | 5 | 398.1 |
| 166 | S | phenyl | (5-phenylthiophen-2-yl)(2-((pyridin-3-yloxy)methyl)piperazin-1-yl)methanone dihydrochloride | 4.9 | 380.1 |
| 167 | S | 3-chlorophenyl | (5-(3-chlorophenyl)thiophen-2-yl)(2-((pyridin-3-yloxy)methyl)piperazin-1-yl)methanone dihydrochloride | 5.39 | 414 |
| 168 | O | 2-methylphenyl | (2-((pyridin-3-yloxy)methyl)piperazin-1-yl)(5-o-tolylfuran-2-yl)methanone dihydrochloride | 4.86 | 378.1 |
| 169 | O | 2-methoxyphenyl | (5-(2-methoxyphenyl)furan-2-yl)(2-((pyridin-3-yloxy)methyl)piperazin-1-yl)methanone dihydrochloride | 4.76 | 394.1 |

TABLE 20-continued

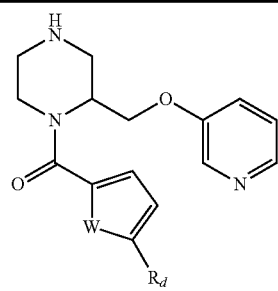

| Example No. | W | $R_d$ | IUPAC Name | HPLC RT (min) | LC-MS $[M + H]^+$ |
|---|---|---|---|---|---|
| 170 | O | 3-methoxyphenyl | (5-(3-methoxyphenyl)furan-2-yl)(2-((pyridin-3-yloxy)methyl)piperazin-1-yl)methanone dihydrochloride | 4.66 | 394.0 |
| 171 | O | 4-(trifluoromethoxy)phenyl | (2-((pyridin-3-yloxy)methyl)piperazin-1-yl)(5-(4-(trifluoromethoxy)phenyl)furan-2-yl)methanone dihydrochloride | 5.52 | 448.0 |
| 172 | O | 4-(trifluoromethyl)phenyl | (2-((pyridin-3-yloxy)methyl)piperazin-1-yl)(5-(4-(trifluoromethyl)phenyl)furan-2-yl)methanone dihydrochloride | 5.32 | 432.0 |
| 173 | O | 4-isopropoxyphenyl | (5-(4-isopropoxyphenyl)furan-2-yl)(2-((pyridin-3-yloxy)methyl)piperazin-1-yl)methanone dihydrochloride | 5.27 | 422.1 |
| 174 | O | 4-fluorophenyl | (5-(4-fluorophenyl)furan-2-yl)(2-((pyridin-3-yloxy)methyl)piperazin-1-yl)methanone dihydrochloride | 4.61 | 382.0 |

TABLE 20-continued

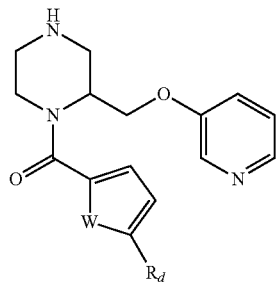

| Example No. | W | R_d | IUPAC Name | HPLC RT (min) | LC-MS [M + H]+ |
|---|---|---|---|---|---|
| 175 | O | 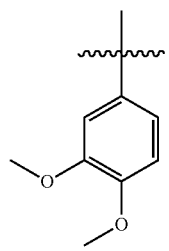 [SMILES: *c1ccc(OC)c(OC)c1] | (5-(3,4-dimethoxyphenyl)furan-2-yl)(2-((pyridin-3-yloxy)methyl)piperazin-1-yl)methanone dihydrochloride | 4.37 | 424.0 |

Example 176

Example 176 was prepared as described for Example 171, substituting Intermediate $C_i$ for Intermediate C.

Example 176

(R)-(2-((pyridin-3-yloxy)methyl)piperazin-1-yl)(5-(4-(trifluoromethoxy)phenyl)furan-2-yl)methanone dihydrochloride LC-MS: RT=5.87 min, [M+H]+=448.1.

Example 177

(2-chlorothiazol-4-yl)(2-((pyridin-3-yloxy)methyl)piperazin-1-yl)methanone dihydrochloride

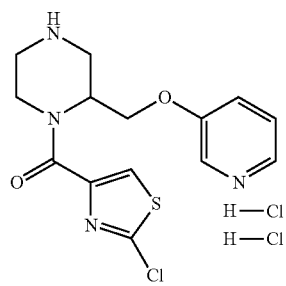

Step 1. Synthesis of 2-chlorothiazole-4-carboxylic acid

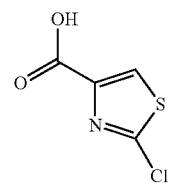

Thiourea (3.69 g, 48.5 mmol) was added to a solution of ethyl bromopyruvate (10 g, 46 mmol) in EtOH (92 mL), and the reaction mixture was heated to 80° C. for 1 h. Upon cooling to rt, the reaction mixture was concentrated under reduced pressure. The resulting solid was dissolved in ice water (100 mL) and brought to pH ~8 with solid $K_2CO_3$. The resulting solid was filtered, washed with water (3×) and air dried. This gave 7.64 g (96%) of a yellow solid that was used without further purification. LC-MS: RT=4.85 min, [M+H]+=173.0.

The solid (7.64 g, 44.4 mmol) was added portionwise to a 60° C. solution of Copper(II) chloride (7.46 g, 55.5 mmol) and t-butyl nitrite (8.2 mL, 66.6 mmol) in acetonitrile (175 mL) while maintaining the reaction temperature between 60 and 65° C. After complete addition, the reaction mixture was heated to 80° C. for 1 h. Upon cooling to rt, the reaction mixture was poured into a mixture of $CH_2Cl_2$ (150 mL), water (150 mL), and HCl (conc., 10 mL). The organics were separated and the aqueous layer was extracted with $CH_2Cl_2$ (2×100 mL). The combined organics were washed with brine (300 mL), dried over $Na_2SO_4$, filtered, and concentrated under reduced pressure. The resulting material was dissolved in EtOH (100 mL) and NaOH (2.13 g, 53.3 mmol) was added followed by water (50 mL). After stirring overnight at rt, the ethanol was removed under reduced pressure and the reaction mixture was diluted with water (50 mL). The mixture was washed with Et₂O (50 mL, discarded) and brought to pH ~2 with conc. HCl. The resulting solid was collected by filtration, washed with water (3×) and dried. This gave 4.73 g (63%) of the title compound as a yellow solid. LC-MS: RT=4.35 min, [M+H]⁺=163.9.

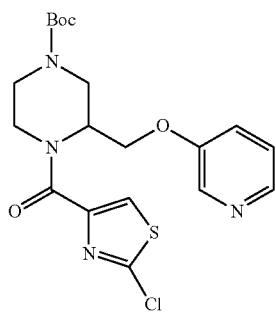 [SMILES: CC(C)(C)OC(=O)N1CCN(C(=O)c2csc(Cl)n2)C(COc2cccnc2)C1]

Step 2. Synthesis of tert-butyl 4-(2-chlorothiazole-4-carbonyl)-3-((pyridin-3-yloxy)methyl)piperazine-1-carboxylate TBTU (592 mg, 1.85 mmol) was added to a solution of Intermediate C (361 mg, 1.23 mmol), 2-chlorothiazole-4-carboxylic acid (221 mg, 1.35 mmol), and triethylamine (0.35 mL, 2.46 mmol) in DMF (4 mL). After stirring overnight, 1N NaOH (2 mL) was added, and the reaction mixture was stirred for 1 h. The reaction mixture was diluted with EtOAc (30 mL) and washed with 1N NaOH (2×20 mL) and brine (20 mL). The organics were dried over Na₂SO₄, filtered, and concentrated under reduced pressure. The material was purified by column chromatography (50 to 70% EtOAc in hexanes gradient), yielding 429.2 mg (79%) of the desired product as a white solid. LC-MS: RT=7.57 min, [M+H]⁺=438.9.

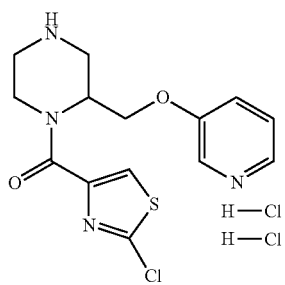

Step 3. Synthesis of (2-chlorothiazol-4-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(2-chlorothiazole-4-carbonyl)-3-((pyridin-3-yloxy)methyl)piperazine-1-carboxylate (36 mg, 0.083 mmol) in MeOH (1 mL). After stirring overnight, the reaction mixture was concentrated under reduced pressure, yielding 33.8 mg (99%) of the desired product as a white solid. LC-MS: RT=3.12 min, (M+H)⁺=338.9.

Example 178

(2-phenylthiazol-4-yl)(2-((pyridin-3-yloxy)methyl)piperazin-1-yl)methanone dihydrochloride

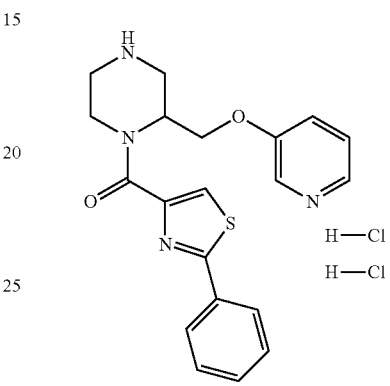

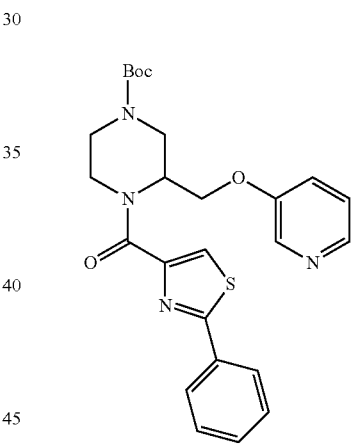

Step 1. Synthesis of tert-butyl 4-(2-phenylthiazole-4-carbonyl)-3-((pyridin-3-yloxy)methyl)piperazine-1-carboxylate

[1,1'-bis(diphenylphosphino)ferrocene]-dichloropalladium(II) complex with dichloromethane (1:1) (7 mg, 0.009 mmol) was added to a mixture of tert-butyl 4-(2-chlorothiazole-4-carbonyl)-3-((pyridin-3-yloxy)methyl)piperazine-1-carboxylate (77 mg, 0.18 mmol), benzeneboronic acid (43 mg, 0.35 mmol) and sodium carbonate (37 mg, 0.35 mmol) in toluene (4 mL), 1,4-dioxane (1 mL), and water (1 mL). The reaction mixture was heated to 80° C. overnight. Upon cooling to room temperature, the reaction mixture was filtered through Celite®, concentrated under reduced pressure, and purified by HPLC (10 to 90% MeCN/0.1% TFA in H₂O/0.1% TFA gradient). This gave 74.9 mg (72%) of the TFA salt of the desired product. LC-MS: RT=8.74 min, [M+H]⁺=481.0.

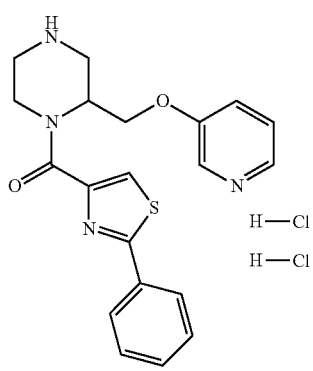

Step 2. Synthesis of (2-phenylthiazol-4-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(2-phenylthiazole-4-carbonyl)-3-((pyridin-3-yloxy)methyl)piperazine-1-carboxylate TFA salt (74.9 mg, 0.126 mmol) in MeOH (1 mL). After stirring overnight, the reaction mixture was concentrated under reduced pressure and purified by HPLC (5 to 50% MeCN/0.1% TFA in $H_2O$/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 40.4 mg (71%) of the desired product as a white solid. LC-MS: RT=4.45 min, $[M+H]^+$=381.0.

Examples 179-182

The examples shown below in Table 21 were prepared by similar methods as described for Example 178, substituting the appropriate boronic acid. All reagents were commercially available unless otherwise noted. All compounds were isolated as the dihydrochloride salts unless otherwise noted.

TABLE 21

| Example No. | $R_d$ | IUPAC Name | HPLC RT (min) | LC-MS $[M + H]^+$ |
|---|---|---|---|---|
| 178 | H | (2-phenylthiazol-4-yl)(2-((pyridin-3-yloxy)methyl)piperazin-1-yl)methanone dihydrochloride | 4.45 | 381.0 |
| 179 | F | (2-(4-fluorophenyl)thiazol-4-yl)(2-((pyridin-3-yloxy)methyl)piperazin-1-yl)methanone dihydrochloride | 4.63 | 398.9 |
| 180 | OMe | (2-(4-methoxyphenyl)thiazol-4-yl)(2-((pyridin-3-yloxy)methyl)piperazin-1-yl)methanone dihydrochloride | 4.60 | 411.0 |
| 181 | $CH_3$ | (2-((pyridin-3-yloxy)methyl)piperazin-1-yl)(2-p-tolylthiazol-4-yl)methanone dihydrochloride | 4.89 | 395.0 |
| 182 | $OCF_3$ | (2-((pyridin-3-yloxy)methyl)piperazin-1-yl)(2-(4-(trifluoromethoxy)phenyl)thiazol-4-yl)methanone dihydrochloride | 5.47 | 464.9 |

Example 183

(2-phenyloxazol-4-yl)(2-((pyridin-3-yloxy)methyl)piperazin-1-yl)methanone dihydrochloride

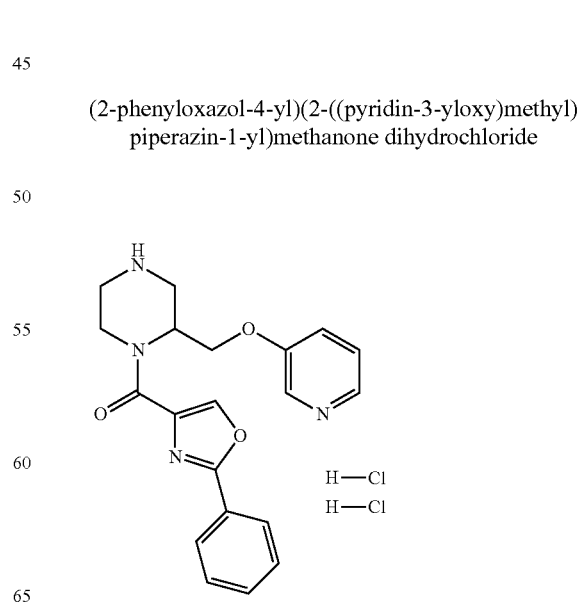

Step 1. Synthesis of 2-chlorooxazole-4-carboxylic acid

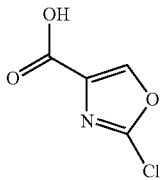

Urea (2.91 g, 48.5 mmol) was added to a solution of ethyl bromopyruvate (10 g, 46 mmol) in EtOH (90 mL), and the reaction mixture was heated to reflux for 2 h. Upon cooling to rt, the reaction mixture was concentrated under reduced pressure. The resulting thick oil was dissolved in ice water (100 mL) and brought to pH ~8 with solid $K_2CO_3$. The resulting solid was filtered, washed with water (2×) and air dried. This gave 3.16 g (44%) of a white solid that was used without further purification. LC-MS: RT=4.47 min, $[M+H]^+$=157.0.

The solid (3.16 g, 20.2 mmol) was added portionwise to a 60° C. solution of Copper(II) chloride (3.40 g, 25.3 mmol) and t-butyl nitrite (3.13 mL, 25.3 mmol) in acetonitrile (100 mL) while maintaining the reaction temperature between 60 and 65° C. After complete addition, the reaction mixture was heated to 80° C. for 1 h. Upon cooling to rt, the reaction mixture was poured into a mixture of $CH_2Cl_2$ (150 mL), water (150 mL), and HCl (conc., 10 mL). The organics were separated and the aqueous layer was extracted with $CH_2Cl_2$ (2×100 mL). The combined organics were washed with brine (300 mL), dried over $Na_2SO_4$, filtered, and concentrated under reduced pressure. The resulting material was dissolved in EtOH (50 mL) and water (25 mL), and NaOH (0.972 g, 24.3 mmol) was added. After stirring overnight at rt, the ethanol was removed under reduced pressure and the reaction mixture was diluted with water (100 mL). The mixture was washed with $Et_2O$ (50 mL, discarded) and brought to pH ~2 with conc. HCl. The aqueous solution was extracted with EtOAc (3×150 mL). The combined organics were dried over $Na_2SO_4$, filtered, and concentrated under reduced pressure. This gave 2.12 g (31%) of the title compound as a yellow solid. LC-MS: RT=3.51 min, $[M+H]^+$=147.9.

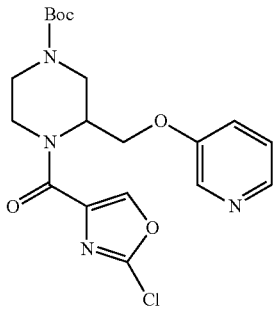

Step 2. Synthesis of tert-butyl 4-(2-chlorooxazole-4-carbonyl)-3-((pyridin-3-yloxy)methyl)piperazine-1-carboxylate TBTU (702 mg, 2.19 mmol) was added to a solution of Intermediate C (428 mg, 1.46 mmol), 2-chlorooxazole-4-carboxylic acid (237 mg, 1.61 mmol), and triethylamine (0.410 mL, 2.92 mmol) in DMF (5 mL). After stirring overnight, 1N NaOH (2 mL) was added, and the reaction mixture was stirred for 1 h. The reaction mixture was diluted with EtOAc (50 mL) and washed with 1N NaOH (2×20 mL) and brine (20 mL). The organics were dried over $Na_2SO_4$, filtered, and concentrated under reduced pressure. The material was purified by HPLC (10 to 90% MeCN/0.1% TFA in $H_2O$/0.1% TFA gradient). The fractions containing the desired material were combined, brought to pH ~12 with 1N NaOH, and extracted with EtOAc (3×). The combined organics were dried over $Na_2SO_4$, filtered, and concentrated under reduced pressure, yielding 139 mg (23%) of the desired product as a white solid. LC-MS: RT=7.33 min, $[M+H]^+$=422.9.

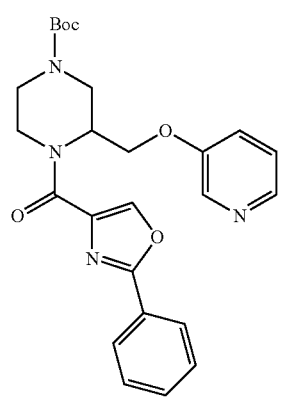 [SMILES: CC(C)(C)OC(=O)N1CCN(C(=O)c2coc(-c3ccccc3)n2)C(COc2cccnc2)C1]

Step 3. Synthesis tert-butyl 4-(2-phenyloxazole-4-carbonyl)-3-((pyridin-3-yloxy)methyl)piperazine-1-carboxylate

[1,1'-bis(diphenylphosphino)ferrocene]-dichloropalladium(II) complex with dichloromethane (1:1) (6.7 mg, 0.0082 mmol) was added to a mixture of tert-butyl 4-(2-chlorooxazole-4-carbonyl)-3-((pyridin-3-yloxy)methyl)piperazine-1-carboxylate (69.5 mg, 0.164 mmol), benzeneboronic acid (40 mg, 0.33 mmol) and sodium carbonate (35 mg, 0.33 mmol) in toluene (4 mL), 1,4-dioxane (1 mL), and water (1 mL). The reaction mixture was heated to 80° C. overnight. Upon cooling to room temperature, the reaction mixture was filtered through Celite®, concentrated under reduced pressure, and purified by HPLC (10 to 90% MeCN/0.1% TFA in $H_2O$/0.1% TFA gradient). This gave 44.8 mg (47%) of the TFA salt of the desired product. LC-MS: RT=8.49 min, $[M+H]^+$=465.0.

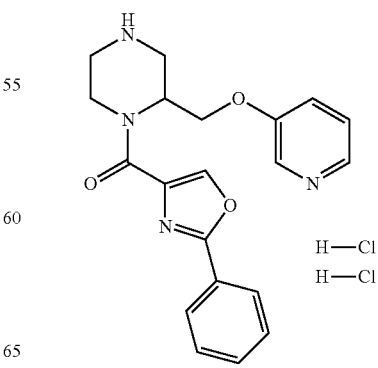

Step 4. Synthesis of (2-phenyloxazol-4-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(2-phenyloxazole-4-carbonyl)-3-((pyridin-3-yloxy)methyl)piperazine-1-carboxylate TFA salt (44.8 mg, 0.077 mmol) in MeOH (1 mL). After stirring overnight, the reaction mixture was concentrated under reduced pressure and purified by HPLC (5 to 50% MeCN/0.1% TFA in $H_2O$/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 22.6 mg (67%) of the desired product as a white solid. LC-MS: RT=4.36 min, $[M+H]^+$=365.0.

Examples 184-192

The examples shown below in Table 22 were prepared by similar methods as described for Example 183, substituting the appropriate boronic acid. All reagents were commercially available unless otherwise noted. All compounds were isolated as the dihydrochloride salts unless otherwise noted.

TABLE 22

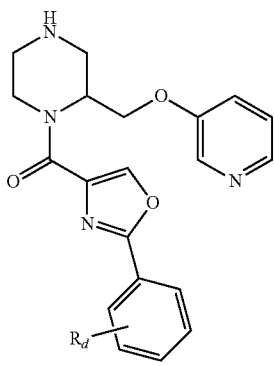

| Example No. | $R_d$ | IUPAC Name | HPLC RT (min) | LC-MS $(M + H)^+$ |
|---|---|---|---|---|
| 183 | H | (2-phenyloxazol-2-yl)(2-((pyridin-3-yloxy)methyl)piperazin-1-yl)methanone dihydrochloride | 4.36 | 365.0 |
| 184 | 4-F | (2-(4-fluorophenyl)oxazol-4-yl)(2-((pyridin-3-yloxy)methyl)piperazin-1-yl)methanone dihydrochloride | 4.45 | 383.6 |
| 185 | 4-OMe | (4-(4-methoxyphenyl)oxazol-2-yl)(2-((pyridin-3-yloxy)methyl)piperazin-1-yl)methanone dihydrochloride | 4.49 | 395.0 |
| 186 | 4-$CH_3$ | (2-((pyridin-3-yloxy)methyl)piperazin-1-yl)(2-p-tolyloxazol-4-yl)methanone dihydrochloride | 4.76 | 379.0 |
| 187 | 3-F | (2-(3-fluorophenyl)oxazol-4-yl)(2-((pyridin-3-yloxy)methyl)piperazin-1-yl)methanone dihydrochloride | 4.47 | 383.6 |
| 188 | 3-Cl | (2-(3-chlorophenyl)oxazol-4-yl)(2-((pyridin-3-yloxy)methyl)piperazin-1-yl)methanone dihydrochloride | 4.79 | 399.6 |

TABLE 22-continued

| Example No. | $R_d$ | IUPAC Name | HPLC RT (min) | LC-MS $(M + H)^+$ |
|---|---|---|---|---|
| 189 | 3-$CH_3$ | (2-((pyridin-3-yloxy)methyl)piperazin-1-yl)(2-m-tolyloxazol-4-yl)methanone dihydrochloride | 4.65 | 379.6 |
| 190 | 3-$OCF_3$ | (2-((pyridin-3-yloxy)methyl)piperazin-1-yl)(2-(3-(trifluoromethoxy)phenyl)oxazol-4-yl)methanone dihydrochloride | 5.12 | 449.7 |
| 191 | 2-F | (2-(2-fluorophenyl)oxazol-4-yl)(2-((pyridin-3-yloxy)methyl)piperazin-1-yl)methanone dihydrochloride | 4.30 | 383.6 |
| 192 | 2-OMe | (2-(2-methoxyphenyl)oxazol-4-yl)(2-((pyridin-3-yloxy)methyl)piperazin-1-yl)methanone dihydrochloride | 4.27 | 395.7 |

Example 193

(2-(phenylamino)oxazol-4-yl)(2-((pyridin-3-yloxy)methyl)piperazin-1-yl)methanone dihydrochloride

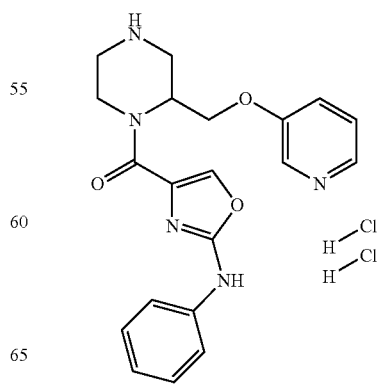

-continued

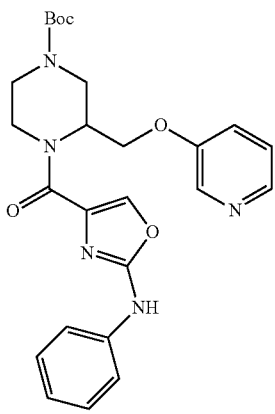

Step 1. Synthesis of tert-butyl 4-(2-(phenylamino)oxazole-4-carbonyl)-3-((pyridin-3-yloxy)methyl)piperazine-1-carboxylate A solution of tert-butyl 4-(2-chlorooxazole-4-carbonyl)-3-((pyridin-3-yloxy)methyl)piperazine-1-carboxylate (117 mg, 0.277 mmol), aniline (51 mg, 0.554 mmol) and potassium carbonate (76 mg, 0.554 mmol) in THF (2 mL) was heated to 70° C. overnight. Upon cooling to rt, the reaction mixture was filtered and concentrated under reduced pressure. The material was purified by HPLC (5 to 50% MeCN/0.1% TFA in H$_2$O/0.1% TFA gradient), yielding 64.8 mg (40%) of the title compound as the TFA salt. LC-MS: RT=6.72 min, [M+H]$^+$=480.0.

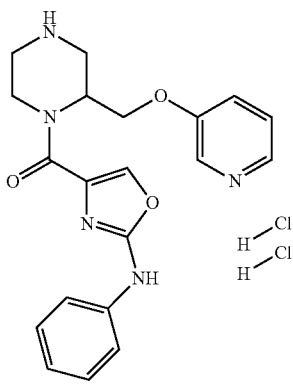

Step 2. Synthesis of (2-(phenylamino)oxazol-4-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(2-(phenylamino)oxazole-4-carbonyl)-3-((pyridin-3-yloxy)methyl)piperazine-1-carboxylate TFA salt (64.8 mg, 0.109 mmol) in MeOH (1 mL). After stirring overnight, the reaction mixture was concentrated under reduced pressure and purified by HPLC (5 to 50% MeCN/0.1% TFA in H$_2$O/0.1% TFA gradient). The fractions containing the desired product were concentrated under reduced pressure, dissolved in MeOH (1 mL), and treated with 4 M HCl in 1,4-dioxane (6 mL). The mixture was concentrated under reduced pressure to give 41 mg (83%) of the title compound as a white solid. LC-MS: RT=3.29 min, [M+H]$^+$=380.0.

Example 194

(2-(4-methoxyphenylamino)oxazol-4-yl)(2-((pyridin-3-yloxy)methyl)piperazin-1-yl)methanone dihydrochloride

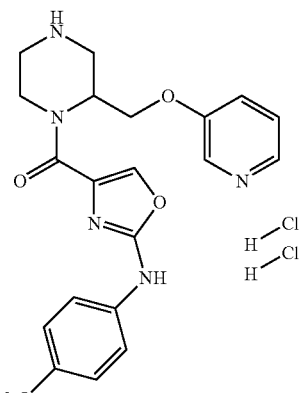

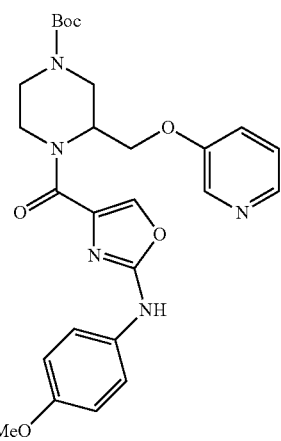

Step 1. Synthesis of tert-butyl 4-(2-(4-methoxyphenylamino)oxazole-4-carbonyl)-3-((pyridin-3-yloxy)methyl)piperazine-1-carboxylate A solution of tert-butyl 4-(2-chlorooxazole-4-carbonyl)-3-((pyridin-3-yloxy)methyl)piperazine-1-carboxylate (117 mg, 0.277 mmol), p-anisidine (68 mg, 0.554 mmol) and potassium carbonate (76 mg, 0.554 mmol) in THF (2 mL) was heated to 70° C. overnight. Upon cooling to rt, the reaction mixture was filtered and concentrated under reduced pressure. The material was purified by HPLC (5 to 50% MeCN/0.1% TFA in H$_2$O/0.1% TFA gradient), yielding 35.5 mg (25%) of the title compound as the TFA salt. LC-MS: RT=6.76 min, [M+H]$^+$=510.0.

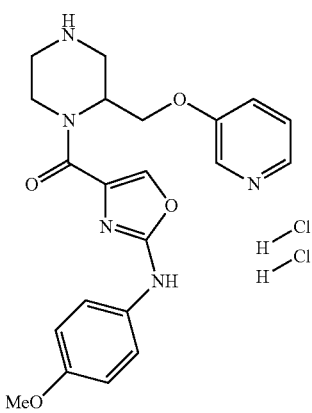

Step 2. Synthesis of (2-(4-methoxyphenylamino) oxazol-4-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(2-(4-methoxyphenylamino)oxazole-4-carbonyl)-3-((pyridin-3-yloxy)methyl)piperazine-1-carboxylate TFA salt (35.5 mg, 0.057 mmol) in MeOH (1 mL). After stirring overnight, the reaction mixture was concentrated under reduced pressure and purified by HPLC (5 to 50% MeCN/0.1% TFA in H$_2$O/0.1% TFA gradient). The fractions containing the desired product were concentrated under reduced pressure, dissolved in MeOH (1 mL), and treated with 4 M HCl in 1,4-dioxane (6 mL). The mixture was concentrated under reduced pressure to give 20 mg (73%) of the title compound as a white solid. LC-MS: RT=3.51 min, [M+H]$^+$=410.0.

Example 195

(2-morpholinooxazol-4-yl)(2-((pyridin-3-yloxy)methyl)piperazin-1-yl)methanone dihydrochloride

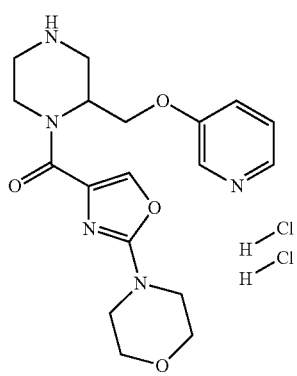

Step 1. Synthesis of tert-butyl 4-(2-morpholinooxazole-4-carbonyl)-3-((pyridin-3-yloxy)methyl)piperazine-1-carboxylate

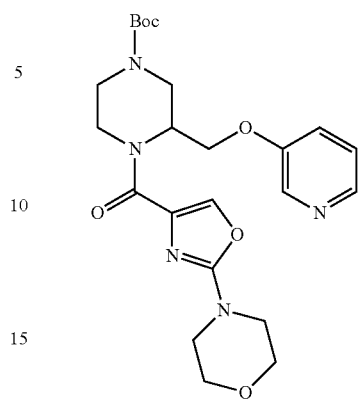

A solution of tert-butyl 4-(2-chlorooxazole-4-carbonyl)-3-((pyridin-3-yloxy)methyl)piperazine-1-carboxylate (117 mg, 0.277 mmol), morpholine (48 mg, 0.554 mmol) and potassium carbonate (76 mg, 0.554 mmol) in THF (2 mL) was heated to 70° C. overnight. Upon cooling to rt, the reaction mixture was filtered and concentrated under reduced pressure. The material was purified by HPLC (5 to 50% MeCN/0.1% TFA in H$_2$O/0.1% TFA gradient), yielding 165 mg (100%) of the title compound as the TFA salt. LC-MS: RT=6.60 min, [M+H]$^+$=474.1.

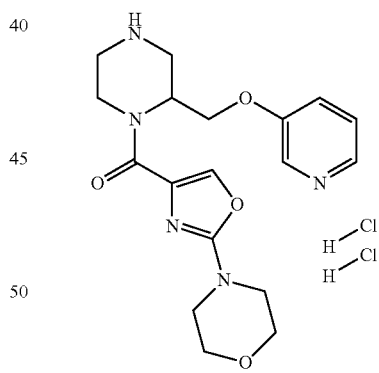

Step 2. Synthesis of (2-morpholinooxazol-4-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(2-morpholinooxazole-4-carbonyl)-3-((pyridin-3-yloxy)methyl)piperazine-1-carboxylate TFA salt (165 mg, 0.277 mmol) in MeOH (1 mL). After stirring overnight, the reaction mixture was concentrated under reduced pressure to give 105.5 mg (85%) of the title compound as a white solid. LC-MS: RT=2.70 min, [M+H]$^+$=374.0.

Example 196

(2-(4-chlorophenyl)-4-methyloxazol-5-yl)(2-((pyridin-3-yloxy)methyl)piperazin-1-yl)methanone trihydrochloride

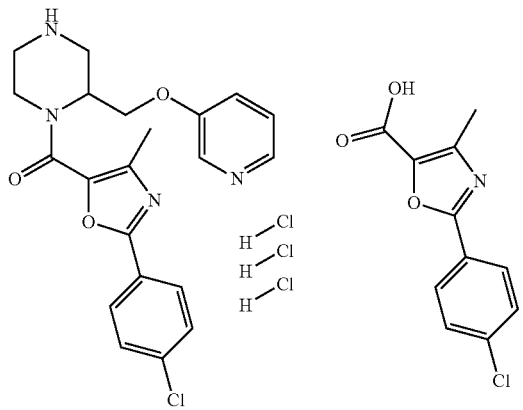

Step 1. Synthesis of 2-(4-chlorophenyl)-4-methyloxazole-5-carboxylic acid

Ethyl 2-chloroacetate (2.0 g, 11.9 mmol) was added to a mixture of 4-chlorobenzamide (5.55 g, 35.7 mmol) in EtOH (10 mL), and the reaction mixture was heated to 80° C. After 2 h, the temperature was increased to 100° C. After 20 h, the temperature was increased to 110° C. After stirring overnight, the reaction mixture was cooled to rt, diluted with EtOAc, and the pH was adjusted to ~10 with 1 N aqueous NaOH. The reaction mixture was extracted with EtOAc (3×), and the combined extracts were dried over $Na_2SO_4$, filtered, and concentrated under reduced pressure. The material was diluted with $CH_2Cl_2$ (40 mL) and the solids removed by filtration. The solids were washed with $CH_2Cl_2$, and the combined $CH_2Cl_2$ filtrates were concentrated under reduced pressure to yield 2.57 g of a light orange solid. The solid was dissolved in THF (10 mL), MeOH (10 mL) and water (5 mL), and lithium hydroxide (1.5 g, 63 mmol) was added. After stirring overnight at rt, the reaction mixture was acidified with 1 N aqueous HCl. The resulting solids were collected by filtration, washed with water (15 mL), and dried, yielding 1.75 g (62%) of the title compound as a white solid. LC-MS: RT=7.48 min, $[M+H]^+$=237.9.

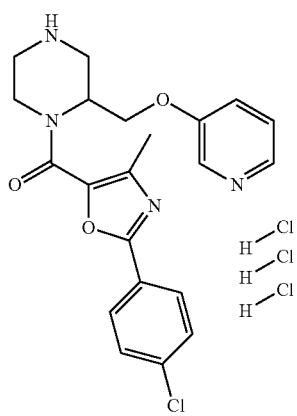

Step 2. Synthesis of (2-(4-chlorophenyl)-4-methyloxazol-5-yl)(2-((pyridin-3-yloxy)methyl)piperazin-1-yl)methanone trihydrochloride TBTU (141 mg, 0.438 mmol) was added to a solution of Intermediate C (86 mg, 0.29 mmol), 2-(4-chlorophenyl)-4-methyloxazole-5-carboxylic acid (76 mg, 0.32 mmol), and triethylamine (0.123 mL, 0.876 mmol) in DMF (4 mL). After stirring overnight, 1N NaOH (3 mL) was added, and the reaction mixture was stirred for 30 min. Water (15 mL) was added, and the reaction mixture was extracted with EtOAc (3×40 mL). The EtOAc extracts were combined, washed with aqueous NaOH (2×10 mL) and brine (10 mL), dried over $Na_2SO_4$, filtered, and concentrated under reduced pressure. The material was purified by HPLC (5 to 95% MeCN/0.1% TFA in $H_2O$/0.1% TFA gradient), yielding a yellow oil. The material was dissolved in MeOH (1 mL) and treated with 4 M HCl in 1,4-dioxane (5 mL, 20 mmol). After stirring for 5 h, the reaction mixture was concentrated under reduced pressure and purified by HPLC (5 to 95% MeCN/0.1% TFA in $H_2O$/0.1% TFA gradient) to give 37.2 mg (24%) of the title compound as a white solid. LC-MS: RT=4.74 min, $[M+H]^+$=413.6.

Examples 197-199

The examples shown below in Table 23 were prepared by similar methods as described for Example 196, substituting the appropriate benzamide. All reagents were commercially available unless otherwise noted. All compounds were isolated as the trihydrochloride salts unless otherwise noted.

TABLE 23

| Example No. | $R_d$ | IUPAC Name | HPLC RT (min) | LC-MS $[M + H]^+$ |
|---|---|---|---|---|
| 196 | Cl | (2-(4-chlorophenyl)-4-methyloxazol-5-yl)(2-((pyridin-3-yloxy)methyl)piperazin-1-yl)methanone trihydrochloride | 4.74 | 413.6 |
| 197 | H | (4-methyl-2-phenyloxazol-5-yl)(2-((pyridin-3-yloxy)methyl)piperazin-1-yl)methanone trihydrochloride | 4.14 | 379.6 |
| 198 | OMe | (2-(4-methoxyphenyl)-4-methyloxazol-5-yl)(2-((pyridin-3-yloxy)methyl)piperazin-1-yl)methanone trihydrochloride | 4.26 | 409.7 |
| 199 | F | (2-(4-fluorophenyl)-4-methyloxazol-5-yl)(2-((pyridin-3-yloxy)methyl)piperazin-1-yl)methanone trihydrochloride | 4.20 | 397.6 |

Example 200

(3-bromophenyl)(2-((pyridin-3-yloxy)methyl)piperazin-1-yl)methanone dihydrochloride

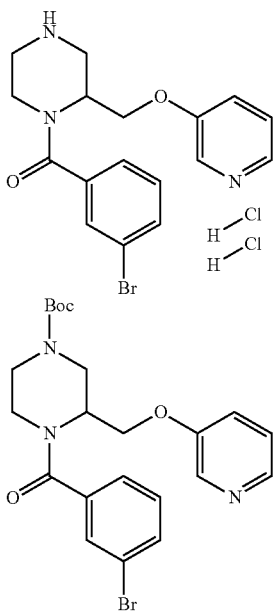

Step 1. Synthesis of tert-butyl 4-(3-bromobenzoyl)-3-((pyridin-3-yloxy)methyl)piperazine-1-carboxylate 3-Bromobenzoyl chloride (0.137 mL, 1.04 mmol) was added to a mixture of Intermediate C (277 mg, 0.945 mmol) and sodium carbonate (110 mg, 1.04 mmol) in THF (4 mL). After stirring overnight at rt, the reaction mixture was heated to 70° C. for 4 h. Upon cooling to rt, the reaction mixture was diluted with water (15 mL) and extracted with EtOAc (3×30 mL). The combined extracts were washed with 1 N aqueous NaOH (15 mL) and brine (15 mL), dried over $Na_2SO_4$, filtered, and concentrated under reduced pressure. The material was purified by HPLC (10 to 90% MeCN/0.1% TFA in $H_2O$/0.1% TFA gradient), yielding 0.502 g of an off-white solid that was contaminated with minor impurities.

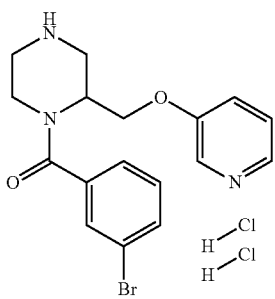

Step 2. Synthesis of (3-bromophenyl)(2-((pyridin-3-yloxy)methyl)piperazin-1-yl)methanone dihydrochloride 4 M HCl in 1,4-dioxane (5 mL, 20 mmol) was added to a solution of tert-butyl 4-(3-bromobenzoyl)-3-((pyridin-3-yloxy)methyl)piperazine-1-carboxylate (126 mg, 0.264 mmol) in MeOH (1 mL). After stirring for 4 h, the reaction mixture was concentrated under reduced pressure and purified by HPLC (5 to 95% MeCN/0.1% TFA in $H_2O$/0.1% TFA gradient). This gave 80.5 mg (68%) of the desired product as a white solid upon conversion to the dihydrochloride salt. LC-MS: RT=3.91 min, $[M+H]^+$=376.5.

Example 201

(4'-fluorobiphenyl-3-yl)(2-((pyridin-3-yloxy)methyl)piperazin-1-yl)methanone dihydrochloride

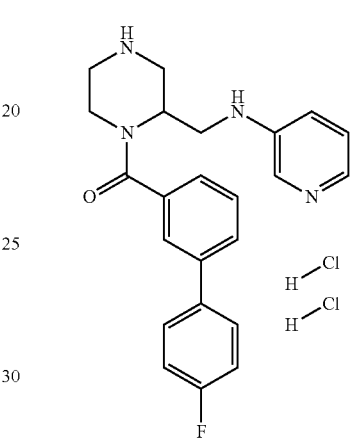

[1,1'-bis(diphenylphosphino)ferrocene]-dichloropalladium(II) complex with dichloromethane (1:1) (11 mg, 0.013 mmol) was added to a mixture of tert-butyl 4-(3-bromobenzoyl)-3-((pyridin-3-yloxy)methyl)piperazine-1-carboxylate (126 mg, 0.264 mmol), 4-fluorobenzeneboronic acid (92 mg, 0.66 mmol) and sodium carbonate (56 mg, 0.52 mmol) in toluene (4 mL), 1,4-dioxane (1 mL), and water (1 mL). The reaction mixture was heated to 70° C. overnight. Upon cooling to room temperature, the reaction mixture was filtered through Celite®, concentrated under reduced pressure, and purified by HPLC (10 to 90% MeCN/0.1% TFA in $H_2O$/0.1% TFA gradient), yielding a yellow oil. The oil was dissolved in MeOH (1 mL) and 4 M HCl in 1,4-dioxane (5 mL, 20 mmol) was added. After stirring for 4 h, the reaction mixture was concentrated under reduced pressure and purified by HPLC (5 to 95% MeCN/0.1% TFA in $H_2O$/0.1% TFA gradient). This gave 80.5 mg (68%) of the desired product as a white solid upon conversion to the dihydrochloride salt. LC-MS: RT=4.92 min, $[M+H]^+$=392.7.

Examples 202 and 203

Examples 202 and 203 were prepared as described for Example 201, substituting the appropriate boronic acids.

Example 202

(4'-chlorobiphenyl-3-yl)(2-((pyridin-3-yloxy)methyl)piperazin-1-yl)methanone dihydrochloride LC-MS: RT=5.10 min, $[M+H]^+$=408.7.

Example 203

(4'-methoxybiphenyl-3-yl)(2-((pyridin-3-yloxy)methyl)piperazin-1-yl)methanone dihydrochloride LC-MS: RT=4.71 min, [M+H]$^+$=404.7.

Examples 204-206

Examples 204-206 were prepared from tert-butyl 4-(4-bromobenzoyl)-3-((pyridin-3-yloxy)methyl)piperazine-1-carboxylate as described for Example 201, substituting the appropriate boronic acids.

Example 204

(4'-fluorobiphenyl-4-yl)(2-((pyridin-3-yloxy)methyl)piperazin-1-yl)methanone dihydrochloride LC-MS: RT=4.84 min, [M+H]$^+$=392.7.

Example 205

(4'-methoxybiphenyl-4-yl)(2-((pyridin-3-yloxy)methyl)piperazin-1-yl)methanone dihydrochloride LC-MS: RT=4.64 min, [M+H]$^+$=404.7.

Example 206

(4'-chlorobiphenyl-4-yl)(2-((pyridin-3-yloxy)methyl)piperazin-1-yl)methanone dihydrochloride LC-MS: RT=5.14 min, [M+H]$^+$=408.7.

Example 207

(6-chloropyridin-2-yl)(2-((pyridin-3-yloxy)methyl)piperazin-1-yl)methanone dihydrochloride

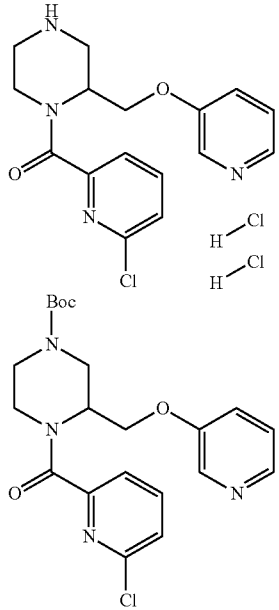

Step 1. Synthesis of tert-butyl 4-(6-chloropicolinoyl)-3-((pyridin-3-yloxy)methyl)piperazine-1-carboxylate TBTU (732 mg, 2.28 mmol) was added to a solution of Intermediate C (445 mg, 1.52 mmol), 6-chloropyridine-2-carboxylic acid (263 mg, 1.67 mmol), and triethylamine (0.43 mL, 3.0 mmol) in DMF (8 mL). After stirring overnight, 1N NaOH was added, and the reaction mixture was stirred for 1 h. The reaction mixture was diluted with EtOAc (50 mL) and washed with 1N NaOH (2×) and brine. The EtOAc layer was dried over Na$_2$SO$_4$, filtered, and concentrated under reduced pressure. The material was purified by HPLC (10 to 90% MeCN/0.1% TFA in H$_2$O/0.1% TFA gradient). The fractions containing the desired product were brought to pH 12 with 1 N NaOH and were extracted with EtOAc (3×). The combined extracts were dried over Na$_2$SO$_4$, filtered, and concentrated under reduced pressure. This gave 590.5 mg (90%) of the title compound as a white solid. LC-MS: RT=7.47 min, [M+H]$^+$=433.7.

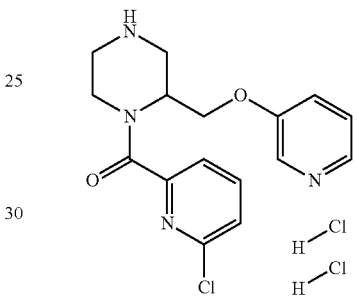

Step 2. Synthesis of (6-chloropyridin-2-yl)(2-((pyridin-3-yloxy)methyl)piperazin-1-yl)methanone dihydrochloride 4 M HCl in 1,4-dioxane (6 mL, 24 mmol) was added to tert-butyl 4-(6-chloropicolinoyl)-3-((pyridin-3-yloxy)methyl)piperazine-1-carboxylate (90.5 mg, 0.209 mmol). After stirring overnight, the reaction mixture was concentrated under reduced pressure, yielding 77.3 mg (91%) of the title compound. LC-MS: RT=2.86 min, [M+H]$^+$=333.5.

Example 208

(6-phenylpyridin-2-yl)(2-((pyridin-3-yloxy)methyl)piperazin-1-yl)methanone dihydrochloride

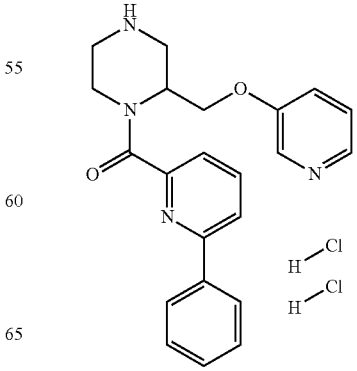

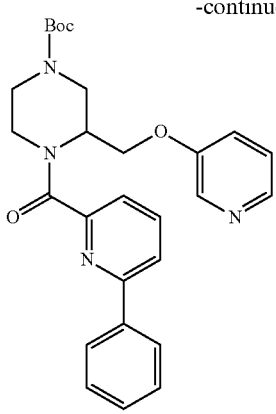

Step 1. Synthesis of tert-butyl 4-(6-phenylpicolinoyl)-3-((pyridin-3-yloxy)methyl)piperazine-1-carboxylate

[1,1'-bis(diphenylphosphino)ferrocene]-dichloropalladium(II) complex with dichloromethane (1:1) (10 mg, 0.012 mmol) was added to a mixture of tert-butyl 4-(6-chloropicolinoyl)-3-((pyridin-3-yloxy)methyl)piperazine-1-carboxylate (100 mg, 0.231 mmol), benzeneboronic acid (56 mg, 0.46 mmol) and sodium carbonate (49 mg, 0.46 mmol) in toluene (4 mL), 1,4-dioxane (1 mL), and water (1 mL). The reaction mixture was heated to 80° C. overnight. Upon cooling to room temperature, the reaction mixture was filtered through Celite®, concentrated under reduced pressure, and purified by HPLC (10 to 90% MeCN/0.1% TFA in H$_2$O/0.1% TFA gradient). This gave 143 mg of the title compound. LC-MS: RT=8.58 min, [M+H]$^+$=475.9.

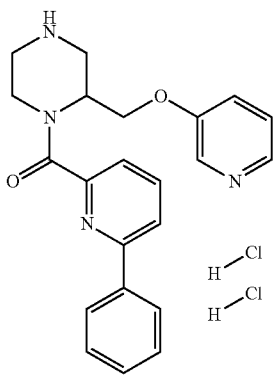

Step 2. Synthesis of (6-phenylpyridin-2-yl)(2-((pyridin-3-yloxy)methyl)piperazin-1-yl)methanone dihydrochloride 4 M HCl in 1,4-dioxane (6 mL, 24 mmol) was added to a solution of tert-butyl 4-(6-phenylpicolinoyl)-3-((pyridin-3-yloxy)methyl)piperazine-1-carboxylate (143 mg, 0.231 mmol) in MeOH (1 mL). After stirring overnight, the reaction mixture was concentrated under reduced pressure, yielding 102.1 mg (99%) of the title compound. LC-MS: RT=4.36 min, [M+H]$^+$=375.6.

Examples 209-212

Examples 209-212 were prepared as described for Example 208, substituting the appropriate boronic acids.

Example 209

(6-(3-methoxyphenyl)pyridin-2-yl)(2-((pyridin-3-yloxy)methyl)piperazin-1-yl)methanone dihydrochloride LC-MS: RT=4.31 min, [M+H]$^+$=405.7.

Example 210

(6-(4-fluorophenyl)pyridin-2-yl)(2-((pyridin-3-yloxy)methyl)piperazin-1-yl)methanone dihydrochloride LC-MS: RT=4.47 min, [M+H]$^+$=393.6.

Example 211

(6-(2-fluorophenyl)pyridin-2-yl)(2-((pyridin-3-yloxy)methyl)piperazin-1-yl)methanone dihydrochloride LC-MS: RT=4.40 min, [M+H]$^+$=393.6.

Example 212

(6-(4-methoxyphenyl)pyridin-2-yl)(2-((pyridin-3-yloxy)methyl)piperazin-1-yl)methanone dihydrochloride LC-MS: RT=4.45 min, [M+H]$^+$=405.7.

Example 213

(3-chloro-2-fluorophenyl)(2-((pyridin-3-yloxy)methyl)piperazin-1-yl)methanone dihydrochloride

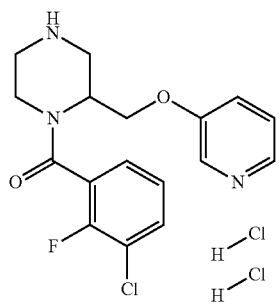

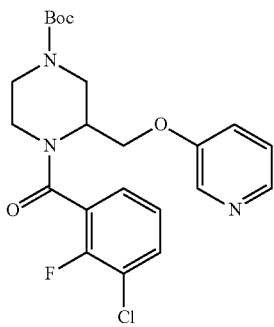

Step 1. Synthesis of tert-butyl 4-(3-chloro-2-fluorobenzoyl)-3-((pyridin-3-yloxy)methyl)piperazine-1-carboxylate TBTU (332 mg, 1.04 mmol) was added to a solution of Intermediate C (203 mg, 0.690 mmol), 2-fluoro-3-chlorobenzoic acid (132 mg, 0.759 mmol), and triethylamine (0.19 mL, 1.4 mmol) in DMF (4 mL). After stirring overnight, 1N NaOH was added, and the reaction mixture was stirred for 1 h. The reaction mixture was diluted with EtOAc and washed with 1N NaOH (2×) and brine. The EtOAc layer was dried over $Na_2SO_4$, filtered, and concentrated under reduced pressure. The material was purified by HPLC (10 to 90% MeCN/0.1% TFA in $H_2O$/0.1% TFA gradient). The fractions containing the desired product were brought to pH 12 with 1 N NaOH and were extracted with EtOAc (3×). The combined extracts were dried over $Na_2SO_4$, filtered, and concentrated under reduced pressure. This gave 269.7 mg (87%) of the title compound as a white solid. LC-MS: RT=8.31 min, [M+H]⁺=450.7.

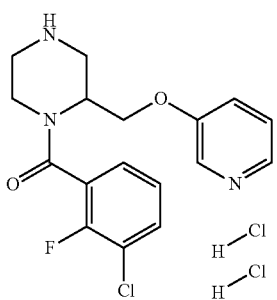

Step 2. Synthesis of (3-chloro-2-fluorophenyl)(2-((pyridin-3-yloxy)methyl)piperazin-1-yl)methanone dihydrochloride 4 M HCl in 1,4-dioxane (6 mL, 24 mmol) was added to tert-butyl 4-(3-chloro-2-fluorobenzoyl)-3-((pyridin-3-yloxy)methyl)piperazine-1-carboxylate (70 mg, 0.16 mmol). After stirring overnight, the reaction mixture was concentrated under reduced pressure, yielding 60.5 mg (92%) of the title compound. LC-MS: RT=3.80 min, [M+H]⁺=350.5.

Example 214

(2-fluorobiphenyl-3-yl)(2-((pyridin-3-yloxy)methyl)piperazin-1-yl)methanone dihydrochloride

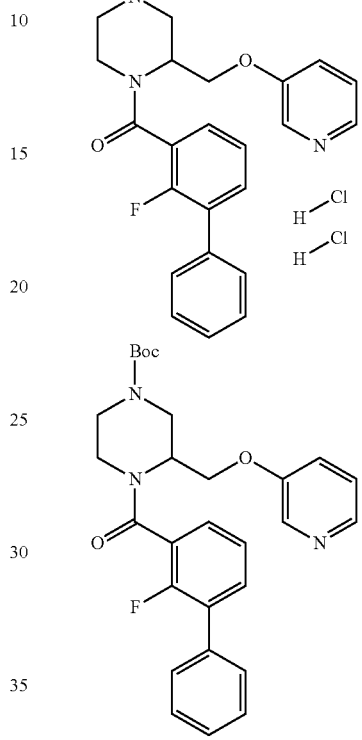

Step 1. Synthesis of tert-butyl 4-(2-fluorobiphenylcarbonyl)-3-((pyridin-3-yloxy)methyl)piperazine-1-carboxylate dihydrochloride

[1,1'-bis(diphenylphosphino)ferrocene]-dichloropalladium(II) complex with dichloromethane (1:1) (18 mg, 0.022 mmol) was added to a mixture of tert-butyl 4-(3-chloro-2-fluorobenzoyl)-3-((pyridin-3-yloxy)methyl)piperazine-1-carboxylate (100 mg, 0.222 mmol), benzeneboronic acid (81 mg, 0.67 mmol) and sodium carbonate (71 mg, 0.67 mmol) in toluene (4 mL), 1,4-dioxane (1 mL), and water (1 mL). The reaction mixture was heated to 110° C. overnight. Additional portions of the palladium catalyst, boronic acid and sodium carbonate were added and heating continued at 110° C. After stirring overnight, additional portions of the palladium catalyst, boronic acid and sodium carbonate were again added and heating continued at 110° C. overnight. Upon cooling to room temperature, the reaction mixture was filtered through Celite®, concentrated under reduced pressure, and purified by HPLC (10 to 90% MeCN/0.1% TFA in $H_2O$/0.1% TFA gradient). This gave 115 mg (86%) of the title compound as the TFA salt that was ~80% pure by LC-MS. LC-MS: RT=9.06 min, [M+H]⁺=492.9. 26.3 mg (22%) of tert-butyl 4-(2-fluorobenzoyl)-3-((pyridin-3-yloxy)methyl)piperazine-1-carboxylate were also isolated as the TFA salt. LC-MS: RT=7.53 min, [M+H]⁺=416.7.

Step 2. Synthesis of (2-fluorobiphenyl-3-yl)(2-((pyridin-3-yloxy)methyl)piperazin-1-yl)methanone dihydrochloride

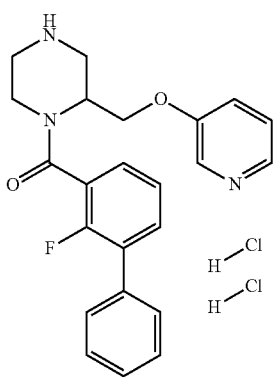

4 M HCl in 1,4-dioxane (6 mL, 24 mmol) was added to a solution of tert-butyl 4-(2-fluorobiphenylcarbonyl)-3-((pyridin-3-yloxy)methyl)piperazine-1-carboxylate TEA salt (115 mg, 0.19 mmol) in MeOH (1 mL). After 1 h, the reaction mixture was concentrated under reduced pressure and purified by HPLC (5 to 50% MeCN/0.1% TFA in H$_2$O/0.1% TFA gradient). The desired chromatography fractions were concentrated under reduced pressure, dissolved in MeOH (1 mL), and treated with 4 M HCl in 1,4-dioxane. This was concentrated under reduced pressure, yielding 70.3 mg (80%) of the title compound as an off-white solid. LC-MS: RT=4.80 min, [M+H]$^+$=392.7.

Example 215

(2-fluorophenyl)(2-((pyridin-3-yloxy)methyl)piperazin-1-yl)methanone dihydrochloride

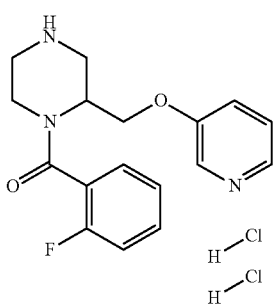

4 M HCl in 1,4-dioxane (6 mL, 24 mmol) was added to a solution of tert-butyl 4-(2-fluorobenzoyl)-3-((pyridin-3-yloxy)methyl)piperazine-1-carboxylate TFA salt (26 mg, 0.050 mmol) in MeOH (1 mL). After 1 h, the reaction mixture was concentrated under reduced pressure and purified by HPLC (5 to 50% MeCN/0.1% TFA in H$_2$O/0.1% TFA gradient). The desired chromatography fractions were concentrated under reduced pressure, dissolved in MeOH (1 mL), and treated with 4 M HCl in 1,4-dioxane. This was concentrated under reduced pressure, yielding 16.3 mg (86%) of the title compound as an off-white solid. LC-MS: RT=3.00 min, [M+H]$^+$=316.3.

Example 216

Phenyl 2-((pyridin-3-yloxy)methyl)piperazine-1-carboxylate dihydrochloride

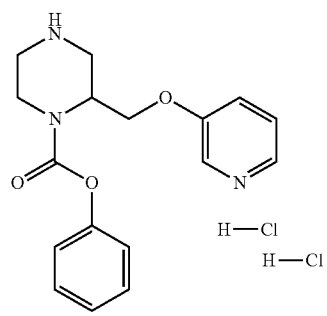

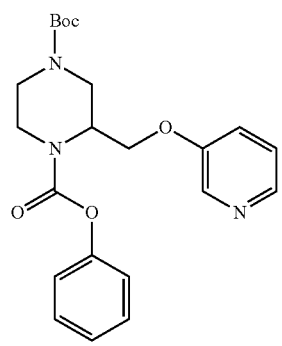

Step 1. Synthesis of 4-tert-butyl 1-phenyl 2-((pyridin-3-yloxy)methyl)piperazine-1,4-dicarboxylate A solution of Intermediate N (108.5 mg, 0.280 mmol), phenol (52.7 mg, 0.560 mmol) and triethylamine (0.078 mL, 0.56 mmol) in MeCN (4 mL) was heated to 70° C. After 12 h, Cs$_2$CO$_3$ (0.182 g, 0.560 mmol) and additional phenol (52.7 mg, 0.560 mmol) were added and heating was continued at 70° C. for 1 h. Upon cooling to rt, the reaction mixture was filtered, concentrated under reduced pressure and purified by HPLC (10 to 70% MeCN/0.1% TFA in H$_2$O/0.1% TFA gradient). This gave 108.2 mg (73%) of the TFA salt of the desired product as a thick, colorless oil. LC-MS: RT=8.54 min, [M+H]$^+$=414.2.

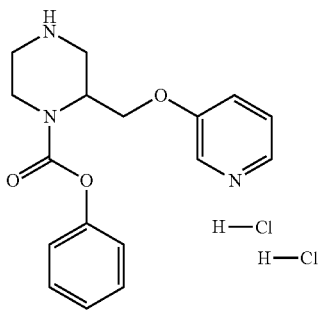

Step 2. Synthesis of phenyl 2-((pyridin-3-yloxy)methyl)piperazine-1-carboxylate dihydrochloride 4 M HCl in 1,4-dioxane (6 mL, 24 mmol) was added to a solution of 4-tert-butyl 1-phenyl 2-((pyridin-3-yloxy)methyl)piperazine-1,4-dicarboxylate TFA salt (108.2 mg, 0.205 mmol) in MeOH (1 mL). After 1 h, the reaction mixture was concentrated under reduced pressure, yielding 72.3 mg (91%) of the desired product as a white solid. LC-MS: RT=3.89 min, [M+H]$^+$=314.1.

Example 217

4-Fluorophenyl 2-((pyridin-3-yloxy)methyl)piperazine-1-carboxylate dihydrochloride

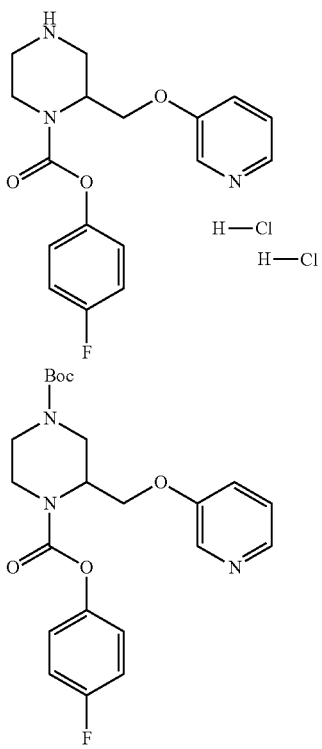

Step 1. Synthesis of 4-tert-butyl 1-(4-fluorophenyl) 2-((pyridin-3-yloxy)methyl)piperazine-1,4-dicarboxylate 4-Fluorophenylchloroformate (46.5 mg, 0.267 mmol) was added to a solution of Intermediate C (78.2 mg, 0.267 mmol) in CH$_2$Cl$_2$ (4 mL). After 16 h, the reaction mixture was concentrated under reduced pressure, and the material was purified by HPLC (10 to 90% MeCN/0.1% TFA in H$_2$O/0.1% TFA gradient). This gave 88.9 mg (61%) of the TFA salt of the desired product as a yellow solid. LC-MS: RT=8.69 min, [M+H]$^+$=432.2.

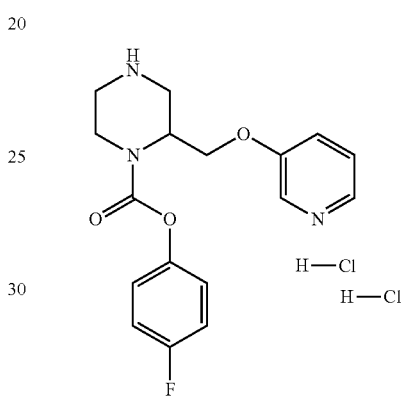

Step 2. Synthesis of 4-Fluorophenyl 2-((pyridin-3-yloxy)methyl)piperazine-1-carboxylate dihydrochloride 4 M HCl in 1,4-dioxane (6 mL, 24 mmol) was added to a solution of 4-tert-butyl 1-(4-fluorophenyl) 2-((pyridin-3-yloxy)methyl)piperazine-1,4-dicarboxylate TFA salt (88.9 mg, 0.163 mmol) in MeOH (1 mL). After 1 h, the reaction mixture was concentrated under reduced pressure, yielding 63.7 mg (97%) of the desired product as a yellow solid. LC-MS: RT=4.07 min, [M+H]$^+$=332.1.

Examples 218-223

The examples shown below in Table 24 were prepared by similar methods as described for Example 216 or Example 217, as indicated, substituting the appropriate phenol or chloroformate, respectively. All reagents were commercially available unless otherwise noted. All compounds were isolated as the dihydrochloride salts unless otherwise noted.

TABLE 24

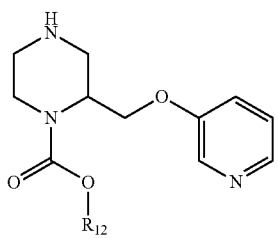

| Example No. | R₁₂ | IUPAC Name | HPLC RT (min) | LC-MS [M + H]⁺ | Prepared using method in Example No. |
|---|---|---|---|---|---|
| 216 | phenyl | phenyl 2-((pyridin-3-yloxy)methyl)piperazine-1-carboxylate dihydrochloride | 3.89 | 314.1 | 208 |
| 217 | 4-fluorophenyl | 4-fluorophenyl 2-((pyridin-3-yloxy)methyl)piperazine-1-carboxylate dihydrochloride | 4.07 | 332.1 | 209 |
| 218 | 3-methoxyphenyl | 3-methoxyphenyl 2-((pyridin-3-yloxy)methyl)piperazine-1-carboxylate dihydrochloride | 4.06 | 344.1 | 208 |
| 219 | 3-chlorophenyl | 3-chlorophenyl 2-((pyridin-3-yloxy)methyl)piperazine-1-carboxylate dihydrochloride | 4.58 | 348.1 | 208 |
| 220 | 4-methoxyphenyl | 4-methoxyphenyl 2-((pyridin-3-yloxy)methyl)piperazine-1-carboxylate dihydrochloride | 4.07 | 344.1 | 208 |

TABLE 24-continued

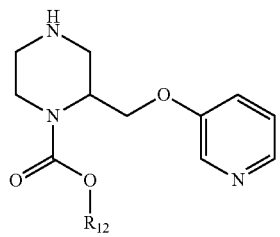

| Example No. | $R_{12}$ | IUPAC Name | HPLC RT (min) | LC-MS $[M + H]^+$ | Prepared using method in Example No. |
|---|---|---|---|---|---|
| 221 | 4-chlorophenyl | 4-chlorophenyl 2-((pyridin-3-yloxy)methyl)piperazine-1-carboxylate dihydrochloride | 4.66 | 348.1 | 208 |
| 222 | p-tolyl | p-tolyl 2-((pyridin-3-yloxy)methyl)piperazine-1-carboxylate dihydrochloride | 4.35 | 328.1 | 209 |
| 223 | 4-bromophenyl | 4-bromophenyl 2-((pyridin-3-yloxy)methyl)piperazine-1-carboxylate dihydrochloride | 4.71 | 392.0 | 209 |

Example 224

4-Chlorobenzyl 2-((pyridin-3-yloxy)methyl)piperazine-1-carboxylate dihydrochloride

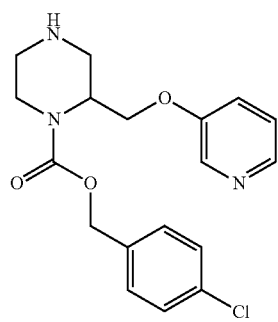

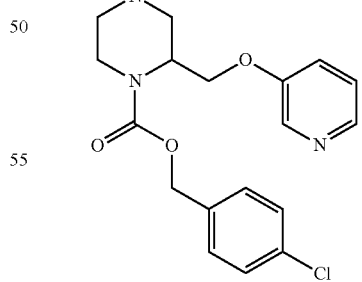

Step 1. Synthesis of 1-(4-chlorobenzyl) 4-tert-butyl 2-((pyridin-3-yloxy)methyl)piperazine-1,4-dicarboxylate A solution of 4-chlorobenzyl alcohol (51 mg, 0.36 mmol) in THF (2 mL) was added to a suspension of sodium hydride (60% dispersion in mineral oil, 15 mg, 0.36 mmol) in THF (2 mL). Upon complete addition, a solution of Intermediate N (114 mg, 0.296 mmol) in THF (2 mL) was added. After 1 h, the reaction mixture was quenched with water (1 mL), diluted with EtOAc (25 mL) and washed with water (3×15 mL) and brine (15 mL). The organics were dried over $Na_2SO_4$, filtered, and concentrated under reduced pressure. The material was purified by HPLC (10 to 95% MeCN/0.1% TFA in $H_2O$/0.1% TFA gradient), yielding 129.0 mg (76%) of the TFA salt of the desired product as a thick oil. LC-MS: RT=9.40 min, $[M+H]^+$=462.1.

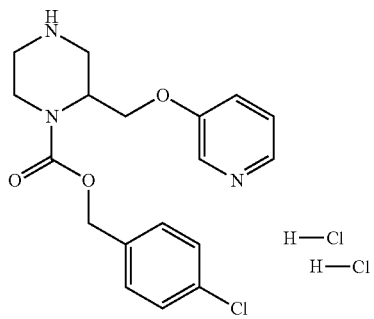

Step 2. Synthesis of 4-chlorobenzyl 2-((pyridin-3-yloxy)methyl)piperazine-1-carboxylate dihydrochloride 4 M HCl in 1,4-dioxane (6 mL, 24 mmol) was added to a solution of 1-(4-chlorobenzyl) 4-tert-butyl 2-((pyridin-3-yloxy)methyl)piperazine-1,4-dicarboxylate TFA salt (129 mg, 0.224 mmol) in MeOH (1 mL). After 12 h, the reaction mixture was concentrated under reduced pressure, yielding 95.7 mg (98%) of the desired product as a white solid. LC-MS: RT=4.74 min, $[M+H]^+$=362.1.

Examples 225-228

The examples found in Table 25 below were prepared by similar methods as described for Example 224, substituting the appropriate alcohol. All reagents were commercially available unless otherwise noted. All compounds were isolated as the dihydrochloride salts unless otherwise noted.

TABLE 25

| Example No. | $R_{12}$ | IUPAC Name | HPLC RT (min) | LC-MS $[M+H]^+$ |
|---|---|---|---|---|
| 224 | 4-chlorobenzyl | 4-chlorobenzyl 2-((pyridin-3-yloxy)methyl)piperazine-1-carboxylate dihydrochloride | 4.74 | 362.1 |
| 225 | 4-bromobenzyl | 4-bromobenzyl 2-((pyridin-3-yloxy)methyl)piperazine-1-carboxylate dihydrochloride | 4.87 | 406 |
| 226 | 3,4-dichlorobenzyl | 3,4-dichlorobenzyl 2-((pyridin-3-yloxy)methyl)piperazine-1-carboxylate dihydrochloride | 5.17 | 396 |

TABLE 25-continued

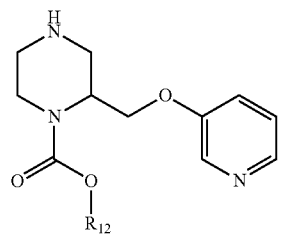

| Example No. | R12 | IUPAC Name | HPLC RT (min) | LC-MS [M + H]+ |
|---|---|---|---|---|
| 227 | cyclohexyl | cyclohexyl 2-((pyridin-3-yloxy)methyl)piperazine-1-carboxylate dihydrochloride | 4.48 | 320.2 |
| 228 | cyclopentyl | cyclopentyl 2-((pyridin-3-yloxy)methyl)piperazine-1-carboxylate dihydrochloride | 3.97 | 306.2 |

Example 229

4-chlorophenyl 2-((3-fluorophenoxy)methyl)piperazine-1-carboxylate dihydrochloride

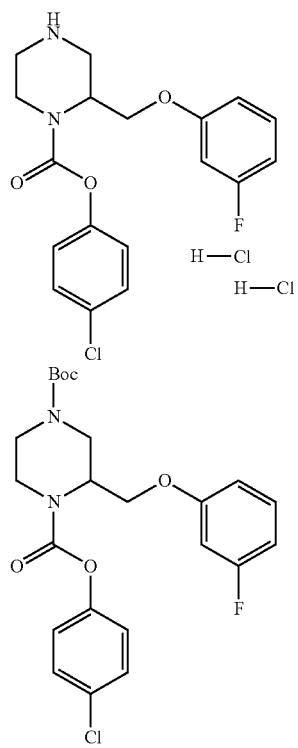

Step 1. Synthesis of 4-tert-butyl 1-(4-chlorophenyl) 2((3-fluorophenoxy)methyl)piperazine-1,4-dicarboxylate 4-Chlorophenylchloroformate (76.5 mg, 0.400 mmol) was added to a solution of Intermediate G (83.0 mg, 0.267 mmol) in CH$_2$Cl$_2$ (4 mL). After 16 h, the reaction mixture was concentrated under reduced pressure, and the material was purified by HPLC (10 to 90% MeCN/0.1% TFA in H$_2$O/0.1% TFA gradient). This gave 38.3 mg (31%) of the desired product. LC-MS: RT=11.14 min, [M+H]$^+$=487.1.

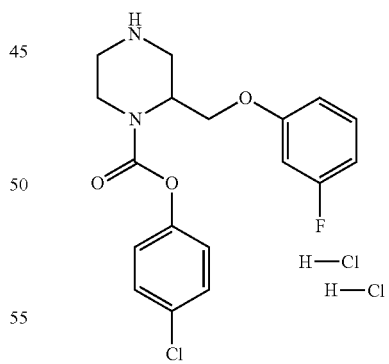

Step 2. Synthesis of 4-chlorophenyl 2-((3-fluorophenoxy)methyl)piperazine-1-carboxylate dihydrochloride 4 M HCl in 1,4-dioxane (6 mL, 24 mmol) was added to a solution of 4-tert-butyl 1-(4-chlorophenyl) 2-((3-fluorophenoxy)methyl)piperazine-1,4-dicarboxylate (38.3 mg, 0.082 mmol) in MeOH (1 mL). After 1 h, the reaction mixture was concentrated under reduced pressure, yielding 32.9 mg (99%) of the desired product as a white solid. LC-MS: RT=5.83 min, [M+H]⁺=365.1.

Example 230

1-(Benzyloxycarbonyl)piperidin-4-yl 2-((pyridin-3-yloxy)methyl)piperazine-1-carboxylate dihydrochloride

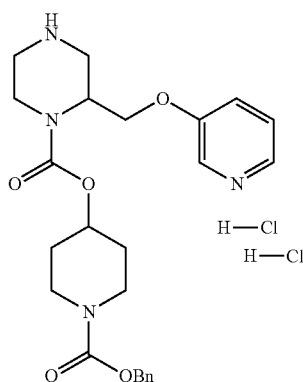

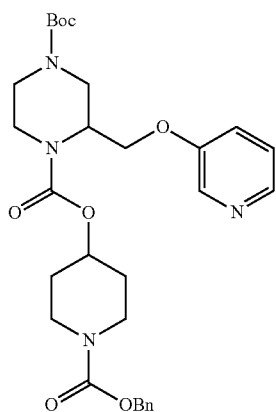

Step 1. Synthesis of 1-(1-(benzyloxycarbonyl)piperidin-4-yl) 4-tert-butyl 2-((pyridin-3-yloxy)methyl)piperazine-1,4-dicarboxylate A solution of benzyl 4-hydroxypiperidine-1-carboxylate (0.883 g, 3.75 mmol) in THF (10 mL) was added to a suspension of sodium hydride (60% dispersion in mineral oil, 0.15 g, 3.75 mmol) in THF (30 mL). Upon complete addition, a solution of Intermediate N (1.60 g, 3.41 mmol) in THF (10 mL) was added. After 16 h, the reaction mixture was quenched with water (10 mL), diluted with EtOAc (150 mL) and washed with water (3×100 mL) and brine (100 mL). The organics were dried over Na₂SO₄, filtered, and concentrated under reduced pressure. The material was purified by column chomatography (10 to 50% EtOAc in Hexanes gradient), yielding 0.765 g (40%) of the desired product as a white solid. LC-MS: RT=9.04 min, [M+H]⁺=555.2.

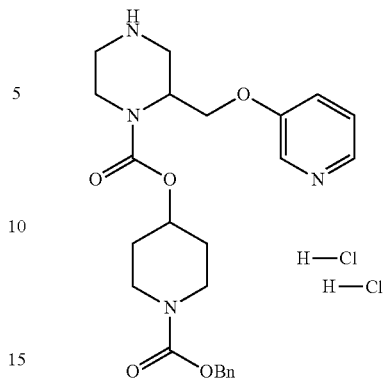

Step 2. Synthesis of 1-(benzyloxycarbonyl)piperidin-4-yl 2-((pyridin-3-yloxy)methyl)piperazine-1-carboxylate dihydrochloride 4 M HCl in 1,4-dioxane (6 mL, 24 mmol) was added to a solution of 1-(1-(benzyloxycarbonyl)piperidin-4-yl) 4-tert-butyl 2-((pyridin-3-yloxy)methyl)piperazine-1,4-dicarboxylate (88.8 mg, 0.160 mmol) in MeOH (1 mL). After 1 h, the reaction mixture was concentrated under reduced pressure, yielding 84.4 mg (100%) of the desired product as a white solid. LC-MS: RT=4.94 min, [M+H]⁺=455.2.

Example 231

Piperidin-4-yl 2-((pyridin-3-yloxy)methyl)piperazine-1-carboxylate trihydrochloride

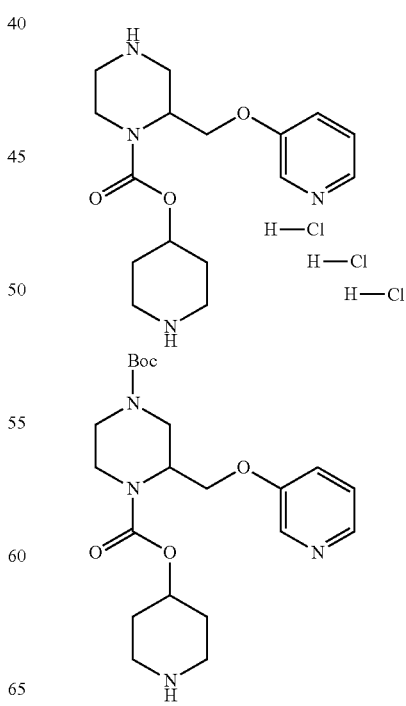

Step 1. Synthesis of 4-tert-butyl 1-piperidin-4-yl 2-((pyridin-3-yloxy)methyl)piperazine-1,4-dicarboxylate Palladium hydroxide on carbon (~10% Pd, 84 mg, 0.06 mmol) was added to a mixture of 1-(1-(benzyloxycarbonyl)piperidin-4-yl) 4-tert-butyl 2-((pyridin-3-yloxy)methyl)piperazine-1,4-dicarboxylate (0.665 g, 1.20 mmol) and ammonium formate (0.151 g, 2.40 mmol) in EtOH (10 mL). The reaction mixture was heated to 70° C. for 2 h. Upon cooling to rt, the reaction mixture was filtered though Celite®, and the filtrate was concentrated under reduced pressure. This gave 0.5278 g of crude product. LC-MS: RT=4.50 min, [M+H]$^+$=421.2.

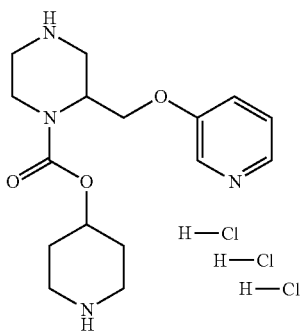

Step 2. Synthesis of piperidin-4-yl 2-((pyridin-3-yloxy)methyl)piperazine-1-carboxylate trihydrochloride 4 M HCl in 1,4-dioxane (6 mL, 24 mmol) was added to a solution of 4-tert-butyl 1-piperidin-4-yl 2-((pyridin-3-yloxy)methyl)piperazine-1,4-dicarboxylate (101.5 mg, 0.241 mmol) in MeOH (1 mL). After 16 h, the reaction mixture was concentrated under reduced pressure, yielding 103.3 mg (99%) of the desired product. LC-MS: RT=1.26 min, [M+H]$^+$=321.2.

Example 232

1-Acetylpiperidin-4-yl 2-((pyridin-3-yloxy)methyl)piperazine-1-carboxylate dihydrochloride

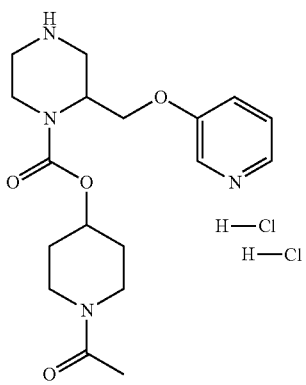

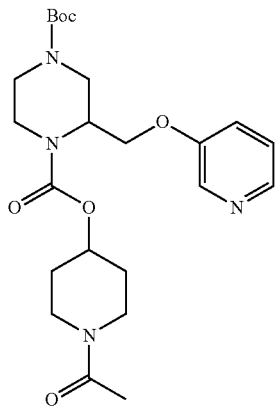

Step 1. Synthesis of 1-(1-acetylpiperidin-4-yl) 4-tert-butyl 2-((pyridin-3-yloxy)methyl)piperazine-1,4-dicarboxylate Acetic anhydride (0.0207 mL, 0.219 mmol) was added to a solution of 4-tert-butyl 1-piperidin-4-yl 2-((pyridin-3-yloxy)methyl)piperazine-1,4-dicarboxylate (83.7 mg, 0.199 mmol) in THF (4 mL). After 16 h, the reaction mixture was concentrated under reduced pressure and purified by HPLC (10 to 90% MeCN/0.1% TFA in H$_2$O/0.1% TFA gradient). This gave 112.5 mg (98%) of the TFA salt of the desired product as a white solid. LC-MS: RT=6.40 min, [M+H]$^+$=463.2.

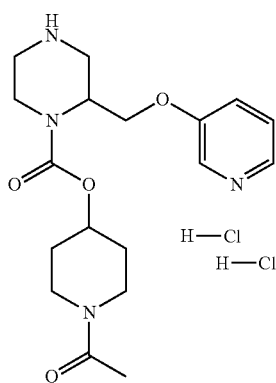

Step 2. Synthesis of 1-acetylpiperidin-4-yl 2-((pyridin-3-yloxy)methyl)piperazine-1-carboxylate dihydrochloride 4 M HCl in 1,4-dioxane (6 mL, 24 mmol) was added to a solution of 1-(1-acetylpiperidin-4-yl) 4-tert-butyl 2-((pyridin-3-yloxy)methyl)piperazine-1,4-dicarboxylate (112.5 mg, 0.195 mmol) in MeOH (1 mL). After 1 h, the reaction mixture was concentrated under reduced pressure, yielding 82.4 mg (97%) of the desired product as a white solid. LC-MS: RT=1.66 min, [M+H]$^+$=363.2.

Example 233 tert-Butyl 2-((pyridin-3-yloxy)methyl)piperazine-1-carboxylate

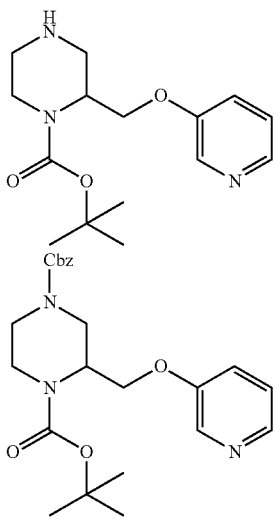

Step 1. Synthesis of 1-tert-butyl 4-benzyl 2-((pyridin-3-yloxy)methyl)piperazine-1,4-dicarboxylate Di-tert-butyl dicarbonate (399 mg, 1.83 mmol) was added to a solution of Intermediate O (544 mg, 1.66 mmol) and triethylamine (0.46 mL, 3.32 mmol) in THF (10 mL). After 12 h, the reaction mixture was diluted with EtOAc (40 mL) and washed with water (3×30 mL) and brine (30 mL). The organics were dried over $Na_2SO_4$, filtered, and concentrated under reduced pressure. The material was purified by column chomatography (10 to 40% EtOAc in Hexanes gradient), yielding 650 mg (92%) of the desired product. $R_f$=0.38 in 80% EtOAc/Hexanes; LC-MS: RT=8.74 min, [M+H]$^+$=428.2.

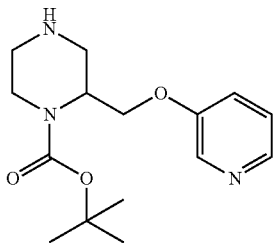 [SMILES: CC(C)(C)OC(=O)N1CCNCC1COc1cccnc1]

Step 2. Synthesis of tert-butyl 2-((pyridin-3-yloxy)methyl)piperazine-1-carboxylate Palladium hydroxide on carbon (~40% palladium, 0.170 g, 0.12 mmol) was added to a solution of 1-tert-butyl 4-benzyl 2-((pyridin-3-yloxy)methyl)piperazine-1,4-dicarboxylate (0.649 g, 1.52 mmol) and ammonium formate (0.191 g, 3.03 mmol) in EtOH (10 mL), and the reaction mixture was heated to 80° C. for 2 h. Upon cooling to rt, the reaction mixture was diluted with EtOAc (40 mL) and washed with water (3×30 mL) and brine (30 mL). The organics were dried over $Na_2SO_4$, filtered, and concentrated under reduced pressure, yielding 388.4 mg (87%) of the desired product as a white, waxy solid. LC-MS: RT=3.90 min, [M+H]$^+$=294.1.

Example 234

Benzyl 2-((pyridin-3-yloxy)methyl)piperazine-1-carboxylate

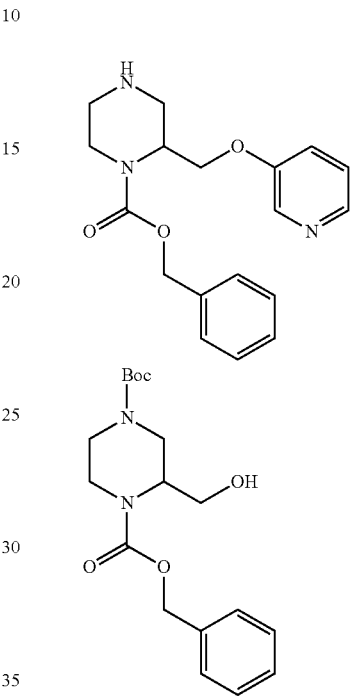

Step 1. Synthesis of 4-tert-butyl 1-benzyl 2-(hydroxymethyl)piperazine-1,4-dicarboxylate Piperazine-2-carboxyilc acid dihydrochloride (5.00 g, 24.6 mmol) was dissolved in $H_2O$ (80 mL) and 1,4-dioxane (80 mL), and the solution was brought to pH 11 with 50% aqueous NaOH. A solution of di-tert-butyl dicarbonate (5.36 g, 30.8 mmol) in 1,4-dioxane (40 mL) was added dropwise while maintaining the pH at 11 with 50% aqueous NaOH. After 12 h, the reaction mixture was extracted with $Et_2O$ (3×125 mL). The aqueous layer was brought to pH 2 with concentrated HCl and was extracted with EtOAc (4×100 mL). The aqueous solution was brought to pH 9.5 with 50% aqueous NaOH. Benzyl chloroformate (3.70 mL, 24.6 mmol) was added at 10° C. while maintaining the pH at 9.5 with 50% aqueous NaOH. The solution was allowed to warm to rt. After 2 h, the reaction mixture was extracted with $Et_2O$ (2×100 mL), brought to pH 1 with concentrated HCl, and extracted with EtOAc (3×150 mL). The combined EtOAc extracts were dried over $Na_2SO_4$, filtered, and concentrated under reduced pressure. The thick oil was dissolved in THF (100 mL) and cooled to 0° C. Borane-THF complex (1.0 M solution in THF, 75 mL, 75 mmol) was added portionwise. After 1 h, the reaction mixture was heated to 50° C. After 1 h, the reaction mixture was cooled to rt and quenched carefully with MeOH. After evolution of gas ceased, additional MeOH (100 mL) was added and the reaction mixture was heated to 70° C. for 1 h. Upon cooling to rt, the reaction mixture was concentrated under reduced pressure. Purification by column chomatography (20 to 40% EtOAc in Hexanes gradient) gave 4.52 g (52%) of the title compound. $R_f$=0.25 in 50% EtOAc/Hexanes; LC-MS: RT=9.53 min; [M+Na]$^+$=373.1; 2.068 g (22%) of dibenzyl 2-(hydroxymethyl)piperazine-1,4-dicarboxylate was also obtained. $R_f$=0.18 in 50% EtOAc/Hexanes; LC-MS: RT=9.47 min; [M+H]$^+$=385.1.

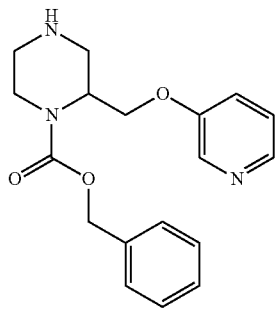 [SMILES: O=C(OCc1ccccc1)N1CCNCC1COc1cccnc1]

Step 2. Synthesis of 4-tert-butyl 1-benzyl 2-((pyridin-3-yloxy)methyl)piperazine-1,4-dicarboxylate A solution of diisopropylazodicarboxylate (2.67 mL, 13.5 mmol) in THF (25 mL) was added dropwise over 1 h to a solution of 4-tert-butyl 1-benzyl 2-(hydroxymethyl)piperazine-1,4-dicarboxylate (4.52 g, 12.9 mmol), 3-hydroxypyridine (1.35 g, 14.2 mmol) and triphenylphosphine (3.55 g, 13.5 mmol) in THF (75 mL) at 15° C. After complete addition, the reaction mixture was allowed to warm to rt and stir overnight. The reaction mixture was concentrated under reduced pressure and purified by column chomatography (10 to 40% EtOAc in Hexanes gradient). This gave 0.9055 g (16%) of the title compound. $R_f$=0.35 in 80% EtOAc/Hexanes; LC-MS: RT=9.85 min; [M+H]$^+$=428.2.

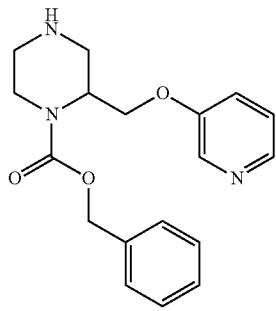 [SMILES: O=C(OCc1ccccc1)N1CCNCC1COc1cccnc1]

Step 3. Synthesis of benzyl 2-((pyridin-3-yloxy)methyl)piperazine-1-carboxylate 4 M HCl in 1,4-dioxane (6 mL, 24 mmol) was added to 4-tert-butyl 1-benzyl 2-((pyridin-3-yloxy)methyl)piperazine-1,4-dicarboxylate (77 mg, 0.18 mmol). After 12 h, the reaction mixture was concentrated under reduced pressure, dissolved in water, and basified with 1 N NaOH in water. The solution was extracted with EtOAc (3×), and the combined organics were dried over Na$_2$SO$_4$, filtered, and concentrated under reduced pressure. This gave 40.5 mg (69%) of the title compound. LC-MS: RT=5.15 min, [M+H]$^+$=328.1.

Example 235

2-(2-((Pyridin-3-yloxy)methyl)piperazin-1-yl)benzo[d]oxazole

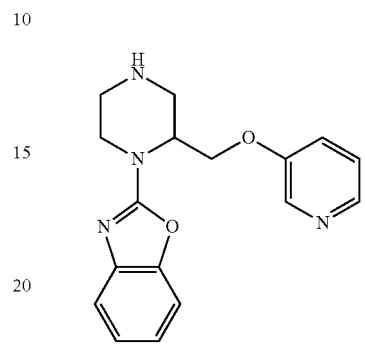

Step 1. Synthesis of tert-butyl 4-(benzo[d]oxazol-2-yl)-3-((pyridin-3-yloxy)methyl)piperazine-1-carboxylate 2-Chlorobenzoxazole (70.3 mg, 0.458 mmol) was added to a solution of Intermediate C (96 mg, 0.33 mmol) and DIEA (0.114 mL, 0.654 mmol) in i-PrOH (4 mL), and the reaction mixture was heated to 80° C. overnight. The reaction mixture was concentrated under reduced pressure and purified by HPLC (10 to 90% MeCN/0.1% TFA in H$_2$O/0.1% TFA gradient). This gave 74.0 mg (43%) of the di-TFA salt of the desired product as a yellow oil. LC-MS: RT=8.43 min, [M+H]$^+$=411.2.

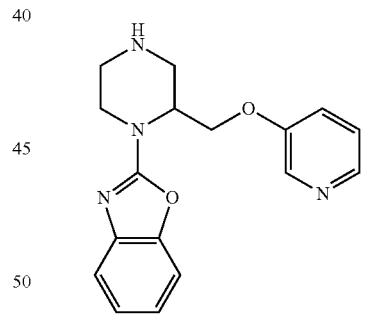

Step 2. Synthesis of 2-(2-((pyridin-3-yloxy)methyl)piperazin-1-yl)benzo[d]oxazole 4 M HCl in 1,4-dioxane (6 mL, 24 mmol) was added to a solution of tert-butyl 4-(benzo[d]oxazol-2-yl)-3-((pyridin-3-yloxy)methyl)piperazine-1-carboxylate di-TFA salt (74 mg, 0.14 mmol) in MeOH (1 mL). After 1 h, the reaction mixture was concentrated under reduced pressure. The material was dissolved in EtOAc (40 mL), washed with 1 N NaOH (2×20 mL) and brine (20 mL), dried over Na$_2$SO$_4$, filtered, and concentrated under reduced pressure. This gave 34.7 mg (79%) of the desired product as a thick yellow oil. LC-MS: RT=4.00 min, [M+H]$^+$=311.1.

Examples 236 and 237

Examples 236 and 237 were prepared as described for Example 235, substituting Intermediates $C_i$ and $C_{ii}$, respectively, for Intermediate C.

Example 236

(R)-2-(2-((pyridin-3-yloxy)methyl)piperazin-1-yl)benzo[d]oxazole hydrochloride

LC-MS: RT=4.04 min, [M+H]$^+$=311.0.

Example 237

(S)-2-(2-((pyridin-3-yloxy)methyl)piperazin-1-yl)benzo[d]oxazole hydrochloride

LC-MS: RT=4.00 min, [M+H]$^+$=311.0.

Example 238

5-chloro-2-(2-((pyridin-3-yloxy)methyl)piperazin-1-yl)benzo[d]oxazole

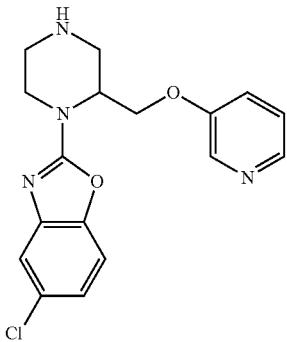 [SMILES: Clc1ccc2oc(N3CCNCC3COc3cccnc3)nc2c1]

Synthesis of 5-chloro-2-(2-((pyridin-3-yloxy)methyl)piperazin-1-yl)benzo[d]oxazole Intermediate AC (147 mg, 0.682 mmol) was added to a solution of Intermediate C (100 mg, 0.341 mmol) and DIEA (0.119 mL, 0.682 mmol) in toluene (5 mL), and the reaction mixture was heated to 50° C. overnight. The reaction mixture was concentrated under reduced pressure and purified by HPLC (10 to 90% MeCN/0.1% TFA in H$_2$O/0.1% TFA gradient). This gave 116.5 mg (51%) of the di-TFA salt of the desired product as an off-white solid. The compound was ~50% pure by HPLC. LC-MS: RT=9.30 min, [M+H]$^+$=445.1. The material was dissolved in MeOH (1 mL) and 4 M HCl in 1,4-dioxane (6 mL, 24 mmol) was added. After 2 h, the reaction mixture was concentrated under reduced pressure and purified by HPLC (5 to 50% MeCN/0.1% TFA in H$_2$O/0.1% TFA gradient). The fractions containing the desired product were brought to pH 12 with 1 N NaOH and were extracted with EtOAc (3×). The combined organics were dried over Na$_2$SO$_4$, filtered, and concentrated under reduced pressure. This gave 8.3 mg (14%) of the desired product. LC-MS: RT=4.62 min, [M+H]$^+$=345.1.

Example 239

6-chloro-2-(2-((pyridin-3-yloxy)methyl)piperazin-1-yl)benzo[d]oxazole

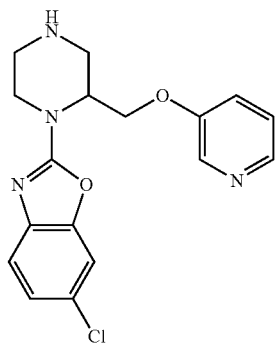 [SMILES: Clc1ccc2nc(N3CCNCC3COc3cccnc3)oc2c1]

Synthesis of 6-chloro-2-(2-((pyridin-3-yloxy)methyl)piperazin-1-yl)benzo[d]oxazole Intermediate AD (147 mg, 0.682 mmol) was added to a solution of Intermediate C (100 mg, 0.341 mmol) and DIEA (0.119 mL, 0.682 mmol) in toluene (5 mL), and the reaction mixture was heated to 50° C. overnight. The reaction mixture was concentrated under reduced pressure and purified by HPLC (10 to 90% MeCN/0.1% TFA in H$_2$O/0.1% TFA gradient). This gave 290.8 mg of the di-TFA salt of the crude product.

The compound was ~50% pure by HPLC. LC-MS: RT=9.29 min, [M+H]$^+$=445.1. The material was dissolved in MeOH (1 mL) and 4 M HCl in 1,4-dioxane (6 mL, 24 mmol) was added. After 2 h, the reaction mixture was concentrated under reduced pressure and purified by HPLC (5 to 50% MeCN/0.1% TFA in H$_2$O/0.1% TFA gradient). The fractions containing the desired product were brought to pH 12 with 1 N NaOH and were extracted with EtOAc (3×). The combined organics were dried over Na$_2$SO$_4$, filtered, and concentrated under reduced pressure. This gave 16.2 mg (22%) of the desired product. LC-MS: RT=4.62 min, [M+H]$^+$=345.1.

Example 240

6-methyl-2-(2-((pyridin-3-yloxy)methyl)piperazin-1-yl)benzo[d]oxazole hydrochloride

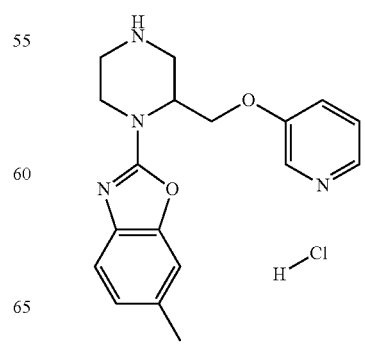

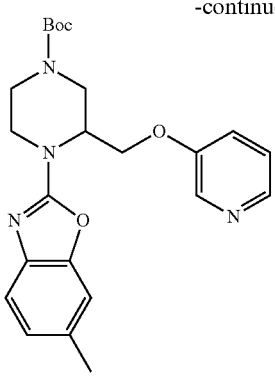

Step 1. Synthesis of tert-butyl 4-(6-methylbenzo[d]oxazol-2-yl)-3-((pyridin-3-yloxy)methyl)piperazine-1-carboxylate A solution of Intermediate S (101 mg, 0.614 mmol) and Intermediate C (150 mg, 0.511 mmol) in DMF (2 mL) was heated to 120° C. overnight. The reaction mixture was concentrated under reduced pressure and purified by HPLC (10 to 90% MeCN/0.1% TFA in H₂O/0.1% TFA gradient). This gave 91.1 mg (27%) of the di-TFA salt of the desired product as a thick oil. LC-MS: RT=8.95 min, [M+H]⁺=425.2.

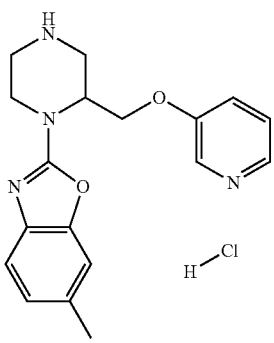 [SMILES: Cc1ccc2nc(N3CCNCC3COc3cccnc3)oc2c1 ; Cl]

Step 2. Synthesis of 6-methyl-2-(2-((pyridin-3-yloxy)methyl)piperazin-1-yl)benzo[d]oxazole hydrochloride 4 M HCl in 1,4-dioxane (6 mL, 24 mmol) was added to a solution of tert-butyl 4-(6-methylbenzo[d]oxazol-2-yl)-3-((pyridin-3-yloxy)methyl)piperazine-1-carboxylate di-TFA salt (91.1 mg, 0.140 mmol) in MeOH (1 mL). After 2 h, the reaction mixture was concentrated under reduced pressure and purified by HPLC (5 to 50% MeCN/0.1% TFA in H₂O/0.1% TFA gradient). The fractions containing the desired product were brought to pH 12 with 1 N NaOH, and brine (20 mL) was added. This was extracted with EtOAc (3×). The combined organics were dried over Na₂SO₄, filtered, and concentrated under reduced pressure, yielding 33.0 mg of the free-base of the desired product. The material was dissolved in MeOH (1 mL) and 4 M HCl in 1,4-dioxane (0.025 mL) was added. The mixture was concentrated under reduced pressure to give 35.5 mg (70%) of the desired product as the hydrochloride salt. LC-MS: RT=4.40 min, [M+H]⁺=325.1.

Example 241

6-methoxy-2-(2-((pyridin-3-yloxy)methyl)piperazin-1-yl)benzo[d]oxazole hydrochloride

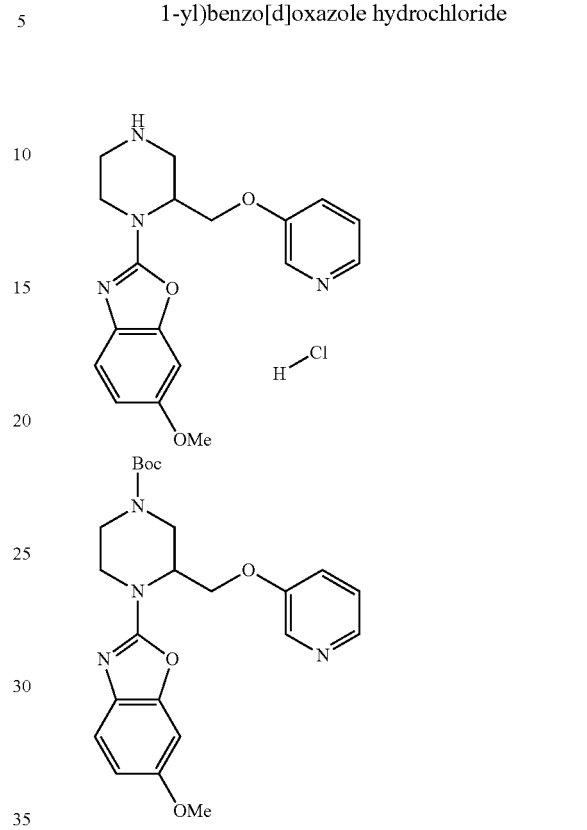

Step 1. Synthesis of tert-butyl 4-(6-methoxybenzo[d]oxazol-2-yl)-3-((pyridin-3-yloxy)methyl)piperazine-1-carboxylate A solution of Intermediate R (222 mg, 1.23 mmol) and Intermediate C (300 mg, 1.02 mmol) in 1,4-dioxane (5 mL) was heated to 140° C. overnight in a sealed tube. Upon cooling to rt, the reaction mixture was concentrated under reduced pressure and purified by HPLC (10 to 90% MeCN/0.1% TFA in H₂O/0.1% TFA gradient). This gave 150.6 mg (22%) of the di-TFA salt of the desired product as a thick oil. LC-MS: RT=8.29 min, [M+H]⁺=441.2.

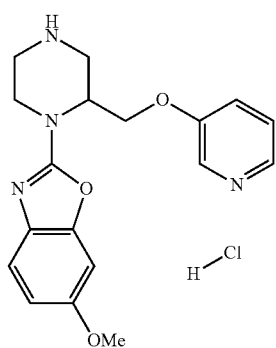 [SMILES: COc1ccc2nc(N3CCNCC3COc3cccnc3)oc2c1 ; Cl]

Step 2. Synthesis of 6-methoxy-2-(2-((pyridin-3-yloxy)methyl)piperazin-1-yl)benzo[d]oxazole hydrochloride 4 M HCl in 1,4-dioxane (6 mL, 24 mmol) was added to a solution of tert-butyl 4-(6-methoxybenzo[d]oxazol-2-yl)-3-((pyridin-3-yloxy)methyl)piperazine-1-carboxylate di-TFA salt (150.6 mg, 0.225 mmol) in MeOH (1 mL). After 2 h, the reaction mixture was concentrated under reduced pressure and purified by HPLC (5 to 50% MeCN/0.1% TFA in H$_2$O/0.1% TFA gradient). The fractions containing the desired product were brought to pH 12 with 1 N NaOH, and brine (20 mL) was added. This was extracted with EtOAc (3×). The combined organics were dried over Na$_2$SO$_4$, filtered, and concentrated under reduced pressure. The material was dissolved in MeOH (1 mL) and 4 M HCl in 1,4-dioxane (0.031 mL) was added. The mixture was concentrated under reduced pressure to give 37.4 mg (44%) of the desired product as the hydrochloride salt. LC-MS: RT=4.00 min, [M+H]$^+$=341.1.

Example 242

5-Methyl-2-(2-((pyridin-3-yloxy)methyl)piperazin-1-yl)benzo[d]oxazole hydrochloride

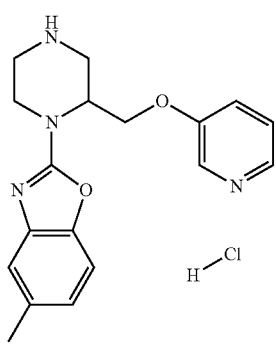 [SMILES: Cc1ccc2oc(N3CCNCC3COc3cccnc3)nc2c1 ; Cl]

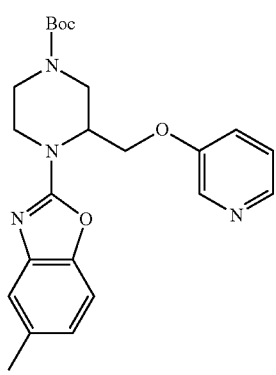

Step 1. Synthesis of tert-butyl 4-(5-methylbenzo[d]oxazol-2-yl)-3-((pyridin-3-yloxy)methyl)piperazine-1-carboxylate A solution of Intermediate T (339 mg, 2.05 mmol) and Intermediate C (200 mg, 0.682 mmol) in toluene (3 mL) was heated to 110° C. overnight. NMP (0.5 mL) was added and heating was continued overnight. Additional Intermediate T (225 mg, 1.36 mmol) was added, and heating was continued overnight. Upon cooling to rt, the reaction mixture was diluted with EtOAc (20 mL) and was washed with 1 N NaOH (2×10 mL) and brine (10 mL). The organics were dried over Na$_2$SO$_4$, filtered, and concentrated under reduced pressure. The material was purified by column chromatography (20 to 50% EtOAc in Hexanes gradient), yielding 212.9 mg (74%) of the desired product as an off-white solid. LC-MS: RT=8.97 min, [M+H]$^+$=425.2. R$_f$=0.29 in 70% EtOAc/Hexanes.

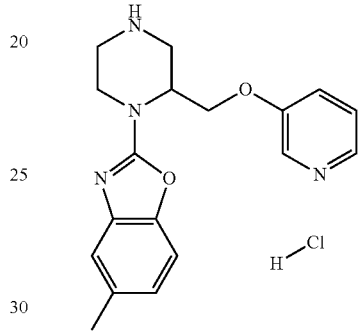

Step 2. Synthesis of 5-methyl-2-(2-((pyridin-3-yloxy)methyl)piperazin-1-yl)benzo[d]oxazole hydrochloride 4 M HCl in 1,4-dioxane (6 mL, 24 mmol) was added to a solution of tert-butyl 4-(5-methylbenzo[d]oxazol-2-yl)-3-((pyridin-3-yloxy)methyl)piperazine-1-carboxylate (212.9 mg, 0.502 mmol) in MeOH (1 mL). After stirring overnight, the reaction mixture was concentrated under reduced pressure and purified by HPLC (5 to 50% MeCN/0.1% TFA in H$_2$O/0.1% TFA gradient). The fractions containing the desired product were brought to pH 12 with 1 N NaOH and were extracted with EtOAc (3×). The combined organics were dried over Na$_2$SO$_4$, filtered, and concentrated under reduced pressure. The material was dissolved in MeOH (1 mL) and 4 M HCl in 1,4-dioxane (1 equiv. HCl, 0.057 mL) was added. The mixture was concentrated under reduced pressure to give 60.8 mg (34%) of the desired product as the hydrochloride salt. LC-MS: RT=4.45 min, [M+H]$^+$=325.1.

Examples 243-249

The examples found in Table 26 below were prepared by similar methods as described for Example 242, substituting Intermediates U through AA for Intermediate T, as indicated. All compounds were isolated as the hydrochloride salts unless otherwise noted.

TABLE 26

| Example No. | Intermediate | $R_d$ | $R_e$ | $R_f$ | IUPAC Name | HPLC RT (min) | LC-MS [M + H]$^+$ |
|---|---|---|---|---|---|---|---|
| 242 | T | H | CH$_3$ | H | 5-methyl-2-(2-((pyridin-3-yloxy)methyl)-piperazin-1-yl)-benzo[d]oxazole hydrochloride | 4.45 | 325.1 |
| 243 | U | H | OMe | H | 5-methoxy-2-(2-((pyridin-3-yloxy)methyl)-piperazin-1-yl)-benzo[d]oxazole hydrochloride | 4.09 | 341.1 |
| 244 | V | H | Ph | H | 5-phenyl-2-(2-((pyridin-3-yloxy)methyl)-piperazin-1-yl)-benzo[d]oxazole hydrochloride | 5.34 | 387.1 |
| 245 | W | H | Br | H | 5-bromo-2-(2-((pyridin-3-yloxy)methyl)-piperazin-1-yl)-benzo[d]oxazole hydrochloride | 4.74 | 389.9 |
| 246 | X | H | H | CH$_3$ | 4-methyl-2-(2-((pyridin-3-yloxy)methyl)-piperazin-1-yl)-benzo[d]oxazole hydrochloride | 4.39 | 325.1 |
| 247 | Z | F | H | H | 6-fluoro-2-(2-((pyridin-3-yloxy)-methyl)piperazin-1-yl)benzo[d]oxazole hydrochloride | 4.13 | 329.0 |
| 248 | Y | H | F | H | 5-fluoro-2-(2-((pyridin-3-yloxy)-methyl)piperazin-1-yl)benzo[d]oxazole hydrochloride | 4.48 | 329.0 |
| 249 | AA | H | CF$_3$ | H | 2-(2-((pyridin-3-yloxy)methyl)-piperazin-1-yl)-5-(trifluoromethyl)-benzo[d]oxazole hydrochloride | 5.55 | 379.6 |

Example 250

2-(2-((pyridin-3-yloxy)methyl)piperazin-1-yl)oxazolo[4,5-b]pyridine hydrochloride Step 1. Synthesis of tert-butyl 4-(oxazolo[4,5-b]pyridin-2-yl)-3-((pyridin-3-yloxy)methyl)piperazine-1-carboxylate A solution of Intermediate AB (369 mg, 2.42 mmol) and Intermediate C (237 mg, 0.808 mmol) in toluene (3 mL) and DMSO (0.3 mL) was heated to 110° C. overnight. Upon cooling to rt, the reaction mixture was concentrated under reduced pressure. The material was purified by column chromatography (30 to 100% EtOAc in Hexanes gradient), yielding 273 mg (82%) of the title compound as an off-white solid. LC-MS: RT=6.59 min, [M+H]$^+$=412.7. $R_f$=0.30 in 10% MeOH in EtOAc.

Step 2. Synthesis of 2-(2-((pyridin-3-yloxy)methyl) piperazin-1-yl)oxazolo[4,5-b]pyridine hydrochloride 4 M HCl in 1,4-dioxane (6 mL, 24 mmol) was added to a solution of tert-butyl 4-(oxazolo[4,5-b]pyridin-2-yl)-3-((pyridin-3-yloxy)methyl)piperazine-1-carboxylate (273 mg, 0.664 mmol) in MeOH (1 mL). After 1 h, the reaction mixture was concentrated under reduced pressure and purified by HPLC (5 to 50% MeCN/0.1% TFA in H$_2$O/0.1% TFA gradient). The fractions containing the desired product were combined and brought to pH 12 with 1 N NaOH and were extracted with EtOAc (3×). The combined organics were dried over Na$_2$SO$_4$, filtered, and concentrated under reduced pressure. The material was dissolved in MeOH (1 mL) and 4 M HCl in 1,4-dioxane (1 equiv. HCl, 0.116 mL) was added. The mixture was concentrated under reduced pressure to give 148 mg (64%) of the desired product as the hydrochloride salt. LC-MS: RT=2.18 min, [M+H]$^+$=312.5.

Examples 251 and 252

Examples 251 and 252 were prepared as described for Example 250, substituting Intermediates BI and BJ, respectively, for Intermediate AB.

Example 251

5-methyl-2-(2-((pyridin-3-yloxy)methyl)piperazin-1-yl)oxazolo[4,5-b]pyridine hydrochloride LC-MS: RT=3.60 min, [M+H]$^+$=326.1.

Example 252

6-methyl-2-(2-((pyridin-3-yloxy)methyl)piperazin-1-yl)oxazolo[4,5-b]pyridine

LC-MS: RT=4.07 min, [M+H]$^+$=326.1.

Examples 253-256

Examples 253-256 were prepared as described for Example 250-252, substituting Intermediates AB, BI or BJ and substituting Intermediates C$_i$ and C$_{ii}$, respectively, for Intermediate C.

Example 253

(R)-2-(2-((pyridin-3-yloxy)methyl)piperazin-1-yl)oxazolo[4,5-b]pyridine hydrochloride LC-MS: RT=3.15 min, [M+H]$^+$=312.1.

Example 254

(S)-2-(2-((pyridin-3-yloxy)methyl)piperazin-1-yl)oxazolo[4,5-b]pyridine hydrochloride LC-MS: RT=2.73 min, [M+H]$^+$=312.1.

Example 255

(R)-5-methyl-2-(2-((pyridin-3-yloxy)methyl)piperazin-1-yl)oxazolo[4,5-b]pyridine hydrochloride LC-MS: RT=3.95 min, [M+H]$^+$=326.1.

Example 256

(R)-6-methyl-2-(2-((pyridin-3-yloxy)methyl)piperazin-1-yl)oxazolo[4,5-b]pyridine hydrochloride LC-MS: RT=4.14 min, [M+H]$^+$=326.1.

Example 257

2-(2-((3-fluorophenoxy)methyl)piperazin-1-yl)oxazolo[4,5-b]pyridine hydrochloride Example 257 was prepared as described for Example 250, substituting Intermediate G for Intermediate C. LC-MS: RT=4.97 min, [M+H]$^+$=329.1.

Example 258

2-(2-((2-methylpyridin-3-yloxy)methyl)piperazin-1-yl)oxazolo[4,5-b]pyridine hydrochloride Example 258 was prepared as described for Example 242, substituting Intermediate M for Intermediate C. LC-MS: RT=2.13 min, [M+H]$^+$=326.1.

Examples 259-263

The examples found in Table 27 below were prepared by similar methods as described for Example 242, substituting Intermediates S, T, U, V, and W for T and Intermediate C$_i$ for Intermediate C. All compounds were isolated as the hydrochloride salts unless otherwise noted.

TABLE 27

| Example No. | R$_d$ | R$_e$ | IUPAC Name | HPLC RT (min) | LC-MS [M + H]$^+$ |
|---|---|---|---|---|---|
| 259 | H | OMe | (R)-5-methoxy-2-(2-((pyridin-3-yloxy)methyl)piperazin-1-yl)benzo[d]oxazole hydrochloride | 4.06 | 341.0 |
| 260 | H | Br | (R)-5-bromo-2-(2-((pyridin-3-yloxy)methyl)piperazin-1-yl)benzo[d]oxazole hydrochloride | 4.65 | 388.9 |
| 261 | CH$_3$ | H | (R)-6-methyl-2-(2-((pyridin-3-yloxy)methyl)piperazin-1-yl)benzo[d]oxazole hydrochloride | 4.94 | 325.1 |
| 262 | H | CH$_3$ | (R)-5-methyl-2-(2-((pyridin-3-yloxy)methyl)piperazin-1-yl)benzo[d]oxazole hydrochloride | 4.89 | 325.1 |
| 263 | H | Ph | (R)-5-phenyl-2-(2-((pyridin-3-yloxy)methyl)piperazin-1-yl)benzo[d]oxazole hydrochloride | 5.68 | 387.1 |

Examples 264-266

The examples found in Table 28 below were prepared by similar methods as described for Example 242, substituting Intermediates R, U and W for Intermediate T and Intermediate C$_{ii}$ for Intermediate C. All compounds were isolated as the hydrochloride salts unless otherwise noted.

TABLE 28

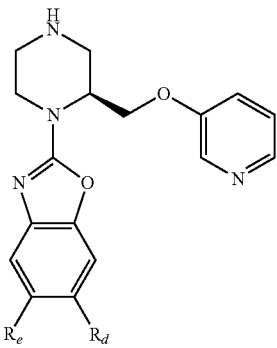

| Example No. | $R_d$ | $R_e$ | IUPAC Name | HPLC RT (min) | LC-MS [M + H]+ |
|---|---|---|---|---|---|
| 264 | H | OMe | (S)-5-methoxy-2-(2-((pyridin-3-yloxy)methyl)piperazin-1-yl)benzo[d]oxazole hydrochloride | 4.05 | 341.0 |
| 265 | H | Br | (S)-5-bromo-2-(2-((pyridin-3-yloxy)methyl)piperazin-1-yl)benzo[d]oxazole hydrochloride | 4.67 | 388.9 |
| 266 | OMe | H | (S)-6-methoxy-2-(2-((pyridin-3-yloxy)methyl)piperazin-1-yl)benzo[d]oxazole hydrochloride | 4.04 | 341.0 |

Examples 267-268

The examples found in Table 29 below were prepared by similar methods as described for Example 242, substituting Intermediate Q for Intermediate T and Intermediate K or Intermediate L for Intermediate C. All compounds were isolated as the hydrochloride salts unless otherwise noted.

TABLE 29

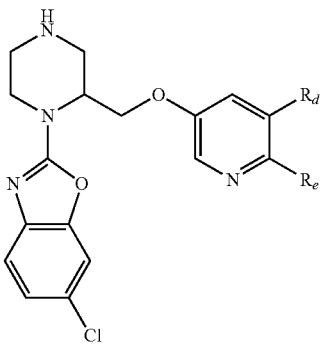

| Example No. | $R_d$ | $R_e$ | IUPAC Name | HPLC RT (min) | LC-MS [M + H]+ |
|---|---|---|---|---|---|
| 267 | Cl | H | 6-chloro-2-(2-((5-chloropyridin-3-yloxy)methyl)piperazin-1-yl)benzo[d]oxazole hydrochloride | 5.39 | 379.0 |
| 268 | H | CH$_3$ | 6-chloro-2-(2-((6-methylpyridin-3-yloxy)methyl)piperazin-1-yl)benzo[d]oxazole hydrochloride | 4.43 | 359.1 |

Example 269

2-(2-((pyridin-3-yloxy)methyl)piperazin-1-yl)thiazole trihydrochloride

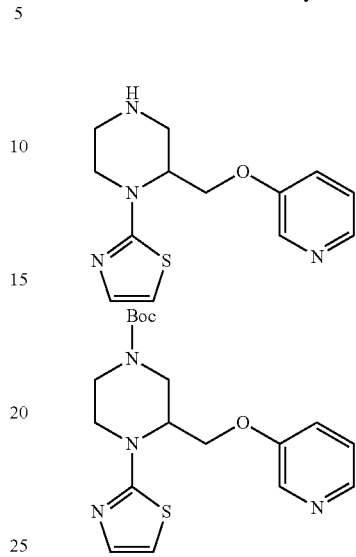

Step 1. Synthesis of tert-butyl 3-((pyridin-3-yloxy)methyl)-4-(thiazol-2-yl)piperazine-1-carboxylate Palladium(II) acetate (6.9 mg, 0.031 mmol) was added to a mixture of Intermediate C (181 mg, 0.617 mmol), 2-bromothiazole (152 mg, 0.925 mmol), sodium tert-butoxide (65.2 mg, 0.679 mmol), and triphenylphosphine (8.1 mg, 0.031 mmol) in toluene (2 mL). The reaction mixture was heated to 110° C. overnight. An additional portion of 2-bromothiazole (151 mg, 0.926 mmol) and Pd(OAc)$_2$ (6.9 mg, 0.031 mmol) were added and heating was continued overnight. Upon cooling to rt, the reaction mixture was diluted with EtOAc (100 mL) and washed with water (50 mL) and brine (50 mL). The organics were dried over Na$_2$SO$_4$, filtered, and concentrated under reduced pressure. The material was purified by HPLC (10 to 90% MeCN/0.1% TFA in H$_2$O/0.1% TFA gradient), yielding 130 mg (35%) of the di-TFA salt of the desired product as a thick oil. LC-MS: RT=7.49 min, [M+H]+=377.1.

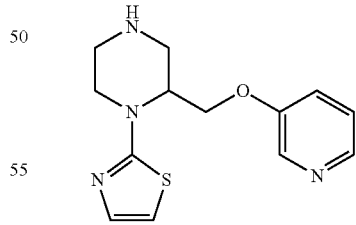

Step 2. Synthesis of 2-(2-((pyridin-3-yloxy)methyl)piperazin-1-yl)thiazole trihydrochloride 4 M HCl in 1,4-dioxane (6 mL, 24 mmol) was added to a solution of tert-butyl 3-((pyridin-3-yloxy)methyl)-4-(thiazol-2-yl)piperazine-1-carboxylate di-TFA salt (130 mg, 0.215 mmol) in MeOH (1 mL). After 1 h, the reaction mixture was concentrated under reduced pressure and purified by HPLC (5 to 50% MeCN/0.1% TFA in H$_2$O/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 37.9 mg (46%) of the desired product as a white solid. LC-MS: RT=2.64 min, [M+H]$^+$=277.0.

Example 270

2-(2-((pyridin-3-yloxy)methyl)piperazin-1-yl)benzo[d]thiazole

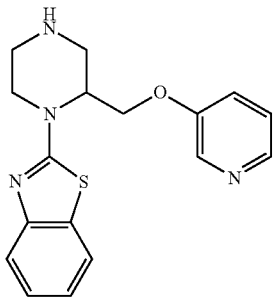

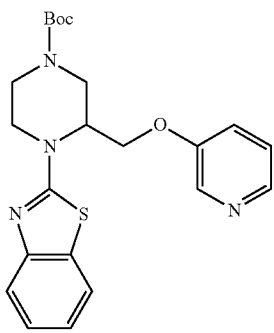

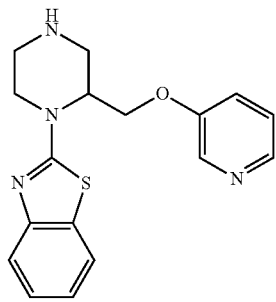

Step 2. Synthesis of 2-(2-((pyridin-3-yloxy)methyl)piperazin-1-yl)benzo[d]thiazole 4 M HCl in 1,4-dioxane (6 mL, 24 mmol) was added to a solution of tert-butyl 4-(benzo[d]thiazol-2-yl)-3-((pyridin-3-yloxy)methyl)piperazine-1-carboxylate di-TFA salt (116.4 mg, 0.215 mmol) in MeOH (1 mL). After 12 h, the reaction mixture was concentrated under reduced pressure and purified by HPLC (5 to 50% MeCN/0.1% TFA in H$_2$O/0.1% TFA gradient). The fractions containing the desired product were brought to pH 12 with 1 N NaOH and were extracted with EtOAc (3×). The combined organics were dried over Na$_2$SO$_4$, filtered, and concentrated under reduced pressure. This gave 41.7 mg (59%) of the desired product as an off-white, sticky solid. LC-MS: RT=4.38 min, [M+H]$^+$=327.1.

Examples 271-291

The examples found in Table 30 below were prepared by similar methods as described for Example 270 substituting the appropriate 2-chlorobenzothiazole.

TABLE 30

| Example No. | $R_d$ | $R_e$ | $R_f$ | $R_g$ | IUPAC Name | HPLC RT (min) | LC-MS [M + H]$^+$ |
|---|---|---|---|---|---|---|---|
| 270 | H | H | H | H | 2-(2-((pyridin-3-yloxy)methyl)-piperazin-1-yl)-benzo[d]thiazole | 4.38 | 327.1 |
| 271 | H | H | Cl | H | 6-chloro-2-(2-((pyridin-3-yloxy)-methyl)piperazin-1-yl)benzo[d]-thiazole | 5.00 | 361.1 |
| 272 | H | H | OMe | H | 6-methoxy-2-(2-((pyridin-3-yloxy)-methyl)piperazin- | 4.34 | 357.1 |

Step 1. Synthesis of tert-butyl 4-(benzo[d]thiazol-2-yl)-3-((pyridin-3-yloxy)methyl)piperazine-1-carboxylate Palladium(II) acetate (3.8 mg, 0.017 mmol) was added to a mixture of Intermediate C (100 mg, 0.341 mmol), 2-chlorobenzothiazole (87 mg, 0.511 mmol), sodium tert-butoxide (36 mg, 0.38 mmol), and triphenylphosphine (4.4 mg, 0.017 mmol) in toluene (1 mL). The reaction mixture was heated to 110° C. overnight. Upon cooling to rt, the reaction mixture was filtered and concentrated under reduced pressure. The material was purified by HPLC (10 to 90% MeCN/0.1% TFA in H$_2$O/0.1% TFA gradient), yielding 116.4 mg (52%) of the di-TFA salt of the desired product as a thick oil. ~85% pure by HPLC. LC-MS: RT=9.14 min, [M+H]$^+$=427.1.

TABLE 30-continued

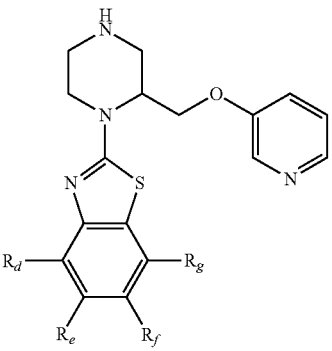

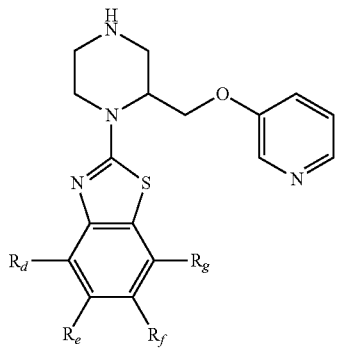

| Example No. | $R_d$ | $R_e$ | $R_f$ | $R_g$ | IUPAC Name | HPLC RT (min) | LC-MS $[M+H]^+$ |
|---|---|---|---|---|---|---|---|
| 273* | Cl | OMe | H | H | 4-chloro-5-methoxy-2-(2-((pyridin-3-yloxy)methyl)piperazin-1-yl)benzo[d]thiazole hydrochloride | 4.71 | 391.0 |
| 274 | H | Cl | H | H | 5-chloro-2-(2-((pyridin-3-yloxy)methyl)piperazin-1-yl)benzo[d]thiazole | 5.01 | 361.0 |
| 275* | H | OMe | H | H | 5-methoxy-2-(2-((pyridin-3-yloxy)methyl)piperazin-1-yl)benzo[d]thiazole hydrochloride | 4.28 | 357.5 |
| 276* | H | $CF_3$ | H | H | 2-(2-((pyridin-3-yloxy)methyl)piperazin-1-yl)-5-(trifluoromethyl)benzo[d]thiazole hydrochloride | 5.18 | 395.6 |
| 277* | H | F | H | H | 5-fluoro-2-(2-((pyridin-3-yloxy)methyl)piperazin-1-yl)benzo[d]thiazole hydrochloride | 4.38 | 345.5 |
| 278* | H | H | i-Pr | H | 6-isopropyl-2-(2-((pyridin-3-yloxy)methyl)piperazin-1-yl)benzo[d]thiazole hydrochloride | 5.31 | 369.9 |
| 279* | H | H | $CF_3$ | H | 2-(2-((pyridin-3-yloxy)methyl)piperazin-1-yl)-6-(trifluoromethyl)benzo[d]thiazole hydrochloride | 5.17 | 395.6 |
| 280* | H | H | $OCF_3$ | H | 2-(2-((pyridin-3-yloxy)methyl)piperazin-1-yl)-6-(trifluoromethoxy)benzo[d]thiazole hydrochloride | 5.25 | 411.6 |
| 281* | H | F | F | H | 5,6-difluoro-2-(2-((pyridin-3-yloxy)methyl)piperazin-1-yl)benzo[d]thiazole hydrochloride | 4.60 | 363.5 |
| 282* | F | H | H | H | 4-fluoro-2-(2-((pyridin-3-yloxy)methyl)piperazin-1-yl)benzo[d]thiazole hydrochloride | 4.35 | 345.5 |
| 283* | H | H | $CH_3$ | H | 6-methyl-2-(2-((pyridin-3-yloxy)methyl)piperazin-1-yl)benzo[d]thiazole hydrochloride | 4.66 | 341.5 |
| 284* | H | H | F | H | 6-fluoro-2-(2-((pyridin-3-yloxy)methyl)piperazin-1-yl)benzo[d]thiazole hydrochloride | 4.47 | 345.5 |
| 285* | H | $CH_3$ | $CH_3$ | H | 5,6-dimethyl-2-(2-((pyridin-3-yloxy)methyl)piperazin-1-yl)benzo[d]thiazole hydrochloride | 5.00 | 355.6 |
| 286* | H | H | $CH_3SO_2$ | H | 6-(methylsulfonyl)-2-(2-((pyridin-3-yloxy)methyl)piperazin-1-yl)benzo[d]thiazole hydrochloride | 3.52 | 405.6 |
| 287* | H | H | O—iPr | H | 6-isopropoxy-2-(2-((pyridin-3-yloxy)methyl)piperazin-1-yl)benzo[d]thiazole hydrochloride | 5.03 | 385.0 |
| 288* | H | H | $OCH_2Ph$ | H | 6-(benzyloxy)-2-(2-((pyridin-3-yloxy)methyl)piperazin-1-yl)benzo[d]thiazole hydrochloride | 5.53 | 433.0 |
| 289* | F | H | F | H | 4,6-difluoro-2-(2-((pyridin-3-yloxy)methyl)piperazin-1-yl)benzo[d]thiazole hydrochloride | 4.65 | 363.5 |
| 290* | H | H | F | F | 6,7-difluoro-2-(2-((pyridin-3-yloxy)methyl)piperazin-1-yl)benzo[d]thiazole hydrochloride | 4.75 | 363.5 |
| 291* | H | H | H | F | 7-fluoro-2-(2-((pyridin-3-yloxy)methyl)piperazin- | 4.55 | 345.5 |

TABLE 30-continued

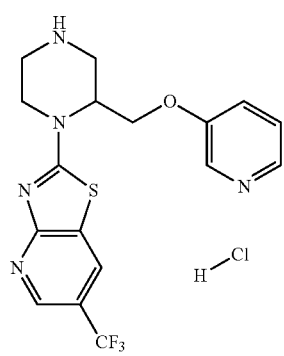 [SMILES: FC(F)(F)c1cnc2nc(N3CCNCC3COc3cccnc3)sc2c1 ; Cl]

| Ex-ample No. | $R_d$ | $R_e$ | $R_f$ | $R_g$ | IUPAC Name | HPLC RT (min) | LC-MS [M+H]$^+$ |
|---|---|---|---|---|---|---|---|
| | | | | | 1-yl)benzo[d]-thiazole hydrochloride | | |

*Compound was converted to the hydrochloride salt by addition of 1 equivalent HCl

Example 292

2-(2-((pyridin-3-yloxy)methyl piperazin-1-yl)thiazolo[4,5-b]pyridine hydrochloride Example 292 was prepared as described for Example 270, substituting Intermediate AZ for 2-chlorobenzothiazole. LC-MS: RT=2.13 min, [M+H]$^+$=326.1.

Example 293

2-(2-((pyridin-3-yloxy)methyl)piperazin-1-yl)-6-(trifluoromethyl)thiazolo[4,5-b]pyridine hydrochloride

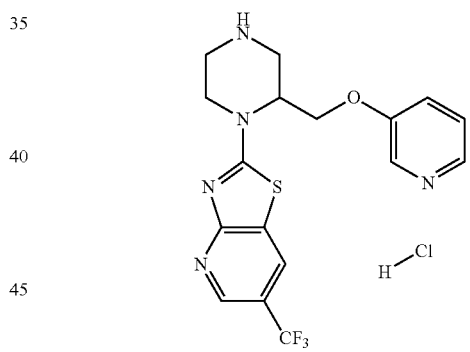

-continued

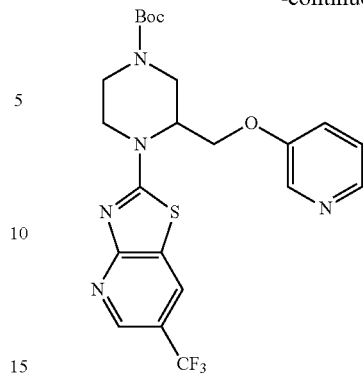

Step 1. Synthesis of tert-butyl 3-((pyridin-3-yloxy)methyl)-4-(6-(trifluoromethyl)thiazolo[4,5-b]pyridin-2-yl)piperazine-1-carboxylate A solution of Intermediate BA (447 mg, 1.87 mmol) and Intermediate C (275 mg, 0.937 mmol) in toluene (2 mL) was heated to 110° C. overnight. Upon cooling to rt, the reaction mixture was diluted with EtOAc (30 mL), washed with 1 N NaOH (2×20 mL) and brine (20 mL), dried over Na$_2$SO$_4$, filtered, and concentrated under reduced pressure. The material was purified by column chromatography (30 to 95% EtOAc in Hexanes gradient), yielding 134 mg (29%) of the title compound. LC-MS: RT=8.70 min, [M+H]$^+$=496.8. R$_f$=0.54 in 100% EtOAc.

Step 2. Synthesis of 2-(2-((pyridin-3-yloxy)methyl)piperazin-1-yl)-6-(trifluoromethyl)thiazolo[4,5-b]pyridine hydrochloride 4 M HCl in 1,4-dioxane (6 mL, 24 mmol) was added to a solution of tert-butyl 3-((pyridin-3-yloxy)methyl)-4-(6-(trifluoromethyl)thiazolo[4,5-b]pyridin-2-yl)piperazine-1-carboxylate (134 mg, 0.271 mmol) in MeOH (1 mL). After stirring overnight, the reaction mixture was concentrated under reduced pressure and purified by HPLC (5 to 50% MeCN/0.1% TFA in H$_2$O/0.1% TFA gradient). The fractions containing the desired product were combined and brought to pH 12 with 1 N NaOH and were extracted with EtOAc (3×). The combined organics were dried over Na$_2$SO$_4$, filtered, and concentrated under reduced pressure. The material was dissolved in MeOH (1 mL) and 4 M HCl in 1,4-dioxane (1 equiv. HCl, 0.036 mL) was added. The mixture was concentrated under reduced pressure to give 60.5 mg (52%) of the desired product as the hydrochloride salt. LC-MS: RT=4.53 min, [M+H]⁺=396.6.

Examples 294-296

The examples found in Table 31 below were prepared by similar methods as described for Example 293, substituting Intermediates BB, BC and AW for Intermediate BA. All compounds were isolated as the hydrochloride salts unless otherwise noted.

TABLE 31

| Example No. | $R_d$ | X | IUPAC Name | HPLC RT (min) | LC-MS [M + H]⁺ |
|---|---|---|---|---|---|
| 294 | Cl | N | 6-chloro-2-(2-((pyridin-3-yloxy)methyl)piperazin-1-yl)thiazolo[4,5-b]pyridine hydrochloride | 4.16 | 362.5 |
| 295 | Br | N | 6-bromo-2-(2-((pyridin-3-yloxy)methyl)piperazin-1-yl)thiazolo[4,5-b]pyridine hydrochloride | 4.33 | 406.0 |
| 296 | Br | C—F | 6-bromo-4-fluoro-2-(2-((pyridin-3-yloxy)methyl)piperazin-1-yl)benzo[d]thiazole hydrochloride | 5.23 | 423.0 |

Example 297

4,6-difluoro-2-(2-((2-methylpyridin-3-yloxy)methyl)piperazin-1-yl)benzo[d]thiazole hydrochloride Example 297 was prepared as described for Example 293, substituting Intermediate AU for Intermediate BA and Intermediate M for Intermediate C. LC-MS: RT=4.19 min, [M+H]⁺=377.1.

Example 298

4-(6-(benzyloxy)benzo[d]thiazol-2-yl)-3-((pyridin-3-yloxy)methyl)piperazine-1-carbaldehyde dihydrochloride

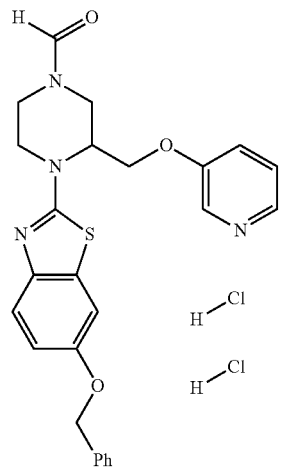 [SMILES: O=CN1CCN(c2nc3ccc(OCc4ccccc4)cc3s2)C(COc2cccnc2)C1 ; Cl ; Cl]

6-(Benzyloxy)-2-(2-((pyridin-3-yloxy)methyl)piperazin-1-yl)benzo[d]thiazole (293 mg, 0.677 mmol), ammonium formate (85 mg, 1.35 mmol) and palladium hydroxide on carbon (~20% Pd, 38 mg, 0.054 mmol) were heated to reflux in EtOH (5 mL). After 2 h, additional ammonium formate was added and heating continued for 2 h. Upon cooling to rt, the reaction mixture was filtered through Celite® and concentrated under reduced pressure. The material was purified by HPLC (10 to 90% MeCN/0.1% TFA in H₂O/0.1% TFA gradient), yielding 157 mg (50%) of the title compound. LC-MS: RT=7.82 min, [M+H]⁺=461.0.

Example 299

4-(6-hydroxybenzo[d]thiazol-2-yl)-3-((pyridin-3-yloxy)methyl)piperazine-1-carbaldehyde dihydrochloride

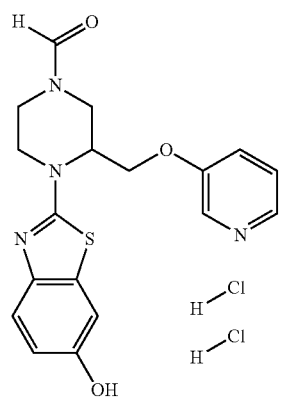

27 mg of the title compound were isolated from the reaction mixture of Example 282 upon HPLC purification and conversion to the di-HCl salt. LC-MS: RT=4.59 min, [M+H]⁺=371.0.

Example 300

2-(2-((pyridin-3-yloxy)methyl)piperazin-1-yl)benzo[d]thiazol-6-ol trihydrochloride

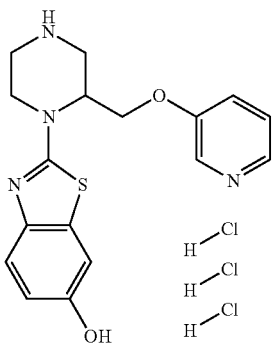

4-(6-(Benzyloxy)benzo[d]thiazol-2-yl)-3-((pyridin-3-yloxy)methyl)piperazine-1-carbaldehyde dihydrochloride (130 mg, 0.244 mmol) and HCl (conc., 1.0 mL) were heated to 100° C. in EtOH (1 mL) and water (1 mL) for 2 h. Upon cooling to rt, the reaction mixture was concentrated under reduced pressure and purified by HPLC (5 to 50% MeCN/0.1% TFA in H₂O/0.1% TFA gradient). The desired fractions were concentrated under reduced pressure, dissolved in MeOH (1 mL) and treated with 4 M HCl in 1,4-dioxane (6 mL). This was concentrated under reduced pressure, yielding 73.8 mg (67%) of the title compound as a white solid. LC-MS: RT=3.45 min, [M+H]⁺=343.

Example 301

1-(4-(6-methoxybenzo[d]thiazol-2-yl)-3-((pyridin-3-yloxy)methyl)piperazin-1-yl)ethanone dihydrochloride

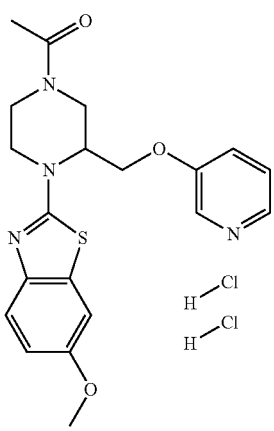

Acetic anhydride (0.100 mL) was added to a solution of 6-methoxy-2-(2-((pyridin-3-yloxy)methyl)piperazin-1-yl) benzo[d]thiazole hydrochloride (73.2 mg, 0.186 mmol) in THF (2 mL), and the mixture was heated to 70° C. for 2 h. Upon cooling to rt, the reaction mixture was concentrated under reduced pressure and purified by HPLC (5 to 50% MeCN/0.1% TFA in H₂O/0.1% TFA gradient). The fractions containing the desired product were brought to pH 12 with 1 N NaOH and were extracted with EtOAc (3×). The combined organics were dried over Na₂SO₄, filtered, and concentrated under reduced pressure. The material was dissolved in MeOH (1 mL) and treated with 4 M HCl in 1,4-dioxane (6 mL). This was concentrated under reduced pressure, yielding 74.3 mg (85%) of the title compound as a white solid. LC-MS: RT=6.10 min, [M+H]⁺=399.0.

Examples 302-307

Examples 302-307 were prepared as described for Example 270, substituting Intermediates Ci and Cii, respectively, for Intermediate C and the appropriately substituted 2-chlorobenzothiazole.

Example 302

(R)-6-methoxy-2-(2-((pyridin-3-yloxy)methyl)piperazin-1-yl)benzo[d]thiazole hydrochloride LC-MS: RT=4.37 min, [M+H]⁺=357.0.

Example 303

(S)-6-methoxy-2-(2-((pyridin-3-yloxy)methyl)piperazin-1-yl)benzo[d]thiazole hydrochloride LC-MS: RT=4.36 min, [M+H]⁺=357.0.

Example 304

(R)-4-fluoro-2-(2-((pyridin-3-yloxy)methyl)piperazin-1-yl)benzo[d]thiazole hydrochloride LC-MS: RT=4.95 min, [M+H]⁺=344.8.

Example 305

(R)-5,6-difluoro-2-(2-((pyridin-3-yloxy)methyl)piperazin-1-yl)benzo[d]thiazole hydrochloride LC-MS: RT=5.19 min, [M+H]⁺=362.7.

Example 306

(R)-6,7-difluoro-2-(2-((pyridin-3-yloxy)methyl)piperazin-1-yl)benzo[d]thiazole hydrochloride LC-MS: RT=5.28 min, [M+H]⁺=362.7.

Example 307

(R)-4,6-difluoro-2-(2-((pyridin-3-yloxy)methyl)piperazin-1-yl)benzo[d]thiazole hydrochloride LC-MS: RT=5.02 min, [M+H]⁺=362.7.

Examples 308-309

The examples found in Table 32 below were prepared by similar methods as described for Example 270, substituting the appropriate 2-chlorobenzothiazole and Intermediate K or Intermediate L for Intermediate C. All reagents were commercially available unless otherwise noted.

TABLE 32

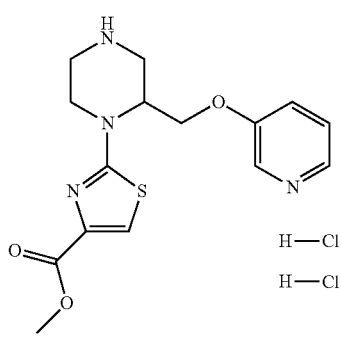

| Example No. | $R_d$ | $R_e$ | IUPAC Name | HPLC RT (min) | LC-MS $[M + H]^+$ |
|---|---|---|---|---|---|
| 308 | Cl | H | 2-(2-((5-chloropyridin-3-yloxy)methyl)piperazin-1-yl)-6-methoxybenzo[d]-thiazole hydrochloride | 5.29 | 391 |
| 309 | H | CH₃ | 6-methoxy-2-(2-((6-methylpyridin-3-yloxy)methyl)piperazin-1-yl)benzo[d]thiazole hydrochloride | 4.16 | 371.1 |

Example 310

Methyl 2-(2-((pyridin-3-yloxy)methyl)piperazin-1-yl)thiazole-4-carboxylate dihydrochloride

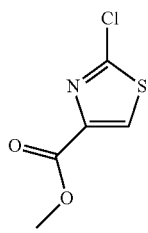

Step 1. Synthesis of methyl 2-chlorothiazole-4-carboxylate

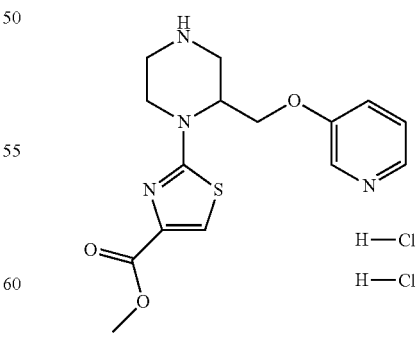

Thionyl chloride (4.4 mL, 61 mmol) was added dropwise to a solution of 2-chlorothiazole-4-carboxylic acid (2.00 g, 12.2 mmol) in MeOH (40 mL) at 0° C., and the reaction mixture was allowed to warm to rt. After stirring overnight, the reaction mixture was concentrated under reduced pressure. The resulting solid was recrystallized from EtOH/H₂O (1:1), yielding 1.40 g (65%) of the title compound as an orange solid. LC-MS: RT=6.17 min, $[M+H]^+$=178.1.

Step 2. Synthesis of methyl 2-(4-(tert-butoxycarbonyl)-2-((pyridin-3-yloxy)methyl)piperazin-1-yl)thiazole-4-carboxylate

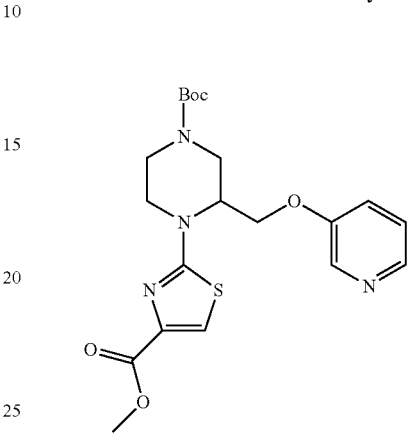

Methyl 2-chlorothiazole-4-carboxylate (0.494 g, 2.78 mmol), Intermediate C (0.680 g, 2.32 mmol), and Na₂CO₃ (0.492 g, 4.64 mmol) were heated to reflux in THF (12 mL). After stirring overnight, little reaction had taken place. The reaction mixture was concentrated under reduced pressure. The material was dissolved in toluene (6 mL), and triphenylphosphine (30 mg, 0.11 mmol), PdOAc₂ (26 mg, 0.11 mmol), and sodium tert-butoxide (245 mg, 2.55 mmol) were added. The reaction mixture was heated to 110° C. overnight. Upon cooling to rt, the reaction mixture was filtered through Celite® and was concentrated under reduced pressure. The material was purified by column chromatography (30 to 70% EtOAc in hexanes gradient), yielding 314 mg (31%) of the title compound. LC-MS: RT=7.58 min, $[M+H]^+$=435.7. $R_f$=0.19 in 100% EtOAc.

Step 3. Synthesis of methyl 2-(2-((pyridin-3-yloxy)methyl)piperazin-1-yl)thiazole-4-carboxylate dihydrochloride 4 M HCl in 1,4-dioxane (6 mL, 24 mmol) was added to a solution of methyl 2-(4-(tert-butoxycarbonyl)-2-((pyridin-3-yloxy)methyl)piperazin-1-yl)thiazole-4-carboxylate (32 mg, 0.074 mmol) in MeOH (1 mL). After stirring overnight, the reaction mixture was concentrated under reduced pressure. The material was dissolved in H₂O (20 mL), and the pH was adjusted to ~2 with concentrated HCl. This was washed with Et₂O (3×5 mL, discarded). The aqueous layer was adjusted to pH ~12 with 1 N NaOH and was extracted with EtOAc (3×20 mL). The combined organics were dried over Na₂SO₄, filtered, and concentrated under reduced pressure, yielding 5.0 mg (17%) of the title compound. LC-MS: RT=3.41 min, (M+H)⁺=335.4.

Example 311

N-Methyl-2-(2-((pyridin-3-yloxy)methyl)piperazin-1-yl)thiazole-4-carboxamide dihydrochloride

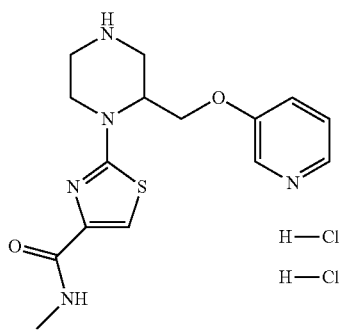

Step 1. Synthesis of 2-(4-(tert-butoxycarbonyl)-2-((pyridin-3-yloxy)methyl)piperazin-1-yl)thiazole-4-carboxylic acid

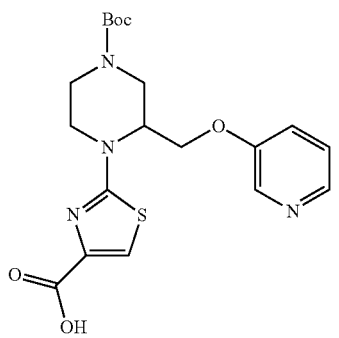 [SMILES: CC(C)(C)OC(=O)N1CCN(c2nc(C(=O)O)cs2)C(COc2cccnc2)C1]

Lithium hydroxide (15.5 mg, 0.649 mmol) was added to a solution of methyl 2-(4-(tert-butoxycarbonyl)-2-((pyridin-3-yloxy)methyl)piperazin-1-yl)thiazole-4-carboxylate (0.282 g, 0.649 mmol) in THF (2 mL), MeOH (2 mL), and H₂O (1 mL). After 5 h, 4M HCl in 1,4-dioxane (0.200 mL) was added, and the reaction mixture was concentrated under reduced pressure. The material was used without further purification. LC-MS: RT=6.35 min, [M+H]⁺=421.7.

Step 2. Synthesis of tert-butyl 4-(4-(methylcarbamoyl)thiazol-2-yl)-3-((pyridin-3-yloxy)methyl)piperazine-1-carboxylate

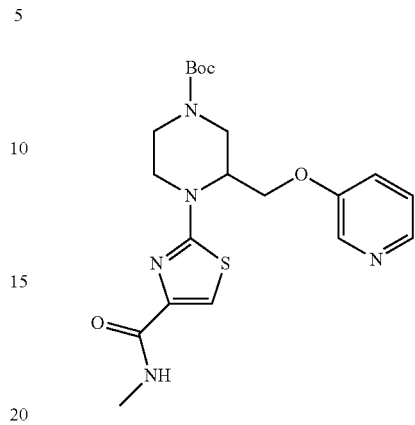

Diisoproylcarbodiimide (0.028 mL, 0.178 mmol) was added to a solution of 2-(4-(tert-butoxycarbonyl)-2-((pyridin-3-yloxy)methyl)piperazin-1-yl)thiazole-4-carboxylic acid (68 mg, 0.162 mmol), methylamine hydrochloride (12 mg, 0.178 mmol), diisopropylethylamine (0.062 mL, 0.357 mmol), and N-hydroxybenzotriazole (24 mg, 0.178 mmol) in CH₂Cl₂ (2 mL). After stirring overnight, little reaction had taken place. TBTU (0.162 mmol) was added, and stirring was continued at rt. After 4 h, additional methylamine hydrochloride (20 mg, 0.296 mmol) was added, and the reaction was heated to 50° C. in a sealed vial overnight. Upon cooling to rt, the reaction mixture was quenched with 1 N NaOH (4 mL) and stirred for 1 h. The reaction mixture was diluted with EtOAc (20 mL) and was washed with 1 N NaOH (2×10 mL) and brine (10 mL), dried over Na₂SO₄, filtered, and concentrated under reduced pressure. The material was purified by column chromatography (40 to 90% EtOAc in hexanes gradient), yielding 35 mg (50%) of the title compound. LC-MS: RT=6.77 min, [M+H]⁺=434.7. R_f=0.10 in 100% EtOAc.

Step 3. Synthesis of N-methyl-2-(2-((pyridin-3-yloxy)methyl)piperazin-1-yl)thiazole-4-carboxamide dihydrochloride

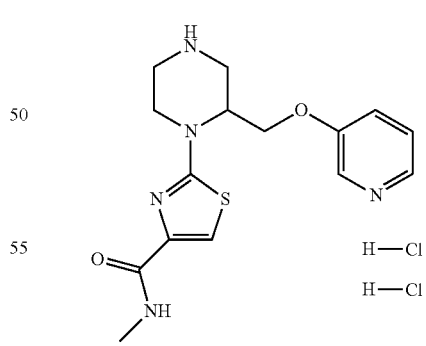

4 M HCl in 1,4-dioxane (6 mL, 24 mmol) was added to a solution of tert-butyl 4-(4-(methylcarbamoyl)thiazol-2-yl)-3-((pyridin-3-yloxy)methyl)piperazine-1-carboxylate (35 mg, 0.081 mmol) in MeOH (1 mL). After stirring for 1 h, the reaction mixture was concentrated under reduced pressure, yielding 31.9 mg (97%) of the title compound. LC-MS: RT=1.37 min, (M+H)⁺=334.2.

Example 312

Morpholino(2-(2-((pyridin-3-yloxy)methyl)piperazin-1-yl)thiazol-4-yl)methanone dihydrochloride

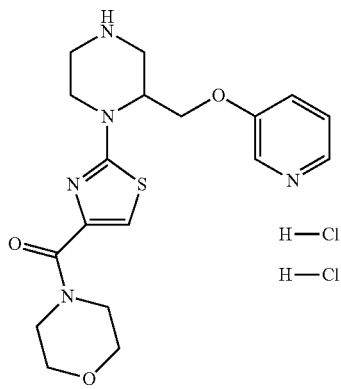

Step 1. Synthesis of tert-butyl 4-(4-(morpholine-4-carbonyl)thiazol-2-yl)-3-((pyridin-3-yloxy)methyl)piperazine-1-carboxylate

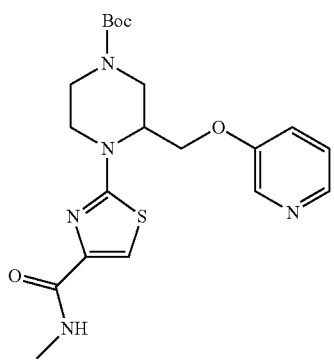 [SMILES: CNC(=O)c1csc(N2CCN(C(=O)OC(C)(C)C)CC2COc2cccnc2)n1]

Diisoproylcarbodiimide (0.028 mL, 0.178 mmol) was added to a solution of 2-(4-(tert-butoxycarbonyl)-2-((pyridin-3-yloxy)methyl)piperazin-1-yl)thiazole-4-carboxylic acid (68 mg, 0.162 mmol), morpholine (16 mg, 0.178 mmol), diisopropylethylamine (0.031 mL, 0.178 mmol), and N-hydroxybenzotriazole (24 mg, 0.178 mmol) in $CH_2Cl_2$ (2 mL). After stirring overnight, little reaction had taken place. TBTU (0.162 mmol) was added, and stirring was continued at rt for 4 h. The reaction mixture was quenched with 1 N NaOH (2 mL) and stirred for 1 h. The reaction mixture was diluted with EtOAc (20 mL) and was washed with 1 N NaOH (2×10 mL) and brine (10 mL), dried over $Na_2SO_4$, filtered, and concentrated under reduced pressure. The material was purified by column chromatography (50 to 100% EtOAc in hexanes gradient), yielding 35.4 mg (45%) of the title compound. LC-MS: RT=6.77 min, [M+H]$^+$=490.9. $R_f$=0.07 in 100% EtOAc.

Step 2. Synthesis of morpholino(2-(2-((pyridin-3-yloxy)methyl)piperazin-1-yl)thiazol-4-yl)methanone dihydrochloride

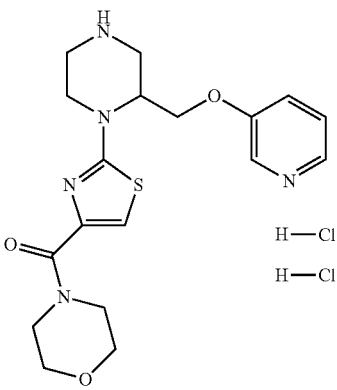

4 M HCl in 1,4-dioxane (6 mL, 24 mmol) was added to a solution of tert-butyl 4-(4-(morpholine-4-carbonyl)thiazol-2-yl)-3-((pyridin-3-yloxy)methyl)piperazine-1-carboxylate (35.4 mg, 0.0723 mmol) in MeOH (1 mL). After stirring overnight, the reaction mixture was concentrated under reduced pressure, yielding 33.2 mg (99%) of the title compound. LC-MS: RT=2.33 min, (M+H)$^+$=390.6.

Examples 313 and 314

Examples 313 and 314 were prepared as described for Example 312 substituting aniline and benzylamine, respectively, for morpholine.

Example 313

N-phenyl-2-(2-((pyridin-3-yloxy)methyl)piperazin-1-yl)thiazole-4-carboxamide dihydrochloride LC-MS: RT=4.45 min, [M+H]$^+$=396.6.

Example 314

N-benzyl-2-(2-((pyridin-3-yloxy)methyl piperazin-1-yl)thiazole-4-carboxamide dihydrochloride LC-MS: RT=4.35 min, [M+H]$^+$=410.7.

Example 315

N-Methyl-N-phenyl-2-((pyridin-3-yloxy)methyl)piperazine-1-carboxamide dihydrochloride

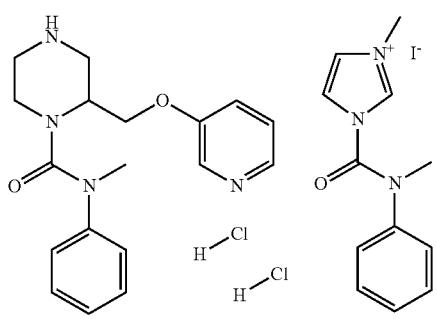

Step 1. Synthesis of 3-methyl-1-(methyl(phenyl)carbamoyl)-1H-imadazol-3-ium iodide N,N'-Carbonyldiimidazole (606 mg, 3.74 mmol) was added to a solution of N-methylaniline (200 mg, 1.87 mmol) in THF (5 mL). After stirring overnight at rt, the reaction mixture was diluted with EtOAc (25 mL) and washed with water (3×15 mL) and brine (15 mL). The organics were dried over Na$_2$SO$_4$, filtered, and concentrated under reduced pressure. The material was dissolved in acetonitrile (4 mL), iodomethane (0.5 mL, 8.02 mmol) was added, and the reaction mixture was heated to 50° C. overnight. The reaction mixture was concentrated under reduced pressure, and the material was recrystallized from 5:1 acetone:Et$_2$O, yielding 110.6 mg (17%) of the desired product as a white solid. LC-MS: RT=2.42 min, (M−I)$^+$=216.1.

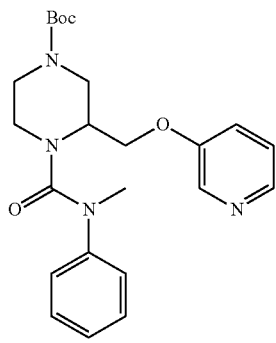 [SMILES: CN(C(=O)N1CCN(C(=O)OC(C)(C)C)CC1COc1cccnc1)c1ccccc1]

Step 2. Synthesis of tert-butyl 4-(N-methyl-N-phenylcarbamoyl)-3-((pyridin-3-yloxy)methyl)piperazine-1-carboxylate The material prepared in step 1 above (89.7 mg (0.261 mmol) was added to a solution of Intermediate C (76.7 mg, 0.261 mmol) in CH$_2$Cl$_2$ (4 mL). After stirring overnight at rt, potassium carbonate (200 mg) was added and the reaction mixture was heated to 80° C. in a sealed tube. After stirring overnight, the reaction mixture was diluted with EtOAc (20 mL) and washed with water (3×15 mL) and brine (15 mL). The organics were dried over Na$_2$SO$_4$, filtered, and concentrated under reduced pressure. The reaction mixture was purified by HPLC (10 to 90% MeCN/0.1% TFA in H$_2$O/0.1% TFA gradient), yielding 28.1 mg (20%) of the TFA salt of the desired product as a yellow oil. LC-MS: RT=8.06 min, [M+H]$^+$=427.2.

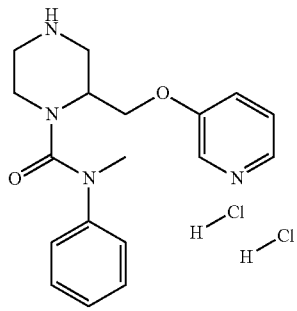

Step 3. Synthesis of N-Methyl-N-phenyl-2-((pyridin-3-yloxy)methyl)piperazine-1-carboxamide dihydrochloride 4 M HCl in 1,4-dioxane (6 mL, 24 mmol) was added to a solution of tert-butyl 4-(N-methyl-N-phenylcarbamoyl)-3-((pyridin-3-yloxy)methyl)piperazine-1-carboxylate TFA salt (28.1 mg, 0.052 mmol) in MeOH (1 mL). After 12 h, the reaction mixture was concentrated under reduced pressure, yielding 16.9 mg (81%) of the desired product as a yellow solid. LC-MS: RT=3.83 min, [M+H]$^+$=327.1.

Examples 316-317

The examples found in Table 33 below were prepared by similar methods as described for Example 315, substituting the appropriate N-methylaniline. All compounds were isolated as the dihydrochloride salts unless otherwise noted.

TABLE 33

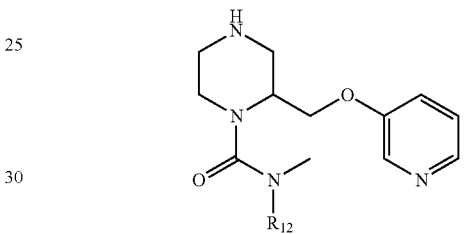

| Example No. | R$_{12}$ | IUPAC Name | HPLC RT (min) | LC-MS [M + H]$^+$ |
|---|---|---|---|---|
| 315 | ⌇phenyl | N-methyl-N-phenyl-2-((pyridin-3-yloxy)methyl)-piperazine-1-carboxamide dihydrochloride | 3.83 | 327.1 |
| 316 | ⌇4-chlorophenyl | N-(4-chlorophenyl)-N-methyl-2-((pyridin-3-yloxy)methyl)piperazine-1-carboxamide dihydrochloride | 4.33 | 361.1 |
| 317 | ⌇4-methoxyphenyl | N-(4-methoxyphenyl)-N-methyl-2-((pyridin-3-yloxy)methyl)piperazine-1-carboxamide dihydrochloride | 3.9 | 357.1 |

Example 318

4-(4-methoxyphenyl)-2-(2-((pyridin-3-yloxy)methyl)piperazin-1-yl)thiazole hydrochloride

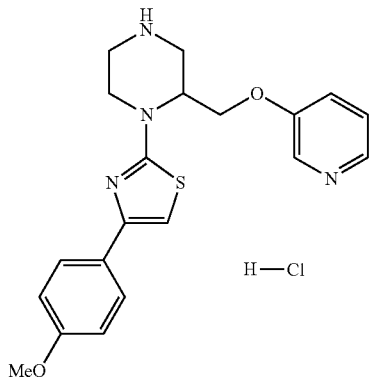 [SMILES: COc1ccc(-c2csc(N3CCNCC3COc3cccnc3)n2)cc1 ; Cl]

Step 1. Synthesis of tert-butyl 4-carbamothioyl-3-((pyridin-3-yloxy)methyl)piperazine-1-carboxylate

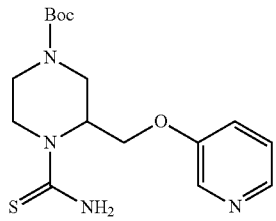

N,N'-Thiocarbonyldiimidazole (0.182 g, 1.02 mmol) and Intermediate C (0.300 g, 1.02 mmol) were heated to 50° C. in THF (4 mL). After 1 h, an additional portion of N,N'-thiocarbonyldiimidazole (0.030 g) was added. After an additional 1 h another portion of N,N'-thiocarbonyldiimidazole (0.030 g) was added, and the reaction mixture was stirred overnight. Ammonium hydroxide (conc., 0.5 mL) was added, and heating was continued at 70° C. for 3 h. Upon cooling to rt, the reaction mixture was diluted with EtOAc (30 mL) and washed with water (2×10 mL) and brine (10 mL). The organics were dried over $Na_2SO_4$, filtered, and concentrated under reduced pressure, yielding 0.390 g (>100% crude yield) of a yellowish solid that was used without further purification. LC-MS: RT=5.89 min, $[M+H]^+$=375.0.

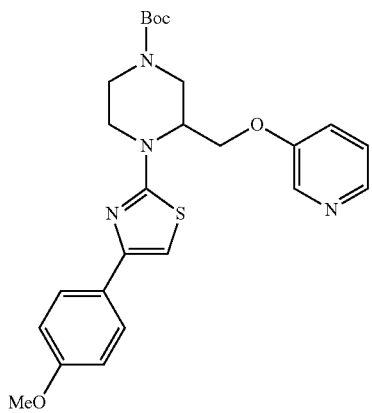 [SMILES: COc1ccc(-c2csc(N3CCN(C(=O)OC(C)(C)C)CC3COc3cccnc3)n2)cc1]

Step 2. Synthesis of tert-butyl 4-(4-(4-methoxyphenyl)thiazol-2-yl)-3-((pyridin-3-yloxy)methyl)piperazine-1-carboxylate 4-Methoxyphenacyl bromide (0.116 g, 0.51 mmol) was added to a solution of tert-butyl 4-carbamothioyl-3-((pyridin-3-yloxy)methyl)piperazine-1-carboxylate (0.195 g, 0.51 mmol) in THF (4 mL), and the reaction mixture was heated to 50° C. overnight. Upon cooling to rt, the reaction mixture was diluted with EtOAc (30 mL) and washed with water (15 mL) and brine (15 mL). The organics were dried over $Na_2SO_4$, filtered, and concentrated under reduced pressure. The material was purified by HPLC (10 to 90% MeCN/0.1% TFA in $H_2O$/0.1% TFA gradient), yielding 199 mg (55%) of the di-TFA salt of the desired product as a yellowish oil. LC-MS: RT=9.95 min, $[M+H]^+$=483.0.

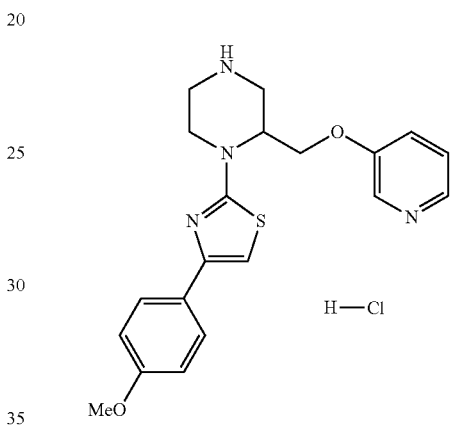

Step 3. Synthesis of 4-(4-methoxyphenyl)-2-(2-((pyridin-3-yloxy)methyl)piperazin-1-yl)thiazole hydrochloride 4 M HCl in 1,4-dioxane (6 mL, 24 mmol) was added to a solution of tert-butyl 4-(4-(4-methoxyphenyl)thiazol-2-yl)-3-((pyridin-3-yloxy)methyl)piperazine-1-carboxylate di-TFA salt (199 mg, 0.280 mmol) in MeOH (1 mL). After 1 h, the reaction mixture was concentrated under reduced pressure and purified by HPLC (5 to 50% MeCN/0.1% TFA in $H_2O$/0.1% TFA gradient). The fractions containing the desired product were brought to pH 12 with 1 N NaOH and were extracted with EtOAc (3×). The combined organics were dried over $Na_2SO_4$, filtered, and concentrated under reduced pressure, yielding 44.2 mg of the free-base of the desired product. The material was dissolved in MeOH (1 mL) and 4 M HCl in 1,4-dioxane (0.029 mL) was added. This was concentrated under reduced pressure, yielding 48.2 mg (41%) of the desired product as an off-white solid. LC-MS: RT=4.98 min, $[M+H]^+$=383.0.

Examples 319-320

The examples found in Table 34 below were prepared by similar methods as described for Example 318, substituting the appropriate phenacyl bromide. All compounds were isolated as the hydrochloride salts unless otherwise noted.

TABLE 34

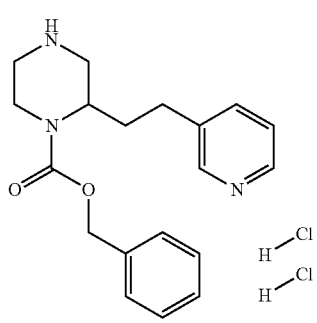

| Example No. | $R_d$ | IUPAC Name | HPLC RT (min) | LC-MS [M + H]+ |
|---|---|---|---|---|
| 318 | OMe | 4-(4-methoxyphenyl)-2-(2-((pyridin-3-yloxy)methyl)piperazin-1-yl)thiazole hydrochloride | 4.98 | 383.0 |
| 319 | H | 4-phenyl-2-(2-((pyridin-3-yloxy)methyl)piperazin-1-yl)thiazole hydrochloride | 5.01 | 353.0 |
| 320 | Cl | 4-(4-chlorophenyl)-2-(2-((pyridin-3-yloxy)methyl)piperazin-1-yl)thiazole hydrochloride | 5.56 | 387.0 |

Example 321

Benzyl 2-(2-(pyridin-3-yl)ethyl)piperazine-1-carboxylate dihydrochloride

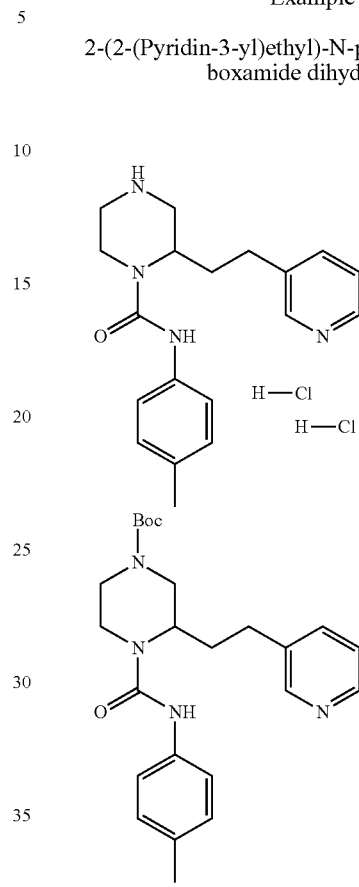

4 M HCl in 1,4-dioxane (6 mL, 24 mmol) was added to a solution of 1-benzyl 4-tert-butyl 2-(2-(pyridin-3-yl)ethyl)piperazine-1,4-dicarboxylate (130.2 mg, 0.306 mmol) in MeOH (1 mL). After 1 h, the reaction mixture was concentrated under reduced pressure and purified by HPLC (5 to 50% MeCN/0.1% TFA in H$_2$O/0.1% TFA gradient). The fractions containing the desired product were concentrated under reduced pressure. The material was dissolved in MeOH (1 mL) and 4 M HCl in 1,4-dioxane (0.015 mL) was added. The mixture was concentrated under reduced pressure to give 71.0 mg (58%) of the desired product. LC-MS: RT=3.50 min, [M+H]+=326.2.

Example 322

2-(2-(Pyridin-3-yl)ethyl)-N-p-tolylpiperazine-1-carboxamide dihydrochloride

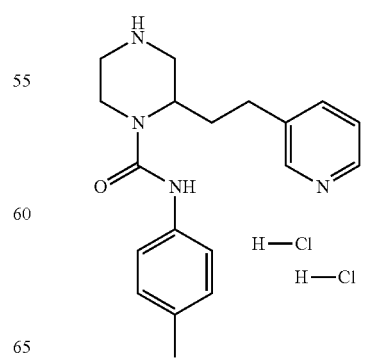

Step 1. Synthesis of tert-butyl 3-(2-(pyridin-3-yl)ethyl)-4-(p-tolylcarbamoyl)piperazine-1-carboxylate p-Tolylisocyanate (39 mg, 0.29 mmol) was added to a solution of Intermediate AE (85.4 mg, 0.293 mmol) in CH$_2$Cl$_2$ (4 mL). After 16 h, the reaction mixture was concentrated under reduced pressure, and the material was purified by HPLC (10 to 90% MeCN/0.1% TFA in H$_2$O/0.1% TFA gradient). This gave 133.9 mg (85%) of the TFA salt of the desired product as a white solid. LC-MS: RT=6.63 min, [M+H]+=425.2.

Step 2. Synthesis of 2-(2-(Pyridin-3-yl)ethyl)-N-p-tolylpiperazine-1-carboxamide dihydrochloride 4 M HCl in 1,4-dioxane (6 mL, 24 mmol) was added to tert-butyl 3-(2-(pyridin-3-yl)ethyl)-4-(p-tolylcarbamoyl)piperazine-1-carboxylate TFA salt (133.9 mg, 0.248 mmol). After 1 h, the reaction mixture was concentrated under reduced pressure, yielding 89.3 mg (90%) of the desired product as a white solid. LC-MS: RT=3.16 min, [M+H]$^+$=325.2.

Examples 323-328

The examples found in Table 35 below were prepared by similar methods as described for Example 322, substituting the appropriate isocyanate. All reagents were commercially available unless otherwise noted. All compounds were isolated as the dihydrochloride salts unless otherwise noted.

TABLE 35

| Example No. | R$_{12}$ | IUPAC Name | HPLC RT (min) | LC-MS [M + H]$^+$ |
|---|---|---|---|---|
| 322 | 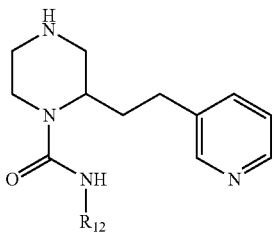 | 2-(2-(pyridin-3-yl)ethyl)-N-p-tolyl-piperazine-1-carboxamide dihydrochloride | 3.16 | 325.2 |
| 323 | (4-Cl-phenyl) | N-(4-chlorophenyl)-2-(2-(pyridin-3-yl)ethyl)piperazine-1-carboxamide dihydrochloride | 3.59 | 345.1 |
| 324 | (4-OMe-phenyl) | N-(4-methoxyphenyl)-2-(2-(pyridin-3-yl)ethyl)piperazine-1-carboxamide dihydrochloride | 2.14 | 341.2 |

TABLE 35-continued

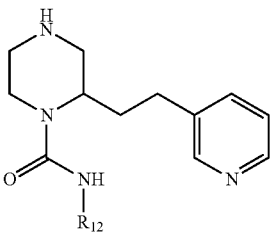

| Example No. | R$_{12}$ | IUPAC Name | HPLC RT (min) | LC-MS [M + H]$^+$ |
|---|---|---|---|---|
| 325 | (4-phenoxyphenyl) | N-(4-phenoxyphenyl)-2-(2-(pyridin-3-yl)ethyl)piperazine-1-carboxamide dihydrochloride | 4.51 | 403.2 |
| 326 | (4-Br-phenyl) | N-(4-bromophenyl)-2-(2-(pyridin-3-yl)ethyl)-piperazine-1-carboxamide dihydrochloride | 3.82 | 389.1 |
| 327 | (4-OEt-phenyl) | N-(4-ethoxyphenyl)-2-(2-(pyridin-3-yl)ethyl)piperazine-1-carboxamide dihydrochloride | 3.05 | 355.2 |
| 328 | (3,4-diCl-phenyl) | N-(3,4-dichlorophenyl)-2-(2-(pyridin-3-yl)ethyl)-piperazine-1-carboxamide dihydrochloride | 4.30 | 379.1 |

Example 329

1-(Phenylsulfonyl)-2-((pyridin-3-yloxy)methyl)piperazine dihydrochloride

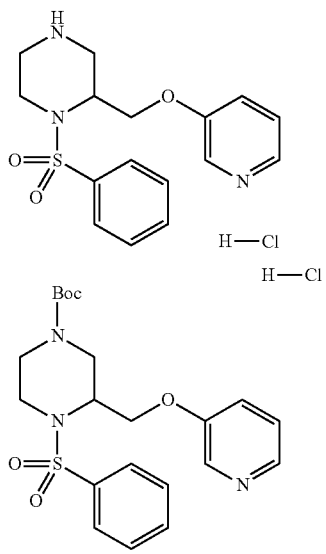

Step 1. Synthesis of tert-butyl 4-(phenylsulfonyl)-3-((pyridin-3-yloxy)methyl)piperazine-1-carboxylate Benzenesulfonyl chloride (51 mg, 0.29 mmol) was added to a solution of Intermediate C (76.8 mg, 0.262 mmol) and DIEA (0.050 mL, 0.29 mmol) in THF (4 mL). After stirring overnight, the reaction mixture was concentrated under reduced pressure, and the material was purified by HPLC (10 to 90% MeCN/0.1% TFA in H$_2$O/0.1% TFA gradient). This gave 122 mg (85%) of the TFA salt of the desired product as a thick oil. LC-MS: RT=8.31 min, [M+H]$^+$=434.1.

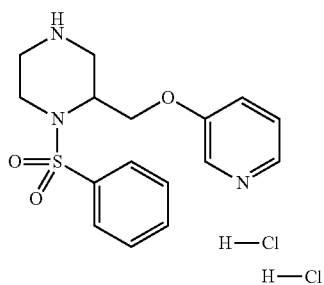

Step 2. Synthesis of 1-(phenylsulfonyl)-2-((pyridin-3-yloxy)methyl)piperazine dihydrochloride 4 M HCl in 1,4-dioxane (6 mL, 24 mmol) was added to tert-butyl 4-(phenylsulfonyl)-3-((pyridin-3-yloxy)methyl)piperazine-1-carboxylate TFA salt (122 mg, 0.223 mmol). After 1 h, the reaction mixture was concentrated under reduced pressure, yielding 82.4 mg (91%) of the desired product as a yellow solid. LC-MS: RT=3.71 min, [M+H]$^+$=334.1.

Examples 330-332

The examples found in Table 36 below were prepared by similar methods as described for Example 329, substituting the appropriate sulfonyl chloride. All reagents were commercially available unless otherwise noted. All compounds were isolated as the dihydrochloride salts unless otherwise noted.

TABLE 36

| Example No. | R$_{12}$ | IUPAC Name | HPLC RT (min) | LC-MS [M + H]$^+$ |
|---|---|---|---|---|
| 329 | phenyl | 1-(phenylsulfonyl)-2-((pyridin-3-yloxy)methyl)piperazine dihydrochloride | 3.05 | 298.1 |
| 330 | 4-chlorophenyl | 1-(4-chlorophenylsulfonyl)-2-((pyridin-3-yloxy)methyl)piperazine dihydrochloride | 4.43 | 368.1 |
| 331 | 4-bromophenyl | 1-(4-bromophenylsulfonyl)-2-((pyridin-3-yloxy)methyl)piperazine dihydrochloride | 4.47 | 412.0 |
| 332 | 4-methoxyphenyl | 1-(4-methoxyphenylsulfonyl)-2-((pyridin-3-yloxy)methyl)piperazine dihydrochloride | 4.04 | 364.1 |

Example 333

N-(4-methoxyphenyl)-2-(pyridin-3-ylmethyl)piperazine-1-carboxamide dihydrochloride

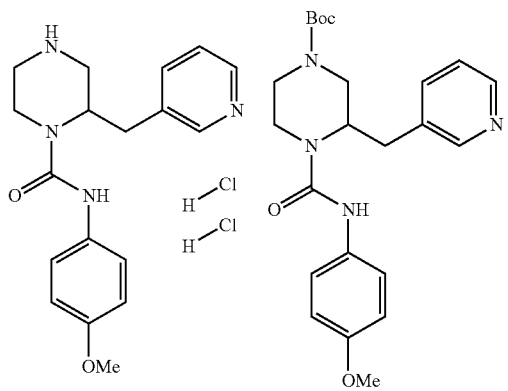

Step 1. Synthesis of tert-butyl 4-(4-methoxyphenylcarbamoyl)-3-(pyridin-3-ylmethyl)piperazine-1-carboxylate 4-Methoxyphenylisocyanate (40 mg, 0.27 mmol) was added to a solution of Intermediate AF (105 mg, 0.27 mmol) in CH$_2$Cl$_2$ (5 mL). After stirring overnight, the reaction mixture was concentrated under reduced pressure, and the material was purified by HPLC (10 to 95% MeCN/0.1% TFA in H$_2$O/0.1% TFA gradient). This gave 76.0 mg (52%) of the TFA salt of the desired product. LC-MS: RT=6.13 min, [M+H]$^+$=427.2.

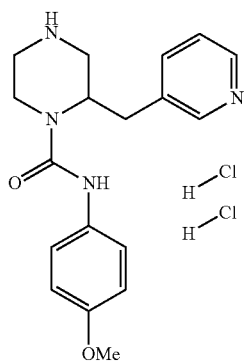

Step 2. Synthesis of N-(4-methoxyphenyl)-2-(pyridin-3-ylmethyl)piperazine-1-carboxamide dihydrochloride 4 M HCl in 1,4-dioxane (6 mL, 24 mmol) was added to tert-butyl 4-(4-methoxyphenylcarbamoyl)-3-(pyridin-3-ylmethyl)piperazine-1-carboxylate (76.0 mg, 0.141 mmol). After stirring overnight, the reaction mixture was concentrated under reduced pressure and purified by HPLC (5 to 50% MeCN/0.1% TFA in H$_2$O/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 30.5 mg (54%) of the desired product as an off-white solid. LC-MS: RT=2.11 min, [M+H]$^+$=327.1.

Example 334

N-(4-chlorophenyl)-2-(pyridin-3-ylmethyl)piperazine-1-carboxamide dihydrochloride

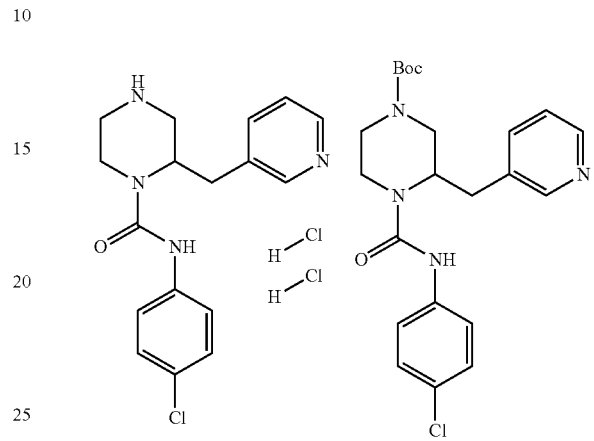

Step 1. Synthesis of tert-butyl 4-(4-chlorophenylcarbamoyl)-3-(pyridin-3-ylmethyl)piperazine-1-carboxylate 4-Chlorophenylisocyanate (41 mg, 0.27 mmol) was added to a solution of Intermediate AF (105 mg, 0.27 mmol) in CH$_2$Cl$_2$ (5 mL). After stirring overnight, the reaction mixture was concentrated under reduced pressure, and the material was purified by HPLC (10 to 95% MeCN/0.1% TFA in H$_2$O/0.1% TFA gradient). This gave 105 mg (72%) of the TFA salt of the desired product as a white solid. LC-MS: RT=7.22 min, [M+H]$^+$=431.1.

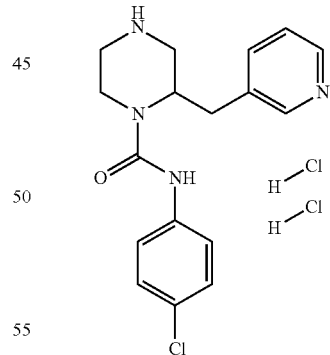

Step 2. Synthesis of N-(4-chlorophenyl)-2-(pyridin-3-ylmethyl)piperazine-1-carboxamide dihydrochloride 4 M HCl in 1,4-dioxane (6 mL, 24 mmol) was added to tert-butyl 4-(4-chlorophenylcarbamoyl)-3-(pyridin-3-ylmethyl)piperazine-1-carboxylate (105 mg, 0.193 mmol). After stirring overnight, the reaction mixture was concentrated under reduced pressure and purified by HPLC (5 to 50%

MeCN/0.1% TFA in H$_2$O/0.1% TFA gradient). The desired chromatography fractions were concentrated under reduced pressure, dissolved in MeOH (1 mL), and treated with 4 M HCl in 1,4-dioxane (6 mL). This was concentrated under reduced pressure, yielding 67.0 mg (86%) of the desired product as an off-white solid. LC-MS: RT=3.66 min, [M+H]$^+$=331.1.

Example 335

N-benzyl-4-methyl-2-(2-((pyridin-3-yloxy)methyl)piperazin-1-yl)oxazole-5-carboxamide trihydrochloride

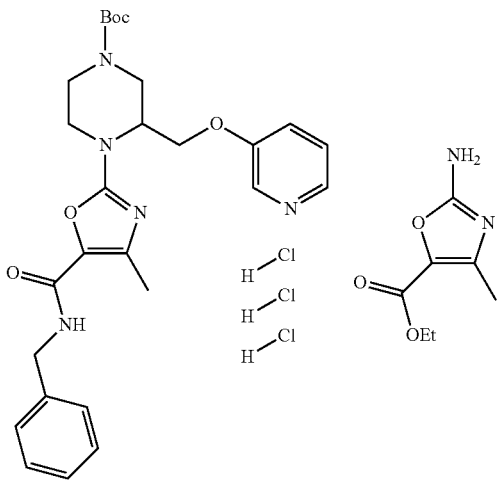

Step 1. Synthesis of ethyl 2-amino-4-methyloxazole-5-carboxylate

Ethyl 2-chloroacetoacetate (8.0 mL, 59 mmol) was added to a mixture of urea (10.6 g, 176 mmol) in MeOH (40 mL), and the reaction mixture was heated to 66° C. overnight. Upon cooling to room temperature, the solids were collected by filtration and suspended in 1 N aqueous NaOH (50 mL). This was extracted with EtOAc (100 mL). The aqueous layer was brought to pH ~11 with NaOH and was extracted with EtOAc (3×100 mL). The EtOAc extracts were combined, dried over Na$_2$SO$_4$, filtered, and concentrated under reduced pressure. This gave 5.02 g (50%) of the title compound as a white solid. LC-MS: RT=5.1 min, [M+H]$^+$=171.

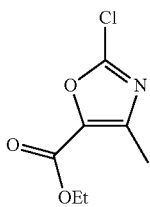

Step 2. Synthesis of ethyl 2-chloro-4-methyloxazole-5-carboxylate

Ethyl 2-amino-4-methyloxazole-5-carboxylate (1.9 g, 11.2 mmol) was added portionwise over ~10 min. to a mixture of t-butyl nitrite (1.5 mL, 12.3 mmol) and copper (II) chloride (1.7 g, 12.3 mmol) in CH$_3$CN (56 mL) at 0° C. After complete addition, the reaction mixture was allowed to warm to rt. After 26 h, the reaction mixture was quenched with 1 M aqueous HCl (45 mL) and stirred at rt for 30 min. The mixture was extracted with Et$_2$O (3×100 mL), and the combined extracts were dried over Na$_2$SO$_4$, filtered, and concentrated under reduced pressure. Purification by column chromatography (3% EtOAc in Hexanes) gave 1.01 g (48%) of the title compound as a white solid. LC-MS: RT=5.19 min, [M+H]$^+$=190.

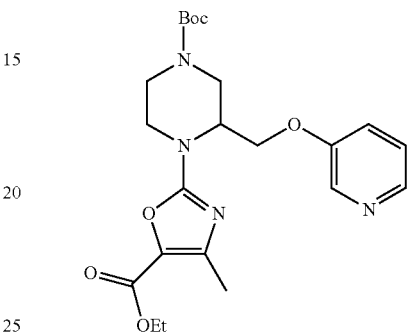

Step 3. Synthesis of ethyl 2-(4-(tert-butoxycarbonyl)-2-((pyridin-3-yloxy)methyl)piperazin-1-yl)-4-methyloxazole-5-carboxylate Ethyl 2-chloro-4-methyloxazole-5-carboxylate (305 mg, 1.61 mmol), Intermediate C (393 mg, 1.34 mmol) and sodium carbonate (171 mg, 1.61 mmol) were heated to 70° C. in THF (10 mL). After 17 h, additional portions of ethyl 2-chloro-4-methyloxazole-5-carboxylate (153 mg, 0.807 mmol) and sodium carbonate (86 mg, 0.81 mmol) were added. After 6 h, the reaction mixture was cooled to rt and diluted with water (15 mL). The mixture was extracted with EtOAc (3×30 mL). The combined extracts were washed with 1 N aqueous NaOH (2×15 mL) and brine (10 mL), dried over Na$_2$SO$_4$, filtered, and concentrated under reduced pressure. Purification by HPLC (10 to 90% MeCN/0.1% TFA in H$_2$O/0.1% TFA gradient) gave 0.200 g (33%) of the title compound as an orange oil.

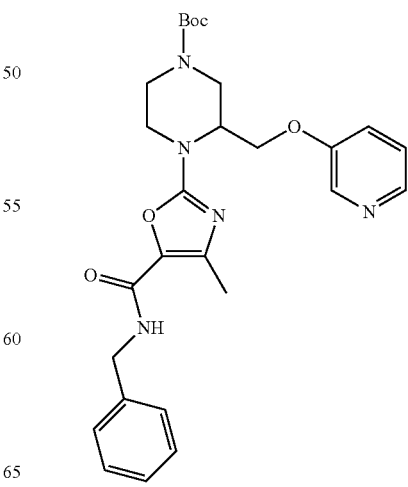

Step 4. Synthesis of tert-butyl 4-(5-(benzylcarbamoyl)-4-methyloxazol-2-yl)-3-((pyridin-3-yloxy)methyl)piperazine-1-carboxylate Lithium hydroxide (56 mg, 1.3 mmol) was added to a solution of ethyl 2-(4-(tert-butoxycarbonyl)-2-((pyridin-3-yloxy)methyl)piperazin-1-yl)-4-methyloxazole-5-carboxylate (200 mg, 0.448 mmol) in THF (2 mL), MeOH (2 mL), and water (1 mL). After 3 h, 2.5 mL of the reaction mixture was removed and acidified to pH ~3 with 1 N aqueous HCl. This was diluted with water (15 mL) and extracted with EtOAc (3×30 mL). The combined extracts were dried over $Na_2SO_4$, filtered, and concentrated under reduced pressure. The resulting yellow oil was dissolved in DMF (3 mL) and benzylamine (0.027 mL, 0.246 mmol), triethylamine (0.094 mL, 0.672 mmol) and TBTU (108 mg, 0.336 mmol) were added. After 14 h, the reaction mixture was concentrated under reduced pressure and purified by HPLC (5 to 95% MeCN/0.1% TFA in $H_2O$/0.1% TFA gradient). This gave the title compound as a brown solid. LC-MS: RT=7.79 min, $[M+H]^+$=508.9.

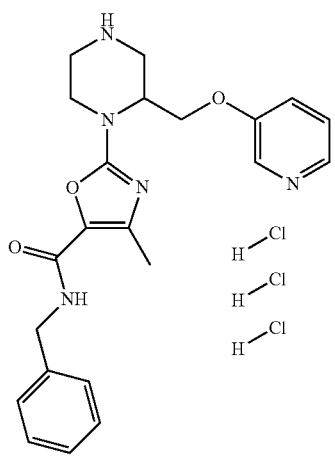

Step 5. Synthesis of N-benzyl-4-methyl-2-(2-((pyridin-3-yloxy)methyl)piperazin-1-yl)oxazole-5-carboxamide trihydrochloride 4 M HCl in 1,4-dioxane (4 mL, 16 mmol) was added to a solution of tert-butyl 4-(5-(benzyl carbamoyl)-4-methyl oxazol-2-yl)-3-((pyridin-3-yloxy)methyl)piperazine-1-carboxylate in MeOH (1 mL). After 1 h, the reaction mixture was concentrated under reduced pressure and purified by HPLC (10 to 90% MeCN/0.1% TFA in $H_2O$/0.1% TFA gradient). The desired chromatography fractions were concentrated under reduced pressure, dissolved in MeOH (1 mL), and treated with 4 M HCl in 1,4-dioxane. This was concentrated under reduced pressure, yielding 3.6 mg (3%) of the title compound as an off-white solid. LC-MS: RT=4.12 min, $[M+H]^+$=408.7.

Example 336

N-(4-Methoxyphenyl)-2-((pyridin-3-ylamino)methyl)piperazine-1-carboxamide dihydrochloride

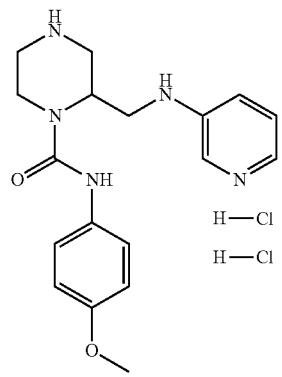

Step 1. Synthesis of tert-butyl 1,3-dioxotetrahydro-1H-oxazolo[3,4-c]pyrazine-7(3H)-carboxylate

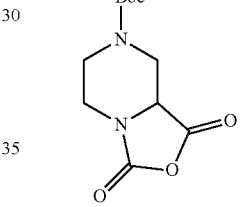

Pyridine (1.4 mL, 17 mmol), DMF (0.29 mL, 3.7 mmol), and thionyl chloride (1.1 mL, 15 mmol) were added in succession to a suspension of 1,4-bis(tert-butoxycarbonyl)piperazine-2-carboxylic acid (3.73 g, 11.3 mmol) in THF (20 mL). The reaction mixture was heated to 40° C. for 3 h. The reaction mixture was diluted with EtOAc (50 mL) and $H_2O$ (50 mL). The layers were separated, and the aqueous layer was extracted with EtOAc (2×50 mL). The combined extracts were dried over $Na_2SO_4$, filtered, and concentrated under reduced pressure. The material was suspended in $Et_2O$ (10 mL) and cooled to −20° C. for 1 h. The solid was collected by filtration, washed with $Et_2O$ (2×10 mL), and air-dried. This gave 1.73 g (60%) of the title compound as a white solid.

Step 2. Synthesis of tert-butyl 3-(pyridin-3-ylcarbamoyl)piperazine-1-carboxylate

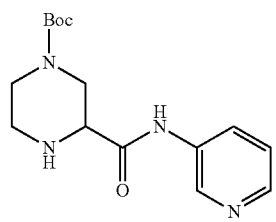 [SMILES: CC(C)(C)OC(=O)N1CCNC(C(=O)Nc2cccnc2)C1]

tert-Butyl 1,3-dioxotetrahydro-1H-oxazolo[3,4-a]pyrazine-7(3H)-carboxylate (1.50 g, 5.85 mmol) and 3-aminopyridine (1.10 g, 11.7 mmol) were heated to reflux in THF (20 mL). After 4 h, the reaction mixture was cooled to rt, diluted with H$_2$O (50 mL), and was extracted with EtOAc (3×75 mL). The combined extracts were dried over Na$_2$SO$_4$, filtered, and concentrated under reduced pressure. The material was purified by column chromatography (0 to 8% MeOH in CH$_2$Cl$_2$ with 0.5% NH$_4$OH gradient), yielding 0.740 g (44%) of the title compound. LC-MS: RT=4.14 min, [M+H]$^+$=307.1.

Step 3. Synthesis of tert-butyl 3-((pyridin-3-ylamino)methyl)piperazine-1-carboxylate

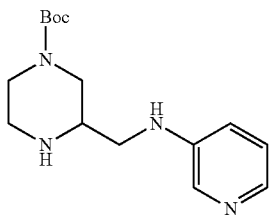 [SMILES: CC(C)(C)OC(=O)N1CCNC(CNc2cccnc2)C1]

Borane-THF complex (1.0 M solution in THF, 3.4 mL, 3.4 mmol) was added to a solution of tert-butyl 3-(pyridin-3-ylcarbamoyl)piperazine-1-carboxylate (522 mg, 1.70 mmol) in THF (4 mL). The reaction mixture was heated to reflux for 5 h. Upon cooling to rt, the reaction mixture was carefully quenched by the dropwise addition of MeOH. After gas evolution ceased, MeOH (10 mL) was added, and the reaction mixture was heated to reflux overnight. Upon cooling to rt, the reaction mixture was concentrated under reduced pressure, yielding the title compound which was used without further purification. LC-MS: RT=2.90 min, [M+H]$^+$=293.1.

Step 4. Synthesis of tert-butyl 4-(4-methoxyphenylcarbamoyl)-3-((pyridin-3-ylamino)methyl)piperazine-1-carboxylate

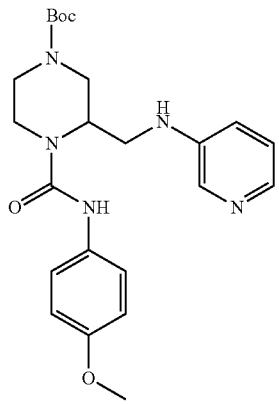 [SMILES: COc1ccc(NC(=O)N2CCN(C(=O)OC(C)(C)C)CC2CNc2cccnc2)cc1]

4-Methoxyphenyl isocyanate (85 mg, 0.567 mmol) was added to a solution of tert-butyl 3-((pyridin-3-ylamino)methyl)piperazine-1-carboxylate (166 mg, 0.567 mmol) in CH$_2$Cl$_2$ (4 mL). After 1 h, the reaction mixture was concentrated under reduced pressure, and the material was purified by HPLC (10 to 90% MeCN/0.1% TFA in H$_2$O/0.1% TFA gradient). This gave 81.7 mg (26%) of the TFA salt of the title compound as a white solid. LC-MS: RT=5.29 min, [M+H]$^+$=442.2.

Step 5. Synthesis of N-(4-methoxyphenyl)-2-((pyridin-3-ylamino)methyl)piperazine-1-carboxamide dihydrochloride

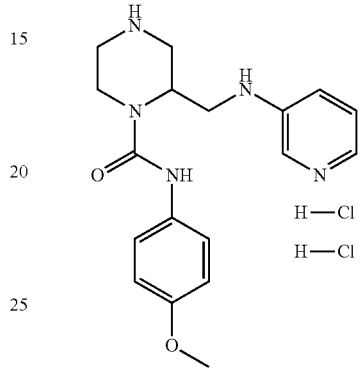

4 M HCl in 1,4-dioxane (6 mL, 24 mmol) was added to a solution of tert-butyl 4-(4-methoxyphenylcarbamoyl)-3-((pyridin-3-ylamino)methyl)piperazine-1-carboxylate TFA salt (81.7 mg, 0.147 mmol) in MeOH (1 mL). After 1 h, the reaction mixture was concentrated under reduced pressure and purified by HPLC (5 to 50% MeCN/0.1% TFA in H$_2$O/0.1% TFA gradient). The fractions containing the desired product were concentrated under reduced pressure. The material was dissolved in MeOH (1 mL) and treated with 4 M HCl in 1,4-dioxane (6 mL). The mixture was concentrated under reduced pressure to give 49.9 mg (82%) of the title compound as a white solid. LC-MS: RT=1.95 min, [M+H]$^+$=342.1.

Examples 337 and 338

Examples 337 and 338 were prepared as described for Example 336 substituting the appropriate isocyanates.

Example 337

N-(3-chloro-4-methoxyphenyl)-2-((pyridin-3-ylamino)methyl)piperazine-1-carboxamide dihydrochloride LC-MS: RT=3.26 min, [M+H]$^+$=376.1.

Example 338

2-((pyridin-3-ylamino)methyl)-N-(4-(trifluoromethoxy)phenyl)piperazine-1-carboxamide dihydrochloride LC-MS: RT=3.97 min, [M+H]$^+$=396.1.

Example 339

2-(2-((pyridin-3-ylamino)methyl)piperazin-1-yl) pyrimidine trihydrochloride

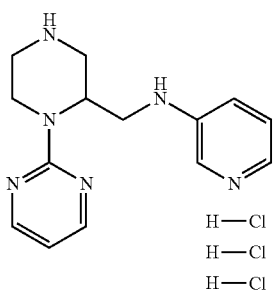

Step 1. Synthesis of tert-butyl 3-((pyridin-3-ylamino) methyl)-4-(pyrimidin-2-yl)piperazine-1-carboxylate

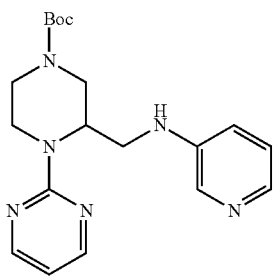 [SMILES: CC(C)(C)OC(=O)N1CCN(c2ncccn2)C(CNc2cccnc2)C1]

Intermediate C (100 mg, 0.341 mmol), 2-chloropyrimidine (39 mg, 0.34 mmol), and diisopropylethylamine (0.060 mL, 0.34 mmol) were heated to 80° C. in isopropanol (1 mL) overnight. Additional 2-chloropyrimidine (78 mg, 0.68 mmol) was added, and heating was continued at 80° C. for 4 days. Upon cooling to rt, the reaction mixture was concentrated under reduced pressure and purified by HPLC (10 to 90% MeCN/0.1% TFA in H$_2$O/0.1% TFA gradient). This gave 100 mg (49%) of the di-TFA salt of the title compound as a white solid. LC-MS: RT=7.60 min, [M+H]$^+$=372.6.

Step 2. Synthesis of 2-(2-((pyridin-3-yloxy)methyl) piperazin-1-yl)pyrimidine trihydrochloride

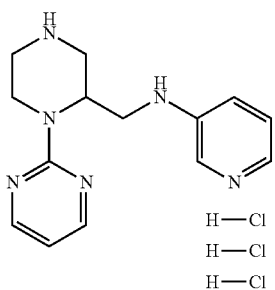

4 M HCl in 1,4-dioxane (6 mL, 24 mmol) was added to a solution of tert-butyl 3-((pyridin-3-ylamino)methyl)-4-(pyrimidin-2-yl)piperazine-1-carboxylate di-TFA salt (100 mg, 0.167 mmol) in MeOH (1 mL). After stirring overnight, the reaction mixture was concentrated under reduced pressure and purified by HPLC (5 to 50% MeCN/0.1% TFA in H$_2$O/ 0.1% TFA gradient). The fractions containing the desired product were concentrated under reduced pressure. The material was dissolved in MeOH (1 mL) and treated with 4 M HCl in 1,4-dioxane (6 mL). The mixture was concentrated under reduced pressure to give 23.5 mg (37%) of the title compound as an off-white solid. LC-MS: RT=2.27 min, [M+H]$^+$=272.4.

Example 340

5-Bromo-2-(2-((pyridin-3-ylamino)methyl)piperazin-1-yl)pyrimidine trihydrochloride Example 320 was prepared as described for Example 319, substituting 2-chloro-5-bromopyrimidine for 2-chloropyrimidine. LC-MS: RT=4.05 min, [M+H]$^+$=350.4.

Example 341

Binding Affinities for α7 nAChR on PC 12 Cells

PC12 cells (ATCC, Manassas, Va.) were resuspended in binding buffer (PBS containing 1.0% FBS and 0.02% sodium azide) and added to a 96-well v-bottom plate at 0.08–1.5×10$^5$ cells per well. Each compound tested was diluted in binding buffer and added to the cells. Each sample contained 0.1% DMSO. Biotinylated α-bungarotoxin (Invitrogen Corporation, Carlsbad, Calif.) was diluted in binding buffer and added to cells to yield a final concentration of 10 nM. An excess of unlabeled α-bungarotoxin was added to the non-specific binding control at a final concentration of 1.5 μM. The samples were incubated at room temperature for one hour. After incubation, the cells were washed one time with binding buffer to remove the unbound α-bungarotoxin.

Phycoerythrin-labeled streptavidin (Becton-Dickinson Biosciences, San Jose, Calif.) was diluted in binding buffer and added to the cells for a final concentration of 1.0 μg/mL. The samples were incubated in the dark at room temperature for 15 minutes. The cells were washed once with binding buffer to remove the excess phycoerythrin-labeled streptavidin. The samples were then resuspended in binding buffer and α-bungarotoxin binding was quantified by FACS analysis.

Compounds were initially tested at 10 uM and 1 uM. Compounds showing 50% or greater inhibition of α-bungarotoxin binding at 10 uM were then tested in an 8-point IC$_{50}$ assay. Briefly, compounds were three-fold serially diluted and added to cells at the following concentrations: compounds showing greater than or equal to 50% inhibition at 10 uM and less than 75% inhibition at 1 uM were serially diluted from a concentration of 50 uM, compounds showing greater than 50% inhibition at 10 uM and between 70 and 95% inhibition at 1 uM were serially diluted from 10 uM and lastly, compounds showing inhibition greater than 50% inhibition at 10 uM and greater than 95% inhibition at 1 uM were serially diluted from 1 uM. IC$_{50}$ curves were then generated from the percent inhibition values at each of the eight concentrations.

The compounds of the invention tested in the above described assay exhibited IC$_{50}$ values between 1 nM and 10 uM.

Example 342

Treatment Prior to/after LPS Challenge Inhibits Circulating TNF in Mice

Male, BALB/c mice, 6-8 weeks of age, were treated with 10 mg/kg of the various compounds of the invention or vehicle control, intraperitoneally (ip). At 5 minutes after treatment with the compounds or vehicle control, the mice were injected with 0.5 mg/kg lipopolysaccharide (LPS) (List Biological Laboratories, Inc., Campbell, Calif.), ip. Mice were sacrificed 1 hour after LPS treatment and blood samples were collected via closed cavity cardiac puncture for TNF-α measurement. Blood was collected into polypropylene tubes containing EDTA and placed into a Microfuge for 10 minutes at 10,000 rpm. Plasma was salvaged from each sample for analysis. TNF-α was measured by ELISA (mouse ELISA kit from R&D Systems Inc., Minneapolis, Minn.) and by multiplexed Luminex analysis using the Bio-Rad Suspension Array System (Bio-Rad Laboratories, Hercules, Calif.) with the Bio-Plex mouse cytokine 5-plex kit (BioRad Laboratories). The compounds tested according to the above described methods inhibited LPS-induced TNF-α values by a minimum of 25% in relation to vehicle-treated control values.

Example 343

Treatment with Compounds Shows Protection Against an LPS-Induced Lethality in Mice Male, BALB/c mice, 8-14 weeks of age, were treated with 10 mg/kg of the various compounds of the invention or vehicle control, intraperitoneally (ip). At 30 minutes after treatment with the inventive compounds or vehicle control, the mice were injected with a dose of LPS (List Biological Laboratories, Inc., Campbell, Calif.) determined by pilot studies to give the $LD_{75}$ specifically defined for each batch of mice utilized. Historically, the LPS dose chosen ranged from 30-40 μg/mouse, i.e. 1.2-1.6 mg/kg, ip. Following the challenge with LPS, the mice were subsequently dosed at 10 mg/kg, bid, for three days with either compound or vehicle. Animals were closely monitored for morbidity and mortality. Each death was recorded by day of event. Animals were followed for at least three, and up to five days following LPS challenge. Protection from lethality was defined by the ability of the inventive compounds to guard the mice from lethality noted in the vehicle control groups. Typically, 60-80% lethality was seen in the vehicle control groups, whereas compound-treated groups showed 0-30% lethality.

Example 344

Treatment with Compounds Inhibited Influx of Eosinophils and Neutrophils in a Murine Model of Allergic Lung Inflammation Male, BALB/c mice, 6-8 weeks of age, were sensitized and challenged with ovalbumin in a model of allergic lung inflammation. Briefly, mice were sensitized intraperitoneally with 10 ug of ovalbumin on Days 1 and 14. Mice were administered compounds orally at the doses indicated below beginning 30 minutes before ovalbumin challenge. Animals were challenged intranasally with 100 ug ovalbumin for 3 days. Eight hours after the final ovalbumin challenge, mice were sacrificed and bronchoalveolar lavage (BAL) was performed. Microscope slides were prepared for each BAL sample and differential cell counts were performed. The immune response associated with the onset of an allergic lung response is histopathologically characterized by the infiltration of the bronchial mucosa with neutrophils and eosinophils.

Groups of six mice were treated with either compounds of the invention, or vehicle control. Sham groups of mice were sensitized with saline and challenged with allergen or sensitized with allergen and challenged with saline. The sham groups were included in the study to assess the effect of the sensitization-challenges procedure on the animals. All compounds were dissolved in saline. The compounds that were tested in the above-described model were dosed at 1, 5, or 10 mg/kg twice a day, at 30 minutes prior to each intranasal alleregen challenge, for the three days prior to BAL. Compound 1 is a racemic mixture of a compound of the present invention, Compound 2 has an R-configuration at the 2-position of the piperazine ring and Compound 3 has an S-configuration at the 2-position of the piperazine ring of that compound. The results of this experiment are presented in FIG. 1. As shown in FIG. 1, the compounds of the present invention designated as Compounds 1 and 2 significantly inhibited influx of both eosinophils and neutrophils.

Example 345

Figure 2:
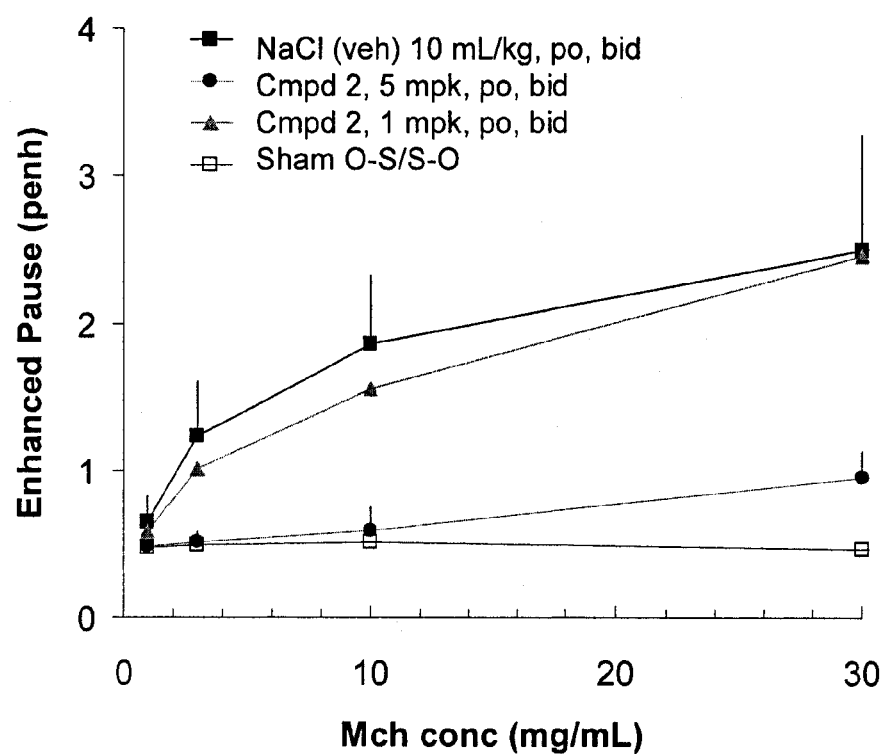
FIG. 2 is a line graph showing enhanced pause (penh) on the y-axis and concentration of methacholine (Mch) in mg/ml in a murine model of allergic lung inflammation where mice were treated with two different concentration of Compound 2 (1 mg/kg and 5 mg/kg), vehicle control or received sham treatment.

Treatment with Compound 2 Attenuates Airway Hyperreactivity in Murine Model of Allergic Lung Inflammation Mice were sensitized and challenged with ovalbumin as described above. Eight hours after the final ovalbumin challenge, mice were challenged with aerosol methacholine at 1, 3, 10 and 30 and 100 mg/ml to test for lung hyperreactivity. Beginning 30 minutes before ovalbumin challenge, mice were treated with vehicle control, sham, Compound 1 at 10 mg/kg (orally, twice a day) or Compound 2 at 5 or 1 mg/kg (orally, twice a day). At 8 hours following the final allergen challenge, airway hyperresponsiveness (AHR) was measured in conscious, unrestrained mice using barometric whole body plethysmography. Enhanced pause, (penh), was taken as a measure of AHR. Penh reflects changes in the waveform of the pressure signal from inspiration and expiration and this was compared to the timing of early and late expiration (pause). Potential changes in penh were measured at a rate of every 2 seconds for each animal by a fully automated, computer based software-hardware system developed by Emka Technologies, Inc (115 Hillwood Ave, Suite 203, Falls Church, Va., 22046). The results of this experiment are shown in FIG. 2. The formula for computing Penh is as follows: Penh=(peak expiratory pressure/peak inspiratory pressure)× expiratory time−relaxation time)/relaxation time. As shown in FIG. 2, Compound 2 administered at 5 mg/kg attenuated airway hyperesponsiveness.

Example 346

Figure 3:
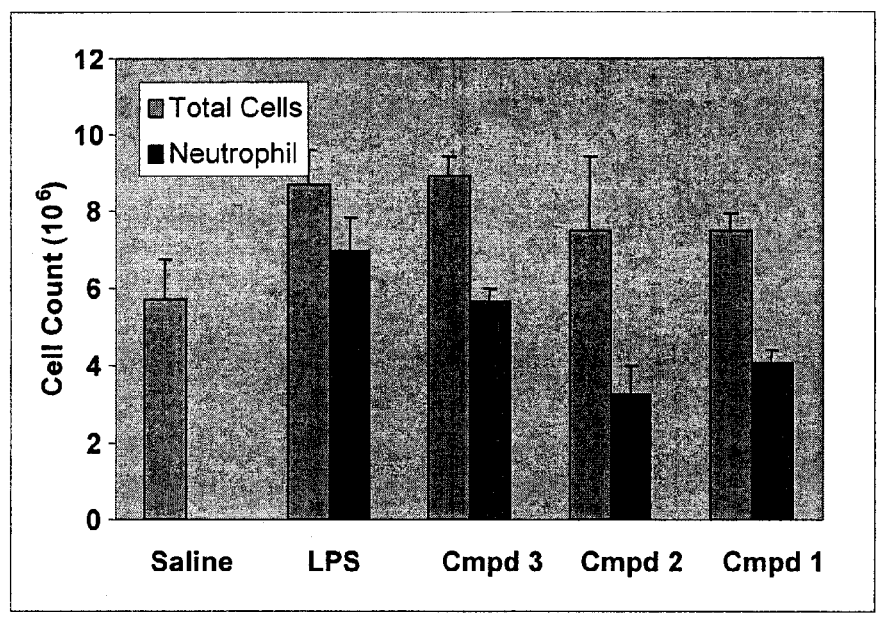
FIG. 3 is a bar graph showing numbers of total cells and neutrophils per mL of BAL fluid from mice treated with saline, LPS as an aerosol alone or LPS plus Compounds 1, 2 or 3 in a murine acute lung injury model.

Treatment with Compounds Inhibited Neutrophil Influx in Bronchoalveolar Lavage Fluid in a Murine Model of LPS-Induced Acute Lung Injury Male, BALB/c mice, 8-10 weeks of age, were challenged with LPS aerosol in a murine model of acute lung injury. Briefly, groups of six mice were challenged with either saline or 75 μg/ml LPS via a 30 minute aerosol. Test compounds were administered orally 15 minutes prior to LPS exposure. Compound 1 was administered orally at 10 mg/kg, Compound 2 was administered orally at 5 mg/kg and Compound 3 was administered at 5 mg/kg. Mice were sacrificed 3 hours after LPS challenge and bronchoalveolar lavage was performed as described above. Neutrophils in the BAL fluid were counted and the results are shown in FIG. 3. As shown in FIG. 3, Compounds 1 and 2 significantly inhibited neutrophil influx.

Example 347

Binding Affinities and Stereoselectivity for α7 nAChR on PC12 and SH-SY5Y Cells

The methods utilized to determine stereoselectivity of compounds of the invention in PC12 cells is described above in Example 341. Stereoselectivity of these compounds were also assessed in the human cell line, SH-SY5Y. Briefly, SH-SY5Y cells (ATCC, Manassas, Va.) were resuspended in binding buffer (PBS containing 1.0% FBS and 0.02% sodium azide) and added to a 96-well v-bottom plate at $1.5$-$2.0 \times 10^5$ cells per well. Each compound tested was diluted in binding buffer and added to the cells. Each sample contained 0.1% DMSO. Biotinylated α-bungarotoxin (Invitrogen Corporation, Carlsbad, Calif.) was diluted in binding buffer and added to cells to yield a final concentration of 5 nM. An excess of unlabeled α-bungarotoxin was added to the non-specific binding control at a final concentration of 1.5 μM. The samples were incubated at room temperature for one hour. After incubation, the cells were washed one time with binding buffer to remove the unbound α-bungarotoxin.

Phycoerythrin-labeled streptavidin (Becton-Dickinson Biosciences, San Jose, Calif.) was diluted in binding buffer and added to the cells for a final concentration of 1.0 μg/mL. The samples were incubated in the dark at room temperature for 15 minutes. The cells were washed once with binding buffer to remove the excess phycoerythrin-labeled streptavidin. The samples were then resuspended in binding buffer and α-bungarotoxin binding was quantified by FACS analysis.

Compounds were initially tested on PC 12 cells as described in Example 321. Using the same concentrations tested in the PC12 $IC_{50}$ assay, compounds were then tested for affinity to the human receptor, which is endogenously expressed on SH-SY5Y cells. Briefly, compounds were three-fold serially diluted and added to cells. $IC_{50}$ curves were generated from the percent inhibition values at each of the eight concentrations.

Figure 4A:
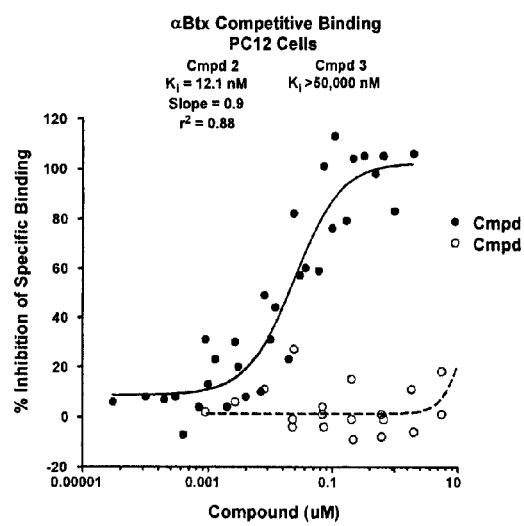
FIG. 4A is a plot showing percent inhibition of specific binding alpha-bungarotoxin in PC 12 cells on y-axis and concentration of Compounds 2 and 3 (uM) on the x-axis.
Figure 4B:
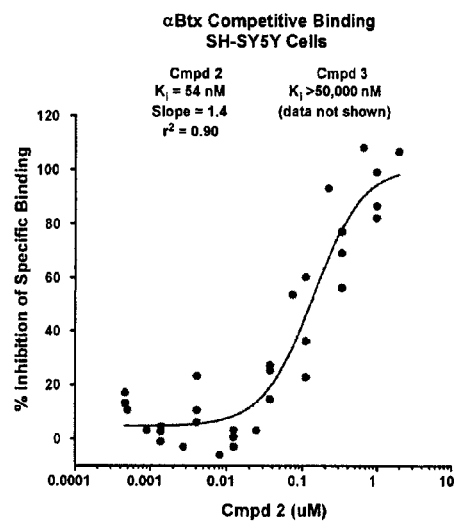
FIG. 4B is a plot showing percent inhibition of specific binding of alpha-bungarotoxin in SH-SY5Y cells and concentration of Compound 2 (uM) on the x-axis.

FIGS. 4A and 4B show data using two specific compounds of the invention. As shown in FIG. 4A, Compound 2 (the R-enantiomer as described in Example 344) and Compound 3 (the S-enantiomer as described in Example 344) showed stereoselectivity in binding affinity for rat alpha-7 receptors. In this experiment, Compound 2 was found to have a $K_i$ of 12.1 nM whereas Compound 3 was found to have a $K_i$ of greater than 50,000 nM in PC12 cells. Other enantiomeric pairs of compounds (enantiomers with R- and S-configurations at the 2-position of the piperazine ring) tested in the PC12 assay have shown similar stereoselectivity in that the R-enantiomers tested bind with greater affinity to the rat alpha-7 receptor than S-enantiomers. As shown in FIG. 4B, Compounds 2 and 3 also showed stereoselective binding affinity for the human alpha-7 receptor. In this experiment, Compound 2 was found to have a $K_i$ of 54 nM whereas Compound 3 was found to have a Ki of greater than 50,000 nM in SH-SY5Y cells.

While this invention has been particularly shown and described with references to specific embodiments thereof, it will be understood by those skilled in the art that various changes in form and details may be made therein without departing from the scope of the invention encompassed by the appended claims.

What is claimed is:
1. A compound of Formula (III) or a pharmaceutically acceptable salt thereof, wherein:

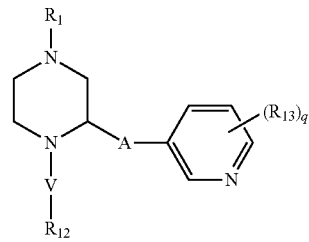

(III)

$R_1$ is selected from the group consisting of H, C1-C10 alkyl, C2-C10 alkenyl, C2-C10 alkynyl, C3-C10 cycloalkyl, C4-C10 cycloalkenyl, C(=O)$R_5$, C(=O)O$R_5$ and C(=O)N$R_5R_5$;

V is selected from the group consisting of a bond, C($R_4$)$_2$, C($R_4$)$_2$C($R_4$)$_2$, C($R_4$)$_2$C($R_4$)$_2R_6$, C($R_4$)$_2$C($R_4$)$_2$C($R_4$)$_2R_6$, C(=O), C(=O)$R_6$, C(=S), C(=S)$R_6$, CH$_2$C(=O), CH$_2$C(=O)$R_6$, CH$_2$C(=S), CH$_2$C(=S)$R_6$, SO$_2$, and SO$_2R_6$;

A is a linking —C($R_a$)$_2$—$X_a$—;

$X_a$ is selected from the group consisting of O, C($R_4$)$_2$O, OC($R_4$)$_2$, N$R_5$, C(=O), C($R_4$)$_2$C(=O), C(=O)N$R_5$, C($R_4$)$_2$N$R_5$, N$R_5$C($R_4$)$_2$, N$R_5$C(=O), N$R_5$C(=O)C($R_4$)$_2$, S, C($R_4$)$_2$S, and SC($R_4$)$_2$;

when $X_a$ is C($R_4$)$_2$O, C($R_4$)$_2$N$R_5$, C(=O), C($R_4$)$_2$C(=O), C(=O)N$R_5$ or C($R_4$)$_2$S, then each $R_a$ is independently selected from the group consisting of H, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, halo, haloalkyl, O$R_5$, S$R_5$, N$R_5R_5$, C(=O)O$R_5$, NO$_2$, CN, C(=O)$R_5$, C(=O)C(=O)$R_5$, C(=O)N$R_5R_5$, N($R_5$)C(=O)$R_5$, N$R_5$S(=O)$_nR_5$, N($R_5$)C(=O)O$R_5$, N$R_5$C(=O)C(=O)$R_5$, N$R_5$C(=O)$R_5$, N$R_5$S(O)$_nN R_5R_5$, N$R_5$S(=O)$_nR_5$, S(=O)$_nR_5$, S(=O)$_nN R_5R_5$ and OC(=O)$R_5$, or both $R_a$ are taken together to form a 3 to 6 membered ring containing 0 to 3 heteroatoms each independently selected from the group consisting of N, O and S, wherein said ring is substituted with one or more $R_8$; and, when $X_a$ is O, OC($R_4$)$_2$, N$R_5$, N$_5$C($R_4$)$_2$N$R_5$C(=O), NC(=O)$R_5$C($R_4$)$_2$, S, or SC($R_4$)$_2$, then each $R_a$ is independently selected from the group consisting of H, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, haloalkyl, C(=O)O$R_5$, CN, C(=O)$R_5$, C(=O)C(=O)$R_5$ and C(=O)N$R_5R_5$, or both $R_a$ are taken together to form a 3 to 6 membered ring containing 0 to 3 heteroatoms each independently selected from the group consisting of N, O and S, wherein said ring is substituted with one or more $R_8$;

each $R_4$ is independently selected from the group consisting of H, C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, halo, haloalkyl, $OR_5$, $SR_5$, $NR_5R_5$, $C(=O)OR_5$, $NO_2$, CN, $C(=O)R_5$, $C(=O)C(=O)R_5$, $C(=O)NR_5R_5$, $N(R_5)C(=O)R_5$, $NR_5S(=O)_nR_5$, $NR_5C(=O)OR_5$, $NR_5C(=O)C(=O)R_5$, $NR_5C(=O)R_5$, $NR_5S(=O)_nNR_5R_5$, $NR_5S(=O)_nR_5$, $S(=O)R_5$, $S(=O)_nNR_5R_5$ and $OC(=O)R_5$, or two $R_4$ are taken together to form a 3-6 membered ring comprising 0-3 heteroatoms, wherein said heteroatom is independently selected from the group consisting of N, O and S, and wherein said ring is substituted with one or more $R_8$;

each $R_5$ is independently selected from the group consisting of H, C1-C10 alkyl and C2-C10 alkenyl;

each $R_6$ is independently selected from the group consisting of $C(R_4)_2$, $C(R_4)_2C(R_4)_2$, $NR_5$, O, $C(=O)$, $C(=O)C(R4)_2$, $C(=O)O$, $OC(R_4)_2$, $C(R_4)_2O$, $C(R_4)_2S$, $C(R_4)_2NR_5$, $NR_5CH_2$, S and $SC(R_4)_2$;

each $R_7$ is independently selected from the group consisting of halo, haloalkyl, $OR_5$, $SR_5$, $C(=O)R_5$, $OC(=O)R_5$, $C(=O)OR_5$, $NR_5R_5$, $NO_2$, CN, $OC(=O)NR_5R_5$, $C(=O)NR_5R_5$, $N(R_5)C(=O)R_5$, $NR_5C(=O)OR_5$, $S(=O)_nNR_5R_5$, C3-C8 cycloalkyl, C4-C10 cycloalkenyl, 3-8 membered heterocycloalkyl, 4-10 membered heterocycloalkenyl, C5-C11 bicycloalkyl, C5-C11 bicycloalkenyl, 5-11 membered heterobicycloalkyl, 5-11 membered heterobicycloalkenyl, aryl, and heteroaryl, wherein said aryl and heteroaryl are each optionally substituted with one or more $R_9$;

each $R_8$ is independently selected from the group consisting of $R_7$, C1-C10 alkyl, C1-C10 alkyl substituted with one or more $R_7$, C2-C10 alkenyl, C2-C10 alkenyl substituted with one or more $R_7$, C2-C10 alkynyl, and C2-C10 alkynyl substituted with one or more $R_7$;

each $R_9$ is independently selected from the group consisting of C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, 3-8 membered heterocycloalkyl, 3-8 membered eterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, halo, $OR_5$, $SR_5$, $NR_5R_5$, $C(=O)OR_5$, $NO_2$, CN, $C(=O)R_5$, $C(=O)C(=O)R_5$, $C(=O)NR_5R_5$, $NR_5C(=O)R_5$, $NR_5S(=O)_nR_5$, $NR_5C(=O)OR_5$, $NR_5C(=O)C(=O)R_5$, $NR_5C(=O)NR_5R_5$, $NR_5S(=O)_nNR_5R_5$, $NR_5S(=O)_nR_5$, $S(=O)_nR_5$, $S(=O)_nNR_5R_5$, $OC(=O)R_5$, optionally substituted aryl, and optionally substituted heteroaryl;

$R_{12}$ is selected from the group consisting of:

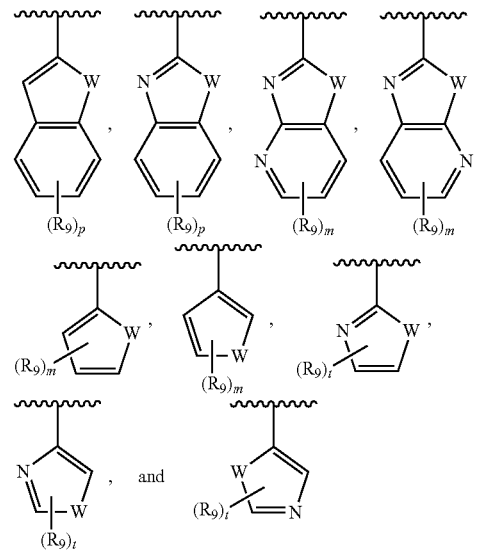

wherein in $R_{12}$:
(a) W is selected from the group consisting of $NR_5$, O and S;
(b) each m is an integer from 0 to 3;
(c) each p is an integer from 0 to 5;
(d) each q is an integer from 0 to 4;
(e) each t is an integer from 0 to 2; and
(f) each $R_9$ is independently selected from the group consisting of C1-C10 alkyl, C1-C10 alkyl substituted with one or more $R_7$, halo, $OR_5$, $NR_5R_5$, $C(=O)OR_5$, $NO_2$, CN, $S(=O)_nR_5$ optionally substituted aryl and optionally substituted heteroaryl; and each $R_{13}$ independently selected from the group consisting of C1-C10 alkyl, C1-C10 alkyl substituted with one or more $R_7$, C2-C10 alkenyl, C2-C10 alkenyl substituted with one or more $R_7$, C2-C10 alkynyl, C2-C10 alkynyl substituted with one or more $R_7$, C3-C10 cycloalkyl, C3-C10 cycloalkyl substituted with one or more $R_8$, C4-C10 cycloalkenyl, C4-C10 cycloalkenyl substituted with one or more $R_8$, 3-8 membered heterocycloalkyl, 3-8 membered heterocycloalkyl substituted with one or more $R_8$, 4-10 membered heterocycloalkenyl, 4-10 membered heterocycloalkenyl substituted with one or more $R_8$, C5-C11 bicycloalkyl, C5-C11 bicycloalkyl substituted with one or more $R_8$, C5-C11 bicycloalkenyl, C5-C11 bicycloalkenyl substituted with one or more $R_8$, 5-11 membered heterobicycloalkyl, 5-11 membered heterobicycloalkyl substituted with one or more $R_8$, 5-11 membered heterobicycloalkenyl, 5-11 membered heterobicycloalkenyl substituted with one or more $R_8$, halo, $OR_5$, $SR_5$, $NR_5R_5$, $C(=O)OR_5$, $NO_2$, CN, $C(=O)R_5$, $C(=O)C(=O)R_5$, $C(=O)NR_5R_5$, $NR_5C(=O)R_5$, $NR_5S(=O)_nR_5$, $NR_5C(=O)OR_5$, $NR_5C(=O)C(=O)R_5$, $NR_5C(=O)NR_5R_5$, $NR_5S(=O)_nNR_5R_5$, $NR_5S(=O)_nR_5$, $S(=O)_nR_5$, $S(=O)_nNR_5R_5$, $OC(=O)R_5$, optionally substituted aryl and optionally substituted heteroaryl;

n is 1 or 2; and
q is an integer from 0 to 4.

2. A pharmaceutical composition comprising at least one pharmaceutically acceptable carrier and the compound of claim 1.

* * * * *